(12) United States Patent
Druilhe et al.

(10) Patent No.: US 8,716,443 B2
(45) Date of Patent: May 6, 2014

(54) SUB-REGION OF A PLASMODIUM PROTEIN WITH IMPROVED VACCINE POTENTIAL, AND MEDICAL USES THEREOF

(75) Inventors: Pierre Druilhe, Paris (FR); Giampietro Corradin, Lausanne (CH); Ali Jafarshad, Paris (FR); Christian Roussilhon, Paris (FR)

(73) Assignees: Institut Pasteur, Paris (FR); Univiersite de Lausanne, Lausanne (CH)

( * ) Notice: Subject to any disclaimer, the term of this patent is extended or adjusted under 35 U.S.C. 154(b) by 135 days.

(21) Appl. No.: 12/991,414

(22) PCT Filed: May 7, 2009

(86) PCT No.: PCT/IB2009/051875
§ 371 (c)(1),
(2), (4) Date: Feb. 28, 2012

(87) PCT Pub. No.: WO2009/136373
PCT Pub. Date: Nov. 12, 2009

(65) Prior Publication Data
US 2012/0164167 A1 Jun. 28, 2012

(30) Foreign Application Priority Data
May 7, 2008 (EP) .................................... 08290433

(51) Int. Cl.
*A61K 39/00* (2006.01)
*C07K 1/00* (2006.01)
*C07K 16/00* (2006.01)

(52) U.S. Cl.
USPC ..................... 530/350; 424/185.1; 530/387.1; 530/388.1

(58) Field of Classification Search
None
See application file for complete search history.

(56) References Cited

U.S. PATENT DOCUMENTS

2004/0137512 A1 * 7/2004 Horii ............................. 435/7.1

FOREIGN PATENT DOCUMENTS

EP 1754717 A1 2/2007

OTHER PUBLICATIONS

European Patent Office, International Search Report and Written Opinion of the International Searching dated Aug. 18, 2009 (16 pgs).
Hall, N et al., Sequence of *Plasmodium falciparum* Chromosomes 1, 3-9 and 13, Nature, vol. 419, Oct. 3, 2002, pp. 527-531.
Ballou, W R et al., Update on the Clinical Development of Candidate Malaria Vaccines, The American Society of Tropical Medicine and Hygiene, vol. 71, Suppl 2, Aug. 1, 2004, pp. 239-247.

* cited by examiner

*Primary Examiner* — Albert Navarro
(74) *Attorney, Agent, or Firm* — Harris Beach PLLC

(57) ABSTRACT

The present application relates to a sub-region of a *Plasmodium* protein, with improved vaccine potential, and to medical uses thereof, notably for treatment or diagnosis of malaria. The present invention notably provides unstructured or unfolded polypeptides deriving from the PFF0165c protein of *P. falciparum* 3D7. The polypeptides of the invention have a high antigenicity, a high immunogenicity, have a high parasite-killing activity in the ADCI assay, and are strongly associated with clinical protection against malaria, and. The present invention thereby provides a vaccine for the palliative and/or curative treatment of malaria, which is specifically intended for infants, toddlers, children under the age of 5, pregnant women.

21 Claims, 9 Drawing Sheets

```
LOCUS       XM_960931               3312 bp    mRNA    linear   INV 07-FEB-2007
DEFINITION  Plasmodium falciparum 3D7 hypothetical protein (PFF0165c) mRNA,
            complete cds.
ACCESSION   XM_960931
VERSION     XM_960931.1  GI:86170479
KEYWORDS    .
SOURCE      Plasmodium falciparum 3D7
  ORGANISM  Plasmodium falciparum 3D7
            Eukaryota; Alveolata; Apicomplexa; Aconoidasida; Haemosporida;
            Plasmodium; Plasmodium (Laverania).
REFERENCE   1  (bases 1 to 3312)
  AUTHORS   Cherevach,I., Davis,P., Goodhead,I., Stevens,K., Mungall,K.,
            Berry,A.E., Berriman,M., RA Pain,A., Hall,N., Atkin,R.,
            Chillingworth,C., Doggett,J., Ormond,D., Sanders,M., Hayes,R.,
            Hall,S., Quail,M. and Barrell,B.G.
  TITLE     Direct Submission
  JOURNAL   Submitted (26-MAR-2004) P.falciparum Genome Sequencing Consortium,
            The Welcome Trust Sanger Institute, Wellcome Trust Genome Campus,
            Hinxton, Cambridge CB10 1SA, UK
COMMENT     PROVISIONAL REFSEQ: This record has not yet been subject to final
            NCBI review. This record is derived from an annotated genomic
            sequence (NC_004327).
            COMPLETENESS: incomplete on both ends.
FEATURES             Location/Qualifiers
     source          1..3312
                     /organism="Plasmodium falciparum 3D7"
                     /mol_type="mRNA"
                     /isolate="3D7"
                     /db_xref="taxon:36329"
                     /chromosome="6"
     gene            1..3312
                     /locus_tag="PFF0165c"
                     /db_xref="GeneID:3885786"
     CDS             1..3312
                     /locus_tag="PFF0165c"
                     /old_locus_tag="MAL6P1.37"
                     /note="Putative Zn-finger motif at the C-terminus"
                     /codon_start=1
                     /product="hypothetical protein"
                     /protein_id="XP_966024.1"
                     /db_xref="GI:86170480"
                     /db_xref="GOA:Q6LFN2"
                     /db_xref="HSSP:P25916"
                     /db_xref="InterPro:IPR001841"
                     /db_xref="UniProtKB/TrEMBL:Q6LFN2"
                     /db_xref="GeneID:3885786"
```

FIGURE 1 (start)

/translation="MSNKKRSKNENDESTSLPLENSELLIEYIHNLKSCLNVYRREIQ
EKNKYISIIKNDLSFHECILTNVNVVWSVFNNDLLNLLCNNEQKEEGEEIIKQRNIGD
EINEYNNLTKLQNDENIKNNNMIKEDLEDDANQNILMKSPYYNIENFLQVFLKYINKK
KKKVKVKVKDEGKKEKIEDKKYEQDDEEENEEEEEEEEEEGEEENKEDEEFFKTFVS
FNLYHNNNEKNISYDKNLVKQENDNKDEARGNDNMCGNYDIHNERGEMLDKGKSYSGD
EKINTSDNAKSCSGDEKVITSDNGKSYDYVKNESEEQEEKENMLNNKKRSLECNPNEA
KKICFSLEEKIGTVQSVKLKEYNELSKENIEKNKHDDNNICNYLSHNEGENVIEREDK
LFNKLNNKNYRNEEEKKKNQINFDYLKKKIKNNQDVFEETIQKCFLINLKKTLNLINK
IMYLKNVEFRKYNLDYIRKINYEKCFYYKNYIDIKKKISELQKDNESLKIQVDRLEKK
KATLIYKLNNDNIRKHILDNNIKDYQNGIDNSKVSYFDEGENPYNRNNKNYRTDNKNS
DDNNNNNNYYYNNYNSDDNYNSEDNEYNNGNYRFRNNYKKDSLNEDDVKKNPLKVCHK
INSDSNIFVNFENIITKQNIIHSEPFRNLLKESNELYITLKEKEKENIILKNEILKME
NKKDEEYEHLLNNTIEDKKELTRSIKELEINMMTCNMEKDKISNKVNTLEYEINVLKN
IDKNQTMQLQQKENDILKMKLYIEKLKLSEKNLKDKIILLENEKDKMLSGIHIKDNSF
NEESKSEEGKIQLRDIQNDNDEKYDDEKKRFKELFIENQKLKEELNKKRNVEEELHSL
RKNYNIINEEIEEITKEFEKKQEQVDEMILQIKNKELELLDKFNNKMNKAYVEEKLKE
LKNTYEEKMKHINNIYKKHDDFVNIYLNLFFQARKNAILSDSQREEQMNLFIKLKDKY
DIIFQKKIELTDILKNVYDCNKKLIGHCQDLEKENSTLQNKLSNEIKNSKMLSKNLSK
NSDDHLLIEENNELRRRLICSVCMENFRNYIIIKCGHIYCNNCIFNNLKTRNRKCPQC
KVPFDKKDLQKIFLD"          (SEQ ID NO: 2)

FIGURE 1 (continued)

```
ORIGIN
        1 atgagtaata agaaaagaag taaaaatgaa aatgacgaat caacatcatt acctttagaa
       61 aattccgagt tattaatcga atatatacat aatttaaaga gctgtttaaa tgtatatagg
      121 cgagagatcc aggaaaagaa taaatatatt agtatcataa agaatgattt aagttttcac
      181 gaatgtatat taacaaatgt aaatgttgta tggagtgtat ttaataacga tttattaaac
      241 ctgctatgta ataatgaaca aaaagaagaa ggggaagaaa taataaaaca aagaaacata
      301 ggtgatgaga taatgaata taataattta acaaaattac aaaatgatga aaatataaaa
      361 aacaataata tgattaaaga agatcttgaa gatgatgcca atcagaatat tttgatgaaa
      421 tcaccttatt ataatataga aaatttttta caagtttttt taaaatatat taataagaag
      481 aagaaaaagg taaaggtaaa ggtaaaggat gaaggtaaga aagaaaaaat agaggacaaa
      541 aaatacgagc aagatgacga agaagaaaat gaagaagagg aggaggagga agaagaagaa
      601 gaaggagaag aagaaaataa agaggatgaa gaattttca aaacatttgt atcttttaat
      661 ttgtatcata ataacaatga aaagaatata tcatatgata aaaatttagt taaacaagaa
      721 aatgataata aagatgaagc acgtggtaac gataacatgt gtggtaatta tgatatacat
      781 aatgagagag gggaaatgtt agataagggt aaatcttatt caggtgacga aaaaataaat
      841 acaagtgata atgctaaatc atgttcaggt gacgaaaaag taattacaag cgataatggt
      901 aaatcttatg attatgtaaa aaatgaaagt gaagaacaag aagaaaaaga aaatatgtta
      961 aataataaaa aaagaagttt ggaatgtaat ccaaatgaag cgaaaaaaat ttgtttctct
     1021 ttagaagaga agataggaac tgtgcaaagt gtaaaattaa aggaatataa tgaattgagt
     1081 aaagaaaata ttgaaaaaaa taaacatgat gataataaca tttgtaatta tctttcacac
     1141 aatgaaggtg agaatgtaat agaaagggaa gataaattat ttaataagct gaataataaa
     1201 aattatagaa atgaagaaga gaaaaaaaaa aatcaaataa attttgatta tttaaaaaaa
     1261 aaaattaaga ataaccaaga tgtttttgag gaaacgatac aaaaatgttt tttgataaat
     1321 ttaaaaaaga cattaaatct tataaacaaa attatgtatt taaaaaatgt tgaatttagg
     1381 aaatataact tagattatat tcgaaaaata aattatgaga aatgttttta ttataaaaat
     1441 tatattgata taaaaagaa aataagcgaa ttacaaaagg ataacgaaag tttaaaaatt
     1501 caggtagata ggctagagaa aaagaaggct acattaatat acaaattgaa taatgataat
     1561 attcgtaaac atattcttga taataatatt aaagattatc aaaatggtat tgataattca
     1621 aaggtaagtt attttagtga aggggagaac ccatataacc gtaataataa aaattatcgt
     1681 acagataata agaatagtga tgataataat aataataata attattatta caataattat
     1741 aatagtgatg ataattataa tagtgaggat aatgaatata ataatggtaa ttatcgattt
     1801 cgtaataatt ataagaagga ttctttgaat gaagatgatg taaaaaaaaa tcctttgaag
     1861 gtatgtcaca aaattaacag tgattctaat atttttgtta attttgaaaa tattataaca
     1921 aaacaaaata ttatacatag tgaaccattt cgaaatttat taaaagaatc taatgaatta
     1981 tatattacat taaaagagaa agaaaaagaa aatatattt taaaaaatga aattctaaag
     2041 atggaaaata aaaggatga agaatatgaa cacttattaa ataataccat tgaagacaag
     2101 aaggaattaa ctagaagtat taagaattat gaaataaata tgatgacatg taatatggaa
     2161 aaagataaaa taagtaataa agtaaataca ttagaatacg aaataaatgt tttaaaaaat
     2221 attgataaga atcaaactat gcaattacaa caaaaggaaa atgatattct aaagatgaag
     2281 ttgtatattg agaaattaaa attatctgag aaaaatttaa aagataaaat tattttatta
     2341 gaaaatgaaa aggataaaat gttgagtggt atacatataaa aagataattc gtttaatgag
     2401 gagtccaaaa gtgaggaagg caaaattcag ctgagagata ttcaaaatga taacgatgaa
     2461 aaatatgatg atgaaaaaaa acgatttaaa gagttattta tagaaaatca gaaattaaaa
     2521 gaagaattga acaaaaaaag aaacgtcgaa gaggaattac acagcttaag gaaaaattat
     2581 aatatcatta atgaagaaat tgaagaaata acaaaagaat tgaaaaaaaa acaagaacaa
     2641 gttgatgaaa tgatattaca aataaaaaat aaagaattag aattattgga taaatttaat
     2701 aataaaatga ataaagcgta tgtagaagag aaattaaaag aattaaaaaa tacatatgaa
     2761 gaaagatga acatataaa taatatatat aaaaaacatg atgattttgt taatatttat
     2821 ttaaatttat tttttcaagc aagaaaaaat gcaatacttt ctgatagtca aagagaagaa
     2881 caaatgaatt tatttataaa attaaaagat aaatatgata tcatatttca aaaaaaaata
     2941 gaattaacag atattttaaa aatgtgtat gattgtaata aaaaattaat aggacattgt
     3001 caagatttag aaaagaaaa ttctactctt cagaataaac tatctaacga aataagaat
     3061 tcaaaaatgc tatccaaaaa tttatctaaa aattctgatg atcatttatt aattgaagaa
     3121 aataatgaat taagaagaag attaatttgt agtgtatgta tggaaaactt tagaaattat
     3181 attattatca aatgtggtca tatttattgt aacaattgta tattcaataa tttaaaaaca
     3241 agaaatagaa agtgtccaca gtgtaaagta ccatttgata aaaggatct acaaaaaatt
     3301 tttctcgact aa            (SEQ ID NO: 1)
//
```

FIGURE 1 (continued)

```
LOCUS       XP_966024               1103 aa            linear   INV 07-FEB-2007
DEFINITION  hypothetical protein PFF0165c [Plasmodium falciparum 3D7].
ACCESSION   XP_966024
VERSION     XP_966024.1  GI:86170480
DBSOURCE    REFSEQ: accession XM_960931.1
KEYWORDS    .
SOURCE      Plasmodium falciparum 3D7
  ORGANISM  Plasmodium falciparum 3D7
            Eukaryota; Alveolata; Apicomplexa; Aconoidasida; Haemosporida;
            Plasmodium; Plasmodium (Laverania).
REFERENCE   1  (residues 1 to 1103)
  AUTHORS   Cherevach,I., Davis,P., Goodhead,I., Stevens,K., Mungall,K.,
            Berry,A.E., Berriman,M., RA Pain,A., Hall,N., Atkin,R.,
            Chillingworth,C., Doggett,J., Ormond,D., Sanders,M., Hayes,R.,
            Hall,S., Quail,M. and Barrell,B.G.
  TITLE     Direct Submission
  JOURNAL   Submitted (26-MAR-2004) P.falciparum Genome Sequencing
Consortium,
            The Welcome Trust Sanger Institute, Wellcome Trust Genome
Campus,
            Hinxton, Cambridge CB10 1SA, UK
COMMENT     PROVISIONAL REFSEQ: This record has not yet been subject to
final
            NCBI review. The reference sequence was derived from CAG25204.
FEATURES             Location/Qualifiers
     source          1..1103
                     /organism="Plasmodium falciparum 3D7"
                     /isolate="3D7"
                     /db_xref="taxon:36329"
                     /chromosome="6"
     Protein         1..1103
                     /product="hypothetical protein"
                     /calculated_mol_wt=132340
     Region          1050..1092
                     /region_name="RING"
                     /note="RING-finger (Really Interesting New Gene)
domain, a
                     specialized type of Zn-finger of 40 to 60 residues
that
                     binds two atoms of zinc; defined by the 'cross-brace'
                     motif C-X2-C-X(9-39)-C-X(1-3)-
                     H-X(2-3)-(N/C/H)-X2-C-X(4-48)C-X2-C; probably involved
in
                     medi; cd00162"
                     /db_xref="CDD:29102"
```

FIGURE 1 (continued)

```
Site            order(1050,1053,1065,1067,1070,1073,1085,1088)
                /site_type="other"
                /note="cross-brace motif"
                /db_xref="CDD:29102"
CDS             1..1103
                /locus_tag="PFF0165c"
                /old_locus_tag="MAL6P1.37"
                /coded_by="XM_960931.1:1..3312"
                /note="Putative Zn-finger motif at the C-terminus"
                /db_xref="GOA:Q6LFN2"
                /db_xref="HSSP:P25916"
                /db_xref="InterPro:IPR001841"
                /db_xref="UniProtKB/TrEMBL:Q6LFN2"
                /db_xref="GeneID:3885786"
ORIGIN
    1 msnkkrskne ndestslple nsellieyih nlksclnvyr reiqeknkyi siikndlsfh
   61 eciltnvnvv wsvfnndlln llcnneqkee geeiikqrni gdeineynnl tklqndenik
  121 nnnmikedle ddanqnilmk spyynienfl qvflkyinkk kkkvkvkvkd egkkekiedk
  181 kyeqddeeen eeeeeeeeee egeeenkede effktfvsfn lyhnnnekni sydknlvkqe
  241 ndnkdeargn dnmcgnydih nergemldkg ksysgdekin tsdnakscsg dekvitsdng
  301 ksydyvknes eeqeekenml nnkkrslecn pneakkicfs leekigtvqs vklkeynels
  361 kenieknkhd dnnicnylsh negenviere dklfnklnnk nyrneeekkk nqinfdylkk
  421 kiknnqdvfe etiqkcflin lkktlnlink imylknvefr kynldyirki nyekcfyykn
  481 yidikkkise lqkdneslki qvdrlekkka tliyklnndn irkhildnni kdyqngidns
  541 kvsyfdegen pynrnnknyr tdknsddnnn nnnnyyynny nsddnynsed neynngnyrf
  601 rnnykkdsln eddvkknplk vchkinsdsn ifvnfeniit kqniihsepf rnllkesnel
  661 yitlkekeke niilkneilk menkkdeeye hllnntiedk keltrsikel einmmtcnme
  721 kdkisnkvnt leyeinvlkn idknqtmqlq qkendilkmk lyieklklse knlkdkiill
  781 enekdkmlsg ihikdnsfne ekskseegkiq lrdiqndnde kyddekkrfk elfienqklk
  841 eelnkkrnve eelhslrkny niineeieei tkefekkqeq vdemilqikn kelelldkfn
  901 nkmnkayvee klkelkntye ekmkhinniy kkhddfvniy lnlffqarkn ailsdsqree
  961 qmnlfiklkd kydiifqkki eltdilknvy dcnkklighc qdlekenstl qnklsneikn
 1021 skmlsknlsk nsddhlliee nnelrrrlic svcmenfrny iiikcghiyc nncifnnlkt
 1081 rnrkcpqckv pfdkkdlqki fld        (SEQ ID NO: 2)
//
```

FIGURE 1 (end)

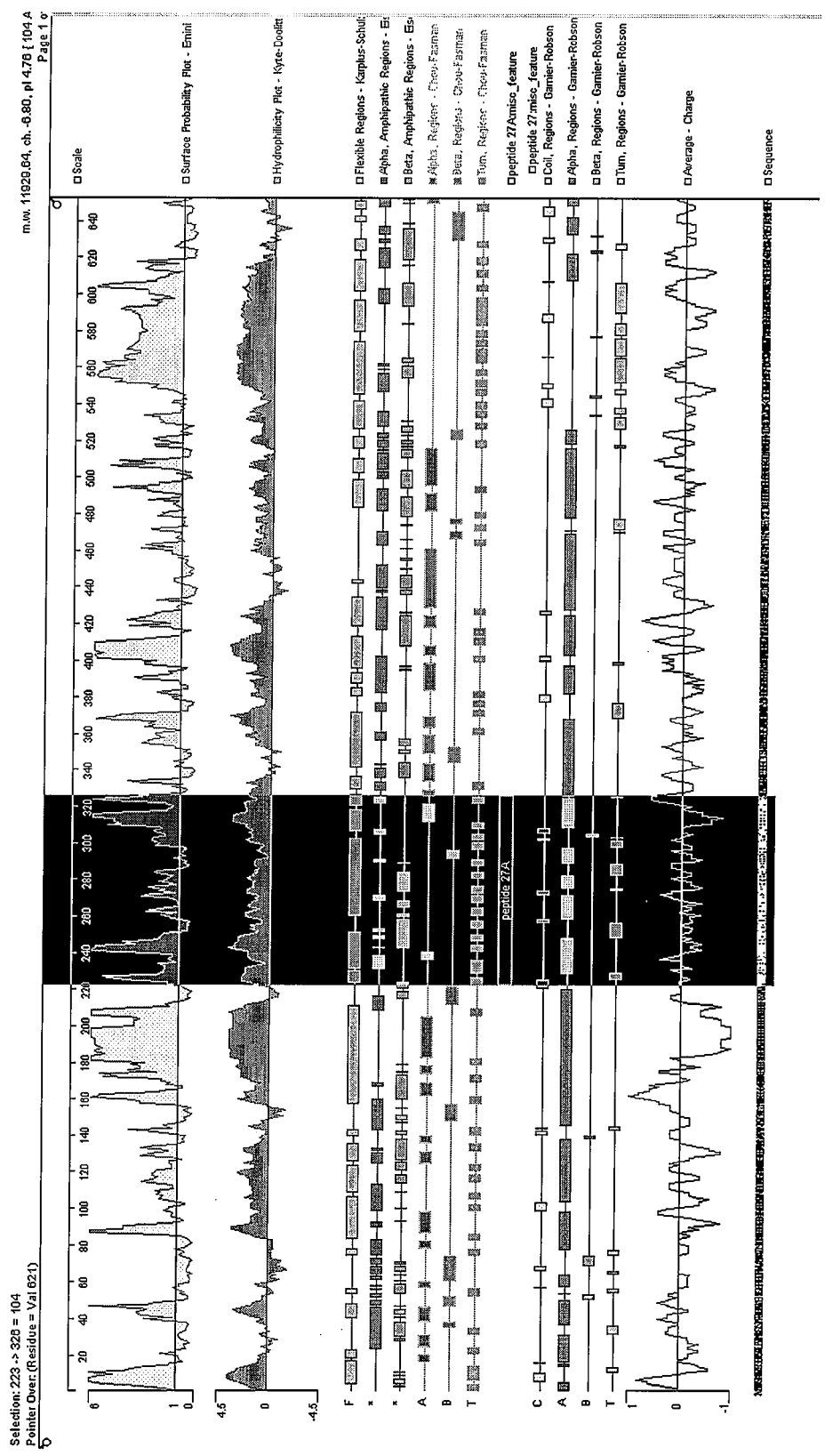
FIGURE 5 (start)

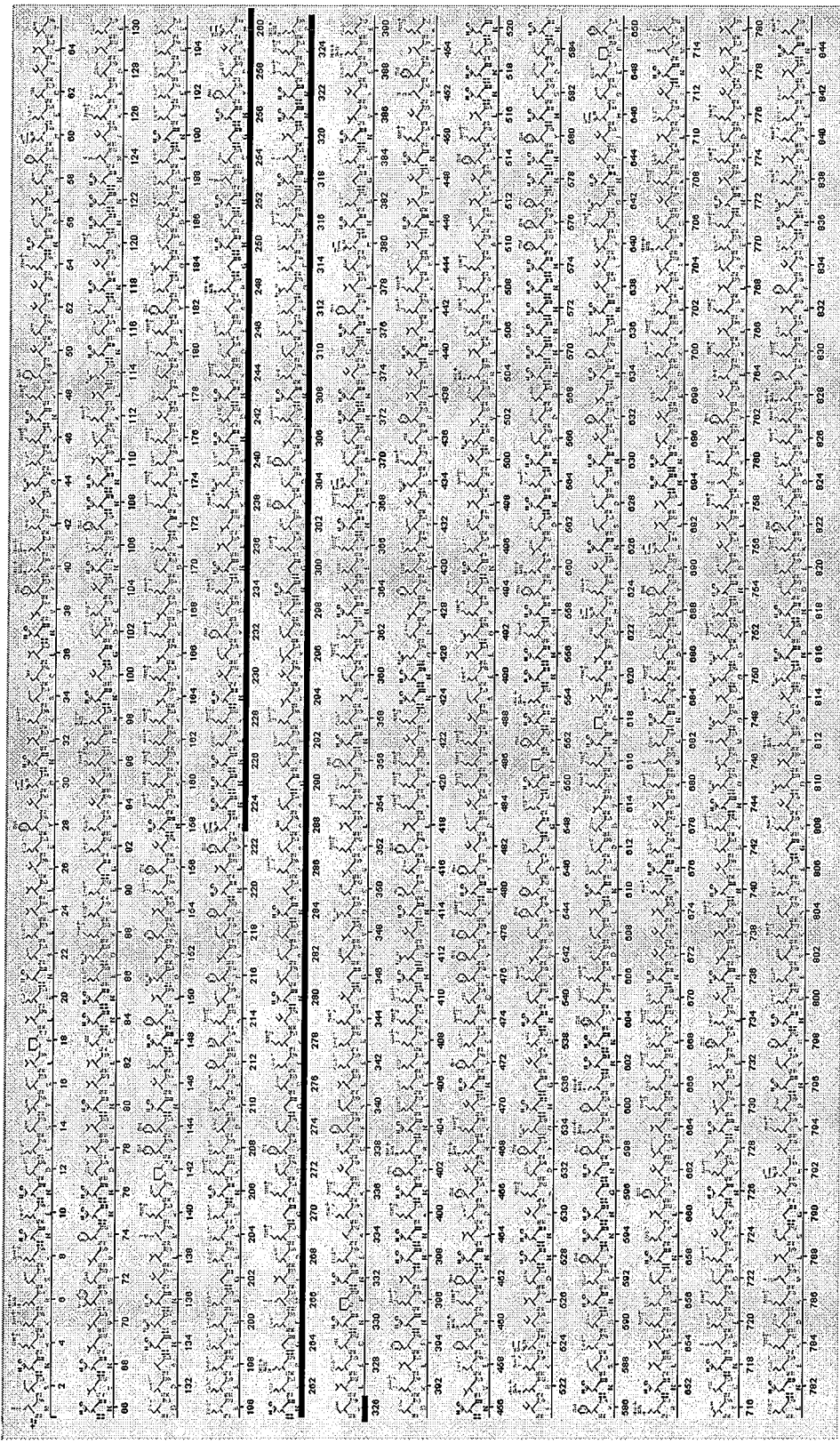
FIGURE 5 (end)

SEQUENCE LISTING

<160> NUMBER OF SEQ ID NOS: 58

<210> SEQ ID NO 1
<211> LENGTH: 3312
<212> TYPE: DNA
<213> ORGANISM: Plasmodium falciparum

<400> SEQUENCE: 1

| | | | | | |
|---|---|---|---|---|---|
| atgagtaata | agaaaagaag | taaaaatgaa | aatgacgaat | caacatcatt | acctttagaa | 60 |
| aattccgagt | tattaatcga | atatatacat | aatttaaaga | gctgtttaaa | tgtatatagg | 120 |
| cgagagatcc | aggaaaagaa | taaatatatt | agtatcataa | agaatgattt | aagttttcac | 180 |
| gaatgtatat | taacaaatgt | aaatgttgta | tggagtgtat | ttaataacga | tttattaaac | 240 |
| ctgctatgta | ataatgaaca | aaaagaagaa | ggggaagaaa | taataaaaca | agaaacata | 300 |
| ggtgatgaga | taaatgaata | taataattta | acaaaattac | aaaatgatga | aaatataaaa | 360 |
| aacaataata | tgattaaaga | agatcttgaa | gatgatgcca | atcagaatat | tttgatgaaa | 420 |
| tcaccttatt | ataatataga | aaattttta | caagttttt | taaaatatat | taataagaag | 480 |
| aagaaaaagg | taaaggtaaa | ggtaaaggat | gaaggtaaga | agaaaaaat | agaggacaaa | 540 |
| aaatacgagc | aagatgacga | agaagaaat | gaagaagagg | aggaggagga | agaagaagaa | 600 |
| gaaggagaag | aagaaaataa | agaggatgaa | gaattttca | aaacatttgt | atctttaat | 660 |
| ttgtatcata | ataacaatga | aaagaatata | tcatatgata | aaaatttagt | aaacaagaa | 720 |
| aatgataata | aagatgaagc | acgtggtaac | gataacatgt | gtggtaatta | tgatatacat | 780 |
| aatgagagag | gggaaatgtt | agataagggt | aaatcttatt | caggtgacga | aaaaataaat | 840 |
| acaagtgata | atgctaaatc | atgttcaggt | gacgaaaaag | taattacaag | cgataatggt | 900 |
| aaatcttatg | attatgtaaa | aaatgaaagt | gaagaacaag | aagaaaaga | aaatatgtta | 960 |
| aataataaaa | aaagaagttt | ggaatgtaat | ccaaatgaag | cgaaaaaat | ttgtttctct | 1020 |
| ttagaagaga | agataggaac | tgtgcaaagt | gtaaaattaa | aggaatataa | tgaattgagt | 1080 |
| aaagaaaata | ttgaaaaaaa | taacatgat | gataataaca | tttgtaatta | tctttcacac | 1140 |
| aatgaaggtg | agaatgtaat | agaaagggaa | gataaattat | ttaataagct | gaataataaa | 1200 |
| aattatagaa | atgaagaaga | gaaaaaaaa | atcaaataa | attttgatta | tttaaaaaaa | 1260 |
| aaaattaaga | ataaccaaga | tgttttgag | gaaacgatac | aaaaatgttt | tttgataaat | 1320 |
| ttaaaaaaga | cattaaatct | tataaacaaa | attatgtatt | taaaaaatgt | tgaatttagg | 1380 |
| aaatataact | tagattatat | tcgaaaaata | aattatgaga | atgttttta | ttataaaat | 1440 |
| tatattgata | taaaaaagaa | aataagcgaa | ttacaaaagg | ataacgaaag | tttaaaaatt | 1500 |
| caggtagata | ggctagagaa | aaagaaggct | acattaatat | acaaattgaa | taatgataat | 1560 |
| attcgtaaac | atattcttga | taataatatt | aaagattatc | aaaatggtat | tgataattca | 1620 |
| aaggtaagtt | attttgatga | agggagaac | ccatataacc | gtaataataa | aaattatcgt | 1680 |
| acagataata | agaatagtga | tgataataat | aataataata | attattatta | caataattat | 1740 |
| aatagtgatg | ataattataa | tagtgaggat | aatgaatata | ataatggtaa | ttatcgattt | 1800 |
| cgtaataatt | ataagaagga | ttctttgaat | gaagatgatg | taaaaaaaaa | tccttttgaag | 1860 |
| gtatgtcaca | aaattaacag | tgattctaat | atttttgtta | attttgaaaa | tattataaca | 1920 |
| aaacaaaata | ttatacatag | tgaaccattt | cgaaatttat | aaagaatc | taatgaatta | 1980 |
| tatattacat | taaagagaa | agaaaagaa | aatattattt | taaaaaatga | aattctaaag | 2040 |

-continued

```
atggaaaata aaaggatga agaatatgaa cacttattaa ataataccat tgaagacaag    2100
aaggaattaa ctagaagtat taagaattaa gaaataaata tgatgacatg taatatggaa    2160
aaagataaaa taagtaataa agtaaataca ttagaatacg aaataaatgt tttaaaaaat    2220
attgataaga atcaaactat gcaattacaa caaaaggaaa atgatattct aaagatgaag    2280
ttgtatattg agaaattaaa attatctgag aaaaatttaa aagataaaat tatttatta    2340 gaaaatgaaa aggataaaat gttgagtggt atacatataa aagataattc gtttaatgag    2400
gagtccaaaa gtgaggaagg caaaattcag ctgagagata ttcaaaatga taacgatgaa    2460
aaatatgatg atgaaaaaaa acgatttaaa gagttattta tagaaaatca gaattaaaa    2520 gaagaattga acaaaaaag aaacgtcgaa gaggaattac acagcttaag gaaaaattat    2580
aatatcatta atgaagaaat tgaagaaata acaaagaat ttgaaaaaaa acaagaacaa    2640
gttgatgaaa tgatattaca ataaaaaat aaagaattag aattattgga taaatttaat    2700
aataaaatga ataaagcgta tgtagaagag aaattaaaag aattaaaaaa tacatatgaa    2760
gaaaagatga acatataaaa taatatatat aaaaaacatg atgattttgt taatatttat    2820
ttaaatttat tttttcaagc aagaaaaaat gcaatacttt ctgatagtca aagaagaa     2880 caaatgaatt tatttataaa attaaaagat aaatatgata tcatatttca aaaaaaata    2940 gaattaacag atattttaaaa aatgtgtat gattgtaata aaaaattaat aggacattgt    3000
caagatttag aaaagaaaa ttctactctt cagaataaac tatctaacga aataaagaat    3060
tcaaaaatgc tatccaaaaa tttatctaaa aattctgatg atcatttatt aattgaagaa    3120
aataatgaat taagaagaag attaattgt agtgtatgta tggaaaactt tagaaattat    3180
attattatca aatgtggtca tatttattgt aacaattgta tattcaataa tttaaaaaca    3240
agaaatagaa agtgtccaca gtgtaaagta ccatttgata aaaaggatct acaaaaaatt    3300
tttctcgact aa                                                        3312
```

<210> SEQ ID NO 2
<211> LENGTH: 1103
<212> TYPE: PRT
<213> ORGANISM: Plasmodium falciparum

<400> SEQUENCE: 2

```
Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Glu Lys Asn Lys
        35                  40                  45

Tyr Ile Ser Ile Ile Lys Asn Asp Leu Ser Phe His Glu Cys Ile Leu
    50                  55                  60

Thr Asn Val Asn Val Val Trp Ser Val Phe Asn Asn Asp Leu Leu Asn
65                  70                  75                  80

Leu Leu Cys Asn Asn Glu Gln Lys Glu Glu Gly Glu Glu Ile Ile Lys
                85                  90                  95

Gln Arg Asn Ile Gly Asp Glu Ile Asn Glu Tyr Asn Asn Leu Thr Lys
            100                 105                 110

Leu Gln Asn Asp Glu Asn Ile Lys Asn Asn Met Ile Lys Glu Asp
        115                 120                 125

Leu Glu Asp Asp Ala Asn Gln Asn Ile Leu Met Lys Ser Pro Tyr Tyr
    130                 135                 140

Asn Ile Glu Asn Phe Leu Gln Val Phe Leu Lys Tyr Ile Asn Lys Lys
```

-continued

```
            145                 150                 155                 160
        Lys Lys Lys Val Lys Val Lys Val Lys Asp Glu Gly Lys Lys Glu Lys
                        165                 170                 175

Ile Glu Asp Lys Lys Tyr Glu Gln Asp Glu Glu Glu Asn Glu Glu
                    180                 185                 190

Glu Glu Glu Glu Glu Glu Glu Gly Glu Glu Glu Asn Lys Glu
                195                 200                 205

Asp Glu Glu Phe Phe Lys Thr Phe Val Ser Phe Asn Leu Tyr His Asn
            210                 215                 220

Asn Asn Glu Lys Asn Ile Ser Tyr Asp Lys Asn Leu Val Lys Gln Glu
        225                 230                 235                 240

Asn Asp Asn Lys Asp Glu Ala Arg Gly Asn Asp Asn Met Cys Gly Asn
                        245                 250                 255

Tyr Asp Ile His Asn Glu Arg Gly Glu Met Leu Asp Lys Gly Lys Ser
                        260                 265                 270

Tyr Ser Gly Asp Glu Lys Ile Asn Thr Ser Asp Asn Ala Lys Ser Cys
                        275                 280                 285

Ser Gly Asp Glu Lys Val Ile Thr Ser Asp Asn Gly Lys Ser Tyr Asp
            290                 295                 300

Tyr Val Lys Asn Glu Ser Glu Glu Gln Glu Glu Lys Glu Asn Met Leu
        305                 310                 315                 320

Asn Asn Lys Lys Arg Ser Leu Glu Cys Asn Pro Asn Glu Ala Lys Lys
                        325                 330                 335

Ile Cys Phe Ser Leu Glu Glu Lys Ile Gly Thr Val Gln Ser Val Lys
                        340                 345                 350

Leu Lys Glu Tyr Asn Glu Leu Ser Lys Glu Asn Ile Glu Lys Asn Lys
                        355                 360                 365

His Asp Asp Asn Asn Ile Cys Asn Tyr Leu Ser His Asn Glu Gly Glu
                        370                 375                 380

Asn Val Ile Glu Arg Glu Asp Lys Leu Phe Asn Lys Leu Asn Asn Lys
        385                 390                 395                 400

Asn Tyr Arg Asn Glu Glu Glu Lys Lys Asn Gln Ile Asn Phe Asp
                        405                 410                 415

Tyr Leu Lys Lys Lys Ile Lys Asn Asn Gln Asp Val Phe Glu Glu Thr
                        420                 425                 430

Ile Gln Lys Cys Phe Leu Ile Asn Leu Lys Lys Thr Leu Asn Leu Ile
                    435                 440                 445

Asn Lys Ile Met Tyr Leu Lys Asn Val Glu Phe Arg Lys Tyr Asn Leu
                    450                 455                 460

Asp Tyr Ile Arg Lys Ile Asn Tyr Glu Lys Cys Phe Tyr Tyr Lys Asn
        465                 470                 475                 480

Tyr Ile Asp Ile Lys Lys Ile Ser Glu Leu Gln Lys Asp Asn Glu
                        485                 490                 495

Ser Leu Lys Ile Gln Val Asp Arg Leu Glu Lys Lys Ala Thr Leu
                    500                 505                 510

Ile Tyr Lys Leu Asn Asn Asp Asn Ile Arg Lys His Ile Leu Asp Asn
            515                 520                 525

Asn Ile Lys Asp Tyr Gln Asn Gly Ile Asp Asn Ser Lys Val Ser Tyr
            530                 535                 540

Phe Asp Glu Gly Glu Asn Pro Tyr Asn Arg Asn Asn Lys Asn Tyr Arg
        545                 550                 555                 560

Thr Asp Asn Lys Asn Ser Asp Asp Asn Asn Asn Asn Asn Asn Tyr Tyr
                        565                 570                 575
```

-continued

```
Tyr Asn Asn Tyr Asn Ser Asp Asp Asn Tyr Asn Ser Glu Asp Asn Glu
            580                 585                 590

Tyr Asn Asn Gly Asn Tyr Arg Phe Arg Asn Asn Tyr Lys Lys Asp Ser
        595                 600                 605

Leu Asn Glu Asp Asp Val Lys Lys Asn Pro Leu Lys Val Cys His Lys
    610                 615                 620

Ile Asn Ser Asp Ser Asn Ile Phe Val Asn Phe Glu Asn Ile Ile Thr
625                 630                 635                 640

Lys Gln Asn Ile Ile His Ser Glu Pro Phe Arg Asn Leu Leu Lys Glu
                645                 650                 655

Ser Asn Glu Leu Tyr Ile Thr Leu Lys Glu Lys Glu Lys Glu Asn Ile
            660                 665                 670

Ile Leu Lys Asn Glu Ile Leu Lys Met Glu Asn Lys Lys Asp Glu Glu
        675                 680                 685

Tyr Glu His Leu Leu Asn Asn Thr Ile Glu Asp Lys Lys Glu Leu Thr
    690                 695                 700

Arg Ser Ile Lys Glu Leu Glu Ile Asn Met Met Thr Cys Asn Met Glu
705                 710                 715                 720

Lys Asp Lys Ile Ser Asn Lys Val Asn Thr Leu Glu Tyr Glu Ile Asn
                725                 730                 735

Val Leu Lys Asn Ile Asp Lys Asn Gln Thr Met Gln Leu Gln Gln Lys
            740                 745                 750

Glu Asn Asp Ile Leu Lys Met Lys Leu Tyr Ile Glu Lys Leu Lys Leu
        755                 760                 765

Ser Glu Lys Asn Leu Lys Asp Lys Ile Ile Leu Glu Asn Glu Lys
    770                 775                 780

Asp Lys Met Leu Ser Gly Ile His Ile Lys Asp Asn Ser Phe Asn Glu
785                 790                 795                 800

Glu Ser Lys Ser Glu Glu Gly Lys Ile Gln Leu Arg Asp Ile Gln Asn
                805                 810                 815

Asp Asn Asp Glu Lys Tyr Asp Asp Glu Lys Lys Arg Phe Lys Glu Leu
            820                 825                 830

Phe Ile Glu Asn Gln Lys Leu Lys Glu Glu Leu Asn Lys Lys Arg Asn
        835                 840                 845

Val Glu Glu Glu Leu His Ser Leu Arg Lys Asn Tyr Asn Ile Ile Asn
    850                 855                 860

Glu Glu Ile Glu Glu Ile Thr Lys Glu Phe Glu Lys Lys Gln Glu Gln
865                 870                 875                 880

Val Asp Glu Met Ile Leu Gln Ile Lys Asn Lys Glu Leu Glu Leu Leu
                885                 890                 895

Asp Lys Phe Asn Asn Lys Met Asn Lys Ala Tyr Val Glu Glu Lys Leu
            900                 905                 910

Lys Glu Leu Lys Asn Thr Tyr Glu Glu Lys Met Lys His Ile Asn Asn
        915                 920                 925

Ile Tyr Lys Lys His Asp Asp Phe Val Asn Ile Tyr Leu Asn Leu Phe
    930                 935                 940

Phe Gln Ala Arg Lys Asn Ala Ile Leu Ser Asp Ser Gln Arg Glu Glu
945                 950                 955                 960

Gln Met Asn Leu Phe Ile Lys Leu Lys Asp Lys Tyr Asp Ile Ile Phe
                965                 970                 975

Gln Lys Lys Ile Glu Leu Thr Asp Ile Leu Lys Asn Val Tyr Asp Cys
            980                 985                 990

Asn Lys Lys Leu Ile Gly His Cys  Gln Asp Leu Glu Lys  Glu Asn Ser
        995                 1000                 1005
```

| | | | | | | | | | | |
|---|---|---|---|---|---|---|---|---|---|---|
| Thr | Leu | Gln | Asn | Lys | Leu | Ser | Asn | Glu | Ile | Lys | Asn | Ser | Lys | Met |
| | 1010 | | | | | 1015 | | | | | 1020 | | | |
| Leu | Ser | Lys | Asn | Leu | Ser | Lys | Asn | Ser | Asp | Asp | His | Leu | Leu | Ile |
| | 1025 | | | | | 1030 | | | | | 1035 | | | |
| Glu | Glu | Asn | Asn | Glu | Leu | Arg | Arg | Arg | Leu | Ile | Cys | Ser | Val | Cys |
| | 1040 | | | | | 1045 | | | | | 1050 | | | |
| Met | Glu | Asn | Phe | Arg | Asn | Tyr | Ile | Ile | Ile | Lys | Cys | Gly | His | Ile |
| | 1055 | | | | | 1060 | | | | | 1065 | | | |
| Tyr | Cys | Asn | Asn | Cys | Ile | Phe | Asn | Asn | Leu | Lys | Thr | Arg | Asn | Arg |
| | 1070 | | | | | 1075 | | | | | 1080 | | | |
| Lys | Cys | Pro | Gln | Cys | Lys | Val | Pro | Phe | Asp | Lys | Lys | Asp | Leu | Gln |
| | 1085 | | | | | 1090 | | | | | 1095 | | | |
| Lys | Ile | Phe | Leu | Asp | | | | | | | | | | |
| | 1100 | | | | | | | | | | | | | |

<210> SEQ ID NO 3
<211> LENGTH: 3312
<212> TYPE: DNA
<213> ORGANISM: Plasmodium falciparum

<400> SEQUENCE: 3

```
atgagtaata agaaaagaag taaaaatgaa aatgacgaat caacatcatt accttagaa     60
aattccgagt tattaatcga atatatacat aatttaaaga gctgtttaaa tgtatatagg    120
cgagagatcc aggaaaagaa taatatatt agtatcataa agaatgattt aagttttcac    180
gaatgtatat taacaaatgt aaatgttgta tggagtgtat ttaataacga tttattaaac    240
ctgctatgta ataatgaaca aaagaagaa ggggaagaaa taataaaaca aagaaacata    300
ggtgatgaga taatgaata aataattta acaaaattac aaaatgatga aaatataaaa    360
aacaataata tgattaaaga agatcttgaa gatgatgcca atcagaatat tttgatgaaa    420
tcaccttatt ataatataga aaattttta caagtttttt taaaatatat taataagaag    480
aagaaaaagg taaggtaaa ggtaaaggat gaaggtaaga agaaaaaat agaggacaaa    540
aaatacgagc aagatgacga agaagaaat gaagaagagg aggaggagga agaagaagaa    600
gaaggagaag aagaaaataa agaggatgaa gaatttttca aaacatttgt atctttaat    660
ttgtatcata ataacaatga aaagaatata tcatatgata aaaatttagt taaacaagaa    720
aatgataata aagatgaagc acgtggtaac gataacatgt gtggtaatta tgatatacat    780
aatgagagag gggaaatgtt agataagggt aaatcttatt caggtgacga aaaaataaat    840
acaagtgata atgctaaatc atgttcaggt gacggaaaag taattacaag cgataatggt    900
aaatcttatg attatgtaaa aaatgaaagt gaagaacaag aagaaaaaga aaatatgtta    960
aataataaaa aagaagtttt ggaatgtaat ccaaatgaag cgaaaaaaat tgtttctct    1020
ttagaagaga agataggaac tgtgcaaagt gtaaattaa aggaatataa tgaattgagt    1080
aaagaaaata ttgaaaaaaa taaacatgat gataataaca tttgtaatta tctttcacac    1140
aatgaaggtg agaatgtaat agaagggaa gataaattat taataagct gaataataaa    1200
aattatagaa atgaagaaga gaaaaaaaaa aatcaaataa attttgatta tttaaaaaaa    1260
aaaattaaga ataccaaga tgttttgag gaaacgatac aaaaatgttt tttgataaat    1320
ttaaaaaaga cattaaatct tataaacaaa attatgtatt taaaaaatgt tgaatttagg    1380
aaatataact tagattatat tcgaaaaata aattatgaga atgtttttta ttataaaaat    1440
tatattgata taaaaaagaa aataagcgaa ttacaaaagg ataacgaaag tttaaaaatt    1500
```

-continued

```
caggtagata ggctagagaa aagaaggct acattaatat acaaattgaa taatgataat    1560
attcgtaaac atattcttga taataatatt aaagattatc aaaatggtat tgataattca    1620
aaggtaagtt attttgatga aggggagaac ccatataacc gtaataataa aaattatcgt    1680
acagataata agaatagtga tgataataat aataataata attattatta caataattat    1740
aatagtgatg ataattataa tagtgaggat aatgaatata ataatggtaa ttatcgattt    1800
cgtaataatt ataagaagga ttcttttgaat gaagatgatg taaaaaaaaa tcctttgaag    1860
gtatgtcaca aaattaacag tgattctaat attttgtta attttgaaaa tattataaca    1920
aaacaaaata ttatacatag tgaaccattt cgaaatttat aaaagaatc taatgaatta    1980 tatattacat aaaagagaaa agaaaagaa atattattt taaaaaatga aattctaaag    2040
atggaaaata aaaaggatga agaatatgaa cacttattaa ataataccat tgaagacaag    2100
aaggaattaa ctagaagtat taaagaatta gaaataaata tgatgacatg taatatggaa    2160
aaagataaaa taagtaataa agtaaataca ttagaatacg aaataaatgt ttaaaaaat    2220 attgataaga atcaaactat gcaattacaa caaaaggaaa atgatattct aaagatgaag    2280
ttgtatattg agaaattaaa attatctgag aaaaatttaa aagataaaat tatttatta    2340 gaaaatgaaa aggataaaat gttgagtggt atacatataa aagataattc gtttaatgag    2400
gagtccaaaa gtgaggaagg caaaattcag ctgagagata ttcaaaatga taacgatgaa    2460
aaatatgatg atgaaaaaaa acgatttaaa gagttatta tagaaaatca gaaattaaaa    2520
gaagaattga acaaaaaaag aaacgtcgaa gaggaattac acagcttaag gaaaaatttat    2580 aatatcatta atgaagaaat tgaagaaata acaaagaat ttgaaaaaaa acaagaacaa    2640
gttgatgaaa tgatattca aataaaaaat aaagaattag aattattgga taaatttaat    2700
aataaaatga ataagcgta tgtagaagag aaattaaaag aattaaaaaa tacatatgaa    2760
gaaagaggta acatataaa taatatat aaaaaacatg atgattttgt taatatttat    2820 ttaaattat tttcaagc aagaaaaaat gcaatactt ctgatagtca aagagaagaa    2880 caatgaatt tatttataaa attaaagat aaatatgata tcatattca aaaaaaaat    2940 gaattaacag atattttaaa aaatgtgtat gattgtaata aaaaattaat aggacattgt    3000
caagatttag aaaagaaaa ttctactctt cagaataaac tatctaacga aataagaat    3060 tcaaaaatgc tatccaaaaa ttatctaaaa aattctgatg atcatttat aattgaagaa    3120 aataatgaat taagaagaag attaatttgt agtgtatgta tggaaaactt tagaaattat    3180
attattatca aatgtggtca tatttattgt aacaattgta tattcaataa tttaaaaca    3240 agaaatagaa agtgtccaca gtgtaaagta ccatttgata aaaaggatct acaaaaaat    3300 tttctcgact aa                                                        3312
```

<210> SEQ ID NO 4
<211> LENGTH: 1103
<212> TYPE: PRT
<213> ORGANISM: Plasmodium falciparum

<400> SEQUENCE: 4

```
Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Glu Lys Asn Lys
        35                  40                  45

Tyr Ile Ser Ile Ile Lys Asn Asp Leu Ser Phe His Glu Cys Ile Leu
```

-continued

```
                50                  55                  60
Thr Asn Val Asn Val Val Trp Ser Val Phe Asn Asn Asp Leu Leu Asn
 65                  70                  75                  80
Leu Leu Cys Asn Glu Gln Lys Glu Glu Gly Glu Ile Ile Lys
                 85                  90                  95
Gln Arg Asn Ile Gly Asp Glu Ile Asn Glu Tyr Asn Asn Leu Thr Lys
                100                 105                 110
Leu Gln Asn Asp Glu Asn Ile Lys Asn Asn Met Ile Lys Glu Asp
                115                 120                 125
Leu Glu Asp Asp Ala Asn Gln Asn Ile Leu Met Lys Ser Pro Tyr Tyr
                130                 135                 140
Asn Ile Glu Asn Phe Leu Gln Val Phe Leu Lys Tyr Ile Asn Lys Lys
145                 150                 155                 160
Lys Lys Lys Val Lys Val Lys Val Lys Asp Gly Lys Lys Glu Lys
                165                 170                 175
Ile Glu Asp Lys Lys Tyr Glu Gln Asp Asp Glu Glu Asn Glu Glu
                180                 185                 190
Glu Glu Glu Glu Glu Glu Glu Glu Gly Glu Glu Glu Asn Lys Glu
                195                 200                 205
Asp Glu Glu Phe Phe Lys Thr Phe Val Ser Phe Asn Leu Tyr His Asn
                210                 215                 220
Asn Asn Glu Lys Asn Ile Ser Tyr Asp Lys Asn Leu Val Lys Gln Glu
225                 230                 235                 240
Asn Asp Asn Lys Asp Glu Ala Arg Gly Asn Asp Asn Met Cys Gly Asn
                245                 250                 255
Tyr Asp Ile His Asn Glu Arg Gly Glu Met Leu Asp Lys Gly Lys Ser
                260                 265                 270
Tyr Ser Gly Asp Glu Lys Ile Asn Thr Ser Asp Asn Ala Lys Ser Cys
                275                 280                 285
Ser Gly Asp Gly Lys Val Ile Thr Ser Asp Asn Gly Lys Ser Tyr Asp
                290                 295                 300
Tyr Val Lys Asn Glu Ser Glu Glu Gln Glu Glu Lys Glu Asn Met Leu
305                 310                 315                 320
Asn Asn Lys Lys Arg Ser Leu Glu Cys Asn Pro Asn Glu Ala Lys Lys
                325                 330                 335
Ile Cys Phe Ser Leu Glu Glu Lys Ile Gly Thr Val Gln Ser Val Lys
                340                 345                 350
Leu Lys Glu Tyr Asn Glu Leu Ser Lys Glu Asn Ile Glu Lys Asn Lys
                355                 360                 365
His Asp Asp Asn Asn Ile Cys Asn Tyr Leu Ser His Asn Glu Gly Glu
                370                 375                 380
Asn Val Ile Glu Arg Glu Asp Lys Leu Phe Asn Lys Leu Asn Asn Lys
385                 390                 395                 400
Asn Tyr Arg Asn Glu Glu Lys Lys Asn Gln Ile Asn Phe Asp
                405                 410                 415
Tyr Leu Lys Lys Lys Ile Lys Asn Asn Gln Asp Val Phe Glu Glu Thr
                420                 425                 430
Ile Gln Lys Cys Phe Leu Ile Asn Leu Lys Lys Thr Leu Asn Leu Ile
                435                 440                 445
Asn Lys Ile Met Tyr Leu Lys Asn Val Glu Phe Arg Lys Tyr Asn Leu
                450                 455                 460
Asp Tyr Ile Arg Lys Ile Asn Tyr Glu Lys Cys Phe Tyr Tyr Lys Asn
465                 470                 475                 480
```

-continued

Tyr Ile Asp Ile Lys Lys Ile Ser Glu Leu Gln Lys Asp Asn Glu
            485                 490                 495

Ser Leu Lys Ile Gln Val Asp Arg Leu Glu Lys Lys Ala Thr Leu
        500                 505                 510

Ile Tyr Lys Leu Asn Asn Asp Asn Ile Arg Lys His Ile Leu Asp Asn
        515                 520                 525

Asn Ile Lys Asp Tyr Gln Asn Gly Ile Asp Asn Ser Lys Val Ser Tyr
        530                 535                 540

Phe Asp Glu Gly Glu Asn Pro Tyr Asn Arg Asn Asn Lys Asn Tyr Arg
545                 550                 555                 560

Thr Asp Asn Lys Asn Ser Asp Asp Asn Asn Asn Asn Asn Tyr Tyr
        565                 570                 575

Tyr Asn Asn Tyr Asn Ser Asp Asp Asn Tyr Asn Ser Glu Asp Asn Glu
        580                 585                 590

Tyr Asn Asn Gly Asn Tyr Arg Phe Arg Asn Asn Tyr Lys Lys Asp Ser
        595                 600                 605

Leu Asn Glu Asp Asp Val Lys Lys Asn Pro Leu Lys Val Cys His Lys
        610                 615                 620

Ile Asn Ser Asp Ser Asn Ile Phe Val Asn Phe Glu Asn Ile Ile Thr
625                 630                 635                 640

Lys Gln Asn Ile Ile His Ser Glu Pro Phe Arg Asn Leu Leu Lys Glu
                645                 650                 655

Ser Asn Glu Leu Tyr Ile Thr Leu Lys Glu Lys Glu Lys Glu Asn Ile
        660                 665                 670

Ile Leu Lys Asn Glu Ile Leu Lys Met Glu Asn Lys Lys Asp Glu Glu
        675                 680                 685

Tyr Glu His Leu Leu Asn Asn Thr Ile Glu Asp Lys Lys Glu Leu Thr
690                 695                 700

Arg Ser Ile Lys Glu Leu Glu Ile Asn Met Met Thr Cys Asn Met Glu
705                 710                 715                 720

Lys Asp Lys Ile Ser Asn Lys Val Asn Thr Leu Glu Tyr Glu Ile Asn
                725                 730                 735

Val Leu Lys Asn Ile Asp Lys Asn Gln Thr Met Gln Leu Gln Gln Lys
        740                 745                 750

Glu Asn Asp Ile Leu Lys Met Lys Leu Tyr Ile Glu Lys Leu Lys Leu
        755                 760                 765

Ser Glu Lys Asn Leu Lys Asp Lys Ile Ile Leu Leu Glu Asn Glu Lys
        770                 775                 780

Asp Lys Met Leu Ser Gly Ile His Ile Lys Asn Ser Phe Asn Glu
785                 790                 795                 800

Glu Ser Lys Ser Glu Glu Gly Lys Ile Gln Leu Arg Asp Ile Gln Asn
                805                 810                 815

Asp Asn Asp Glu Lys Tyr Asp Asp Glu Lys Lys Arg Phe Lys Glu Leu
        820                 825                 830

Phe Ile Glu Asn Gln Lys Leu Lys Glu Glu Leu Asn Lys Lys Arg Asn
        835                 840                 845

Val Glu Glu Glu Leu His Ser Leu Arg Lys Asn Tyr Asn Ile Ile Asn
        850                 855                 860

Glu Glu Ile Glu Glu Ile Thr Lys Glu Phe Glu Lys Lys Gln Glu Gln
865                 870                 875                 880

Val Asp Glu Met Ile Leu Gln Ile Lys Asn Lys Glu Leu Glu Leu Leu
                885                 890                 895

Asp Lys Phe Asn Asn Lys Met Asn Lys Ala Tyr Val Glu Glu Lys Leu
        900                 905                 910

| | | | | | | | | | | | | |
|---|---|---|---|---|---|---|---|---|---|---|---|---|
|Lys|Glu|Leu|Lys|Asn|Thr|Tyr|Glu|Glu|Lys|Met|Lys|His|Ile|Asn|Asn|
| | |915| | | |920| | | |925| | | | | |

Ile Tyr Lys Lys His Asp Asp Phe Val Asn Ile Tyr Leu Asn Leu Phe
    930             935             940

Phe Gln Ala Arg Lys Asn Ala Ile Leu Ser Asp Ser Gln Arg Glu Glu
945             950             955             960

Gln Met Asn Leu Phe Ile Lys Leu Lys Asp Lys Tyr Asp Ile Ile Phe
            965             970             975

Gln Lys Lys Ile Glu Leu Thr Asp Ile Leu Lys Asn Val Tyr Asp Cys
            980             985             990

Asn Lys Lys Leu Ile Gly His Cys  Gln Asp Leu Glu Lys  Glu Asn Ser
            995             1000             1005

Thr Leu  Gln Asn Lys Leu Ser  Asn Glu Ile Lys Asn  Ser Lys Met
    1010             1015             1020

Leu Ser  Lys Asn Leu Ser Lys  Asn Ser Asp Asp His  Leu Leu Ile
    1025             1030             1035

Glu Glu  Asn Asn Glu Leu Arg  Arg Arg Leu Ile Cys  Ser Val Cys
    1040             1045             1050

Met Glu  Asn Phe Arg Asn Tyr  Ile Ile Ile Lys Cys  Gly His Ile
    1055             1060             1065

Tyr Cys  Asn Asn Cys Ile Phe  Asn Asn Leu Lys Thr  Arg Asn Arg
    1070             1075             1080

Lys Cys  Pro Gln Cys Lys Val  Pro Phe Asp Lys Lys  Asp Leu Gln
    1085             1090             1095

Lys Ile  Phe Leu Asp
    1100

<210> SEQ ID NO 5
<211> LENGTH: 2532
<212> TYPE: DNA
<213> ORGANISM: Plasmodium falciparum

<400> SEQUENCE: 5

```
atgagtaata agaaaagaag taaaaatgaa atgacgaat  caacatcatt acctttagaa      60
aattccgagt tattaatcga atatatacat aatttaaaga gctgtttaaa tgtatatagg     120
cgagagatcc aggaaaagaa taatatatt agtatcataa agaatgattt aagttttcac     180
gaatgtatat taacaaatgt aaatgttgta tggagtgtat ttaataacga tttattaaac     240
ctgctatgta ataatgaaca aaagaagaa ggggaagaaa taataaaaca agaaacata      300
ggtgatgaga taaatgaata taataattta acaaaattac aaaatgatga aaatataaaa     360
aacaataata tgattaaaga agatcttgaa gatgatgcca atcagaatat tttgatgaaa     420
tcaccttatt ataatataga aaatttttta caagttttt taaaatatat taataagaag     480
aagaaaaagg taaaggtaaa ggtaaaggat gaaggtaaga agaaaaaaat agaggacaaa     540
aaatacgagc aagatgacga agaagaaaat gaagaagagg aggaggagga agaagaagaa     600
gaaggagaag aagaaaataa agaggatgaa gaatttttca aaacatttgt atcttttaat     660
ttgtatcata taacaatga aaagaatata tcatatgata aaaatttagt taaacaagaa     720
aatgataata aagatgaagc acgtggtaac gataacatgt gtggtaatta tgatatacat     780
aatgagagag gggaaatgtt agataagggt aaatcttatt caggtgacga aaaaataaat     840
acaagtgata atgctaaatc atgttcaggt gacgaaaaag taattacaag cgataatggt     900
aaatcttatg attatgtaaa aaatgaaagt gaagaacaag aagaaaaaga aaatatgtta     960
```

-continued

```
aataataaaa aaagaagttt ggaatgtaat ccaaatgaag cgaaaaaaat ttgtttctct   1020
ttagaagaga agataggaac tgtgcaaagt gtaaaattaa aggaatataa tgaattgagt   1080
aaagaaaata ttgaaaaaaa taaacatgat gataataaca tttgtaatta tctttcacac   1140
aatgaaggtg agaatgtaat agaaagggaa gataaaattat ttaataagct gaataataaa   1200
aattatagaa atgaagaaga gaaaaaaaaa aatcaaataa attttgatta tttaaaaaaa   1260
aaaattaaga ataaccaaga tgttttttgag gaaacgatac aaaaatgttt tttgataaat   1320
ttaaaaaaga cattaaatct tataaacaaa attatgtatt taaaaaatgt tgaatttagg   1380
aaatataact tagattatat tcgaaaaata aattatgaga atgtttttta ttataaaaat   1440
tatattgata taaaaaagaa aataagcgaa ttacaaaagg ataacgaaag tttaaaaatt   1500
caggtagata ggctagagaa aaagaaggct acattaatat acaaattgaa taatgataat   1560
attcgtaaac atattcttga taataatatt aaagattatc aaaatggtat tgataattca   1620
aaggtaagtt attttgatga aggggagaac ccatataacc gtaataataa aaattatcgt   1680
acagataata agaatagtga tgataataat aataataata attattatta caataattat   1740
aatagtgatg ataattataa tagtgaggat aatgaatata ataatggtaa ttatcgattt   1800
cgtaataatt ataagaagga ttctttgaat gaagatgatg taaaaaaaaa tcctttgaag   1860
gtatgtcaca aaattaacag tgattctaat attttttgtta attttgaaaa tattataaca   1920
aaacaaaata ttatacatag tgaaccattt cgaaatttat taaaagaatc taatgaatta   1980
tatattacat taaagagaa agaaaaagaa aatattattt taaaaaatga aattctaaag   2040
atggaaaata aaaaggatga agaatatgaa cacttattaa ataataccat tgaagacaag   2100
aaggaattaa ctagaagtat taaagaatta gaaataaata tgatgacatg taatatggaa   2160
aaagataaaa taagtaataa agtaaataca ttagaatacg aaataaatgt tttaaaaaat   2220
attgataaga atcaaactat gcaattacaa caaaaggaaa atgatattct aaagatgaag   2280
ttgtatattg agaaattaaa attatctgag aaaaatttaa agataaaat tatttttatta   2340 gaaaatgaaa aggataaaat gttgagtggt atacatataa aagataattc gtttaatgag   2400
gagtccaaaa gtgaggaagg caaaattcag ctgagagata ttcaaaatga taacgatgaa   2460
aaatatgatg atgaaaaaaa acgatttaaa gagttatttta tagaaaatca gaaattaaaa   2520
gaagaattga ac   2532
```

<210> SEQ ID NO 6
<211> LENGTH: 844
<212> TYPE: PRT
<213> ORGANISM: Plasmodium falciparum

<400> SEQUENCE: 6

```
Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Glu Lys Asn Lys
        35                  40                  45

Tyr Ile Ser Ile Ile Lys Asn Asp Leu Ser Phe His Glu Cys Ile Leu
    50                  55                  60

Thr Asn Val Asn Val Val Trp Ser Val Phe Asn Asn Asp Leu Leu Asn
65                  70                  75                  80

Leu Leu Cys Asn Asn Glu Gln Lys Glu Glu Gly Glu Glu Ile Ile Lys
            85                  90                  95
```

```
Gln Arg Asn Ile Gly Asp Glu Ile Asn Glu Tyr Asn Asn Leu Thr Lys
            100                 105                 110

Leu Gln Asn Asp Glu Asn Ile Lys Asn Asn Met Ile Lys Glu Asp
        115                 120                 125

Leu Glu Asp Asp Ala Asn Gln Asn Ile Leu Met Lys Ser Pro Tyr Tyr
        130                 135                 140

Asn Ile Glu Asn Phe Leu Gln Val Phe Leu Lys Tyr Ile Asn Lys Lys
145                 150                 155                 160

Lys Lys Lys Val Lys Val Lys Val Lys Asp Glu Gly Lys Lys Glu Lys
                165                 170                 175

Ile Glu Asp Lys Lys Tyr Glu Gln Asp Asp Glu Glu Asn Glu Glu
        180                 185                 190

Glu Glu Glu Glu Glu Glu Glu Glu Gly Glu Glu Glu Asn Lys Glu
        195                 200                 205

Asp Glu Glu Phe Phe Lys Thr Phe Val Ser Phe Asn Leu Tyr His Asn
        210                 215                 220

Asn Asn Glu Lys Asn Ile Ser Tyr Asp Lys Asn Leu Val Lys Gln Glu
225                 230                 235                 240

Asn Asp Asn Lys Asp Glu Ala Arg Gly Asn Asp Asn Met Cys Gly Asn
                245                 250                 255

Tyr Asp Ile His Asn Glu Arg Gly Glu Met Leu Asp Lys Gly Lys Ser
        260                 265                 270

Tyr Ser Gly Asp Glu Lys Ile Asn Thr Ser Asp Asn Ala Lys Ser Cys
        275                 280                 285

Ser Gly Asp Glu Lys Val Ile Thr Ser Asp Asn Gly Lys Ser Tyr Asp
        290                 295                 300

Tyr Val Lys Asn Glu Ser Glu Glu Gln Glu Glu Lys Glu Asn Met Leu
305                 310                 315                 320

Asn Asn Lys Lys Arg Ser Leu Glu Cys Asn Pro Asn Glu Ala Lys Lys
                325                 330                 335

Ile Cys Phe Ser Leu Glu Glu Lys Ile Gly Thr Val Gln Ser Val Lys
        340                 345                 350

Leu Lys Glu Tyr Asn Glu Leu Ser Lys Glu Asn Ile Glu Lys Asn Lys
        355                 360                 365

His Asp Asp Asn Asn Ile Cys Asn Tyr Leu Ser His Asn Glu Gly Glu
        370                 375                 380

Asn Val Ile Glu Arg Glu Asp Lys Leu Phe Asn Lys Leu Asn Asn Lys
385                 390                 395                 400

Asn Tyr Arg Asn Glu Glu Lys Lys Asn Gln Ile Asn Phe Asp
                405                 410                 415

Tyr Leu Lys Lys Lys Ile Lys Asn Asn Gln Asp Val Phe Glu Glu Thr
        420                 425                 430

Ile Gln Lys Cys Phe Leu Ile Asn Leu Lys Lys Thr Leu Asn Leu Ile
        435                 440                 445

Asn Lys Ile Met Tyr Leu Lys Asn Val Glu Phe Arg Lys Tyr Asn Leu
        450                 455                 460

Asp Tyr Ile Arg Lys Ile Asn Tyr Glu Lys Cys Phe Tyr Tyr Lys Asn
465                 470                 475                 480

Tyr Ile Asp Ile Lys Lys Ile Ser Glu Leu Gln Lys Asp Asn Glu
        485                 490                 495

Ser Leu Lys Ile Gln Val Asp Arg Leu Glu Lys Lys Ala Thr Leu
        500                 505                 510

Ile Tyr Lys Leu Asn Asn Asp Asn Ile Arg Lys His Ile Leu Asp Asn
        515                 520                 525
```

Asn Ile Lys Asp Tyr Gln Asn Gly Ile Asp Asn Ser Lys Val Ser Tyr
         530                 535                 540

Phe Asp Glu Gly Glu Asn Pro Tyr Asn Arg Asn Asn Lys Asn Tyr Arg
545                 550                 555                 560

Thr Asp Asn Lys Asn Ser Asp Asp Asn Asn Asn Asn Asn Asn Tyr Tyr
                565                 570                 575

Tyr Asn Asn Tyr Asn Ser Asp Asp Asn Tyr Asn Ser Glu Asp Asn Glu
                580                 585                 590

Tyr Asn Asn Gly Asn Tyr Arg Phe Arg Asn Asn Tyr Lys Lys Asp Ser
                595                 600                 605

Leu Asn Glu Asp Asp Val Lys Lys Asn Pro Leu Lys Val Cys His Lys
         610                 615                 620

Ile Asn Ser Asp Ser Asn Ile Phe Val Asn Phe Glu Asn Ile Ile Thr
625                 630                 635                 640

Lys Gln Asn Ile Ile His Ser Glu Pro Phe Arg Asn Leu Leu Lys Glu
                645                 650                 655

Ser Asn Glu Leu Tyr Ile Thr Leu Lys Glu Lys Glu Lys Glu Asn Ile
                660                 665                 670

Ile Leu Lys Asn Glu Ile Leu Lys Met Glu Asn Lys Lys Asp Glu Glu
                675                 680                 685

Tyr Glu His Leu Leu Asn Asn Thr Ile Glu Asp Lys Lys Glu Leu Thr
         690                 695                 700

Arg Ser Ile Lys Glu Leu Glu Ile Asn Met Met Thr Cys Asn Met Glu
705                 710                 715                 720

Lys Asp Lys Ile Ser Asn Lys Val Asn Thr Leu Glu Tyr Glu Ile Asn
                725                 730                 735

Val Leu Lys Asn Ile Asp Lys Asn Gln Thr Met Gln Leu Gln Gln Lys
                740                 745                 750

Glu Asn Asp Ile Leu Lys Met Lys Leu Tyr Ile Glu Lys Leu Lys Leu
                755                 760                 765

Ser Glu Lys Asn Leu Lys Asp Lys Ile Ile Leu Leu Glu Asn Glu Lys
         770                 775                 780

Asp Lys Met Leu Ser Gly Ile His Ile Lys Asp Asn Ser Phe Asn Glu
785                 790                 795                 800

Glu Ser Lys Ser Glu Glu Gly Lys Ile Gln Leu Arg Asp Ile Gln Asn
                805                 810                 815

Asp Asn Asp Glu Lys Tyr Asp Asp Glu Lys Lys Arg Phe Lys Glu Leu
                820                 825                 830

Phe Ile Glu Asn Gln Lys Leu Lys Glu Glu Leu Asn
         835                 840

<210> SEQ ID NO 7
<211> LENGTH: 2532
<212> TYPE: DNA
<213> ORGANISM: Plasmodium falciparum

<400> SEQUENCE: 7
atgagtaata agaaaagaag taaaaatgaa atgacgaat caacatcatt acctttagaa      60
aattccgagt tattaatcga atatatacat aatttaaaga gctgtttaaa tgtatatagg    120
cgagagatcc aggaaaagaa taatatatt agtatcataa agaatgattt aagttttcac     180
gaatgtatat taacaaatgt aaatgttgta tggagtgtat ttaataacga tttattaaac    240
ctgctatgta ataatgaaca aaagaagaa ggggaagaaa taataaaaca agaaacata      300 ggtgatgaga taatgaata taataattta acaaaattac aaaatgatga aaatataaaa    360

-continued

```
aacaataata tgattaaaga agatcttgaa gatgatgcca atcagaatat tttgatgaaa    420
tcaccttatt ataatataga aaattttta caagttttt taaaatatat taataagaag     480
aagaaaaagg taaaggtaaa ggtaaaggat gaaggtaaga aagaaaaaat agaggacaaa    540
aaatacgagc aagatgacga agaagaaaat gaagaagagg aggaggagga agaagaagaa    600
gaaggagaag aagaaaataa agaggatgaa gaattttca aaacatttgt atcttttaat    660
ttgtatcata ataacaatga aagaatata tcatatgata aaaatttagt taaacaagaa    720
aatgataata aagatgaagc acgtggtaac gataacatgt gtggtaatta tgatatacat    780
aatgagagag gggaaatgtt agataagggt aaatcttatt caggtgacga aaaaataaat    840
acaagtgata atgctaaatc atgttcaggt gacggaaaag taattacaag cgataatggt    900
aaatcttatg attatgtaaa aaatgaaagt gaagaacaag aagaaaaaga aaatatgtta    960
aataataaaa aaagaagttt ggaatgtaat ccaaatgaag cgaaaaaaat ttgtttctct   1020
ttagaagaga agataggaac tgtgcaaagt gtaaaattaa aggaatataa tgaattgagt   1080
aaagaaaata ttgaaaaaaa taaacatgat gataataaca tttgtaatta tctttcacac   1140
aatgaaggtg agaatgtaat agaaagggaa gataaaattat ttaataagct gaataataaa   1200
aattatagaa atgaagaaga gaaaaaaaaa aatcaaataa attttgatta tttaaaaaaa   1260
aaaattaaga ataaccaaga tgttttgag gaaacgatac aaaaatgttt tttgataaat   1320
ttaaaaaaga cattaaatct tataaacaaa attatgtatt taaaaaatgt tgaatttagg   1380
aaatataact tagattatat tcgaaaata aatttatgaga aatgttttta ttataaaaat   1440
tatattgata taaaaaagaa aataagcgaa ttacaaaagg ataacgaaag tttaaaaatt   1500
caggtagata ggctagagaa aaagaaggct acattaatat acaaattgaa taatgataat   1560
attcgtaaac atattcttga taataatatt aaagattatc aaaatggtat tgataattca   1620
aaggtaagtt atttttgatga aggggagaac ccatataacc gtaataataa aaattatcgt   1680
acagataata agaatagtga tgataataat aataataata attattatta caataattat   1740
aatagtgatg ataattataa tagtgaggat aatgaatata ataatggtaa ttatcgattt   1800
cgtaataatt ataagaagga ttctttgaat gaagatgatg taaaaaaaa tcctttgaag   1860 gtatgtcaca aaattaacag tgattctaat attttgtta attttgaaaa tattataaca   1920
aaacaaaata ttatacatag tgaaccattt cgaaatttat taaaagaatc taatgaatta   1980
tatattacat aaaagagaa agaaaaagaa aatattattt taaaaaatga aattctaaag   2040
atggaaaata aaaggatga agaatatgaa cacttattaa ataataccat tgaagacaag   2100
aaggaattaa ctagaagtat taaagaatta gaaataaata tgatgacatg taatatggaa   2160
aaagataaaa taagtaataa agtaaataca ttagaatacg aaataaatgt tttaaaaaat   2220
attgataaga atcaaactat gcaattacaa caaaaggaaa atgatattct aaagatgaag   2280
ttgtatattg agaaattaaa attatctgag aaaaatttaa agataaaat tatttttatta   2340 gaaaatgaaa aggataaaat gttgagtggt atacatataa aagataattc gtttaatgag   2400
gagtccaaaa gtgaggaagg caaaattcag ctgagagata ttcaaaatga taacgatgaa   2460
aaatatgatg atgaaaaaaa acgatttaaa gagttatta tagaaaatca gaaattaaaa   2520
gaagaattga ac                                                      2532
```

<210> SEQ ID NO 8
<211> LENGTH: 844
<212> TYPE: PRT
<213> ORGANISM: Plasmodium falciparum

<400> SEQUENCE: 8

```
Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Glu Lys Asn Lys
        35                  40                  45

Tyr Ile Ser Ile Ile Lys Asn Asp Leu Ser Phe His Glu Cys Ile Leu
    50                  55                  60

Thr Asn Val Asn Val Val Trp Ser Val Phe Asn Asn Asp Leu Leu Asn
65                  70                  75                  80

Leu Leu Cys Asn Asn Glu Gln Lys Glu Glu Gly Glu Glu Ile Ile Lys
                85                  90                  95

Gln Arg Asn Ile Gly Asp Glu Ile Asn Glu Tyr Asn Asn Leu Thr Lys
            100                 105                 110

Leu Gln Asn Asp Glu Asn Ile Lys Asn Asn Asn Met Ile Lys Glu Asp
        115                 120                 125

Leu Glu Asp Asp Ala Asn Gln Asn Ile Leu Met Lys Ser Pro Tyr Tyr
130                 135                 140

Asn Ile Glu Asn Phe Leu Gln Val Phe Leu Lys Tyr Ile Asn Lys Lys
145                 150                 155                 160

Lys Lys Lys Val Lys Val Lys Val Lys Asp Glu Gly Lys Lys Glu Lys
                165                 170                 175

Ile Glu Asp Lys Lys Tyr Glu Gln Asp Asp Glu Glu Glu Asn Glu Glu
            180                 185                 190

Glu Glu Glu Glu Glu Glu Glu Glu Glu Gly Glu Glu Glu Asn Lys Glu
        195                 200                 205

Asp Glu Glu Phe Phe Lys Thr Phe Val Ser Phe Asn Leu Tyr His Asn
    210                 215                 220

Asn Asn Glu Lys Asn Ile Ser Tyr Asp Lys Asn Leu Val Lys Gln Glu
225                 230                 235                 240

Asn Asp Asn Lys Asp Glu Ala Arg Gly Asn Asp Asn Met Cys Gly Asn
                245                 250                 255

Tyr Asp Ile His Asn Glu Arg Gly Glu Met Leu Asp Lys Gly Lys Ser
            260                 265                 270

Tyr Ser Gly Asp Glu Lys Ile Asn Thr Ser Asp Asn Ala Lys Ser Cys
        275                 280                 285

Ser Gly Asp Gly Lys Val Ile Thr Ser Asp Asn Gly Lys Ser Tyr Asp
    290                 295                 300

Tyr Val Lys Asn Glu Ser Glu Glu Gln Glu Glu Lys Glu Asn Met Leu
305                 310                 315                 320

Asn Asn Lys Lys Arg Ser Leu Glu Cys Asn Pro Asn Glu Ala Lys Lys
                325                 330                 335

Ile Cys Phe Ser Leu Glu Glu Lys Ile Gly Thr Val Gln Ser Val Lys
            340                 345                 350

Leu Lys Glu Tyr Asn Glu Leu Ser Lys Glu Asn Ile Glu Lys Asn Lys
        355                 360                 365

His Asp Asp Asn Asn Ile Cys Asn Tyr Leu Ser His Asn Glu Gly Glu
    370                 375                 380

Asn Val Ile Glu Arg Glu Asp Lys Leu Phe Asn Lys Leu Asn Lys
385                 390                 395                 400

Asn Tyr Arg Asn Glu Glu Glu Lys Lys Lys Asn Gln Ile Asn Phe Asp
                405                 410                 415
```

```
Tyr Leu Lys Lys Lys Ile Lys Asn Asn Gln Asp Val Phe Glu Glu Thr
            420                 425                 430

Ile Gln Lys Cys Phe Leu Ile Asn Leu Lys Lys Thr Leu Asn Leu Ile
        435                 440                 445

Asn Lys Ile Met Tyr Leu Lys Asn Val Glu Phe Arg Lys Tyr Asn Leu
    450                 455                 460

Asp Tyr Ile Arg Lys Ile Asn Tyr Glu Lys Cys Phe Tyr Tyr Lys Asn
465                 470                 475                 480

Tyr Ile Asp Ile Lys Lys Ile Ser Glu Leu Gln Lys Asp Asn Glu
                485                 490                 495

Ser Leu Lys Ile Gln Val Asp Arg Leu Glu Lys Lys Ala Thr Leu
            500                 505                 510

Ile Tyr Lys Leu Asn Asn Asp Asn Ile Arg Lys His Ile Leu Asp Asn
        515                 520                 525

Asn Ile Lys Asp Tyr Gln Asn Gly Ile Asp Asn Ser Lys Val Ser Tyr
    530                 535                 540

Phe Asp Glu Gly Glu Asn Pro Tyr Asn Arg Asn Asn Lys Asn Tyr Arg
545                 550                 555                 560

Thr Asp Asn Lys Asn Ser Asp Asp Asn Asn Asn Asn Asn Tyr Tyr
                565                 570                 575

Tyr Asn Asn Tyr Asn Ser Asp Asp Asn Tyr Ser Glu Asp Asn Glu
            580                 585                 590

Tyr Asn Asn Gly Asn Tyr Arg Phe Arg Asn Asn Tyr Lys Lys Asp Ser
        595                 600                 605

Leu Asn Glu Asp Asp Val Lys Lys Asn Pro Leu Lys Val Cys His Lys
    610                 615                 620

Ile Asn Ser Asp Ser Asn Ile Phe Val Asn Phe Glu Asn Ile Ile Thr
625                 630                 635                 640

Lys Gln Asn Ile Ile His Ser Glu Pro Phe Arg Asn Leu Leu Lys Glu
                645                 650                 655

Ser Asn Glu Leu Tyr Ile Thr Leu Lys Glu Lys Glu Lys Glu Asn Ile
            660                 665                 670

Ile Leu Lys Asn Glu Ile Leu Lys Met Glu Asn Lys Lys Asp Glu Glu
        675                 680                 685

Tyr Glu His Leu Leu Asn Asn Thr Ile Glu Asp Lys Lys Glu Leu Thr
    690                 695                 700

Arg Ser Ile Lys Glu Leu Glu Ile Asn Met Met Thr Cys Asn Met Glu
705                 710                 715                 720

Lys Asp Lys Ile Ser Asn Lys Val Asn Thr Leu Glu Tyr Glu Ile Asn
                725                 730                 735

Val Leu Lys Asn Ile Asp Lys Asn Gln Thr Met Gln Leu Gln Gln Lys
            740                 745                 750

Glu Asn Asp Ile Leu Lys Met Lys Leu Tyr Ile Glu Lys Leu Lys Leu
        755                 760                 765

Ser Glu Lys Asn Leu Lys Asp Lys Ile Ile Leu Glu Asn Glu Lys
    770                 775                 780

Asp Lys Met Leu Ser Gly Ile His Ile Lys Asp Asn Ser Phe Asn Glu
785                 790                 795                 800

Glu Ser Lys Ser Glu Glu Gly Lys Ile Gln Leu Arg Asp Ile Gln Asn
                805                 810                 815

Asp Asn Asp Glu Lys Tyr Asp Asp Glu Lys Lys Arg Phe Lys Glu Leu
            820                 825                 830

Phe Ile Glu Asn Gln Lys Leu Lys Glu Glu Leu Asn
```

<210> SEQ ID NO 9
<211> LENGTH: 312
<212> TYPE: DNA
<213> ORGANISM: Plasmodium falciparum

<400> SEQUENCE: 9

```
cataataaca atgaaaagaa tatatcatat gataaaaatt tagttaaaca agaaaatgat    60
aataaagatg aagcacgtgg taacgataac atgtgtggta attatgatat acataatgag   120
agagggaaa tgttagataa gggtaaatct tattcaggtg acgaaaaaat aaatacaagt    180
gataatgcta atcatgttc agtgacgaa aaagtaatta caagcgataa tggtaaatct    240
tatgattatg taaaaaatga aagtgaagaa caagaagaaa agaaaatat gttaaataat    300
aaaaaagaa gt                                                        312
```

<210> SEQ ID NO 10
<211> LENGTH: 104
<212> TYPE: PRT
<213> ORGANISM: Plasmodium falciparum

<400> SEQUENCE: 10

```
His Asn Asn Asn Glu Lys Asn Ile Ser Tyr Asp Lys Asn Leu Val Lys
1               5                   10                  15

Gln Glu Asn Asp Asn Lys Asp Glu Ala Arg Gly Asn Asp Asn Met Cys
            20                  25                  30

Gly Asn Tyr Asp Ile His Asn Glu Arg Gly Glu Met Leu Asp Lys Gly
        35                  40                  45

Lys Ser Tyr Ser Gly Asp Glu Lys Ile Asn Thr Ser Asp Asn Ala Lys
    50                  55                  60

Ser Cys Ser Gly Asp Glu Lys Val Ile Thr Ser Asp Asn Gly Lys Ser
65                  70                  75                  80

Tyr Asp Tyr Val Lys Asn Glu Ser Glu Glu Gln Glu Glu Lys Glu Asn
                85                  90                  95

Met Leu Asn Asn Lys Lys Arg Ser
            100
```

<210> SEQ ID NO 11
<211> LENGTH: 312
<212> TYPE: DNA
<213> ORGANISM: Plasmodium falciparum

<400> SEQUENCE: 11

```
cataataaca atgaaaagaa tatatcatat gataaaaatt tagttaaaca agaaaatgat    60
aataaagatg aagcacgtgg taacgataac atgtgtggta attatgatat acataatgag   120
agagggaaa tgttagataa gggtaaatct tattcaggtg acgaaaaaat aaatacaagt    180
gataatgcta atcatgttc agtgacgga aaagtaatta caagcgataa tggtaaatct    240
tatgattatg taaaaaatga aagtgaagaa caagaagaaa agaaaatat gttaaataat    300
aaaaaagaa gt                                                        312
```

<210> SEQ ID NO 12
<211> LENGTH: 104
<212> TYPE: PRT
<213> ORGANISM: Plasmodium falciparum

<400> SEQUENCE: 12

```
His Asn Asn Asn Glu Lys Asn Ile Ser Tyr Asp Lys Asn Leu Val Lys
```

```
                1               5                  10                 15
Gln Glu Asn Asp Asn Lys Asp Glu Ala Arg Gly Asn Asp Asn Met Cys
                20                 25                 30

Gly Asn Tyr Asp Ile His Asn Glu Arg Gly Glu Met Leu Asp Lys Gly
                35                 40                 45

Lys Ser Tyr Ser Gly Asp Glu Lys Ile Asn Thr Ser Asp Asn Ala Lys
                50                 55                 60

Ser Cys Ser Gly Asp Gly Lys Val Ile Thr Ser Asp Asn Gly Lys Ser
 65                 70                 75                 80

Tyr Asp Tyr Val Lys Asn Glu Ser Glu Glu Gln Glu Glu Lys Glu Asn
                85                 90                 95

Met Leu Asn Asn Lys Lys Arg Ser
                100

<210> SEQ ID NO 13
<211> LENGTH: 81
<212> TYPE: DNA
<213> ORGANISM: Plasmodium falciparum

<400> SEQUENCE: 13
aaaaaaagaa acgtcgaaga ggaattacac agcttaagga aaaattataa tatcattaat     60
gaagaaattg aagaaataac a                                               81

<210> SEQ ID NO 14
<211> LENGTH: 27
<212> TYPE: PRT
<213> ORGANISM: Plasmodium falciparum

<400> SEQUENCE: 14

Lys Lys Arg Asn Val Glu Glu Glu Leu His Ser Leu Arg Lys Asn Tyr
 1               5                  10                 15

Asn Ile Ile Asn Glu Glu Ile Glu Glu Ile Thr
                20                 25

<210> SEQ ID NO 15
<211> LENGTH: 1866
<212> TYPE: DNA
<213> ORGANISM: Plasmodium falciparum

<400> SEQUENCE: 15
cataataaca atgaaaagaa tatatcatat gataaaaatt tagttaaaca agaaaatgat     60
aataaagatg aagcacgtgg taacgataac atgtgtggta attatgatat acataatgag    120 agagggaaa tgttagataa gggtaaatct tattcaggtg acgaaaaaat aaatacaagt    180
gataatgcta aatcatgttc aggtgacgaa aagtaatta caagcgataa tggtaaatct    240
tatgattatg taaaaaatga aagtgaagaa caagaagaaa agaaaatat gttaaataat    300 aaaaaaagaa gtttggaatg taatccaaat gaagcgaaaa aatttgtttt ctctttagaa    360
gagaagatag gaactgtgca aagtgtaaaa ttaaggaat ataatgaatt gagtaaagaa    420
aatattgaaa aaaataaaca tgatgataat aacatttgta attatctttc acacaatgaa    480
ggtgagaatg taatagaaag ggaagataaa ttatttaata agctgaataa taaaaattat    540
agaaatgaag aagagaaaaa aaaaaatcaa ataaattttg attatttaaa aaaaaaaatt    600
aagaataacc aagatgtttt tgaggaaacg atacaaaaat gttttttgat aaatttaaaa    660 aagcattaa atcttataaa caaaattatg tatttaaaaa atgttgaatt taggaaatat    720
aacttagatt atattcgaaa aataaattat gagaaatgtt tttattataa aaattatatt    780
```

-continued

```
gatataaaaa agaaaataag cgaattacaa aaggataacg aaagtttaaa aattcaggta    840
gataggctag agaaaagaa ggctacatta atatacaaat tgaataatga taatattcgt    900
aaacatattc ttgataataa tattaaagat tatcaaaatg gtattgataa ttcaaaggta    960
agttattttg atgaagggga gaacccatat aaccgtaata ataaaaatta tcgtacagat   1020
aataagaata gtgatgataa taataataat aataattatt attacaataa ttataatagt   1080
gatgataatt ataatagtga ggataatgaa tataataatg gtaattatcg atttcgtaat   1140
aattataaga aggattcttt gaatgaagat gatgtaaaaa aaaatccttt gaaggtatgt   1200
cacaaaatta acagtgattc taatatttt gttaattttg aaaatattat aacaaaacaa    1260
aatattatac atagtgaacc atttcgaaat ttattaaaag aatctaatga attatatatt   1320
acattaaaag agaagaaaa agaaaatatt atttaaaaa atgaaattct aaagatggaa     1380
aataaaaagg atgaagaata tgaacactta ttaaataata ccattgaaga caagaaggaa   1440
ttaactagaa gtattaaaga attagaaata aatatgatga catgtaatat ggaaaaagat   1500
aaaataagta ataaagtaaa tacattagaa tacgaaataa atgttttaaa aaatattgat   1560
aagaatcaaa ctatgcaatt acaacaaaag gaaaatgata ttctaaagat gaagttgtat   1620
attgagaaat taaaattatc tgagaaaaat ttaaaagata aaattatttt attagaaaat   1680
gaaaaggata aatgttgag tggtatacat ataaaagata attcgtttaa tgaggagtcc    1740
aaaagtgagg aaggcaaaat tcagctgaga gatattcaaa atgataacga tgaaaaatat   1800
gatgatgaaa aaaacgatt taagagtta tttatagaaa atcagaaatt aaagaagaa     1860 ttgaac                                                              1866
```

<210> SEQ ID NO 16
<211> LENGTH: 622
<212> TYPE: PRT
<213> ORGANISM: Plasmodium falciparum

<400> SEQUENCE: 16

```
His Asn Asn Asn Glu Lys Asn Ile Ser Tyr Asp Lys Asn Leu Val Lys
1               5                   10                  15

Gln Glu Asn Asp Asn Lys Asp Glu Ala Arg Gly Asn Asp Asn Met Cys
            20                  25                  30

Gly Asn Tyr Asp Ile His Asn Glu Arg Gly Glu Met Leu Asp Lys Gly
        35                  40                  45

Lys Ser Tyr Ser Gly Asp Glu Lys Ile Asn Thr Ser Asp Asn Ala Lys
    50                  55                  60

Ser Cys Ser Gly Asp Glu Lys Val Ile Thr Ser Asp Asn Gly Lys Ser
65                  70                  75                  80

Tyr Asp Tyr Val Lys Asn Glu Ser Glu Glu Gln Glu Glu Lys Glu Asn
                85                  90                  95

Met Leu Asn Asn Lys Lys Arg Ser Leu Glu Cys Asn Pro Asn Glu Ala
            100                 105                 110

Lys Lys Ile Cys Phe Ser Leu Glu Glu Lys Ile Gly Thr Val Gln Ser
        115                 120                 125

Val Lys Leu Lys Glu Tyr Asn Glu Leu Ser Lys Glu Asn Ile Glu Lys
    130                 135                 140

Asn Lys His Asp Asp Asn Asn Ile Cys Asn Tyr Leu Ser His Asn Glu
145                 150                 155                 160

Gly Glu Asn Val Ile Glu Arg Glu Asp Lys Leu Phe Asn Lys Leu Asn
                165                 170                 175

Asn Lys Asn Tyr Arg Asn Glu Glu Glu Lys Lys Lys Asn Gln Ile Asn
```

```
                180                 185                 190
Phe Asp Tyr Leu Lys Lys Lys Ile Lys Asn Asn Gln Asp Val Phe Glu
            195                 200                 205

Glu Thr Ile Gln Lys Cys Phe Leu Ile Asn Leu Lys Lys Thr Leu Asn
    210                 215                 220

Leu Ile Asn Lys Ile Met Tyr Leu Lys Asn Val Glu Phe Arg Lys Tyr
225                 230                 235                 240

Asn Leu Asp Tyr Ile Arg Lys Ile Asn Tyr Glu Lys Cys Phe Tyr Tyr
                245                 250                 255

Lys Asn Tyr Ile Asp Ile Lys Lys Ile Ser Glu Leu Gln Lys Asp
            260                 265                 270

Asn Glu Ser Leu Lys Ile Gln Val Asp Arg Leu Glu Lys Lys Ala
    275                 280                 285

Thr Leu Ile Tyr Lys Leu Asn Asn Asp Asn Ile Arg Lys His Ile Leu
    290                 295                 300

Asp Asn Asn Ile Lys Asp Tyr Gln Asn Gly Ile Asp Asn Ser Lys Val
305                 310                 315                 320

Ser Tyr Phe Asp Glu Gly Glu Asn Pro Tyr Asn Arg Asn Asn Lys Asn
                325                 330                 335

Tyr Arg Thr Asp Asn Lys Asn Ser Asp Asp Asn Asn Asn Asn Asn
            340                 345                 350

Tyr Tyr Tyr Asn Asn Tyr Asn Ser Asp Asp Asn Tyr Asn Ser Glu Asp
                355                 360                 365

Asn Glu Tyr Asn Asn Gly Asn Tyr Arg Phe Arg Asn Asn Tyr Lys Lys
    370                 375                 380

Asp Ser Leu Asn Glu Asp Asp Val Lys Lys Asn Pro Leu Lys Val Cys
385                 390                 395                 400

His Lys Ile Asn Ser Asp Ser Asn Ile Phe Val Asn Phe Glu Asn Ile
                405                 410                 415

Ile Thr Lys Gln Asn Ile Ile His Ser Glu Pro Phe Arg Asn Leu Leu
            420                 425                 430

Lys Glu Ser Asn Glu Leu Tyr Ile Thr Leu Lys Glu Lys Glu Lys Glu
    435                 440                 445

Asn Ile Ile Leu Lys Asn Glu Ile Leu Lys Met Glu Asn Lys Lys Asp
450                 455                 460

Glu Glu Tyr Glu His Leu Leu Asn Asn Thr Ile Glu Asp Lys Lys Glu
465                 470                 475                 480

Leu Thr Arg Ser Ile Lys Glu Leu Glu Ile Asn Met Met Thr Cys Asn
                485                 490                 495

Met Glu Lys Asp Lys Ile Ser Asn Lys Val Asn Thr Leu Glu Tyr Glu
            500                 505                 510

Ile Asn Val Leu Lys Asn Ile Asp Lys Asn Gln Thr Met Gln Leu Gln
    515                 520                 525

Gln Lys Glu Asn Asp Ile Leu Lys Met Lys Leu Tyr Ile Glu Lys Leu
    530                 535                 540

Lys Leu Ser Glu Lys Asn Leu Lys Asp Lys Ile Ile Leu Leu Glu Asn
545                 550                 555                 560

Glu Lys Asp Lys Met Leu Ser Gly Ile His Ile Lys Asp Asn Ser Phe
                565                 570                 575

Asn Glu Glu Ser Lys Ser Glu Glu Gly Lys Ile Gln Leu Arg Asp Ile
            580                 585                 590

Gln Asn Asp Asn Asp Glu Lys Tyr Asp Asp Glu Lys Lys Arg Phe Lys
            595                 600                 605
```

```
Glu Leu Phe Ile Glu Asn Gln Lys Leu Lys Glu Glu Leu Asn
    610                 615                 620
```

<210> SEQ ID NO 17
<211> LENGTH: 1866
<212> TYPE: DNA
<213> ORGANISM: Plasmodium falciparum

<400> SEQUENCE: 17

| | | | | |
|---|---|---|---|---|
| cataataaca | atgaaaagaa | tatatcatat | gataaaaatt | tagttaaaca | agaaaatgat | 60 |
| aataaagatg | aagcacgtgg | taacgataac | atgtgtggta | attatgatat | acataatgag | 120 |
| agagggaaaa | tgttagataa | gggtaaatct | tattcaggtg | acgaaaaaat | aaatacaagt | 180 |
| gataatgcta | aatcatgttc | aggtgacgga | aaagtaatta | caagcgataa | tggtaaatct | 240 |
| tatgattatg | taaaaaatga | aagtgaagaa | caagaagaaa | agaaaatat | gttaaataat | 300 |
| aaaaaaagaa | gtttggaatg | taatccaaat | gaagcgaaaa | aaatttgttt | ctctttagaa | 360 |
| gagaagatag | gaactgtgca | aagtgtaaaa | ttaaggaat | ataatgaatt | gagtaaagaa | 420 |
| aatattgaaa | aaataaaca | tgatgataat | aacatttgta | attatctttc | acacaatgaa | 480 |
| ggtgagaatg | taatagaaag | ggaagataaa | ttatttaata | agctgaataa | taaaaattat | 540 |
| agaaatgaag | aagagaaaaa | aaaaatcaa | ataaattttg | attatttaaa | aaaaaaatt | 600 |
| aagaataacc | aagatgtttt | tgaggaaacg | atacaaaaat | gttttttgat | aaatttaaaa | 660 |
| aagacattaa | atcttataaa | caaaattatg | tatttaaaaa | atgttgaatt | taggaaatat | 720 |
| aacttagatt | atattcgaaa | aataaattat | gagaaatgtt | tttattataa | aaattatatt | 780 |
| gatataaaaa | agaaaataag | cgaattacaa | aaggataacg | aaagtttaaa | aattcaggta | 840 |
| gataggctag | agaaaaagaa | ggctacatta | atatacaaat | tgaataatga | taatattcgt | 900 |
| aaacatattc | ttgataataa | tattaaagat | tatcaaaatg | gtattgataa | ttcaaaggta | 960 |
| agttattttg | atgaagggga | gaacccatat | aaccgtaata | ataaaaatta | tcgtacagat | 1020 |
| aataagaata | gtgatgataa | taataataat | aataattatt | attacaataa | ttataatagt | 1080 |
| gatgataatt | ataatagtga | ggataatgaa | tataataatg | gtaattatcg | atttcgtaat | 1140 |
| aattataaga | aggattcttt | gaatgaagat | gatgtaaaaa | aaatcctttt | gaaggtatgt | 1200 |
| cacaaaatta | acagtgattc | taatattttt | gttaattttg | aaaatattat | aacaaaacaa | 1260 |
| aatattatac | atagtgaacc | atttcgaaat | ttattaaaag | aatctaatga | attatatatt | 1320 |
| acattaaaag | agaaagaaaa | agaaatatt | attttaaaaa | atgaaattct | aaagatggaa | 1380 |
| aataaaaagg | atgaagaata | tgaacactta | ttaaataata | ccattgaaga | caagaaggaa | 1440 |
| ttaactagaa | gtattaaaga | attagaaata | aatatgatga | catgtaatat | ggaaaaagat | 1500 |
| aaaataagta | ataaagtaaa | tacattagaa | tacgaaataa | atgttttaaa | aaatattgat | 1560 |
| aagaatcaaa | ctatgcaatt | acaacaaaag | gaaaatgata | ttctaaagat | gaagttgtat | 1620 |
| attgagaaat | taaattatc | tgagaaaaat | ttaaagata | aaattattt | attagaaaat | 1680 |
| gaaaaggata | aaatgttgag | tggtatacat | ataaaagata | attcgtttaa | tgaggagtcc | 1740 |
| aaaagtgagg | aaggcaaaat | tcagctgaga | gatattcaaa | atgataacga | tgaaaaatat | 1800 |
| gatgatgaaa | aaaacgatt | taaagagtta | tttatagaaa | atcagaaatt | aaaagaagaa | 1860 |
| ttgaac | | | | | 1866 |

<210> SEQ ID NO 18
<211> LENGTH: 622
<212> TYPE: PRT
<213> ORGANISM: Plasmodium falciparum

<400> SEQUENCE: 18

```
His Asn Asn Asn Glu Lys Asn Ile Ser Tyr Asp Lys Asn Leu Val Lys
1               5                   10                  15

Gln Glu Asn Asp Asn Lys Asp Glu Ala Arg Gly Asn Asp Asn Met Cys
            20                  25                  30

Gly Asn Tyr Asp Ile His Asn Glu Arg Gly Glu Met Leu Asp Lys Gly
        35                  40                  45

Lys Ser Tyr Ser Gly Asp Glu Lys Ile Asn Thr Ser Asp Asn Ala Lys
    50                  55                  60

Ser Cys Ser Gly Asp Gly Lys Val Ile Thr Ser Asp Asn Gly Lys Ser
65                  70                  75                  80

Tyr Asp Tyr Val Lys Asn Glu Ser Glu Glu Gln Glu Glu Lys Glu Asn
                85                  90                  95

Met Leu Asn Asn Lys Lys Arg Ser Leu Glu Cys Asn Pro Asn Glu Ala
            100                 105                 110

Lys Lys Ile Cys Phe Ser Leu Glu Glu Lys Ile Gly Thr Val Gln Ser
        115                 120                 125

Val Lys Leu Lys Glu Tyr Asn Glu Leu Ser Lys Glu Asn Ile Glu Lys
130                 135                 140

Asn Lys His Asp Asp Asn Asn Ile Cys Asn Tyr Leu Ser His Asn Glu
145                 150                 155                 160

Gly Glu Asn Val Ile Glu Arg Glu Asp Lys Leu Phe Asn Lys Leu Asn
                165                 170                 175

Asn Lys Asn Tyr Arg Asn Glu Glu Lys Lys Asn Gln Ile Asn
            180                 185                 190

Phe Asp Tyr Leu Lys Lys Lys Ile Lys Asn Asn Gln Asp Val Phe Glu
        195                 200                 205

Glu Thr Ile Gln Lys Cys Phe Leu Ile Asn Leu Lys Lys Thr Leu Asn
    210                 215                 220

Leu Ile Asn Lys Ile Met Tyr Leu Lys Asn Val Glu Phe Arg Lys Tyr
225                 230                 235                 240

Asn Leu Asp Tyr Ile Arg Lys Ile Asn Tyr Glu Lys Cys Phe Tyr Tyr
                245                 250                 255

Lys Asn Tyr Ile Asp Ile Lys Lys Ile Ser Glu Leu Gln Lys Asp
            260                 265                 270

Asn Glu Ser Leu Lys Ile Gln Val Asp Arg Leu Glu Lys Lys Lys Ala
        275                 280                 285

Thr Leu Ile Tyr Lys Leu Asn Asn Asp Asn Ile Arg Lys His Ile Leu
    290                 295                 300

Asp Asn Asn Ile Lys Asp Tyr Gln Asn Gly Ile Asp Asn Ser Lys Val
305                 310                 315                 320

Ser Tyr Phe Asp Glu Gly Glu Asn Pro Tyr Asn Arg Asn Asn Lys Asn
                325                 330                 335

Tyr Arg Thr Asp Asn Lys Asn Ser Asp Asp Asn Asn Asn Asn Asn
            340                 345                 350

Tyr Tyr Tyr Asn Asn Tyr Asn Ser Asp Asp Asn Tyr Asn Ser Glu Asp
        355                 360                 365

Asn Glu Tyr Asn Asn Gly Asn Tyr Arg Phe Arg Asn Asn Tyr Lys Lys
    370                 375                 380

Asp Ser Leu Asn Glu Asp Asp Val Lys Lys Asn Pro Leu Lys Val Cys
385                 390                 395                 400

His Lys Ile Asn Ser Asp Ser Asn Ile Phe Val Asn Phe Glu Asn Ile
                405                 410                 415
```

Ile Thr Lys Gln Asn Ile Ile His Ser Glu Pro Phe Arg Asn Leu Leu
        420                 425                 430

Lys Glu Ser Asn Glu Leu Tyr Ile Thr Leu Lys Glu Lys Glu Lys Glu
        435                 440                 445

Asn Ile Ile Leu Lys Asn Glu Ile Leu Lys Met Glu Asn Lys Lys Asp
        450                 455                 460

Glu Glu Tyr Glu His Leu Leu Asn Asn Thr Ile Glu Asp Lys Lys Glu
465                 470                 475                 480

Leu Thr Arg Ser Ile Lys Glu Leu Glu Ile Asn Met Met Thr Cys Asn
                485                 490                 495

Met Glu Lys Asp Lys Ile Ser Asn Lys Val Asn Thr Leu Glu Tyr Glu
        500                 505                 510

Ile Asn Val Leu Lys Asn Ile Asp Lys Asn Gln Thr Met Gln Leu Gln
        515                 520                 525

Gln Lys Glu Asn Asp Ile Leu Lys Met Lys Leu Tyr Ile Glu Lys Leu
        530                 535                 540

Lys Leu Ser Glu Lys Asn Leu Lys Asp Lys Ile Ile Leu Leu Glu Asn
545                 550                 555                 560

Glu Lys Asp Lys Met Leu Ser Gly Ile His Ile Lys Asp Asn Ser Phe
                565                 570                 575

Asn Glu Glu Ser Lys Ser Glu Glu Gly Lys Ile Gln Leu Arg Asp Ile
        580                 585                 590

Gln Asn Asp Asn Asp Glu Lys Tyr Asp Asp Glu Lys Lys Arg Phe Lys
        595                 600                 605

Glu Leu Phe Ile Glu Asn Gln Lys Leu Lys Glu Glu Leu Asn
        610                 615                 620

<210> SEQ ID NO 19
<211> LENGTH: 978
<212> TYPE: DNA
<213> ORGANISM: Plasmodium falciparum

<400> SEQUENCE: 19
atgagtaata agaaaagaag taaaaatgaa atgacgaat caacatcatt acctttagaa        60
aattccgagt tattaatcga atatatacat aatttaaaga gctgttaaa tgtatatagg       120 cgagagatcc aggaaaagaa taatatatt agtatcataa agaatgattt aagttttcac       180
gaatgtatat aacaaatgt aaatgttgta tggagtgtat ttaataacga tttattaaac       240
ctgctatgta ataatgaaca aaagaagaa ggggaagaaa taataaaaca agaaacata        300 ggtgatgaga taaatgaata taataattta acaaaattac aaaatgatga aaatataaaa       360
aacaataata tgattaaaga agatcttgaa gatgatgcca atcagaatat tttgatgaaa       420
tcaccttatt ataatataga aaatttttta caagtttttt taaaatatat taataagaag       480
aagaaaaagg taaaggtaaa ggtaaaggat gaaggtaaga agaaaaat agaggacaaa       540 aaatacgagc aagatgacga agaagaaat gaagaagagg aggaggagga agaagaagaa       600
gaaggagaag aagaaaataa agaggatgaa gaattttca aaacatttgt atcttttaat       660
ttgtatcata taacaatga aagaatata tcatatgata aaatttagt taaacaagaa       720 aatgataata aagatgaagc acgtggtaac gataacatgt gtggtaatta tgatatacat       780
aatgagagag gggaaatgtt agataagggt aaatcttatt caggtgacga aaaaataaat       840
acaagtgata tgctaaaatc atgttcaggt gacgaaaaag taattacaag cgataatggt       900
aaatcttatg attatgtaaa aaatgaaagt gaagaacaag aagaaaaaga aaatatgtta       960
aataataaaa aaagaagt                                                           978

<210> SEQ ID NO 20
<211> LENGTH: 326
<212> TYPE: PRT
<213> ORGANISM: Plasmodium falciparum

<400> SEQUENCE: 20

Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Glu Lys Asn Lys
        35                  40                  45

Tyr Ile Ser Ile Ile Lys Asn Asp Leu Ser Phe His Glu Cys Ile Leu
    50                  55                  60

Thr Asn Val Asn Val Val Trp Ser Val Phe Asn Asn Asp Leu Leu Asn
65                  70                  75                  80

Leu Leu Cys Asn Asn Glu Gln Lys Glu Glu Gly Glu Ile Ile Lys
                85                  90                  95

Gln Arg Asn Ile Gly Asp Glu Ile Glu Tyr Asn Asn Leu Thr Lys
            100                 105                 110

Leu Gln Asn Asp Glu Asn Ile Lys Asn Asn Met Ile Lys Glu Asp
        115                 120                 125

Leu Glu Asp Asp Ala Asn Gln Asn Ile Leu Met Lys Ser Pro Tyr Tyr
    130                 135                 140

Asn Ile Glu Asn Phe Leu Gln Val Phe Leu Lys Tyr Ile Asn Lys Lys
145                 150                 155                 160

Lys Lys Lys Val Lys Val Lys Val Lys Asp Glu Gly Lys Lys Glu Lys
                165                 170                 175

Ile Glu Asp Lys Lys Tyr Glu Gln Asp Asp Glu Glu Glu Asn Glu Glu
            180                 185                 190

Glu Glu Glu Glu Glu Glu Glu Glu Gly Glu Glu Asn Lys Glu
        195                 200                 205

Asp Glu Glu Phe Phe Lys Thr Phe Val Ser Phe Asn Leu Tyr His Asn
    210                 215                 220

Asn Asn Glu Lys Asn Ile Ser Tyr Asp Lys Asn Leu Val Lys Gln Glu
225                 230                 235                 240

Asn Asp Asn Lys Asp Glu Ala Arg Gly Asn Asp Asn Met Cys Gly Asn
                245                 250                 255

Tyr Asp Ile His Asn Glu Arg Gly Glu Met Leu Asp Lys Gly Lys Ser
            260                 265                 270

Tyr Ser Gly Asp Glu Lys Ile Asn Thr Ser Asp Asn Ala Lys Ser Cys
        275                 280                 285

Ser Gly Asp Glu Lys Val Ile Thr Ser Asp Asn Gly Lys Ser Tyr Asp
    290                 295                 300

Tyr Val Lys Asn Glu Ser Glu Glu Gln Glu Glu Lys Glu Asn Met Leu
305                 310                 315                 320

Asn Asn Lys Lys Arg Ser
                325

<210> SEQ ID NO 21
<211> LENGTH: 978
<212> TYPE: DNA
<213> ORGANISM: Plasmodium falciparum

<400> SEQUENCE: 21

```
atgagtaata agaaaagaag taaaaatgaa aatgacgaat caacatcatt acctttagaa        60
aattccgagt tattaatcga atatatacat aatttaaaga gctgtttaaa tgtatatagg       120
cgagagatcc aggaaaagaa taaatatatt agtatcataa agaatgattt aagttttcac       180
gaatgtatat taacaaatgt aaatgttgta tggagtgtat ttaataacga tttattaaac       240
ctgctatgta ataatgaaca aaagaagaa ggggaagaaa taataaaaca aagaaacata        300
ggtgatgaga taaatgaata taataattta acaaaattac aaaatgatga aaatataaaa       360
aacaataata tgattaaaga agatcttgaa gatgatgcca atcagaatat tttgatgaaa       420
tcaccttatt ataatataga aaatttttta caagtttttt taaaatatat taataagaag       480
aagaaaaagg taaaggtaaa ggtaaaggat gaaggtaaga aagaaaaaat agaggacaaa       540
aaatacgagc aagatgacga agaagaaaat gaagaagagg aggaggagga agaagaagaa       600
gaaggagaag aagaaaataa agaggatgaa gaattttttca aaacatttgt atcttttaat      660
ttgtatcata ataacaatga aaagaatata tcatatgata aaaatttagt taaacaagaa       720
aatgataata agatgaagc acgtggtaac gataacatgt gtggtaatta tgatatacat        780
aatgagagag gggaaatgtt agataagggt aaatcttatt caggtgacga aaaaataaat       840
acaagtgata atgctaaatc atgttcaggt gacggaaaag taattacaag cgataatggt       900
aaatcttatg attatgtaaa aaatgaaagt gaagaacaag aagaaaaaga aaatatgtta       960
aataataaaa aaagaagt                                                     978
```

<210> SEQ ID NO 22
<211> LENGTH: 326
<212> TYPE: PRT
<213> ORGANISM: Plasmodium falciparum

<400> SEQUENCE: 22

```
Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Glu Lys Asn Lys
        35                  40                  45

Tyr Ile Ser Ile Ile Lys Asn Asp Leu Ser Phe His Glu Cys Ile Leu
    50                  55                  60

Thr Asn Val Asn Val Val Trp Ser Val Phe Asn Asn Asp Leu Leu Asn
65                  70                  75                  80

Leu Leu Cys Asn Asn Glu Gln Lys Glu Glu Gly Glu Ile Ile Lys
            85                  90                  95

Gln Arg Asn Ile Gly Asp Glu Ile Asn Glu Tyr Asn Asn Leu Thr Lys
            100                 105                 110

Leu Gln Asn Asp Glu Asn Ile Lys Asn Asn Met Ile Lys Glu Asp
        115                 120                 125

Leu Glu Asp Asp Ala Asn Gln Asn Ile Leu Met Lys Ser Pro Tyr Tyr
    130                 135                 140

Asn Ile Glu Asn Phe Leu Gln Val Phe Leu Lys Tyr Ile Asn Lys Lys
145                 150                 155                 160

Lys Lys Lys Val Lys Val Lys Val Lys Asp Glu Gly Lys Lys Glu Lys
                165                 170                 175

Ile Glu Asp Lys Lys Tyr Glu Gln Asp Asp Glu Glu Glu Asn Glu Glu
            180                 185                 190

Glu Glu Glu Glu Glu Glu Glu Glu Glu Gly Glu Glu Glu Asn Lys Glu
```

```
                195                 200                 205
Asp Glu Glu Phe Phe Lys Thr Phe Val Ser Phe Asn Leu Tyr His Asn
            210                 215                 220
Asn Asn Glu Lys Asn Ile Ser Tyr Asp Lys Asn Leu Val Lys Gln Glu
225                 230                 235                 240
Asn Asp Asn Lys Asp Glu Ala Arg Gly Asn Asp Asn Met Cys Gly Asn
                245                 250                 255
Tyr Asp Ile His Asn Glu Arg Gly Glu Met Leu Asp Lys Gly Lys Ser
            260                 265                 270
Tyr Ser Gly Asp Glu Lys Ile Asn Thr Ser Asp Asn Ala Lys Ser Cys
            275                 280                 285
Ser Gly Asp Gly Lys Val Ile Thr Ser Asp Asn Gly Lys Ser Tyr Asp
        290                 295                 300
Tyr Val Lys Asn Glu Ser Glu Glu Gln Glu Glu Lys Glu Asn Met Leu
305                 310                 315                 320
Asn Asn Lys Lys Arg Ser
            325

<210> SEQ ID NO 23
<211> LENGTH: 1920
<212> TYPE: DNA
<213> ORGANISM: Plasmodium falciparum

<400> SEQUENCE: 23
atgagtaata agaaaagaag taaaaatgaa aatgacgaat caacatcatt acctttagaa      60
aattccgagt tattaatcga atatatacat aatttaaaga gctgtttaaa tgtatatagg     120
cgagagatcc aggaaaagaa taatatatt agtatcataa agaatgattt aagttttcac      180
gaatgtatat taacaaatgt aaatgttgta tggagtgtat ttaataacga tttattaaac     240
ctgctatgta ataatgaaca aaagaagaa ggggaagaaa taataaaaca aagaaacata      300
ggtgatgaga taatgaata aataattta acaaaattac aaaatgatga aaatataaaa       360
aacaataata tgattaaaga agatcttgaa gatgatgcca atcagaatat tttgatgaaa     420
tcaccttatt ataatataga aaatttttta caagtttttt taaatatat taataagaag      480 aagaaaaagg taaggtaaa ggtaaaggat gaaggtaaga agaaaaaat agaggacaaa       540 aaatacgagc aagatgacga agaagaaat gaagaagagg aggaggagga agaagaagaa      600
gaaggagaag aagaaaataa agaggatgaa gaatttttca aaacatttgt atctttta at    660 ttgtatcata ataacaatga aaagaatata tcatatgata aaaatttagt aaacaagaa      720 aatgataata agatgaagc acgtggtaac gataacatgt gtggtaatta tgatatacat      780
aatgagagag gggaaatgtt agataaggt aaatcttatt caggtgacga aaaaataaat      840
acaagtgata atgctaaatc atgttcaggt gacgaaaaag taattacaag cgataatggt      900
aaatcttatg attatgtaaa aaatgaaagt gaagaacaag aagaaaaga aaatatgtta      960 aataataaaa aaagaagttt ggaatgtaat ccaaatgaag cgaaaaaat tgtttctct      1020 ttagaagaga gataggaac tgtgcaaagt gtaaaattaa aggaatataa tgaattgagt     1080
aaagaaaata ttgaaaaaaa taaacatgat gataataaca tttgtaatta tctttcacac     1140
aatgaaggtg agaatgtaat agaaagggaa gataaattat ttaataagct gaataataaa     1200
aattatagaa atgaagaaga gaaaaaaaaa aatcaaataa attttgatta tttaaaaaaa     1260
aaaattaaga ataaccaaga tgtttttgag gaaacgatac aaaaatgttt tttgataaat     1320
ttaaaaaaga cattaaatct tataaacaaa attatgtatt taaaaaatgt tgaatttagg     1380
```

| | | | | | |
|---|---|---|---|---|---|
| aaatataact | tagattatat | tcgaaaaata | aattatgaga | atgttttta | ttataaaaat | 1440
| tatattgata | taaaaaagaa | ataagcgaa | ttacaaagg | ataacgaaag | tttaaaaatt | 1500
| caggtagata | ggctagagaa | aaagaaggct | acattaatat | acaaattgaa | taatgataat | 1560
| attcgtaaac | atattcttga | taataatatt | aaagattatc | aaaatggtat | tgataattca | 1620
| aaggtaagtt | attttgatga | aggggagaac | ccatataacc | gtaataataa | aaattatcgt | 1680
| acagataata | agaatagtga | tgataataat | aataataata | attattatta | caataattat | 1740
| aatagtgatg | ataattataa | tagtgaggat | aatgaatata | ataatggtaa | ttatcgattt | 1800
| cgtaataatt | ataagaagga | ttctttgaat | gaagatgatg | taaaaaaaaa | tcctttgaag | 1860
| gtatgtcaca | aaattaacag | tgattctaat | attttttgtta | attttgaaaa | tattataaca | 1920

<210> SEQ ID NO 24
<211> LENGTH: 640
<212> TYPE: PRT
<213> ORGANISM: Plasmodium falciparum

<400> SEQUENCE: 24

```
Met Ser Asn Lys Lys Arg Ser Lys Asn Glu Asn Asp Glu Ser Thr Ser
1               5                  10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Lys Asn Lys
        35                  40                  45

Tyr Ile Ser Ile Ile Lys Asn Asp Leu Ser Phe His Glu Cys Ile Leu
    50                  55                  60

Thr Asn Val Asn Val Val Trp Ser Val Phe Asn Asn Asp Leu Leu Asn
65                  70                  75                  80

Leu Leu Cys Asn Asn Glu Gln Lys Glu Glu Gly Glu Ile Ile Lys
                85                  90                  95

Gln Arg Asn Ile Gly Asp Glu Ile Asn Glu Tyr Asn Asn Leu Thr Lys
            100                 105                 110

Leu Gln Asn Asp Glu Asn Ile Lys Asn Asn Met Ile Lys Glu Asp
        115                 120                 125

Leu Glu Asp Asp Ala Asn Gln Asn Ile Leu Met Lys Ser Pro Tyr Tyr
    130                 135                 140

Asn Ile Glu Asn Phe Leu Gln Val Phe Leu Lys Tyr Ile Asn Lys Lys
145                 150                 155                 160

Lys Lys Lys Val Lys Val Lys Val Lys Asp Glu Gly Lys Lys Glu Lys
                165                 170                 175

Ile Glu Asp Lys Lys Tyr Glu Gln Asp Asp Glu Glu Asn Glu Glu
            180                 185                 190

Glu Glu Glu Glu Glu Glu Glu Glu Gly Glu Glu Glu Asn Lys Glu
        195                 200                 205

Asp Glu Glu Phe Phe Lys Thr Phe Val Ser Phe Asn Leu Tyr His Asn
    210                 215                 220

Asn Asn Glu Lys Asn Ile Ser Tyr Asp Lys Asn Leu Val Lys Gln Glu
225                 230                 235                 240

Asn Asp Asn Lys Asp Glu Ala Arg Gly Asn Asp Asn Met Cys Gly Asn
                245                 250                 255

Tyr Asp Ile His Asn Glu Arg Gly Glu Met Leu Asp Lys Gly Lys Ser
            260                 265                 270

Tyr Ser Gly Asp Glu Lys Ile Asn Thr Ser Asp Asn Ala Lys Ser Cys
        275                 280                 285
```

```
Ser Gly Asp Glu Lys Val Ile Thr Ser Asp Asn Gly Lys Ser Tyr Asp
    290                 295                 300

Tyr Val Lys Asn Glu Ser Glu Glu Gln Glu Lys Glu Asn Met Leu
305                 310                 315                 320

Asn Asn Lys Lys Arg Ser Leu Glu Cys Asn Pro Asn Glu Ala Lys Lys
                325                 330                 335

Ile Cys Phe Ser Leu Glu Glu Lys Ile Gly Thr Val Gln Ser Val Lys
                340                 345                 350

Leu Lys Glu Tyr Asn Glu Leu Ser Lys Glu Asn Ile Glu Lys Asn Lys
                355                 360                 365

His Asp Asp Asn Asn Ile Cys Asn Tyr Leu Ser His Asn Glu Gly Glu
                370                 375                 380

Asn Val Ile Glu Arg Glu Asp Lys Leu Phe Asn Lys Leu Asn Asn Lys
385                 390                 395                 400

Asn Tyr Arg Asn Glu Glu Lys Lys Asn Gln Ile Asn Phe Asp
                405                 410                 415

Tyr Leu Lys Lys Lys Ile Lys Asn Asn Gln Asp Val Phe Glu Glu Thr
                420                 425                 430

Ile Gln Lys Cys Phe Leu Ile Asn Leu Lys Lys Thr Leu Asn Leu Ile
                435                 440                 445

Asn Lys Ile Met Tyr Leu Lys Asn Val Glu Phe Arg Lys Tyr Asn Leu
450                 455                 460

Asp Tyr Ile Arg Lys Ile Asn Tyr Glu Lys Cys Phe Tyr Tyr Lys Asn
465                 470                 475                 480

Tyr Ile Asp Ile Lys Lys Lys Ile Ser Glu Leu Gln Lys Asp Asn Glu
                485                 490                 495

Ser Leu Lys Ile Gln Val Asp Arg Leu Glu Lys Lys Ala Thr Leu
                500                 505                 510

Ile Tyr Lys Leu Asn Asn Asp Asn Ile Arg Lys His Ile Leu Asp Asn
                515                 520                 525

Asn Ile Lys Asp Tyr Gln Asn Gly Ile Asp Asn Ser Lys Val Ser Tyr
                530                 535                 540

Phe Asp Glu Gly Glu Asn Pro Tyr Asn Arg Asn Asn Lys Asn Tyr Arg
545                 550                 555                 560

Thr Asp Asn Lys Asn Ser Asp Asp Asn Asn Asn Asn Asn Tyr Tyr
                565                 570                 575

Tyr Asn Asn Tyr Asn Ser Asp Asp Asn Tyr Asn Ser Glu Asp Asn Glu
                580                 585                 590

Tyr Asn Asn Gly Asn Tyr Arg Phe Arg Asn Asn Tyr Lys Lys Asp Ser
                595                 600                 605

Leu Asn Glu Asp Asp Val Lys Lys Asn Pro Leu Lys Val Cys His Lys
610                 615                 620

Ile Asn Ser Asp Ser Asn Ile Phe Val Asn Phe Glu Asn Ile Ile Thr
625                 630                 635                 640

<210> SEQ ID NO 25
<211> LENGTH: 1920
<212> TYPE: DNA
<213> ORGANISM: Plasmodium falciparum

<400> SEQUENCE: 25
atgagtaata agaaaagaag taaaaatgaa atgacgaat caacatcatt acctttagaa      60
aattccgagt tattaatcga atatatacat aatttaaaga gctgtttaa tgtatatagg      120 cgagagatcc aggaaaagaa taatatatt agtatcataa agaatgattt aagttttcac      180
```

-continued

| | | | | |
|---|---|---|---|---|
| gaatgtatat | taacaaatgt | aaatgttgta | tggagtgtat | ttaataacga tttattaaac | 240 |
| ctgctatgta | ataatgaaca | aaaagaagaa | ggggaagaaa | taataaaaca aagaaacata | 300 |
| ggtgatgaga | taaatgaata | taataattta | acaaaattac | aaaatgatga aaatataaaa | 360 |
| aacaataata | tgattaaaga | gatcttgaa | gatgatgcca | atcagaatat tttgatgaaa | 420 |
| tcaccttatt | ataatataga | aattttttta | caagtttttt | taaaatatat taataagaag | 480 |
| aagaaaaagg | taaaggtaaa | ggtaaaggat | gaaggtaaga | agaaaaaat agaggacaaa | 540 |
| aaatacgagc | aagatgacga | agaagaaaat | gaagaagagg | aggaggagga agaagaagaa | 600 |
| gaaggagaag | aagaaaataa | agaggatgaa | gaatttttca | aaacatttgt atcttttaat | 660 |
| ttgtatcata | ataacaatga | aaagaatata | tcatatgata | aaaatttagt taaacaagaa | 720 |
| aatgataata | aagatgaagc | acgtggtaac | gataacatgt | gtggtaatta tgatatacat | 780 |
| aatgagagag | gggaaatgtt | agataagggt | aaatcttatt | caggtgacga aaaaataaat | 840 |
| acaagtgata | atgctaaatc | atgttcaggt | gacggaaaag | taattacaag cgataatggt | 900 |
| aaatcttatg | attatgtaaa | aaatgaaagt | gaagaacaag | aagaaaaaga aaatatgtta | 960 |
| aataataaaa | aaagaagttt | ggaatgtaat | ccaaatgaag | cgaaaaaaat ttgtttctct | 1020 |
| ttagaagaga | agataggaac | tgtgcaaagt | gtaaaattaa | aggaatataa tgaattgagt | 1080 |
| aaagaaaata | ttgaaaaaaa | taacatgat | gataataaca | tttgtaatta tctttcacac | 1140 |
| aatgaaggtg | agaatgtaat | agaaagggaa | gataaattat | ttaataagct gaataataaa | 1200 |
| aattatagaa | atgaagaaga | gaaaaaaaaa | aatcaaataa | attttgatta tttaaaaaaa | 1260 |
| aaaattaaga | ataaccaaga | tgttttgag | gaaacgatac | aaaaatgttt tttgataaat | 1320 |
| ttaaaaaaga | cattaaatct | tataaacaaa | attatgtatt | taaaaaatgt tgaatttagg | 1380 |
| aaatataact | tagattatat | tcgaaaaata | aattatgaga | atgttttta ttataaaaat | 1440 |
| tatattgata | taaaaaagaa | aataagcgaa | ttacaaaagg | ataacgaaag tttaaaaatt | 1500 |
| caggtagata | ggctagagaa | aaagaaggct | acattaatat | acaaattgaa taatgataat | 1560 |
| attcgtaaac | atattcttga | taataatatt | aaagattatc | aaaatggtat tgataattca | 1620 |
| aaggtaagtt | attttgatga | aggggagaac | ccatataacc | gtaataataa aaattatcgt | 1680 |
| acagataata | agaatagtga | tgataataat | aataataata | attattatta caataattat | 1740 |
| aatagtgatg | ataattataa | tagtgaggat | aatgaatata | ataatggtaa ttatcgattt | 1800 |
| cgtaataatt | ataagaagga | ttcttgaat | gaagatgatg | taaaaaaaaa tcctttgaag | 1860 |
| gtatgtcaca | aaattaacag | tgattctaat | attttttgtta | attttgaaaa tattataaca | 1920 |

<210> SEQ ID NO 26
<211> LENGTH: 640
<212> TYPE: PRT
<213> ORGANISM: Plasmodium falciparum

<400> SEQUENCE: 26

Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Glu Lys Asn Lys
        35                  40                  45

Tyr Ile Ser Ile Ile Lys Asn Asp Leu Ser Phe His Glu Cys Ile Leu
    50                  55                  60

Thr Asn Val Asn Val Val Trp Ser Val Phe Asn Asn Asp Leu Leu Asn
65                  70                  75                  80

```
Leu Leu Cys Asn Asn Glu Gln Lys Glu Glu Gly Glu Ile Ile Lys
                85                  90                  95
Gln Arg Asn Ile Gly Asp Glu Ile Asn Glu Tyr Asn Asn Leu Thr Lys
            100                 105                 110
Leu Gln Asn Asp Glu Asn Ile Lys Asn Asn Met Ile Lys Glu Asp
        115                 120                 125
Leu Glu Asp Asp Ala Asn Gln Asn Ile Leu Met Lys Ser Pro Tyr Tyr
130                 135                 140
Asn Ile Glu Asn Phe Leu Gln Val Phe Leu Lys Tyr Ile Asn Lys Lys
145                 150                 155                 160
Lys Lys Lys Val Lys Val Lys Val Lys Asp Glu Gly Lys Lys Glu Lys
                165                 170                 175
Ile Glu Asp Lys Lys Tyr Glu Gln Asp Asp Glu Glu Asn Glu Glu
            180                 185                 190
Glu Glu Glu Glu Glu Glu Glu Glu Gly Glu Glu Glu Asn Lys Glu
        195                 200                 205
Asp Glu Glu Phe Phe Lys Thr Phe Val Ser Phe Asn Leu Tyr His Asn
        210                 215                 220
Asn Asn Glu Lys Asn Ile Ser Tyr Asp Lys Asn Leu Val Lys Gln Glu
225                 230                 235                 240
Asn Asp Asn Lys Asp Glu Ala Arg Gly Asn Asp Asn Met Cys Gly Asn
                245                 250                 255
Tyr Asp Ile His Asn Glu Arg Gly Glu Met Leu Asp Lys Gly Lys Ser
            260                 265                 270
Tyr Ser Gly Asp Glu Lys Ile Asn Thr Ser Asp Asn Ala Lys Ser Cys
        275                 280                 285
Ser Gly Asp Gly Lys Val Ile Thr Ser Asp Asn Gly Lys Ser Tyr Asp
        290                 295                 300
Tyr Val Lys Asn Glu Ser Glu Glu Gln Glu Glu Lys Glu Asn Met Leu
305                 310                 315                 320
Asn Asn Lys Lys Arg Ser Leu Glu Cys Asn Pro Asn Glu Ala Lys Lys
                325                 330                 335
Ile Cys Phe Ser Leu Glu Glu Lys Ile Gly Thr Val Gln Ser Val Lys
            340                 345                 350
Leu Lys Glu Tyr Asn Glu Leu Ser Lys Glu Asn Ile Glu Lys Asn Lys
        355                 360                 365
His Asp Asp Asn Asn Ile Cys Asn Tyr Leu Ser His Asn Glu Gly Glu
        370                 375                 380
Asn Val Ile Glu Arg Glu Asp Lys Leu Phe Asn Lys Leu Asn Asn Lys
385                 390                 395                 400
Asn Tyr Arg Asn Glu Glu Lys Lys Asn Gln Ile Asn Phe Asp
                405                 410                 415
Tyr Leu Lys Lys Lys Ile Lys Asn Asn Gln Asp Val Phe Glu Glu Thr
            420                 425                 430
Ile Gln Lys Cys Phe Leu Ile Asn Leu Lys Lys Thr Leu Asn Leu Ile
        435                 440                 445
Asn Lys Ile Met Tyr Leu Lys Asn Val Glu Phe Arg Lys Tyr Asn Leu
        450                 455                 460
Asp Tyr Ile Arg Lys Ile Asn Tyr Glu Lys Cys Phe Tyr Tyr Lys Asn
465                 470                 475                 480
Tyr Ile Asp Ile Lys Lys Ile Ser Glu Leu Gln Lys Asp Asn Glu
            485                 490                 495
Ser Leu Lys Ile Gln Val Asp Arg Leu Glu Lys Lys Lys Ala Thr Leu
```

```
                500             505             510
Ile Tyr Lys Leu Asn Asn Asp Asn Ile Arg Lys His Ile Leu Asp Asn
            515                 520                 525

Asn Ile Lys Asp Tyr Gln Asn Gly Ile Asp Asn Ser Lys Val Ser Tyr
            530                 535                 540

Phe Asp Glu Gly Glu Asn Pro Tyr Asn Arg Asn Asn Lys Asn Tyr Arg
545                 550                 555                 560

Thr Asp Asn Lys Asn Ser Asp Asp Asn Asn Asn Asn Asn Asn Tyr Tyr
                565                 570                 575

Tyr Asn Asn Tyr Asn Ser Asp Asp Asn Tyr Asn Ser Glu Asp Asn Glu
            580                 585                 590

Tyr Asn Asn Gly Asn Tyr Arg Phe Arg Asn Asn Tyr Lys Lys Asp Ser
            595                 600                 605

Leu Asn Glu Asp Asp Val Lys Lys Asn Pro Leu Lys Val Cys His Lys
            610                 615                 620

Ile Asn Ser Asp Ser Asn Ile Phe Val Asn Phe Glu Asn Ile Ile Thr
625                 630                 635                 640

<210> SEQ ID NO 27
<211> LENGTH: 1103
<212> TYPE: PRT
<213> ORGANISM: Plasmodium falciparum

<400> SEQUENCE: 27

Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Glu Lys Asn Lys
        35                  40                  45

Tyr Ile Ser Ile Ile Lys Asn Asp Leu Ser Phe His Glu Cys Ile Leu
    50                  55                  60

Thr Asn Val Asn Val Val Trp Ser Val Phe Asn Asn Asp Leu Leu Asn
65                  70                  75                  80

Leu Leu Cys Asn Asn Glu Gln Lys Glu Glu Gly Glu Glu Ile Ile Lys
                85                  90                  95

Gln Arg Asn Ile Gly Asp Glu Ile Asn Glu Tyr Asn Asn Leu Thr Lys
            100                 105                 110

Leu Gln Asn Asp Glu Asn Ile Lys Asn Asn Met Ile Lys Glu Asp
        115                 120                 125

Leu Glu Asp Asp Ala Asn Gln Asn Ile Leu Met Lys Ser Pro Tyr Tyr
    130                 135                 140

Asn Ile Glu Asn Phe Leu Gln Val Phe Leu Lys Tyr Ile Asn Lys Lys
145                 150                 155                 160

Lys Lys Lys Val Lys Val Lys Val Lys Asp Glu Gly Lys Lys Glu Lys
                165                 170                 175

Ile Glu Asp Lys Lys Tyr Glu Gln Asp Asp Glu Glu Glu Asn Glu Glu
            180                 185                 190

Glu Glu Glu Glu Glu Glu Glu Glu Gly Glu Glu Glu Asn Lys Glu
        195                 200                 205

Asp Glu Glu Phe Phe Lys Thr Phe Val Ser Phe Asn Leu Tyr His Asn
    210                 215                 220

Asn Asn Glu Lys Asn Ile Ser Tyr Asp Lys Asn Leu Val Lys Gln Glu
225                 230                 235                 240

Asn Asp Asn Lys Asp Glu Ala Arg Gly Asn Asp Asn Met Cys Gly Asn
```

-continued

```
                245                 250                 255
Tyr Asp Ile His Asn Glu Arg Gly Glu Met Leu Asp Lys Gly Lys Ser
            260                 265                 270

Tyr Ser Gly Asp Glu Lys Ile Asn Thr Ser Asp Asn Ala Lys Ser Cys
            275                 280                 285

Ser Gly Asp Glu Lys Val Ile Thr Ser Asp Asn Gly Lys Ser Tyr Asp
            290                 295                 300

Tyr Val Lys Asn Glu Ser Glu Gln Glu Lys Glu Asn Met Leu
305                 310                 315                 320

Asn Asn Lys Lys Arg Ser Leu Glu Cys Asn Pro Asn Glu Ala Lys Lys
                325                 330                 335

Ile Cys Phe Ser Leu Glu Glu Lys Ile Gly Thr Val Gln Ser Val Lys
            340                 345                 350

Leu Lys Glu Tyr Asn Glu Leu Ser Glu Asn Ile Glu Lys Asn Lys
            355                 360                 365

His Asp Asp Asn Asn Ile Cys Asn Tyr Leu Ser His Asn Glu Gly Glu
            370                 375                 380

Asn Val Ile Glu Arg Glu Asp Lys Leu Phe Asn Lys Leu Asn Asn Lys
385                 390                 395                 400

Asn Tyr Arg Asn Glu Glu Lys Lys Asn Gln Ile Asn Phe Asp
                405                 410                 415

Tyr Leu Lys Lys Lys Ile Lys Asn Asn Gln Asp Val Phe Glu Glu Thr
            420                 425                 430

Ile Gln Lys Cys Phe Leu Ile Asn Leu Lys Lys Thr Leu Asn Leu Ile
            435                 440                 445

Asn Lys Ile Met Tyr Leu Lys Asn Val Glu Phe Arg Lys Tyr Asn Leu
450                 455                 460

Asp Tyr Ile Arg Lys Ile Asn Tyr Glu Lys Cys Phe Tyr Tyr Lys Asn
465                 470                 475                 480

Tyr Ile Asp Ile Lys Lys Lys Ile Ser Glu Leu Gln Lys Asp Asn Glu
            485                 490                 495

Ser Leu Lys Ile Gln Val Asp Arg Leu Glu Lys Lys Ala Thr Leu
            500                 505                 510

Ile Tyr Lys Leu Asn Asn Asp Asn Ile Arg Lys His Ile Leu Asp Asn
            515                 520                 525

Asn Ile Lys Asp Tyr Gln Asn Gly Ile Asp Asn Ser Lys Val Ser Tyr
            530                 535                 540

Phe Asp Glu Gly Glu Asn Pro Tyr Asn Arg Asn Asn Asn Tyr Arg
545                 550                 555                 560

Thr Asp Asn Lys Asn Ser Asp Asp Asn Asn Asn Asn Tyr Tyr
                565                 570                 575

Tyr Asn Asn Tyr Asn Ser Asp Asp Asn Tyr Asn Ser Glu Asp Asn Glu
            580                 585                 590

Tyr Asn Asn Gly Asn Tyr Arg Phe Arg Asn Asn Tyr Lys Lys Asp Ser
            595                 600                 605

Leu Asn Glu Asp Asp Val Lys Lys Asn Pro Leu Lys Val Cys His Lys
            610                 615                 620

Ile Asn Ser Asp Ser Asn Ile Phe Val Asn Phe Glu Asn Ile Ile Thr
625                 630                 635                 640

Lys Gln Asn Ile Ile His Ser Glu Pro Phe Arg Asn Leu Leu Lys Glu
                645                 650                 655

Ser Asn Glu Leu Tyr Ile Thr Leu Lys Glu Lys Glu Lys Glu Asn Ile
            660                 665                 670
```

-continued

```
Ile Leu Lys Asn Glu Ile Leu Lys Met Glu Asn Lys Lys Asp Glu
            675                 680                 685
Tyr Glu His Leu Leu Asn Asn Thr Ile Glu Asp Lys Lys Glu Leu Thr
    690                 695                 700
Arg Ser Ile Lys Glu Leu Glu Ile Asn Met Met Thr Cys Asn Met Glu
705                 710                 715                 720
Lys Asp Lys Ile Ser Asn Lys Val Asn Thr Leu Glu Tyr Glu Ile Asn
                725                 730                 735
Val Leu Lys Asn Ile Asp Lys Asn Gln Thr Met Gln Leu Gln Gln Lys
            740                 745                 750
Glu Asn Asp Ile Leu Lys Met Lys Leu Tyr Ile Glu Lys Leu Lys Leu
            755                 760                 765
Ser Glu Lys Asn Leu Lys Asp Lys Ile Ile Leu Leu Glu Asn Glu Lys
    770                 775                 780
Asp Lys Met Leu Ser Gly Ile His Ile Lys Asp Asn Ser Phe Asn Glu
785                 790                 795                 800
Glu Ser Lys Ser Glu Glu Gly Lys Ile Gln Leu Arg Asp Ile Gln Asn
                805                 810                 815
Asp Asn Asp Glu Lys Tyr Asp Asp Glu Lys Lys Arg Phe Lys Glu Leu
            820                 825                 830
Phe Ile Glu Asn Gln Lys Leu Lys Glu Glu Leu Asn Lys Lys Arg Asn
            835                 840                 845
Val Glu Glu Glu Leu His Ser Leu Arg Lys Asn Tyr Asn Ile Ile Asn
850                 855                 860
Glu Glu Ile Glu Glu Ile Thr Lys Glu Phe Glu Lys Lys Gln Glu Gln
865                 870                 875                 880
Val Asp Glu Met Ile Leu Gln Ile Lys Asn Lys Glu Leu Glu Leu Leu
            885                 890                 895
Asp Lys Phe Asn Asn Lys Met Asn Lys Ala Tyr Val Glu Glu Lys Leu
            900                 905                 910
Lys Glu Leu Lys Asn Thr Tyr Glu Glu Lys Met Lys His Ile Asn Asn
            915                 920                 925
Ile Tyr Lys Lys His Asp Asp Phe Val Asn Ile Tyr Leu Asn Leu Phe
    930                 935                 940
Phe Gln Ala Arg Lys Asn Ala Ile Leu Ser Asp Ser Gln Arg Glu Glu
945                 950                 955                 960
Gln Met Asn Leu Phe Ile Lys Leu Lys Asp Lys Tyr Asp Ile Ile Phe
                965                 970                 975
Gln Lys Lys Ile Glu Leu Thr Asp Ile Leu Lys Asn Val Tyr Asp Cys
            980                 985                 990
Asn Lys Lys Leu Ile Gly His Cys Gln Asp Leu Glu Lys Glu Asn Ser
    995                 1000                1005
Thr Leu Gln Asn Lys Leu Ser Asn Glu Ile Lys Asn Ser Lys Met
    1010                1015                1020
Leu Ser Lys Asn Leu Ser Lys Asn Ser Asp Asp His Leu Leu Ile
    1025                1030                1035
Glu Glu Asn Asn Glu Leu Arg Arg Arg Leu Ile Cys Ser Val Cys
    1040                1045                1050
Met Glu Asn Phe Arg Asn Tyr Ile Ile Ile Lys Cys Gly His Ile
    1055                1060                1065
Tyr Cys Asn Asn Cys Ile Phe Asn Asn Leu Lys Thr Arg Asn Arg
    1070                1075                1080
Lys Cys Pro Gln Cys Lys Val Pro Phe Asp Lys Lys Asp Leu Gln
    1085                1090                1095
```

```
Lys Ile  Phe Leu Asp
    1100

<210> SEQ ID NO 28
<211> LENGTH: 27
<212> TYPE: PRT
<213> ORGANISM: Plasmodium falciparum

<400> SEQUENCE: 28

Lys Lys Arg Asn Val Glu Glu Leu His Ser Leu Arg Lys Asn Tyr
1               5                   10                  15

Asn Ile Ile Asn Glu Glu Ile Glu Ile Thr
            20                  25

<210> SEQ ID NO 29
<211> LENGTH: 1103
<212> TYPE: PRT
<213> ORGANISM: Plasmodium falciparum

<400> SEQUENCE: 29

Met Ser Asn Lys Lys Arg Ser Lys Asn Glu Asn Asp Glu Ser Thr Ser
1               5                   10                  15

Leu Pro Leu Glu Asn Ser Glu Leu Leu Ile Glu Tyr Ile His Asn Leu
            20                  25                  30

Lys Ser Cys Leu Asn Val Tyr Arg Arg Glu Ile Gln Lys Asn Lys
            35                  40                  45

Tyr Ile Ser Ile Ile Lys Asn Asp Leu Ser Phe His Glu Cys Ile Leu
            50                  55                  60

Thr Asn Val Asn Val Val Trp Ser Val Phe Asn Asn Asp Leu Leu Asn
65                  70                  75                  80

Leu Leu Cys Asn Asn Glu Gln Lys Glu Glu Gly Glu Ile Ile Lys
                    85                  90                  95

Gln Arg Asn Ile Gly Asp Glu Ile Asn Glu Tyr Asn Asn Leu Thr Lys
                100                 105                 110

Leu Gln Asn Asp Glu Asn Ile Lys Asn Asn Met Ile Lys Glu Asp
            115                 120                 125

Leu Glu Asp Asp Ala Asn Gln Asn Ile Leu Met Lys Ser Pro Tyr Tyr
130                 135                 140

Asn Ile Glu Asn Phe Leu Gln Val Phe Leu Lys Tyr Ile Asn Lys Lys
145                 150                 155                 160

Lys Lys Lys Val Lys Val Lys Val Lys Asp Glu Gly Lys Lys Glu Lys
                165                 170                 175

Ile Glu Asp Lys Lys Tyr Glu Gln Asp Asp Glu Glu Glu Asn Glu Glu
            180                 185                 190

Glu Glu Glu Glu Glu Glu Glu Glu Gly Glu Glu Glu Asn Lys Glu
            195                 200                 205

Asp Glu Glu Phe Phe Lys Thr Phe Val Ser Phe Asn Leu Tyr His Asn
        210                 215                 220

Asn Asn Glu Lys Asn Ile Ser Tyr Asp Lys Asn Leu Val Lys Gln Glu
225                 230                 235                 240

Asn Asp Asn Lys Asp Glu Ala Arg Gly Asn Asp Asn Met Cys Gly Asn
                245                 250                 255

Tyr Asp Ile His Asn Glu Arg Gly Glu Met Leu Asp Lys Gly Lys Ser
            260                 265                 270

Tyr Ser Gly Asp Glu Lys Ile Asn Thr Ser Asp Asn Ala Lys Ser Cys
        275                 280                 285
```

-continued

Ser Gly Asp Glu Lys Val Ile Thr Ser Asp Asn Gly Lys Ser Tyr Asp
    290                 295                 300

Tyr Val Lys Asn Glu Ser Glu Glu Gln Glu Lys Glu Asn Met Leu
305                 310                 315                 320

Asn Asn Lys Lys Arg Ser Leu Glu Cys Asn Pro Asn Glu Ala Lys Lys
                325                 330                 335

Ile Cys Phe Ser Leu Glu Glu Lys Ile Gly Thr Val Gln Ser Val Lys
            340                 345                 350

Leu Lys Glu Tyr Asn Glu Leu Ser Lys Glu Asn Ile Glu Lys Asn Lys
            355                 360                 365

His Asp Asp Asn Asn Ile Cys Asn Tyr Leu Ser His Asn Glu Gly Glu
    370                 375                 380

Asn Val Ile Glu Arg Glu Asp Lys Leu Phe Asn Lys Leu Asn Asn Lys
385                 390                 395                 400

Asn Tyr Arg Asn Glu Glu Lys Lys Asn Gln Ile Asn Phe Asp
                405                 410                 415

Tyr Leu Lys Lys Lys Ile Lys Asn Asn Gln Asp Val Phe Glu Glu Thr
            420                 425                 430

Ile Gln Lys Cys Phe Leu Ile Asn Leu Lys Lys Thr Leu Asn Leu Ile
    435                 440                 445

Asn Lys Ile Met Tyr Leu Lys Asn Val Glu Phe Arg Lys Tyr Asn Leu
450                 455                 460

Asp Tyr Ile Arg Lys Ile Asn Tyr Glu Lys Cys Phe Tyr Tyr Lys Asn
465                 470                 475                 480

Tyr Ile Asp Ile Lys Lys Ile Ser Glu Leu Gln Lys Asp Asn Glu
            485                 490                 495

Ser Leu Lys Ile Gln Val Asp Arg Leu Glu Lys Lys Ala Thr Leu
            500                 505                 510

Ile Tyr Lys Leu Asn Asn Asp Asn Ile Arg Lys His Ile Leu Asp Asn
    515                 520                 525

Asn Ile Lys Asp Tyr Gln Asn Gly Ile Asp Asn Ser Lys Val Ser Tyr
    530                 535                 540

Phe Asp Glu Gly Glu Asn Pro Tyr Asn Arg Asn Asn Lys Asn Tyr Arg
545                 550                 555                 560

Thr Asp Asn Lys Asn Ser Asp Asp Asn Asn Asn Asn Asn Tyr Tyr
                565                 570                 575

Tyr Asn Asn Tyr Asn Ser Asp Asp Asn Tyr Asn Ser Glu Asp Asn Glu
            580                 585                 590

Tyr Asn Asn Gly Asn Tyr Arg Phe Arg Asn Asn Tyr Lys Lys Asp Ser
            595                 600                 605

Leu Asn Glu Asp Asp Val Lys Lys Asn Pro Leu Lys Val Cys His Lys
    610                 615                 620

Ile Asn Ser Asp Ser Asn Ile Phe Val Asn Phe Glu Asn Ile Ile Thr
625                 630                 635                 640

Lys Gln Asn Ile Ile His Ser Glu Pro Phe Arg Asn Leu Leu Lys Glu
                645                 650                 655

Ser Asn Glu Leu Tyr Ile Thr Leu Lys Glu Lys Glu Lys Glu Asn Ile
            660                 665                 670

Ile Leu Lys Asn Glu Ile Leu Lys Met Glu Asn Lys Lys Asp Glu Glu
            675                 680                 685

Tyr Glu His Leu Leu Asn Asn Thr Ile Glu Asp Lys Lys Glu Leu Thr
    690                 695                 700

Arg Ser Ile Lys Glu Leu Glu Ile Asn Met Met Thr Cys Asn Met Glu
705                 710                 715                 720

Lys Asp Lys Ile Ser Asn Lys Val Asn Thr Leu Glu Tyr Glu Ile Asn
            725                 730                 735

Val Leu Lys Asn Ile Asp Lys Asn Gln Thr Met Gln Leu Gln Gln Lys
            740                 745                 750

Glu Asn Asp Ile Leu Lys Met Lys Leu Tyr Ile Glu Lys Leu Lys Leu
            755                 760                 765

Ser Glu Lys Asn Leu Lys Asp Lys Ile Ile Leu Leu Glu Asn Glu Lys
            770                 775                 780

Asp Lys Met Leu Ser Gly Ile His Ile Lys Asp Asn Ser Phe Asn Glu
785                 790                 795                 800

Glu Ser Lys Ser Glu Glu Gly Lys Ile Gln Leu Arg Asp Ile Gln Asn
            805                 810                 815

Asp Asn Asp Glu Lys Tyr Asp Asp Glu Lys Lys Arg Phe Lys Glu Leu
            820                 825                 830

Phe Ile Glu Asn Gln Lys Leu Lys Glu Glu Leu Asn Lys Lys Arg Asn
            835                 840                 845

Val Glu Glu Glu Leu His Ser Leu Arg Lys Asn Tyr Asn Ile Ile Asn
            850                 855                 860

Glu Glu Ile Glu Glu Ile Thr Lys Glu Phe Glu Lys Lys Gln Glu Gln
865                 870                 875                 880

Val Asp Glu Met Ile Leu Gln Ile Lys Asn Lys Glu Leu Glu Leu Leu
            885                 890                 895

Asp Lys Phe Asn Asn Lys Met Asn Lys Ala Tyr Val Glu Glu Lys Leu
            900                 905                 910

Lys Glu Leu Lys Asn Thr Tyr Glu Glu Lys Met Lys His Ile Asn Asn
            915                 920                 925

Ile Tyr Lys Lys His Asp Asp Phe Val Asn Ile Tyr Leu Asn Leu Phe
            930                 935                 940

Phe Gln Ala Arg Lys Asn Ala Ile Leu Ser Asp Ser Gln Arg Glu Glu
945                 950                 955                 960

Gln Met Asn Leu Phe Ile Lys Leu Lys Asp Lys Tyr Asp Ile Ile Phe
            965                 970                 975

Gln Lys Lys Ile Glu Leu Thr Asp Ile Leu Lys Asn Val Tyr Asp Cys
            980                 985                 990

Asn Lys Lys Leu Ile Gly His Cys Gln Asp Leu Glu Lys Glu Asn Ser
            995                 1000                1005

Thr Leu Gln Asn Lys Leu Ser Asn Glu Ile Lys Asn Ser Lys Met
    1010                1015                1020

Leu Ser Lys Asn Leu Ser Lys Asn Ser Asp Asp His Leu Leu Ile
    1025                1030                1035

Glu Glu Asn Asn Glu Leu Arg Arg Arg Leu Ile Cys Ser Val Cys
    1040                1045                1050

Met Glu Asn Phe Arg Asn Tyr Ile Ile Ile Lys Cys Gly His Ile
    1055                1060                1065

Tyr Cys Asn Asn Cys Ile Phe Asn Asn Leu Lys Thr Arg Asn Arg
    1070                1075                1080

Lys Cys Pro Gln Cys Lys Val Pro Phe Asp Lys Lys Asp Leu Gln
    1085                1090                1095

Lys Ile Phe Leu Asp
    1100

<210> SEQ ID NO 30
<211> LENGTH: 104
<212> TYPE: PRT

<213> ORGANISM: Plasmodium falciparum

<400> SEQUENCE: 30

His Asn Asn Asn Glu Lys Asn Ile Ser Tyr Asp Lys Asn Leu Val Lys
1               5                   10                  15

Gln Glu Asn Asp Asn Lys Asp Glu Ala Arg Gly Asn Asp Asn Met Cys
            20                  25                  30

Gly Asn Tyr Asp Ile His Asn Glu Arg Gly Glu Met Leu Asp Lys Gly
        35                  40                  45

Lys Ser Tyr Ser Gly Asp Glu Lys Ile Asn Thr Ser Asp Asn Ala Lys
    50                  55                  60

Ser Cys Ser Gly Asp Glu Lys Val Ile Thr Ser Asp Asn Gly Lys Ser
65                  70                  75                  80

Tyr Asp Tyr Val Lys Asn Glu Ser Glu Glu Gln Glu Glu Lys Glu Asn
                85                  90                  95

Met Leu Asn Asn Lys Lys Arg Ser
            100

<210> SEQ ID NO 31
<211> LENGTH: 3933
<212> TYPE: PRT
<213> ORGANISM: Plasmodium falciparum

<400> SEQUENCE: 31

Met Ile Lys Lys Ser Glu Glu Ser Lys Arg Leu Leu Arg Lys Lys Leu
1               5                   10                  15

Asn Asn Asp Ile Thr Asn Ile Leu Leu Leu Phe Glu Lys Val Gln Glu
            20                  25                  30

Trp Ala Asp Leu Ser Asn Ile Leu Gln Lys Leu Tyr Leu Thr Ile Glu
        35                  40                  45

Lys Tyr Glu Leu Phe Val Asn Val Ser Ser Lys Phe Leu Leu Phe Arg
    50                  55                  60

Arg Leu Ser Gln Cys Leu Asn Pro Leu Leu Pro Ser Gly Val His Ser
65                  70                  75                  80

Lys Ala Leu Ile Ile Tyr Ser Ser Ile Phe Lys Lys Val Glu Met Asp
                85                  90                  95

Phe Phe Ile Asn Asn Ile His Ile Leu Cys Ser Gly Ile Phe Glu Phe
            100                 105                 110

Met Leu His Cys Thr Ile Asn Leu Lys Thr Ile Tyr Phe Lys Asn Ile
        115                 120                 125

Lys Ser Ile Leu Arg Leu Lys Glu Asn Val Tyr Ile Phe Ala Tyr Ala
    130                 135                 140

Leu Leu Leu Ser Leu Phe Asn Val Val Asp Ser Asp Asn Asn Ile Leu
145                 150                 155                 160

Leu Tyr Ile Tyr Ser Ile Asn Asn Tyr Ile Gly Glu Asn Ile Phe Phe
                165                 170                 175

Asn Asn Ile Trp Leu Leu Leu Arg His Pro Glu Ile Arg Thr Asn
            180                 185                 190

Ile Leu Asn Phe Leu Glu Ala Ser Phe Ser Pro Gln Ile Tyr Leu Leu
        195                 200                 205

Ser Lys Glu Arg Ile Lys Met Leu Leu Pro Tyr Lys Asp His Leu Val
    210                 215                 220

Leu Ser Ser Ile Ile Tyr Cys Leu Asn Asp Lys Asn Ile Leu Asn Gln
225                 230                 235                 240

Arg Ile Thr Leu Ser Leu Leu Ile Asn Asn Phe Pro Leu Ser His Val
                245                 250                 255

Pro Asn Lys Lys Asn Lys Lys Ile Ile Asp Lys Ser Lys Ser Asn
            260                 265                 270

Asp Tyr His Met Asp Lys Pro Pro Tyr Ser Pro Phe Asn Ala Ser Thr
            275                 280                 285

Ser Ser Val Ile Leu Asn Asn Ser Asn Met Asp Ser Met Asn Asp Asn
290                 295                 300

Arg Ile Asn Glu Asn Asn Ile Asn Asn Asn Asp Asn Lys Arg His Asn
305                 310                 315                 320

Ile Gln Ile Asn Asn Asp Tyr Leu Phe Gly Asp Met Met Asn Lys Gln
            325                 330                 335

Asn Asp Thr Thr Ile Met Gln Ser Asn Lys Met Leu Asn Arg His Asn
            340                 345                 350

Ile Ile Gly Glu Gln His Leu Asp Asp Leu Leu Ser Ser Ile His
            355                 360                 365

Asp Asp Asn Ser Glu Lys Lys Asn Asn Asn Phe Met Leu Leu Asn
370                 375                 380

Glu Asn Asn Lys Ile Ser Thr Ser Lys Glu His Leu Asp Asn Met His
385                 390                 395                 400

Asn Arg Gly Ile Lys Ser His Glu Asp Ile Met Gly Ser Asn Gln Asn
            405                 410                 415

Lys Met Asn Leu Ser Asn Asp Glu Lys Asp His Trp Gly Gly Asn Leu
            420                 425                 430

Asn Ser Lys Val Gly Asn Tyr Asp Asp Lys Asn Ile Cys Gly Lys Lys
            435                 440                 445

His Leu Gly Leu Lys Ser Glu Tyr Gly Gln Val Ser Tyr Asp Glu Ser
            450                 455                 460

Leu Glu Arg Arg Leu Asn Asn Asn Asn Asn Asn Asn Asn Asn Asn
465                 470                 475                 480

Asn Asn Asn Asn Asn Asn Gly Asp Asn Leu Lys Tyr Gln Gly Ser Val
                    485                 490                 495

Asp Tyr Asp Glu His Asp Ile Ser Met Ser Thr Glu Asn Asp Lys Tyr
            500                 505                 510

Gly Lys Met Gly Asn Glu Asn Met Asn Asp Val Phe Ile Ser Lys Gly
            515                 520                 525

Lys Met Met Arg Lys Gly Tyr Glu Asp Gly His His His Ile Asn
            530                 535                 540

Ile Asn Asp Asp Asp Asn Leu Asn Tyr Asp Asp Asn Glu Asp Glu
545                 550                 555                 560

Tyr Gly Asn Tyr His Asn Asn Tyr Asn Asp Arg Asn Tyr Phe Asn
                    565                 570                 575

Glu Tyr Asp Glu Asp Asp Gln Tyr Glu Asn Asn Asn Asn Asn His
            580                 585                 590

Ser Asn Asn Asn Asn Met Leu His Leu Gly Ser Val Asp Arg Asn Arg
            595                 600                 605

Arg Lys Gln Leu Lys Lys Lys Ile Asn Asn Ile Gly Gln Thr Asn Asn
            610                 615                 620

Tyr Asp Asp Asp Glu Glu Glu Asp Glu Glu Glu Asp Asn Asn
625                 630                 635                 640

Asn Asn Thr Ser Tyr Asn Asn Asn Asn Asn Ser Ser Ser Ser
                    645                 650                 655

Ser Ile Phe Phe Ser Asp Thr Ser Lys Lys Leu Ile Ala Arg Asn Val
            660                 665                 670

Ile Phe Leu Leu Lys Lys Ser Asp Ile Gly Leu Asn Arg Arg Ile Phe

-continued

```
              675                 680                 685
Lys Tyr Leu Tyr Leu Tyr Glu Ser Asn Asp Glu Lys Asn Phe Lys Asp
690                 695                 700
Lys Glu Ile Asn Phe Glu Asn Tyr Lys Ile Tyr Cys Glu Thr Ile Ile
705                 710                 715                 720
Asp Ile Leu Glu Asn Lys Ser Asp Asp Asn Tyr Asn Ser Ile Ala Glu
                    725                 730                 735
Val Ile Tyr Ile Leu Phe Lys Asn Lys Asp Tyr Ile Asn Ile Asn Arg
                740                 745                 750
Tyr Ile Met Glu Gln Val Phe Leu Tyr Leu Leu Asn Phe Cys Tyr Lys
            755                 760                 765
Asn Arg Glu Asp Thr Ser Ile Lys Ser Phe Leu Lys Asn Met Leu Asn
        770                 775                 780
Leu Asn Leu Ile Ser Tyr Glu Asn Ile Leu Asn Ile Phe Leu Tyr Thr
785                 790                 795                 800
Phe Tyr Tyr Leu Arg Arg Asn Asp Asp Leu Phe Val His Tyr Thr Asn
                    805                 810                 815
Ile Tyr Ile Lys Lys Tyr Ile Asn Leu Leu Asn Ile Met Thr Phe Phe
                820                 825                 830
Val Glu Phe Ile Lys His Met Asn Lys Tyr Leu Tyr Ile Gln Phe Leu
            835                 840                 845
Phe His Phe Asn Leu Ala Thr Leu Lys Leu Met Asn Phe Leu Asn Leu
        850                 855                 860
Lys Ile Ile Asn Ile Ile Lys Lys Tyr Ser His Val Lys Asp Leu Asn
865                 870                 875                 880
Glu Lys Tyr Phe Ile Asp Ser Asn Asp Val Val Ser Gly Arg His Ser
                    885                 890                 895
Thr Leu Tyr Tyr Phe Tyr Phe Phe Val Thr His Tyr Asn Asn Tyr Tyr
                900                 905                 910
Leu Asn Lys Cys Leu Ser Ile Ile Val Lys Asp Ile Leu Pro Gln Asn
            915                 920                 925
Pro Ser Asn Arg Lys Met Gly Asn Tyr Gln Ser His Tyr Tyr Ala Asn
        930                 935                 940
Asn Lys His Met Leu Tyr Met Asn Thr His Glu Ile His Ser Ala Arg
945                 950                 955                 960
Met Glu Glu Tyr Ser Asn Lys Ile Gln Lys Val Gly Phe Lys Asn Glu
                    965                 970                 975
Ile Val Asp Arg Lys Asn Lys Tyr Asp Asn Glu Tyr Ser Glu Ser
                980                 985                 990
Glu Ile Lys Met Arg Ala Val Asp Asn Ser Met Asn Tyr Ile Lys Arg
            995                 1000                1005
Lys Val Lys Lys Lys Asn Met Glu Ser Lys Asp Ser Ser Asn Ser
1010                1015                1020
Met Ser Asn Met Glu Ile Asn Thr Asn Ser Thr Met Ala Asn Arg
        1025                1030                1035
Leu Asn His Met Gln His Ile Gln His Asp Gly Ile Ser Ser Met
        1040                1045                1050
Glu His Met Asn Asn Lys Ile Asn Asp Asn Asn Asn Asn Asn
        1055                1060                1065
Val Asn Tyr Phe Phe Asp Gly Asn Asn Ser Asn Asn Asn Asn Asn
        1070                1075                1080
Asn Asn Ile Leu Glu Asn Asn Asn Lys Leu Tyr Phe Asp Lys Gly
        1085                1090                1095
```

-continued

```
Tyr Asn Gly Asn Tyr Ser Lys Ile Glu Asn Asp Gln Ser Phe His
1100                1105                1110

Asn Ile Leu Met Lys Tyr Lys Phe Lys Leu Lys Gln Asn Leu Ile
1115                1120                1125

Asp Ala Ile Ile Lys Asn His Glu Leu Tyr Phe Phe Thr Asn Asn
1130                1135                1140

Cys Glu Tyr Ile Ile Phe Leu Phe Tyr Asn Tyr His Leu Leu Ile
1145                1150                1155

Glu Lys Glu Lys Leu Asn Lys Ser Cys Phe Tyr Phe Leu Lys Asn
1160                1165                1170

Ile Leu Asn Asn Cys Thr Cys Glu Asn Lys Asn Lys Phe Tyr Phe
1175                1180                1185

Trp Cys Phe Leu Phe Leu His Ile Ile Arg Ile Asn Phe Asn Lys
1190                1195                1200

Ser Leu Leu Lys Asn Tyr Lys Ile Lys Glu Ala Gly Asp Asp Thr
1205                1210                1215

Asp Asp Asp Asp Asp Asp Asp Asp Asp Asp Asp Glu Glu Glu
1220                1225                1230

Asp Asp Asp Asp Glu Asp Asp Asp Glu Asp Asp Glu Glu Glu
1235                1240                1245

Asp Asp Glu Glu Asp Leu Gly Val Asp Gly Leu Lys Asn Met Ser
1250                1255                1260

Ser Lys Lys Gly Lys Lys Lys Lys Lys Ser Val His Lys Asn
1265                1270                1275

Lys Leu Met Asn Lys Lys Tyr Gly Arg Gly Gly Ser Ser Lys Tyr
1280                1285                1290

Tyr Tyr Tyr Leu Thr Ser Asp Lys Glu Ile Met Leu His Gly Gly
1295                1300                1305

Met Met Gly Gly Val Asn Tyr Ser Asp Met Glu His Asp Glu Asp
1310                1315                1320

Asn Leu Asp Val Asp Asp Glu Asp Glu Gln Met Phe Ser Tyr Asn
1325                1330                1335

Lys Asn Lys Ile Arg Asn Lys His Phe Gly Glu Leu Asn Lys Met
1340                1345                1350

Lys Tyr Met Asn Glu Asp Ile Thr Asn Asn Asn Asn Ile Asn
1355                1360                1365

Asn Asn Ser Asn Asn Asn Asn Asn Asn Lys Asn Asn Ile Asn Asn
1370                1375                1380

Asn Asn Asn Asn Asn Asn Asn Asn Asn Asn Asn Asn Asn Leu
1385                1390                1395

Asn Asn Leu Asn Asn Phe Asn Asn Asn Val Ser Ile Asn Asn Gly
1400                1405                1410

Asn Asn Lys Tyr Arg Asn Tyr Phe Arg Ser Thr Glu Glu Glu Leu
1415                1420                1425

Leu Phe Asn Lys Arg Phe Val Glu Phe Leu Leu Pro Tyr Ser Asn
1430                1435                1440

Asn Ile Ala Lys Tyr Ile Phe Gln Tyr Ile Lys Ile Leu Lys Lys
1445                1450                1455

Asn Lys Lys Phe Ile Lys Leu Phe Phe Asp Ile Asn Tyr Leu Tyr
1460                1465                1470

Phe Phe Cys Asp Asn Met Phe Cys Leu Lys Ile Leu Lys Lys Ser
1475                1480                1485

Leu Lys Cys Lys Asp Asn His Glu Leu Thr Ile Asn Val Lys Val
1490                1495                1500
```

```
Ile Leu Glu Tyr Ile Ile Asn Ser Lys Thr Asn Glu Tyr His Ile
1505                 1510                1515

Ile His Ser Asn Phe Tyr Asn Leu Thr His Asp Val Phe Lys Leu
1520                 1525                1530

Tyr Asn Arg Arg Asn Asn Leu Ile Asn Tyr Tyr Leu Ile Lys Tyr
1535                 1540                1545

Ile Met Arg Asn Lys Glu Asn Leu Ser Tyr Ile Phe Asp Asn Ile
1550                 1555                1560

Ile Ile Ser Met Phe Asp Leu Ile Thr Glu Ile Glu Asn Leu Tyr
1565                 1570                1575

Glu Lys Ile Glu Met Met Lys Lys Asp Leu Ser Tyr Ser Met Met
1580                 1585                1590

Asn Asn Asn Asp His Val Tyr Asp Pro Asn Gly Met Ile Glu Ala
1595                 1600                1605

Ala Asp Gln Arg Lys Ser His Tyr Val Ser Leu Lys Asp Asn Met
1610                 1615                1620

Asn Asn Met Asn Asn Met Asn Asn Val Asn Asn Met Asn Asn Val
1625                 1630                1635

Asn Asn Met Asn Asn Val Asn Asn Val Asn Asn Val Asn Asn Val
1640                 1645                1650

Asn Tyr His Asn Asn Thr Ile Asn Asn Asn Asn Asn Asn Asn Asn
1655                 1660                1665

Phe Ser Asn His Thr Ser Tyr Val Asn Glu Lys Thr Gln Glu Asn
1670                 1675                1680

Asn Tyr His Asn Leu Met Asn Thr Tyr Glu Lys Tyr Leu Lys Lys
1685                 1690                1695

Leu Lys Cys Lys Phe Asp Tyr Ile Ser Tyr Phe Phe Leu Asn Met
1700                 1705                1710

Glu Asn Phe Met Leu Trp Leu Tyr Lys His Lys Ile Ser Lys Lys
1715                 1720                1725

Ile Tyr His Ser Arg Asn Lys Met Thr Leu Thr Asn Tyr Glu Lys
1730                 1735                1740

Asn Met Ala Ile Ile Ile Cys Tyr Ile Cys Thr Glu Gly Asn Ile
1745                 1750                1755

Asn Ser Phe Phe Phe Arg Asn Tyr Leu Asp Val Phe Phe Ile Leu
1760                 1765                1770

Phe Leu Lys Ile Ile Tyr Leu Asn Glu Asn Ile Ser Glu Leu Asn
1775                 1780                1785

Asn Ser Ala Asn Asn Ile Ile Gln Lys Glu Lys Asn Asn Leu Lys
1790                 1795                1800

His Asn Ser Leu Leu Glu Phe Lys Arg Asp Thr Leu Ser Met Leu
1805                 1810                1815

Asn Asn Ile Phe Asn Ile Asn His Asn Lys Lys Phe Glu Tyr Met
1820                 1825                1830

Lys Ile Leu Asn Leu Tyr Tyr Arg Gln Ile Ile His His Leu Leu
1835                 1840                1845

Phe Leu Tyr Tyr Tyr Phe Thr Val Lys Lys Tyr Val Leu Gln
1850                 1855                1860

Leu Gln Leu Val His Phe Ile Arg Tyr Ile Leu Pro Leu Tyr Glu
1865                 1870                1875

Lys Asn Ile Asp Lys Lys Phe Leu Thr Asn Glu Ser Thr Glu Lys
1880                 1885                1890

Asp Lys Val Phe Lys Arg Met Lys Tyr Asn Asn Tyr Glu Glu Phe
```

-continued

|  | 1895 |  |  |  | 1900 |  |  |  | 1905 |  |  |
| --- | --- | --- | --- | --- | --- | --- | --- | --- | --- | --- | --- |
| Ile | Ser | Ala | Ser | Lys | Tyr | His | Phe | Glu | Ile | Ile | Asn | Arg | Asn | Asn |
| 1910 |  |  |  |  | 1915 |  |  |  | 1920 |  |  |
| Tyr | Asn | Met | Lys | Asn | Asp | Val | Phe | Ile | Phe | Ser | Ile | Leu | Arg | Lys |
| 1925 |  |  |  |  | 1930 |  |  |  | 1935 |  |  |
| Ser | Met | Thr | Ile | Ile | Phe | Asn | Leu | Asn | Glu | Gln | Val | Leu | Tyr | Lys |
| 1940 |  |  |  |  | 1945 |  |  |  | 1950 |  |  |
| Glu | Val | Leu | Lys | Thr | Ile | Ile | Asp | Leu | Ile | Glu | Asn | Ile | Ile | Asp |
| 1955 |  |  |  |  | 1960 |  |  |  | 1965 |  |  |
| Glu | Lys | Glu | Val | Lys | Asn | Tyr | Tyr | Leu | Thr | Val | Phe | Phe | Leu | Asp |
| 1970 |  |  |  |  | 1975 |  |  |  | 1980 |  |  |
| Leu | Leu | Tyr | Ile | Ile | Lys | Met | Glu | Asp | Gln | Lys | Lys | Lys | Lys | Asn |
| 1985 |  |  |  |  | 1990 |  |  |  | 1995 |  |  |
| Ile | Phe | Phe | Ile | Met | Lys | Phe | Cys | Gln | Phe | Leu | Ile | Glu | Ile | Phe |
| 2000 |  |  |  |  | 2005 |  |  |  | 2010 |  |  |
| Lys | Leu | Ile | Tyr | Arg | Asp | Glu | Met | Lys | Asn | Glu | Leu | Lys | Cys | Asp |
| 2015 |  |  |  |  | 2020 |  |  |  | 2025 |  |  |
| Lys | Lys | Phe | Gln | Asp | Asp | Asn | Ile | Thr | Ile | Asp | Ile | Ile | Glu | Asn |
| 2030 |  |  |  |  | 2035 |  |  |  | 2040 |  |  |
| Ala | Leu | Ser | Asn | Asn | Lys | Met | Ser | Thr | Ala | Ser | Phe | Cys | Thr | Ile |
| 2045 |  |  |  |  | 2050 |  |  |  | 2055 |  |  |
| Phe | Ser | Ile | Lys | Thr | Asp | Asp | Lys | Phe | Val | Asn | Val | Gln | His | Lys |
| 2060 |  |  |  |  | 2065 |  |  |  | 2070 |  |  |
| Asn | Ile | Ser | Asn | Leu | Phe | Ser | Val | Ile | Phe | Asn | Leu | Tyr | Ala | Phe |
| 2075 |  |  |  |  | 2080 |  |  |  | 2085 |  |  |
| Leu | Lys | Lys | Lys | Ile | Lys | Leu | Tyr | Tyr | Lys | His | Asn | Lys | His | Leu |
| 2090 |  |  |  |  | 2095 |  |  |  | 2100 |  |  |
| Ile | Asn | Asn | Asp | Asp | Lys | Asn | Asn | Val | Val | Asn | Asn | Asn | Ser | Tyr |
| 2105 |  |  |  |  | 2110 |  |  |  | 2115 |  |  |
| Ile | Tyr | Tyr | Asp | Asn | Asn | Ser | Asn | Val | Tyr | Asn | Asn | Asn | Asn | Thr |
| 2120 |  |  |  |  | 2125 |  |  |  | 2130 |  |  |
| Asn | Ile | Tyr | Asn | Asn | Asn | Asn | Asn | Asn | Glu | Asn | Asn | Ala | Phe | Asn |
| 2135 |  |  |  |  | 2140 |  |  |  | 2145 |  |  |
| Asn | Asn | Met | Pro | Asn | Asn | Ser | Asn | Ile | Met | Asn | Asn | Met | Asn | Asn |
| 2150 |  |  |  |  | 2155 |  |  |  | 2160 |  |  |
| Met | Asn | Asp | Ile | Tyr | His | Ile | Ser | Gln | His | Thr | Asn | Asn | Asn | Ile |
| 2165 |  |  |  |  | 2170 |  |  |  | 2175 |  |  |
| Arg | Tyr | Asn | Asp | Val | Ser | Ser | Cys | Gly | Ala | Arg | Gly | His | Asn | Ile |
| 2180 |  |  |  |  | 2185 |  |  |  | 2190 |  |  |
| Asn | Ser | Asn | Glu | Asn | Val | Asn | Gln | Asn | Asp | Leu | Asn | Asn | Asn | Ser |
| 2195 |  |  |  |  | 2200 |  |  |  | 2205 |  |  |
| Asn | Tyr | Asn | Tyr | Asn | Arg | Gly | Met | Asn | Asn | Met | Asn | Gly | Asp | Ile |
| 2210 |  |  |  |  | 2215 |  |  |  | 2220 |  |  |
| Asn | Asn | Ile | Asn | Gly | Asp | Ile | Asn | Asn | Met | Asn | Gly | Asp | Ile | Asn |
| 2225 |  |  |  |  | 2230 |  |  |  | 2235 |  |  |
| Asn | Met | Asn | Gly | Asp | Ile | Asn | Asn | Met | Asn | Gly | Asp | Ile | Asn | Asn |
| 2240 |  |  |  |  | 2245 |  |  |  | 2250 |  |  |
| Met | Asn | Gly | Asp | Ile | Asn | Asn | Met | Asn | Gly | Gly | Asn | Phe | Lys | Asn |
| 2255 |  |  |  |  | 2260 |  |  |  | 2265 |  |  |
| Pro | Asn | Ser | Tyr | Asn | Asn | Asn | Asn | Asn | Met | Asn | Ser | Tyr | Tyr | Ser |
| 2270 |  |  |  |  | 2275 |  |  |  | 2280 |  |  |
| His | Asn | Ser | Ser | Asp | Tyr | His | Lys | Asp | Asn | Asp | Asn | Met | Arg | Asn |
| 2285 |  |  |  |  | 2290 |  |  |  | 2295 |  |  |

-continued

```
Asn Val Asn Ser Ser Asn Ser Asn Phe His Asn Asn Gln Asp
    2300            2305            2310

Val Gln Ile Met Asn Arg Lys Asn Asp Ser Asp Gly Asn Val Gly
    2315            2320            2325

Asn Phe Asp Asn Asn Ser Thr Tyr Ser Tyr Met Asn Asn Val Asn
    2330            2335            2340

Asn Asp Ile Ser Met Arg Leu Thr Asn Ile Asn Asn Asn Asn Asn
    2345            2350            2355

Ile Asn Ile Asn Asn Asn Asn Asn Asn Asn Asn Leu Phe Ala
    2360            2365            2370

Tyr Asn Lys Asn Asn Pro Asn Ala Leu Val Asn Asn Met Asn Asn
    2375            2380            2385

Gln Asp Lys Pro Asp Gln His Asn Asn Ser His Gln Tyr Met Tyr
    2390            2395            2400

Lys Glu Asn Asp Met Asn Gln Phe Gly Asn Ser Asn Tyr Asn Asn
    2405            2410            2415

Met Asp Asn Thr Asn Asn Lys Phe Tyr Asn Asn Tyr Asn Tyr Gly
    2420            2425            2430

Lys Asn Val Glu Gly His Thr Ile Tyr Asp Asn Asn Asn Asn Asn
    2435            2440            2445

Asn Asn Asn Ser Asn Asn Gly Ala Val Asn Ile Asn Ser Val Gln
    2450            2455            2460

Gly Glu Asn Asn Val Met Ser Arg Asn Asn Ile Leu Phe Asn His
    2465            2470            2475

Asn Val Asn Asn Asn Glu Tyr Tyr Phe Ser Gln Lys Asn Glu Asp
    2480            2485            2490

Asn Met Ala Ser Met Asn Asn Asn His His Asn Asn Tyr His Asn
    2495            2500            2505

Asn Asn Asn Asn His His Asn Asn Ile Asn Asn His His Asn
    2510            2515            2520

Asn Asn Ile Asn Asn His His Asn Met Asn Arg Asn Asn Asn Ile
    2525            2530            2535

Tyr Ser Glu Asp Ser Lys Thr Asn Glu Cys Tyr Ser Met Arg Glu
    2540            2545            2550

Lys Met Gly Asp Val Asn Val Ala Tyr Asn Ser Asn Phe Tyr Asp
    2555            2560            2565

Asp Lys Asn Asn Tyr Thr His Met Lys Asn Asp Leu Ile Lys Asn
    2570            2575            2580

Glu Gln Lys Asn Asn Tyr Gly Phe Cys Asn Asn His Glu Asn Thr
    2585            2590            2595

Phe Ile Tyr Asn Cys Lys Asn Arg Met Asn Arg Asn Asn Tyr Ala
    2600            2605            2610

Phe Asn Met Gly Ser Lys Lys Asn Lys Lys Ile Met Leu Leu Lys
    2615            2620            2625

Val Cys Leu Ser Asn Ile Ile Ser Ile Asn Lys Leu Leu Tyr Phe
    2630            2635            2640

Ile Thr Arg Pro Glu Phe Leu Phe Ile Asp Asn Leu Tyr Ser Ile
    2645            2650            2655

Phe Lys Asp Tyr Ile Lys Asn Arg Asn Glu Tyr Asn Lys Glu Arg
    2660            2665            2670

Leu Ser Lys Ser Asp Tyr Tyr Tyr Glu Gln Arg Glu Lys Leu Tyr
    2675            2680            2685

Lys Glu His Arg Arg Lys Met Asn Arg Gln Asn Ile Arg Thr Asp
    2690            2695            2700
```

-continued

```
Ser Ser Asn Asn Asn Asn Asn Asn Ile Asn Ser Asn Asn Asn
    2705                2710                2715
Asn Asn Asn Asn Asn Asn Asn Asn Asn Asn Asn Asn
    2720                2725                2730
Asn Asn Asn Ile Tyr Asn Asn Asn Tyr Tyr Tyr Ser Ser Ser
    2735                2740                2745
Ile Asn Lys Val Ser Phe Asp Asp Glu Lys Ile Glu Val Glu
    2750                2755                2760
Ser Phe Leu Asp His Asn Gly Val Val Gly Ser Asn Lys Lys Ile
    2765                2770                2775
Lys Arg Glu Lys Ile Arg Glu Tyr Phe Lys Lys Glu Lys Asn Leu
    2780                2785                2790
Leu Lys Lys Leu Asn Phe Met Thr Lys Phe Ser Lys Asn Thr Ile
    2795                2800                2805
Lys Lys Ser Met Ile Val Met Asn Asn Ser Asp Glu Cys Ile Glu
    2810                2815                2820
Lys Lys Lys Leu Ser Phe Ser Leu Thr Leu Leu Thr Glu Phe Asp
    2825                2830                2835
Asp Val Ile Leu Ile Lys Ile Ile Asp Asp Leu Leu Asn Tyr Tyr
    2840                2845                2850
Glu Lys Tyr Lys Ser Lys Ile Asn Leu Asn Glu Phe Met Tyr Phe
    2855                2860                2865
Leu Phe Asn Ile Tyr Leu Asn Ile Cys Thr Leu Thr Lys Arg Ile
    2870                2875                2880
Ile Asn His Phe Ile Asp Phe Ile Phe Ser Phe Ile Lys Lys Ile
    2885                2890                2895
Thr Gln Thr Ser Gln Asn Ile Met Ser Ser Leu Trp Phe Leu Tyr
    2900                2905                2910
Ile Leu Phe Ile Ile Glu Asn Asn His Ile Tyr Val Phe Asn Asp
    2915                2920                2925
Lys Leu Gln Lys Lys Ile Ile Val Glu Gln Ile Ser Ile Leu Ile
    2930                2935                2940
Gln Ile Ser Leu Tyr Ser Tyr Tyr Ser Lys Asn Val Lys Asn Asn
    2945                2950                2955
Tyr Asn Ile Gln Thr Pro Leu Pro Asn Phe Val Gln Pro Phe Asn
    2960                2965                2970
Ile Tyr Tyr Ile Ile Gln Asn Tyr Phe Ile Asn Asn Asn Tyr Phe
    2975                2980                2985
His Ile Lys Lys Asn Asn Lys Asn Ile Arg Tyr Phe Tyr Ile Lys
    2990                2995                3000
Asn Leu Lys Leu Ile Glu Lys Asn Phe Asn Ile Asn Asp Tyr Ser
    3005                3010                3015
Glu Ile Ala Ala Ile Asn Ala Leu Ser Phe Leu Leu Met Cys Phe
    3020                3025                3030
Tyr His Thr Val Asn Tyr Asn Gly Thr Asn Lys Ser Tyr Ile Cys
    3035                3040                3045
Glu Ser Ser Val Asn Ile Phe Tyr Glu His Phe Ser Lys Tyr Ile
    3050                3055                3060
Ser Leu Ile Tyr Asn Asn Ser Leu Gln Asn Ile Phe Tyr Arg Tyr
    3065                3070                3075
Val Phe Leu Leu Ile Met Asn Leu Leu Ile Asp Tyr Asn Ala Asn
    3080                3085                3090
Ser Lys Tyr Tyr Ile Lys Lys Ile Thr Phe Asp Leu Tyr Ser Tyr
```

```
                  3095                3100                3105
Ile Thr Asn Val Asp Ile Arg Cys Ile Lys Ala Leu Ser Thr Leu
    3110                3115                3120
Phe Lys Lys Leu Asn Glu Thr Asn Ile Asp Glu Leu Leu Leu Val
    3125                3130                3135
Pro Thr Ser Ser Ile Phe Ser Leu Lys Phe Asn Ile Ile Asn Ser
    3140                3145                3150
Arg Ile Asn Tyr Ile Asn Lys Leu Ser Leu Ile Ile Leu Ala Gly
    3155                3160                3165
Asn Arg Asn Phe Tyr Leu Cys His Leu Pro Lys Ile Ala Glu Asn
    3170                3175                3180
Ile Ser Glu Tyr Ile Lys Phe Cys Asn Asp Leu Lys Leu Tyr Arg
    3185                3190                3195
Glu Ile Leu Ile Leu Ile Cys Ile Ile Ile Lys Asn Asp Glu
    3200                3205                3210
Asn Glu Ile Tyr Ile Ile Ile Pro Thr Phe Ile Ser Leu Ile Leu
    3215                3220                3225
Gln Ile Tyr His Val Glu Arg Ile Lys Tyr Lys Met Ala Val Glu
    3230                3235                3240
Asn Ile Asn Asn Ile Asp Lys Asp Asp Asp Asn Tyr Ile Tyr Asp
    3245                3250                3255
Phe Asn Ser Tyr Asn Asn Lys Asp Val Leu Ser Leu Leu Lys Thr
    3260                3265                3270
Leu Leu Ile Ile Ile Asn Ile Leu Ile Lys Arg Asn Val Ser Phe
    3275                3280                3285
Ile Asn Phe Tyr Ser Trp Ile Phe Phe Lys Asp Ile Ser Ile Lys
    3290                3295                3300
Lys Asn Arg Leu Glu Gln Gln Asn Arg Glu Pro Gly Asn Leu Met
    3305                3310                3315
Ile Tyr Pro Gly His Lys Thr Leu Val Tyr Asn Asn Lys Lys Lys
    3320                3325                3330
Lys Gln Lys Asn Val Val Arg Tyr Val Ser Ser Ser Asp Lys
    3335                3340                3345
Asp Glu Ser Ser Val Tyr Asn Ile Ser Val Asp Glu Glu Asn Ser
    3350                3355                3360
Leu Lys Thr Gln Gly Arg Phe Phe Asp Asp Thr Tyr Tyr Lys Arg
    3365                3370                3375
Lys Asp Asn Ser Gly Tyr Thr Asn Lys Met Lys Asn Phe Asn Ser
    3380                3385                3390
Leu Thr Tyr Glu Asp Lys Ser Ser Leu Met Thr Gly Asn Gln Thr
    3395                3400                3405
Ser Ser Thr Lys Asp Val Gly Gly Met Val Asn Asn Ala Ile Arg
    3410                3415                3420
Gln Asn Ile Glu Gln Asn Asn Met Ile His Pro Asn Gln Ile Asn
    3425                3430                3435
Asn Asn Asn Asn Asn Asn Asn Asn Asn Asn Val Tyr Asn Phe
    3440                3445                3450
Asn Asp Phe Thr Asn Ser Met Asn Gln Pro Asn Val Ile Asn Asn
    3455                3460                3465
Asn Lys Lys Lys Lys Ala Phe Thr Thr Asp Asp Tyr Phe Val Lys
    3470                3475                3480
Tyr Asp Glu Asn Gln Lys Val Thr Lys Gln Thr Lys Leu Asn His
    3485                3490                3495
```

```
His Asn Glu Asp Asn Leu Asn Asp Thr Ile Thr Val Tyr Leu Asn
    3500                3505                3510

Ser Asn Gln Glu Asp Tyr Leu Tyr Glu Ser Lys Asn Asn Phe Thr
    3515                3520                3525

Ser Ile Arg Ser Glu His Ile Ser Ser Met Val Asp Ile Lys Lys
    3530                3535                3540

Gly Ser Ile Leu Asn Ser Asn Ile Leu Thr Asn Asp Asn Asn
    3545                3550                3555

Thr Asn Asn Asn Ile His Ser Asn Ile His Asn Gly Ser Ser Ser
    3560                3565                3570

Asn Asn Asn Asn Asn Asn Ser Val Cys Thr Gly Ile Lys Leu
    3575                3580                3585

Asp Glu Ser Lys Phe Val Pro Phe Leu Asp Ile Ile Glu Arg Ile
    3590                3595                3600

Tyr Ser Pro Asn Asn Ile Leu Asn Lys Lys Tyr Val Ser Ser Glu
    3605                3610                3615

Glu Leu Lys Asn Glu Lys Ser Thr Arg Thr Tyr Asn Ser Ser Leu
    3620                3625                3630

Gln Glu Gly Ser Asp Tyr Asp Glu Glu Asp Glu Glu Tyr Asp
    3635                3640                3645

Val Asp Ala Asp Val Asp Val Asp Val Asp Asp Asp Asp
    3650                3655                3660

Asp Asp Asp Val Asp Ile Val Asp Val Asp Val Asp Asp Val Val
    3665                3670                3675

Val Asp Tyr Asn Tyr Tyr Asp Asn Glu Asn Asn Ser Val Lys Ile
    3680                3685                3690

Ile Asp Val Asp Glu Arg Lys Arg Ser Val His Phe Tyr Pro Gln
    3695                3700                3705

His Leu Asp Gly Asn Thr Leu Lys Lys Asn Leu Tyr Tyr Asn Asp
    3710                3715                3720

Asn Tyr Leu Arg Glu Tyr Ile Leu Ser Thr Lys Asn Glu Leu Ser
    3725                3730                3735

Gly Tyr Ser Ser Phe Glu Asn Asn Leu Ser Ser Ser Ser Val Asn
    3740                3745                3750

Ser Ile Lys Ser Asn Phe Ser Asn Thr Phe Ser Lys Asp Asn Ile
    3755                3760                3765

Asn Lys Asn Ile Ile Thr Asp Asp Thr Ser Asp Asp Asn Asp Met
    3770                3775                3780

Met Asn Ser Asn Asn Asn Met Asn Ser Met Met Val Pro Tyr Asn
    3785                3790                3795

Met His Met Thr Asp Asp Glu Phe Gln Glu Asn Ile Asn Asn Asn
    3800                3805                3810

Asn Asn Asn Asn Asn Asn Asn Asp Asn Met Tyr Leu Ser Ser
    3815                3820                3825

Asp Asp Gly Tyr Pro Ser Gln Ser Asn His Lys Trp Ile His Phe
    3830                3835                3840

Asn Ser Leu Leu Asn Tyr Asp Ile His Glu Leu Ser Lys Lys Lys
    3845                3850                3855

Lys Lys Lys Lys Lys Lys Ile Ser Ile His Ser Cys Lys Asn Leu
    3860                3865                3870

Pro Leu Val Leu Val Tyr Leu Ser Lys Lys Ile Lys Leu Asn Phe
    3875                3880                3885

Tyr Lys Tyr Ser Met Lys Lys Pro Lys Glu Glu Thr Ile Ile Leu
    3890                3895                3900
```

```
Leu Lys  Glu Leu Asn Ser Val  Glu Asn Asp Ile Asn  Asp Leu Phe
    3905             3910                 3915

Leu Glu  Val Asp Leu Asn Glu  Val Tyr Tyr Asp Phe  Leu Ile Arg
    3920             3925                 3930

<210> SEQ ID NO 32
<211> LENGTH: 41
<212> TYPE: PRT
<213> ORGANISM: Plasmodium falciparum

<400> SEQUENCE: 32

Gly Met Asn Asn Met Asn Gly Asp Ile Asn Asn Ile Asn Gly Asp Ile
1               5                   10                  15

Asn Asn Met Asn Gly Asp Ile Asn Asn Met Gly Asp Ile Asn Asn
            20                  25                  30

Met Asn Gly Asp Ile Asn Asn Met Asn
        35                  40

<210> SEQ ID NO 33
<211> LENGTH: 781
<212> TYPE: PRT
<213> ORGANISM: Plasmodium falciparum

<400> SEQUENCE: 33

Met Ser Tyr Asn Asp Gly Ser Glu Glu Asn Asp Ser Asn Thr Tyr
1               5                   10                  15

Ile Pro Asp Glu Lys Lys Lys Lys Lys Asn Asn Lys Asn Ala
            20                  25                  30

Tyr Ala Leu Ile Asn Glu Val Asn Tyr Ser Gln Glu Asp Gln Glu
            35                  40                  45

Val Ile His Asn Thr Asn Ser Glu Asp Glu Thr Ser Asn Arg Lys Gly
    50                  55                  60

Asn Gly Cys Val Tyr Ser Leu Ser Asp Gln Asn Val Glu Asp His Ile
65                  70                  75                  80

Ile Ser Leu Pro Glu Tyr Leu Asp Leu Ile Asn Asn Asn Asn Asn
                85                  90                  95

Ser Asn Ser Tyr Lys Met Lys Lys Glu Lys Lys Lys Lys Lys Lys
                100                 105                 110

Lys Lys Asn Gln Thr Asp Glu Glu Asn Met Lys Asn Lys Lys Asp His
            115                 120                 125

Ile Tyr Gln Asn Asn Ile Thr Asn Gln Gln Asn Asp Ile Lys Asn Asp
            130                 135                 140

Tyr Lys Lys Ile Asn His His Asn Met Asn Asn Lys Lys Asn Lys Ile
145                 150                 155                 160

Phe Cys Gln Asp Asp Gln Asn Ile Phe Asn Ile Asn His Thr Phe Gln
                165                 170                 175

Ile His Glu Thr Val Gln Asn Asn Leu Ile Ile Pro Ser Glu Thr
            180                 185                 190

Cys Leu Ala Ser Asp Ile Ile Gln Pro Ser Asp Thr Thr Gln Ser Asn
            195                 200                 205

Thr Tyr Leu Asn Glu Ala Thr Ala Ser Gln Asn Asp Asp Asn Asn
            210                 215                 220

Glu Asp Ser Ser Asn Glu Met Gly Met Phe Lys Lys Ile Phe Tyr Arg
225                 230                 235                 240

Ile Lys Lys Ile Ile Val Asp Lys Lys Gly Thr Pro Ile Thr Asn Glu
                245                 250                 255
```

-continued

```
Asn Asp Val Asp Asn Asp Met Cys Glu Leu Asn Val Met Glu Asn Asn
            260                 265                 270
Met Asn Ile His Ser Asn Asn Asn Ile Ser Thr His Met Asp
        275                 280                 285
Asp Val Ile Glu Asp Glu Ser Asn Glu Val Phe Val Ile Asn Arg
    290                 295                 300
Asn Thr Asp Gly Tyr Ile Asn Thr Arg Glu Asn Ile Asn Val Ser Thr
305                 310                 315                 320
His Val Thr Arg Gln Met Ile Asn Leu Ser Glu Leu Asn Pro Asn Asp
                325                 330                 335
Leu Leu Cys Asn Val Ser Glu Tyr Glu Glu Gly Gln Asn Ile Asn Ser
            340                 345                 350
Leu Trp Asn Asp Asn Asn Asn Asn Asn Asn Asn Asn Asn Phe
        355                 360                 365
Leu Val Gly Ser Leu Asn Ala Leu His Pro Ile Asn His Asn Leu Arg
    370                 375                 380
Asn Glu Asn Ile His Asn Asp Asn Ile Asn Asn Thr His Ile Asn Tyr
385                 390                 395                 400
Asp Asn Asn Asn Ser Tyr Glu Ser Pro Ile His Ile Leu Ser Phe Ser
                405                 410                 415
Phe Lys Asn Ile Tyr Asn Lys Ile Ser Ser Tyr Ile Asn Glu His Ile
            420                 425                 430
Thr His Ile Lys Glu Lys Ile Lys Lys Tyr Trp Leu Glu Arg Val Gln
        435                 440                 445
Glu Ala Asn Thr Gln Leu Asn Ser Pro Arg Pro Val His Thr Arg Asn
    450                 455                 460
Thr Thr Asn Ile Asn Thr Asn Ile Asn Ile Asn Glu Asp Glu Asn Asp
465                 470                 475                 480
Asp Pro Ser Cys Val Gln Ile Leu Phe Phe Met Gly Leu Ile Cys Lys
                485                 490                 495
Phe Pro Ile Leu Trp Ile Ile Gly Ser Ile Val Phe Cys Ile Thr Pro
            500                 505                 510
Ser Glu His Arg Lys Thr Lys Thr Trp Ser Leu Val Asn Thr Phe Phe
        515                 520                 525
Ala Leu Leu Ser Ile Ile Tyr Phe Ile Thr Thr Thr Asn Phe Arg Leu
    530                 535                 540
Arg Lys Pro Thr Phe Phe Val Ile Leu Glu Gln Asn Val Glu Asn Lys
545                 550                 555                 560
Asn Thr Tyr Pro Lys Gly Ile Leu Lys Tyr Asn Asn Met Ile His His
                565                 570                 575
Lys His Ile Ile Ile Asp Gln Ser Ser Leu His Lys Trp Lys Asp Leu
            580                 585                 590
His Thr Asn Lys Val Tyr Lys Thr Ser Glu Asn Tyr Phe Leu Asn Arg
        595                 600                 605
Asn Phe Leu Ser Ser Gln Lys Pro Asp Ser Asn Ile Leu Leu Ser Asp
    610                 615                 620
Thr Ile Tyr Lys Leu Leu Asn Arg Ile Gln Val Thr Val Thr Phe Gly
625                 630                 635                 640
Lys Gly Asn Ile Tyr Ser Ser Asp Asn Ile Glu Lys Ile Lys Pro Phe
                645                 650                 655
Phe Gln Asn Leu Arg Ile Asn Met Asp Pro Ile Ser Tyr Asp Lys Leu
            660                 665                 670
Thr Met Thr Asp Glu Asp Ile Pro Asp Asp Phe Phe Gly Ser Gly Leu
        675                 680                 685
```

```
Arg Cys Glu Arg Thr Tyr Asn Asn His Asn Gln Asn Ile Asn Glu Pro
    690                 695                 700

Gln Gln Asn Lys Glu Lys Gly Lys Trp Tyr Leu Phe Trp Lys Glu Glu
705                 710                 715                 720

Glu Ile Asn Asn Ser His Asn Lys Asn Ile Tyr Asn Ile Ser Ile Pro
                725                 730                 735

Val Gly Glu Ile Phe Phe Phe Lys Ser Glu Tyr Asn Cys Arg Ile Ala
            740                 745                 750

Phe Leu Tyr Pro Lys Ser Ile Leu Tyr Asp Gln Asn Asp Ile Pro Ser
        755                 760                 765

Asn Phe Val Glu Ile Gln Lys Ile Ile Ile Lys Pro Phe
    770                 775                 780

<210> SEQ ID NO 34
<211> LENGTH: 30
<212> TYPE: PRT
<213> ORGANISM: Plasmodium falciparum

<400> SEQUENCE: 34

Met Cys Glu Leu Asn Val Met Glu Asn Met Asn Asn Ile His Ser
1               5                   10                  15

Asn Asn Asn Asn Ile Ser Thr His Met Asp Asp Val Ile Glu
            20                  25                  30

<210> SEQ ID NO 35
<211> LENGTH: 1979
<212> TYPE: PRT
<213> ORGANISM: Plasmodium falciparum

<400> SEQUENCE: 35

Met Val Phe Thr Phe Lys Asn Lys Lys Lys Lys Glu Ala Ser Ser
1               5                   10                  15

Asp Lys Val Ser Lys Glu Ser Phe Asn Glu Asp Asn Glu Asn Asn
            20                  25                  30

Glu Lys Arg Glu Lys Ser Asp Ser Trp Tyr Lys Lys Ile Ile Glu Thr
            35                  40                  45

Lys Gly Lys Ser Lys Thr Lys Tyr Lys Asn Asp Asn Ser Leu Asp Asp
    50                  55                  60

Asn Ile Asn Glu Asp Ile Ile Asn Asn Asn Asn Asn Asn Asn Asn Asp
65                  70                  75                  80

Asn Asn Asn Asp Asn Asn Asp Asn Asn Asp Asn Asn Asn Asp
            85                  90                  95

Asn Asn Asn Asp Asn Asn Asn Glu Asn Asn Asn Asp Asn Asn Asn Phe
            100                 105                 110

Asn Asn Tyr Ser Asp Glu Ile Ser Lys Asn Ile Ile His Lys Asp Asn
        115                 120                 125

Glu Leu Glu Asn Gln Leu Lys Asp Thr Leu Lys Ser Ile Ser Ser Leu
    130                 135                 140

Ser Asn Lys Ile Val Asn Tyr Glu Ser Lys Ile Glu Glu Leu Glu Lys
145                 150                 155                 160

Glu Leu Lys Glu Val Lys Asp Lys Asn Ile Asp Asn Asn Asp Tyr Glu
                165                 170                 175

Asn Lys Leu Lys Glu Lys Glu Asp Phe Val Lys Gln Lys Ile Asp Met
            180                 185                 190

Leu Asn Glu Lys Glu Asn Leu Leu Gln Glu Lys Glu Leu Asp Ile Asn
        195                 200                 205
```

-continued

```
Lys Arg Glu Lys Lys Ile Asn Glu Lys Glu Lys Asn Ile Ile Lys Lys
            210                 215                 220

Glu Glu Thr Phe His Asn Ile Glu Lys Glu Tyr Leu Glu Lys Asn Lys
225                 230                 235                 240

Glu Arg Glu Thr Ile Ser Ile Glu Ile Asp Ile Lys Lys His Leu
                245                 250                 255

Glu Lys Leu Lys Ile Glu Ile Lys Glu Lys Glu Asp Leu Glu Asn
            260                 265                 270

Leu Asn Lys Lys Leu Leu Ser Lys Glu Asn Val Leu Lys Glu Leu Lys
            275                 280                 285

Gly Cys Val Lys Glu Lys Asn Glu Thr Ile Asn Ser Leu Asn Asp Asn
290                 295                 300

Ile Ile Glu Lys Glu Lys Lys Tyr Lys Leu Leu Glu Tyr Glu Leu Glu
305                 310                 315                 320

Glu Lys Asn Lys Gln Ile Asp Leu Leu Asn Lys Gln Glu Lys Glu Lys
                325                 330                 335

Glu Lys Glu Lys Glu Arg Glu Lys Lys Glu Arg Glu Lys Glu Lys
            340                 345                 350

Glu Lys Glu Tyr Asp Thr Leu Ile Lys Glu Leu Lys Asp Glu Lys Ile
            355                 360                 365

Ser Ile Leu Glu Lys Val His Ser Ile Lys Val Arg Glu Met Asp Ile
370                 375                 380

Glu Lys Arg Glu His Asn Phe Leu His Met Glu Asp Gln Leu Lys Asp
385                 390                 395                 400

Leu Lys Asn Ser Phe Val Lys Asn Asn Gln Leu Lys Val Tyr Lys
                405                 410                 415

Cys Glu Ile Lys Asn Leu Lys Thr Glu Leu Lys Lys Glu Lys Glu
            420                 425                 430

Leu Lys Asp Ile Glu Asn Val Ser Lys Glu Ile Asn Lys Leu Ile
            435                 440                 445

Asn Gln Leu Asn Glu Lys Glu Lys Gln Ile Leu Ala Phe Asn Lys Asn
450                 455                 460

His Lys Glu Glu Ile His Gly Leu Lys Glu Glu Leu Lys Glu Ser Val
465                 470                 475                 480

Lys Ile Thr Lys Ile Glu Thr Gln Glu Leu Gln Glu Met Val Asp Ile
                485                 490                 495

Lys Gln Lys Glu Leu Asp Gln Leu Gln Glu Lys Tyr Asn Ala Gln Ile
            500                 505                 510

Glu Ser Ile Ser Ile Glu Leu Ser Lys Lys Glu Lys Tyr Asn Gln
            515                 520                 525

Tyr Lys Asn Thr Tyr Ile Glu Leu Ile Asn Asn Leu Asn Glu Lys Leu
530                 535                 540

Glu Glu Thr Asn Lys Glu Tyr Thr Asn Leu Gln Asn Asn Tyr Thr Asn
545                 550                 555                 560

Glu Ile Asn Met Leu Asn Asn Asp Ile His Met Leu Asn Gly Asn Ile
                565                 570                 575

Lys Thr Met Asn Thr Gln Ile Ser Thr Leu Lys Asn Asp Val His Leu
            580                 585                 590

Leu Asn Glu Gln Ile Asp Lys Leu Asn Asn Lys Gly Thr Leu Asn
            595                 600                 605

Ser Lys Ile Ser Glu Leu Asn Val Gln Ile Met Asp Leu Lys Glu Glu
610                 615                 620

Lys Asp Phe Leu Asn Asn Gln Ile Val Asp Leu Ser Asn Gln Ile Asp
625                 630                 635                 640
```

```
Leu Leu Thr Arg Lys Met Glu Glu Lys Glu Asn Lys Met Leu Glu Gln
            645                 650                 655

Glu Asn Lys Tyr Lys Gln Glu Met Glu Leu Leu Arg Gly Asn Ile Lys
            660                 665                 670

Ser Ser Glu Asn Ile Leu Asn Asn Asp Glu Glu Val Cys Asp Leu Lys
            675                 680                 685

Arg Lys Leu Ser Leu Lys Glu Ser Glu Met Lys Met Met Lys Glu Glu
            690                 695                 700

His Asp Lys Lys Leu Ala Glu Leu Lys Asp Asp Cys Asp Val Arg Ile
705                 710                 715                 720

Arg Glu Met Asn Glu Lys Asn Glu Asp Lys Ile Asn Met Leu Lys Glu
                    725                 730                 735

Glu Tyr Glu Asp Lys Ile Asn Thr Leu Lys Glu Gln Asn Glu Asp Lys
            740                 745                 750

Ile Asn Thr Leu Lys Glu Gln Asn Glu Asp Lys Ile Asn Thr Leu Lys
            755                 760                 765

Glu Glu Tyr Glu His Lys Ile Asn Thr Met Lys Glu Glu Tyr Glu His
            770                 775                 780

Lys Ile Asn Thr Leu Asn Glu Gln Asn Glu His Lys Ile Asn Thr Leu
785                 790                 795                 800

Asn Glu Gln Asn Glu His Lys Ile Asn Thr Met Lys Glu Glu Tyr Glu
                    805                 810                 815

Asp Lys Met Asn Thr Leu Asn Glu Gln Asn Glu Asp Lys Met Asn Ser
            820                 825                 830

Leu Lys Glu Glu Tyr Glu Asn Lys Ile Asn Gln Ile Asn Ser Asn Asn
            835                 840                 845

Glu Ile Lys Ile Lys Asp Val Val Asn Glu Tyr Ile Glu Glu Val Asp
            850                 855                 860

Lys Leu Lys Val Thr Leu Asp Glu Lys Lys Lys Gln Phe Asp Lys Glu
865                 870                 875                 880

Ile Asn Tyr Ala His Ile Lys Ala His Glu Lys Glu Gln Ile Leu Leu
                    885                 890                 895

Thr Glu Met Glu Glu Leu Lys Cys Gln Arg Asp Asn Lys Tyr Ser Asp
            900                 905                 910

Leu Tyr Glu Lys Tyr Ile Lys Leu Ile Lys Ser Ile Cys Met Ile Ile
            915                 920                 925

Asn Ile Glu Cys Cys Asp Asp Ile Glu Asn Glu Asp Ile Ile Arg Arg
930                 935                 940

Ile Glu Glu Tyr Ile Asn Asn Asn Lys Gly Leu Lys Lys Glu Val Glu
945                 950                 955                 960

Glu Lys Glu His Lys Arg His Ser Ser Phe Asn Ile Leu Lys Ser Lys
                    965                 970                 975

Glu Lys Phe Phe Lys Asn Ser Ile Glu Asp Lys Ser His Glu Leu Lys
            980                 985                 990

Lys Lys His Glu Lys Asp Leu Leu  Ser Lys Asp Lys Glu  Ile Glu Glu
            995                 1000                1005

Lys Asn  Lys Lys Ile Lys Glu  Leu Asn Asn Asp Ile  Lys Lys Leu
    1010                1015                1020

Gln Asp  Glu Ile Leu Val Tyr  Lys Lys Gln Ser Asn  Ala Gln Gln
    1025                1030                1035

Val Asp  His Lys Lys Lys Ser  Trp Ile Leu Leu Lys  Asp Lys Ser
    1040                1045                1050

Lys Glu  Lys Ile Lys Asp Lys  Glu Asn Gln Ile Asn  Val Glu Lys
```

-continued

```
            1055                1060                1065

Asn Glu Glu Lys Asp Leu Lys Lys Lys Asp Asp Glu Ile Arg Ile
        1070                1075                1080

Leu Asn Glu Glu Leu Val Lys Tyr Lys Thr Ile Leu Tyr Asn Leu
        1085                1090                1095

Lys Lys Asp Pro Leu Leu Gln Asn Gln Asp Leu Leu Ser Lys Ile
        1100                1105                1110

Asp Ile Asn Ser Leu Thr Ile Asn Glu Gly Met Cys Val Asp Lys
        1115                1120                1125

Ile Glu Glu His Ile Leu Asp Tyr Asp Glu Glu Ile Asn Lys Ser
        1130                1135                1140

Arg Ser Asn Leu Phe Gln Leu Lys Asn Glu Ile Cys Ser Leu Thr
        1145                1150                1155

Thr Glu Val Met Glu Leu Asn Asn Lys Lys Asn Glu Leu Ile Glu
        1160                1165                1170

Glu Asn Asn Lys Leu Asn Leu Val Asp Gln Gly Lys Lys Lys Leu
        1175                1180                1185

Lys Lys Asp Val Glu Lys Gln Lys Lys Glu Ile Glu Lys Leu Asn
        1190                1195                1200

Lys Gln Leu Thr Lys Cys Asn Lys Gln Ile Asp Glu Leu Asn Glu
        1205                1210                1215

Glu Val Glu Lys Leu Asn Asn Glu Asn Ile Glu Leu Ile Thr Tyr
        1220                1225                1230

Ser Asn Asp Leu Asn Asn Lys Phe Asp Met Lys Glu Asn Asn Leu
        1235                1240                1245

Met Met Lys Leu Asp Glu Asn Glu Asp Asn Ile Lys Lys Met Lys
        1250                1255                1260

Ser Lys Ile Asp Asp Met Glu Lys Glu Ile Lys Tyr Arg Glu Asp
        1265                1270                1275

Glu Lys Lys Arg Asn Leu Asn Glu Ile Asn Asn Leu Lys Lys Lys
        1280                1285                1290

Asn Glu Asp Met Cys Ile Lys Tyr Asn Glu Met Asn Ile Lys Tyr
        1295                1300                1305

Gly Asp Ile Cys Val Lys Tyr Glu Glu Met Ser Leu Thr Tyr Lys
        1310                1315                1320

Glu Thr Ser Leu Lys Tyr Glu Gln Ile Lys Val Lys Tyr Asp Glu
        1325                1330                1335

Lys Cys Ser Gln Tyr Asp Glu Ile Arg Phe Gln Tyr Asp Glu Lys
        1340                1345                1350

Cys Phe Gln Tyr Asp Glu Ile Asn Lys Lys Tyr Gly Ala Leu Leu
        1355                1360                1365

Asn Ile Asn Ile Thr Asn Lys Met Val Asp Ser Lys Val Asp Arg
        1370                1375                1380

Asn Asn Asn Glu Ile Ile Ser Val Asp Asn Lys Val Glu Gly Ile
        1385                1390                1395

Ala Asn Tyr Leu Lys Gln Ile Phe Glu Leu Asn Glu Glu Ile Ile
        1400                1405                1410

Arg Leu Lys Gly Glu Ile Asn Lys Ile Ser Leu Leu Tyr Ser Asn
        1415                1420                1425

Glu Leu Asn Glu Lys Asn Ser Tyr Asp Ile Asn Met Lys His Ile
        1430                1435                1440

Gln Glu Gln Leu Leu Phe Leu Glu Lys Thr Asn Lys Glu Asn Glu
        1445                1450                1455
```

-continued

```
Glu Lys Ile Ile Asn Leu Thr Ser Gln Tyr Ser Asp Ala Tyr Lys
    1460                1465                1470

Lys Lys Ser Asp Glu Ser Lys Leu Cys Gly Ala Gln Phe Val Asp
    1475                1480                1485

Asp Val Asn Ile Tyr Gly Asn Ile Ser Asn Asn Asn Ile Arg Thr
    1490                1495                1500

Asn Glu Tyr Lys Tyr Glu Glu Met Phe Asp Thr Asn Ile Glu Glu
    1505                1510                1515

Lys Asn Gly Met His Leu Ser Lys Tyr Ile His Leu Leu Glu Glu
    1520                1525                1530

Asn Lys Phe Arg Cys Met Lys Ile Ile Tyr Glu Asn Glu Asn Ile
    1535                1540                1545

Lys Ser Ser Asn Lys Ile Ile Gly Leu Tyr Asn Tyr Ser Arg Tyr
    1550                1555                1560

Tyr Gly Leu Arg Glu Asp Leu Cys Lys Glu Glu Ile Val Pro Ser
    1565                1570                1575

Lys Ile Gly Asn Ile Ser Asn Lys Asn Glu Asn Asn Asn Lys Lys
    1580                1585                1590

Asn Asn Thr Cys Asp Gly Tyr Asp Glu Lys Val Thr Ile Val Leu
    1595                1600                1605

Cys Ile Ile Leu Asn Glu Ile Ile Lys Phe Leu Phe Leu Asn Asp
    1610                1615                1620

Glu Tyr Val Leu Leu Phe Glu Lys Ile His Lys Asn Val Trp Lys
    1625                1630                1635

Arg Met Tyr Ile Pro Glu Glu Ile Lys Phe Phe Ile Leu Lys Tyr
    1640                1645                1650

Ile Thr Leu Leu Asn Asn Leu Arg Asp Tyr Ile Ile Ser Val His
    1655                1660                1665

Asn Asn Met Lys Asn Glu Lys Tyr Asp Glu Cys Trp Phe Leu Phe
    1670                1675                1680

Gln His Tyr Phe Glu Arg Ser Ser Asp Val Arg Lys Glu Met Val
    1685                1690                1695

His Phe Leu Leu Glu Arg Lys Ser Gln Glu Asn Leu Ile Ser Phe
    1700                1705                1710

Lys Ser Lys Leu Lys Ser Lys Lys Glu Lys Ile Leu Thr Met Asp
    1715                1720                1725

Ile Leu Asn Phe Ser Lys Glu His Met Gln Leu Lys Thr Ile Ala
    1730                1735                1740

His Leu Arg Lys Glu Ile Asn Tyr Glu Lys Leu Ser Lys Asp Thr
    1745                1750                1755

Leu Asn Arg Asp Tyr Asn Leu Leu Leu Tyr Lys Tyr Gln Glu Cys
    1760                1765                1770

Val Ser Lys Leu Lys Arg Val Lys Asn Leu Met Lys Glu Ile Asn
    1775                1780                1785

Gln Asn Val Phe Ile Glu Lys Tyr Asp Asp Ile Ser Lys Glu Leu
    1790                1795                1800

Asp Asn Phe Ser Asp Gly Tyr Asn Glu Gln Asn Glu Gln His Val
    1805                1810                1815

Met Asp Pro Ile Leu Leu Asn Asn Asn Lys Asn Lys Asn Asn Lys
    1820                1825                1830

Leu Ile Thr Glu His Asn Asn Pro Ile Ile Asn Arg Leu Thr Asn
    1835                1840                1845

Phe Thr Gln Asn Arg Asp Ser Lys Tyr Lys Asn Lys Ile Met Asp
    1850                1855                1860
```

```
Asp Val Lys Gln Arg Lys Ile Asn Ser Thr Met Asn Asn Thr Asn
    1865                1870                1875

Lys Asn Gly Ile Asn Ile Ile Tyr Asn His Tyr Glu Asn Leu Asn
    1880                1885                1890

Lys Pro Asn Tyr Asn Asp Asn Ile Asn Arg Leu Asn Ser Tyr His
    1895                1900                1905

Gln Asn Ile His Ile Ala Asn Ser Ile His Pro Asn Arg Asn Gln
    1910                1915                1920

Asn Lys Ser Phe Leu Thr Asn Gln Ala Asn Ser Thr Tyr Ser Val
    1925                1930                1935

Met Lys Asn Tyr Ile Asn Ser Asp Lys Pro Asn Leu Asn Gly Lys
    1940                1945                1950

Lys Ser Val Arg Asn Ile Phe Asn Glu Ile Val Asp Glu Asn Val
    1955                1960                1965

Asn Lys Thr Phe Val His Lys Ser Val Phe Phe
    1970                1975

<210> SEQ ID NO 36
<211> LENGTH: 25
<212> TYPE: PRT
<213> ORGANISM: Plasmodium falciparum

<400> SEQUENCE: 36

Leu Leu Ser Lys Asp Lys Glu Ile Glu Glu Lys Asn Lys Lys Ile Lys
1               5                   10                  15

Glu Leu Asn Asn Asp Ile Lys Lys Leu
            20                  25

<210> SEQ ID NO 37
<211> LENGTH: 964
<212> TYPE: PRT
<213> ORGANISM: Plasmodium falciparum

<400> SEQUENCE: 37

Met Ala Lys Lys Lys Gln Ile His Leu Asn Ile Ile Asp Phe Gln
1               5                   10                  15

Lys Tyr Tyr Gln Thr Asp Asp Leu Leu Leu Asp Thr Ser Ile Ser Thr
                20                  25                  30

Glu Lys Lys Thr Val Asp Asn Gln Lys Phe Ile Arg Lys Asn Arg Thr
                35                  40                  45

Leu Glu Lys Asp Glu Val Val Gln Asn Ile Asp Trp Arg Thr Phe Asp
            50                  55                      60

Asn Glu Lys Glu Lys Glu Thr Asn Asn Glu Asn Thr Ser Asn Val Asn
65                  70                  75                  80

Lys Ile Lys Ser Pro Gly Leu Glu Lys Lys Asn Phe Lys Lys Ser Asn
                85                  90                  95

Asp Val Ile Thr Leu Gly Ala Arg Asn Lys Asn Lys Ser Thr Asn Leu
                100                 105                 110

Asn Ala Asp Asp Ile Asp Phe Thr Asn Leu Arg Asn Lys Lys Lys Glu
            115                 120                 125

Asp Asp Ile Asp Phe Thr Asn Leu Arg Asn Lys Lys Lys Glu Asp Asp
        130                 135                 140

Leu Asp Phe Ser Asn Leu Arg Asn Lys Lys Lys Glu Glu Glu Asp Val
145                 150                 155                 160

Asp Phe Ser Asn Leu Arg Asn Lys Lys Lys Glu Asp Asp Val Asp Phe
                165                 170                 175
```

```
Ser Asn Val Arg Asn Lys Lys Glu Asp Asp Leu Asp Phe Ser Asn
            180                 185                 190
Val Arg Asn Lys Lys Glu Asp Asp Val Asn Phe Ser Asp Val Arg
            195                 200                 205
Asn Lys Lys Lys Glu Asp Asp Leu Asp Phe Ser Asn Val Arg Asn Lys
            210                 215                 220
Lys Lys Glu Asp Asp Val Asn Phe Ser Asp Val Arg Asn Lys Lys
225                 230                 235                 240
Glu Asp Asp Leu Asp Phe Ser Asn Val Arg Asn Lys Lys Glu Asp
                245                 250                 255
Asp Val Asn Phe Ser Asp Val Arg Asn Lys Lys Glu Asp Ala Leu
            260                 265                 270
Asp Phe Ser Asn Val Arg Asn Lys Lys Glu Asp Asp Leu Asp Phe
            275                 280                 285
Ser Asn Val Arg Asn Lys Asn Lys Glu Asp Asp Met Asp Phe Ser Asn
            290                 295                 300
Val Arg Asn Lys Lys Lys Glu Asp Asp Leu Asp Phe Ser Asn Val Arg
305                 310                 315                 320
Asn Lys Lys Lys Glu Asp Asp Leu Asp Phe Ser Asn Val Arg Asn Lys
                325                 330                 335
Lys Lys Glu Asp Asp Leu Asn Phe Ser Asn Val Arg Asn Lys Lys
            340                 345                 350
Glu Asp Asp Leu Asp Phe Ser Asn Val Arg Asn Lys Asn Lys Glu Asp
                355                 360                 365
Asp Met Asp Phe Ser Asn Val Arg Asn Lys Lys Glu Asp Asp Met
            370                 375                 380
Asp Phe Ser Asn Val Arg Asn Lys Lys Lys Glu Asp Asp Leu Asp Phe
385                 390                 395                 400
Ser Asn Val Arg Asn Lys Lys Glu Asp Asp Leu Asp Phe Ser Asn
                405                 410                 415
Val Arg Asn Lys Lys Lys Glu Asp Asp Leu Asp Phe Ser Asn Leu Arg
            420                 425                 430
Asn Lys Lys Lys Glu Glu Ser Lys Glu Asn Asp Thr Asn Lys Ser Glu
                435                 440                 445
Lys Pro Leu Tyr Leu Arg Arg Leu Glu Glu Tyr Arg Lys Lys Lys
450                 455                 460
Leu Glu Ser Gln Ala Asn Asp Thr Ala Met Lys Met His Glu Lys Glu
465                 470                 475                 480
Gln Ile Asp Asp Ile Gln Glu Arg Lys Glu Glu Ile Lys Glu Glu Phe
                485                 490                 495
Lys Glu Glu Val Lys Glu Glu Ile Lys Glu Ile Lys Glu Glu Ile Lys
                500                 505                 510
Glu Val Lys Glu Glu Ile Lys Glu Glu Ile Lys Glu Glu Ile Lys Glu
                515                 520                 525
Val Lys Glu Glu Ile Lys Glu Glu Ile Lys Glu Glu Ile Lys Glu Val
                530                 535                 540
Lys Glu Glu Ile Lys Glu Val Lys Glu Glu Ile Lys Glu Val Lys Glu
545                 550                 555                 560
Glu Ile Lys Glu Val Lys Glu Glu Ile Lys Glu Glu Ile Lys Glu Val
                565                 570                 575
Lys Glu Glu Ile Lys Glu Glu Ile Lys Glu Glu Ile Lys Glu Val Lys
                580                 585                 590
Glu Glu Ile Lys Glu Glu Val Lys Glu Glu Ile Lys Glu Val Lys Glu
                595                 600                 605
```

Glu Ile Lys Glu Val Lys Glu Glu Ile Lys Glu Glu Val Lys Glu Glu
            610                 615                 620

Ile Lys Glu Val Lys Glu Glu Ile Lys Glu Val Lys Glu Glu Ile Lys
625                 630                 635                 640

Glu Glu Ile Lys Glu Val Lys Glu Glu Ile Lys Glu Glu Val Lys Glu
                645                 650                 655

Glu Ile Lys Glu Glu Ile Lys Glu Ile Lys Glu Glu Leu Lys Asn Asp
            660                 665                 670

Ile Ser Ser Glu Thr Thr Lys Glu Glu Lys Asn Thr Glu His Lys Lys
        675                 680                 685

Glu Glu Thr Glu Lys Lys Lys Phe Ile Pro Lys Arg Val Ile Met Tyr
690                 695                 700

Gln Gln Glu Leu Lys Glu Lys Glu Arg Asn Leu Lys Leu Leu Glu
705                 710                 715                 720

Gln Gln Arg Lys Glu Arg Glu Met Arg Leu Gln Leu Ile Arg Ser Lys
                725                 730                 735

Thr Gln Gly Thr Ser Thr Phe Ile Pro Ser Ala Lys Leu Lys His
            740                 745                 750

Leu Glu Ser Leu Lys Glu Lys Lys Lys Glu Val Lys Thr Asn Ile
        755                 760                 765

Gln Pro Lys Asp Asn Asn Asn Asn Asn Asn Asn Asn Asn Asn Asn
770                 775                 780

Asn Asn Ile Ala Val Leu Lys Asn Asn Lys Asn Glu Glu Gln Asn Val
785                 790                 795                 800

Ile Lys Lys Lys Ser Ile Phe Leu Glu Ile Ala Glu Lys Thr Glu Asn
                805                 810                 815

Ala Lys Ile Val Glu Lys Thr Asp Ile Glu Ile Ala Lys Lys Lys
            820                 825                 830

Arg Glu Glu Leu Tyr Lys Lys Gln Leu Glu Lys Ile Thr Lys Lys Asn
        835                 840                 845

Glu Glu His Leu Lys Tyr Asn Asn Ile Tyr Lys His Asp Val Asn Ile
850                 855                 860

Ile Lys Asn Phe Tyr Asn Glu Ile Lys Asp Lys Ile Ile Gln Asn Tyr
865                 870                 875                 880

Tyr Phe Asn Gln Asp Asp Cys Ile Ser Leu Cys Ser Ile Leu Lys Thr
                885                 890                 895

Asp Asp Cys Asn Tyr Met Glu Ser His Val Pro Phe Tyr Val Ile
            900                 905                 910

Ser Ile Phe Met Leu Ser Leu Pro Gln Lys Leu Gln Asn Asp Asp Tyr
        915                 920                 925

Phe Lys Arg Ala Ser Asn Ile Lys Asn Leu Leu Ile Tyr Leu Lys Glu
930                 935                 940

Val Gln Phe Tyr Pro Tyr Lys Val Lys Ile Ser Thr Leu Ile Arg Arg
945                 950                 955                 960

Asn Ile Ile Asn

<210> SEQ ID NO 38
<211> LENGTH: 37
<212> TYPE: PRT
<213> ORGANISM: Plasmodium falciparum

<400> SEQUENCE: 38

Glu Glu Ile Lys Glu Glu Ile Lys Glu Val Lys Glu Glu Ile Lys Glu
1               5                   10                  15

Val Lys Glu Glu Ile Lys Glu Val Lys Glu Ile Lys Glu Val Lys
            20                  25                  30

Glu Glu Ile Lys Glu
        35

<210> SEQ ID NO 39
<211> LENGTH: 213
<212> TYPE: PRT
<213> ORGANISM: Plasmodium falciparum

<400> SEQUENCE: 39

Met Arg His Lys Ile Ser Glu Asn Glu Ile Asn Lys Ile Asp Ser
1               5                   10                  15

Ile Asn Leu Lys Glu Val Lys Asp Ala Ser Ala Cys Met Asn Asn Tyr
            20                  25                  30

Thr Asn Phe Ile Ser Ile Lys Leu Lys Lys Asn Arg Glu Gly Ile Ile
            35                  40                  45

His Ser Ile Gln Arg Ile Lys His Leu Glu Gly Leu Thr Lys Leu Leu
    50                  55                  60

Asn Lys Glu Leu Ser Glu Gly Asn Lys Glu Leu Glu Lys Leu Glu Lys
65                  70                  75                  80

Asn Ile Lys Glu Leu Glu Glu Thr Asn Asn Thr Leu Glu Asn Asp Ile
                85                  90                  95

Lys Val Glu Met Asn Lys Gly Asn Leu Tyr Lys Ser Arg Leu Ala Leu
            100                 105                 110

Leu Lys Lys Asn Lys Val Arg Ile Ser Lys Ala Gln Glu Ile Ile Asp
            115                 120                 125

Lys Asp Ile Ile Tyr Met Lys Ser Arg Ile Asn Ile Met Arg Glu Asn
    130                 135                 140

Ala Asp Lys Asn Asn Gln Lys Tyr Asp Lys Ile Val Ser Gln Lys Asp
145                 150                 155                 160

Lys Met His Gln Glu Met Glu Lys Phe Lys Lys Asp Arg Lys Asn Leu
                165                 170                 175

Gln Leu Asn Leu Lys Asn Thr Arg Lys Asn His Glu Phe Leu Lys Asn
            180                 185                 190

Lys Met Gln Asn Leu Val Leu Thr Met Lys Lys Ser Thr Ala Asp Asp
            195                 200                 205

Lys Arg Phe Gln Tyr
    210

<210> SEQ ID NO 40
<211> LENGTH: 38
<212> TYPE: PRT
<213> ORGANISM: Plasmodium falciparum

<400> SEQUENCE: 40

Thr Lys Lys Leu Asn Lys Glu Leu Ser Glu Gly Asn Lys Glu Leu Glu
1               5                   10                  15

Lys Leu Glu Lys Asn Ile Lys Glu Leu Glu Glu Thr Asn Asn Thr Leu
            20                  25                  30

Glu Asn Asp Ile Lys Val
        35

<210> SEQ ID NO 41
<211> LENGTH: 1979
<212> TYPE: PRT
<213> ORGANISM: Plasmodium falciparum

<400> SEQUENCE: 41

-continued

```
Met Val Phe Thr Phe Lys Asn Lys Lys Lys Lys Glu Ala Ser Ser
1               5                   10                  15

Asp Lys Val Ser Lys Glu Ser Phe Asn Glu Glu Asp Asn Glu Asn Asn
            20                  25                  30

Glu Lys Arg Glu Lys Ser Asp Ser Trp Tyr Lys Lys Ile Ile Glu Thr
            35                  40                  45

Lys Gly Lys Ser Lys Thr Lys Tyr Lys Asn Asp Asn Ser Leu Asp Asp
        50                  55                  60

Asn Ile Asn Glu Asp Ile Ile Asn Asn Asn Asn Asn Asn Asn Asn Asp
65                  70                  75                  80

Asn Asn Asn Asp Asn Asn Asp Asn Asn Asn Asp Asn Asn Asn Asp
                85                  90                  95

Asn Asn Asn Asp Asn Asn Asn Glu Asn Asn Asp Asn Asn Asn Phe
                100                 105                 110

Asn Asn Tyr Ser Asp Glu Ile Ser Lys Asn Ile Ile His Lys Asp Asn
        115                 120                 125

Glu Leu Glu Asn Gln Leu Lys Asp Thr Leu Lys Ser Ile Ser Ser Leu
    130                 135                 140

Ser Asn Lys Ile Val Asn Tyr Glu Ser Lys Ile Glu Glu Leu Glu Lys
145                 150                 155                 160

Glu Leu Lys Glu Val Lys Asp Lys Asn Ile Asp Asn Asn Asp Tyr Glu
                165                 170                 175

Asn Lys Leu Lys Glu Lys Glu Asp Phe Val Lys Gln Lys Ile Asp Met
            180                 185                 190

Leu Asn Glu Lys Glu Asn Leu Leu Gln Glu Lys Glu Leu Asp Ile Asn
        195                 200                 205

Lys Arg Glu Lys Lys Ile Asn Glu Lys Glu Lys Asn Ile Ile Lys Lys
    210                 215                 220

Glu Glu Thr Phe His Asn Ile Glu Lys Glu Tyr Leu Glu Lys Asn Lys
225                 230                 235                 240

Glu Arg Glu Thr Ile Ser Ile Glu Ile Ile Asp Ile Lys Lys His Leu
                245                 250                 255

Glu Lys Leu Lys Ile Glu Ile Lys Glu Lys Lys Glu Asp Leu Glu Asn
            260                 265                 270

Leu Asn Lys Lys Leu Leu Ser Lys Glu Asn Val Leu Lys Glu Leu Lys
        275                 280                 285

Gly Cys Val Lys Glu Lys Asn Glu Thr Ile Asn Ser Leu Asn Asp Asn
    290                 295                 300

Ile Ile Glu Lys Glu Lys Lys Tyr Lys Leu Leu Glu Tyr Glu Leu Glu
305                 310                 315                 320

Glu Lys Asn Lys Gln Ile Asp Leu Leu Asn Lys Gln Glu Lys Glu Lys
                325                 330                 335

Glu Lys Glu Lys Glu Arg Glu Lys Glu Lys Glu Arg Glu Lys Glu Lys
            340                 345                 350

Glu Lys Glu Tyr Asp Thr Leu Ile Lys Glu Leu Lys Asp Glu Lys Ile
        355                 360                 365

Ser Ile Leu Glu Lys Val His Ser Ile Lys Val Arg Glu Met Asp Ile
    370                 375                 380

Glu Lys Arg Glu His Asn Phe Leu His Met Glu Asp Gln Leu Lys Asp
385                 390                 395                 400

Leu Lys Asn Ser Phe Val Lys Asn Asn Gln Leu Lys Val Tyr Lys
                405                 410                 415

Cys Glu Ile Lys Asn Leu Lys Thr Glu Leu Glu Lys Lys Glu Lys Glu
```

```
                420             425              430
Leu Lys Asp Ile Glu Asn Val Ser Lys Glu Ile Asn Lys Leu Ile
            435             440             445
Asn Gln Leu Asn Glu Lys Glu Lys Gln Ile Leu Ala Phe Asn Lys Asn
            450             455             460
His Lys Glu Glu Ile His Gly Leu Lys Glu Glu Leu Lys Glu Ser Val
465             470             475             480
Lys Ile Thr Lys Ile Glu Thr Gln Glu Leu Gln Glu Met Val Asp Ile
            485             490             495
Lys Gln Lys Glu Leu Asp Gln Leu Gln Glu Lys Tyr Asn Ala Gln Ile
            500             505             510
Glu Ser Ile Ser Ile Glu Leu Ser Lys Lys Glu Lys Glu Tyr Asn Gln
            515             520             525
Tyr Lys Asn Thr Tyr Ile Glu Glu Ile Asn Asn Leu Asn Glu Lys Leu
            530             535             540
Glu Glu Thr Asn Lys Glu Tyr Thr Asn Leu Gln Asn Asn Tyr Thr Asn
545             550             555             560
Glu Ile Asn Met Leu Asn Asn Asp Ile His Met Leu Asn Gly Asn Ile
            565             570             575
Lys Thr Met Asn Thr Gln Ile Ser Thr Leu Lys Asn Asp Val His Leu
            580             585             590
Leu Asn Glu Gln Ile Asp Lys Leu Asn Asn Glu Lys Gly Thr Leu Asn
            595             600             605
Ser Lys Ile Ser Glu Leu Asn Val Gln Ile Met Asp Leu Lys Glu Glu
            610             615             620
Lys Asp Phe Leu Asn Asn Gln Ile Val Asp Leu Ser Asn Gln Ile Asp
625             630             635             640
Leu Leu Thr Arg Lys Met Glu Glu Lys Glu Asn Lys Met Leu Glu Gln
            645             650             655
Glu Asn Lys Tyr Lys Gln Glu Met Glu Leu Leu Arg Gly Asn Ile Lys
            660             665             670
Ser Ser Glu Asn Ile Leu Asn Asn Asp Glu Glu Val Cys Asp Leu Lys
            675             680             685
Arg Lys Leu Ser Leu Lys Glu Ser Glu Met Lys Met Met Lys Glu Glu
            690             695             700
His Asp Lys Lys Leu Ala Glu Leu Lys Asp Asp Cys Asp Val Arg Ile
705             710             715             720
Arg Glu Met Asn Glu Lys Asn Glu Asp Lys Ile Asn Met Leu Lys Glu
            725             730             735
Glu Tyr Glu Asp Lys Ile Asn Thr Leu Lys Glu Gln Asn Glu Asp Lys
            740             745             750
Ile Asn Thr Leu Lys Glu Gln Asn Glu Asp Lys Ile Asn Thr Leu Lys
            755             760             765
Glu Glu Tyr Glu His Lys Ile Asn Thr Met Lys Glu Glu Tyr Glu His
            770             775             780
Lys Ile Asn Thr Leu Asn Glu Gln Asn Glu His Lys Ile Asn Thr Leu
785             790             795             800
Asn Glu Gln Asn Glu His Lys Ile Asn Thr Met Lys Glu Glu Tyr Glu
            805             810             815
Asp Lys Met Asn Thr Leu Asn Glu Gln Asn Glu Asp Lys Met Asn Ser
            820             825             830
Leu Lys Glu Glu Tyr Glu Asn Lys Ile Asn Gln Ile Asn Ser Asn Asn
            835             840             845
```

```
Glu Ile Lys Ile Lys Asp Val Val Asn Glu Tyr Ile Glu Val Asp
850                 855                 860
Lys Leu Lys Val Thr Leu Asp Glu Lys Lys Gln Phe Asp Lys Glu
865                 870                 875                 880
Ile Asn Tyr Ala His Ile Lys Ala His Glu Lys Glu Gln Ile Leu Leu
                    885                 890                 895
Thr Glu Met Glu Glu Leu Lys Cys Gln Arg Asp Asn Lys Tyr Ser Asp
                900                 905                 910
Leu Tyr Glu Lys Tyr Ile Lys Leu Ile Lys Ser Ile Cys Met Ile Ile
                915                 920                 925
Asn Ile Glu Cys Cys Asp Ile Glu Asn Glu Asp Ile Ile Arg Arg
930                 935                 940
Ile Glu Glu Tyr Ile Asn Asn Asn Lys Gly Leu Lys Lys Glu Val Glu
945                 950                 955                 960
Glu Lys Glu His Lys Arg His Ser Ser Phe Asn Ile Leu Lys Ser Lys
                965                 970                 975
Glu Lys Phe Phe Lys Asn Ser Ile Glu Asp Lys Ser His Glu Leu Lys
                980                 985                 990
Lys Lys His Glu Lys Asp Leu Leu  Ser Lys Asp Lys Glu  Ile Glu Glu
                995                 1000                1005
Lys Asn  Lys Lys Lys Ile Lys Glu  Leu Asn Asn Asp Ile  Lys Lys Leu
    1010                1015                1020
Gln Asp  Glu Ile Leu Val Tyr  Lys Lys Gln Ser Asn  Ala Gln Gln
    1025                1030                1035
Val Asp  His Lys Lys Lys Ser  Trp Ile Leu Leu Lys  Asp Lys Ser
    1040                1045                1050
Lys Glu  Lys Ile Lys Asp Lys  Glu Asn Gln Ile Asn  Val Glu Lys
    1055                1060                1065
Asn Glu  Glu Lys Asp Leu Lys  Lys Lys Asp Asp Glu  Ile Arg Ile
    1070                1075                1080
Leu Asn  Glu Glu Leu Val Lys  Tyr Lys Thr Ile Leu  Tyr Asn Leu
    1085                1090                1095
Lys Lys  Asp Pro Leu Leu Gln  Asn Gln Asp Leu Leu  Ser Lys Ile
    1100                1105                1110
Asp Ile  Asn Ser Leu Thr Ile  Asn Glu Gly Met Cys  Val Asp Lys
    1115                1120                1125
Ile Glu  Glu His Ile Leu Asp  Tyr Asp Glu Glu Ile  Asn Lys Ser
    1130                1135                1140
Arg Ser  Asn Leu Phe Gln Leu  Lys Asn Glu Ile Cys  Ser Leu Thr
    1145                1150                1155
Thr Glu  Val Met Glu Leu Asn  Asn Lys Lys Asn Glu  Leu Ile Glu
    1160                1165                1170
Glu Asn  Asn Lys Leu Asn Leu  Val Asp Gln Gly Lys  Lys Lys Leu
    1175                1180                1185
Lys Lys  Asp Val Glu Lys Gln  Lys Lys Glu Ile Glu  Lys Leu Asn
    1190                1195                1200
Lys Gln  Leu Thr Lys Cys Asn  Lys Gln Ile Asp Glu  Leu Asn Glu
    1205                1210                1215
Glu Val  Glu Lys Leu Asn Asn  Glu Asn Ile Glu Leu  Ile Thr Tyr
    1220                1225                1230
Ser Asn  Asp Leu Asn Asn Lys  Phe Asp Met Lys Glu  Asn Asn Leu
    1235                1240                1245
Met Met  Lys Leu Asp Glu Asn  Glu Asp Asn Ile Lys  Lys Met Lys
    1250                1255                1260
```

```
Ser Lys Ile Asp Asp Met Glu Lys Glu Ile Lys Tyr Arg Glu Asp
    1265                 1270                1275
Glu Lys Lys Arg Asn Leu Asn Glu Ile Asn Asn Leu Lys Lys Lys
    1280                 1285                1290
Asn Glu Asp Met Cys Ile Lys Tyr Asn Glu Met Asn Ile Lys Tyr
    1295                 1300                1305
Gly Asp Ile Cys Val Lys Tyr Glu Glu Met Ser Leu Thr Tyr Lys
    1310                 1315                1320
Glu Thr Ser Leu Lys Tyr Glu Gln Ile Lys Val Lys Tyr Asp Glu
    1325                 1330                1335
Lys Cys Ser Gln Tyr Asp Glu Ile Arg Phe Gln Tyr Asp Glu Lys
    1340                 1345                1350
Cys Phe Gln Tyr Asp Glu Ile Asn Lys Lys Tyr Gly Ala Leu Leu
    1355                 1360                1365
Asn Ile Asn Ile Thr Asn Lys Met Val Asp Ser Lys Val Asp Arg
    1370                 1375                1380
Asn Asn Asn Glu Ile Ile Ser Val Asp Asn Lys Val Glu Gly Ile
    1385                 1390                1395
Ala Asn Tyr Leu Lys Gln Ile Phe Glu Leu Asn Glu Glu Ile Ile
    1400                 1405                1410
Arg Leu Lys Gly Glu Ile Asn Lys Ile Ser Leu Leu Tyr Ser Asn
    1415                 1420                1425
Glu Leu Asn Glu Lys Asn Ser Tyr Asp Ile Asn Met Lys His Ile
    1430                 1435                1440
Gln Glu Gln Leu Leu Phe Leu Glu Lys Thr Asn Lys Glu Asn Glu
    1445                 1450                1455
Glu Lys Ile Ile Asn Leu Thr Ser Gln Tyr Ser Asp Ala Tyr Lys
    1460                 1465                1470
Lys Lys Ser Asp Glu Ser Lys Leu Cys Gly Ala Gln Phe Val Asp
    1475                 1480                1485
Asp Val Asn Ile Tyr Gly Asn Ile Ser Asn Asn Asn Ile Arg Thr
    1490                 1495                1500
Asn Glu Tyr Lys Tyr Glu Glu Met Phe Asp Thr Asn Ile Glu Glu
    1505                 1510                1515
Lys Asn Gly Met His Leu Ser Lys Tyr Ile His Leu Leu Glu Glu
    1520                 1525                1530
Asn Lys Phe Arg Cys Met Lys Ile Ile Tyr Glu Asn Glu Asn Ile
    1535                 1540                1545
Lys Ser Ser Asn Lys Ile Ile Gly Leu Tyr Asn Tyr Ser Arg Tyr
    1550                 1555                1560
Tyr Gly Leu Arg Glu Asp Leu Cys Lys Glu Glu Ile Val Pro Ser
    1565                 1570                1575
Lys Ile Gly Asn Ile Ser Asn Lys Asn Glu Asn Asn Lys Lys
    1580                 1585                1590
Asn Asn Thr Cys Asp Gly Tyr Asp Glu Lys Val Thr Ile Val Leu
    1595                 1600                1605
Cys Ile Ile Leu Asn Glu Ile Ile Lys Phe Leu Phe Leu Asn Asp
    1610                 1615                1620
Glu Tyr Val Leu Leu Phe Glu Lys Ile His Lys Asn Val Trp Lys
    1625                 1630                1635
Arg Met Tyr Ile Pro Glu Glu Ile Lys Phe Phe Ile Leu Lys Tyr
    1640                 1645                1650
Ile Thr Leu Leu Asn Asn Leu Arg Asp Tyr Ile Ile Ser Val His
```

-continued

```
            1655                1660                1665

Asn Asn Met Lys Asn Glu Lys Tyr Asp Glu Cys Trp Phe Leu Phe
            1670                1675                1680

Gln His Tyr Phe Glu Arg Ser Ser Asp Val Arg Lys Glu Met Val
            1685                1690                1695

His Phe Leu Leu Glu Arg Lys Ser Gln Glu Asn Leu Ile Ser Phe
            1700                1705                1710

Lys Ser Lys Leu Lys Ser Lys Lys Glu Lys Ile Leu Thr Met Asp
            1715                1720                1725

Ile Leu Asn Phe Ser Lys Glu His Met Gln Leu Lys Thr Ile Ala
            1730                1735                1740

His Leu Arg Lys Glu Ile Asn Tyr Glu Lys Leu Ser Lys Asp Thr
            1745                1750                1755

Leu Asn Arg Asp Tyr Asn Leu Leu Leu Tyr Lys Tyr Gln Glu Cys
            1760                1765                1770

Val Ser Lys Leu Lys Arg Val Lys Asn Leu Met Lys Glu Ile Asn
            1775                1780                1785

Gln Asn Val Phe Ile Glu Lys Tyr Asp Asp Ile Ser Lys Glu Leu
            1790                1795                1800

Asp Asn Phe Ser Asp Gly Tyr Asn Glu Gln Asn Glu Gln His Val
            1805                1810                1815

Met Asp Pro Ile Leu Leu Asn Asn Asn Lys Asn Lys Asn Asn Lys
            1820                1825                1830

Leu Ile Thr Glu His Asn Asn Pro Ile Ile Asn Arg Leu Thr Asn
            1835                1840                1845

Phe Thr Gln Asn Arg Asp Ser Lys Tyr Lys Asn Lys Ile Met Asp
            1850                1855                1860

Asp Val Lys Gln Arg Lys Ile Asn Ser Thr Met Asn Asn Thr Asn
            1865                1870                1875

Lys Asn Gly Ile Asn Ile Ile Tyr Asn His Tyr Glu Asn Leu Asn
            1880                1885                1890

Lys Pro Asn Tyr Asn Asp Asn Ile Asn Arg Leu Asn Ser Tyr His
            1895                1900                1905

Gln Asn Ile His Ile Ala Asn Ser Ile His Pro Asn Arg Asn Gln
            1910                1915                1920

Asn Lys Ser Phe Leu Thr Asn Gln Ala Asn Ser Thr Tyr Ser Val
            1925                1930                1935

Met Lys Asn Tyr Ile Asn Ser Asp Lys Pro Asn Leu Asn Gly Lys
            1940                1945                1950

Lys Ser Val Arg Asn Ile Phe Asn Glu Ile Val Asp Glu Asn Val
            1955                1960                1965

Asn Lys Thr Phe Val His Lys Ser Val Phe Phe
            1970                1975

<210> SEQ ID NO 42
<211> LENGTH: 77
<212> TYPE: PRT
<213> ORGANISM: Plasmodium falciparum

<400> SEQUENCE: 42

Val Asp Lys Ile Glu Glu His Ile Leu Asp Tyr Asp Glu Glu Ile Asn
1               5                   10                  15

Lys Ser Arg Ser Asn Leu Phe Gln Leu Lys Asn Glu Ile Cys Ser Leu
            20                  25                  30

Thr Thr Glu Val Met Glu Leu Asn Asn Lys Lys Asn Glu Leu Ile Glu
```

```
                35                  40                  45
Glu Asn Asn Lys Leu Asn Leu Val Asp Gln Gly Lys Lys Leu Lys
 50                  55                  60
Lys Asp Val Glu Lys Gln Lys Lys Glu Ile Glu Lys Leu
 65                  70                  75

<210> SEQ ID NO 43
<211> LENGTH: 1979
<212> TYPE: PRT
<213> ORGANISM: Plasmodium falciparum

<400> SEQUENCE: 43

Met Val Phe Thr Phe Lys Asn Lys Lys Lys Lys Glu Ala Ser Ser
 1               5                  10                  15

Asp Lys Val Ser Lys Glu Ser Phe Asn Glu Glu Asp Asn Glu Asn
                20                  25                  30

Glu Lys Arg Glu Lys Ser Asp Ser Trp Tyr Lys Lys Ile Ile Glu Thr
                35                  40                  45

Lys Gly Lys Ser Lys Thr Lys Tyr Lys Asn Asp Asn Ser Leu Asp Asp
 50                  55                  60

Asn Ile Asn Glu Asp Ile Ile Asn Asn Asn Asn Asn Asn Asn Asp
 65                  70                  75                  80

Asn Asn Asn Asp Asn Asn Asn Asp Asn Asn Asp Asn Asn Asn Asp
                85                  90                  95

Asn Asn Asn Asp Asn Asn Asn Glu Asn Asn Asp Asn Asn Asn Phe
                100                 105                 110

Asn Asn Tyr Ser Asp Glu Ile Ser Lys Asn Ile Ile His Lys Asp Asn
                115                 120                 125

Glu Leu Glu Asn Gln Leu Lys Asp Thr Leu Lys Ser Ile Ser Ser Leu
                130                 135                 140

Ser Asn Lys Ile Val Asn Tyr Glu Ser Lys Ile Glu Glu Leu Glu Lys
145                 150                 155                 160

Glu Leu Lys Glu Val Lys Asp Lys Asn Ile Asp Asn Asn Asp Tyr Glu
                165                 170                 175

Asn Lys Leu Lys Glu Lys Glu Asp Phe Val Lys Gln Lys Ile Asp Met
                180                 185                 190

Leu Asn Glu Lys Glu Asn Leu Leu Gln Glu Lys Glu Leu Asp Ile Asn
                195                 200                 205

Lys Arg Glu Lys Lys Ile Asn Glu Lys Glu Lys Asn Ile Ile Lys Lys
                210                 215                 220

Glu Glu Thr Phe His Asn Ile Glu Lys Glu Tyr Leu Glu Lys Asn Lys
225                 230                 235                 240

Glu Arg Glu Thr Ile Ser Ile Glu Ile Ile Asp Ile Lys Lys His Leu
                245                 250                 255

Glu Lys Leu Lys Ile Glu Ile Lys Glu Lys Lys Glu Asp Leu Glu Asn
                260                 265                 270

Leu Asn Lys Lys Leu Leu Ser Lys Glu Asn Val Leu Lys Glu Leu Lys
                275                 280                 285

Gly Cys Val Lys Glu Lys Asn Glu Thr Ile Asn Ser Leu Asn Asp Asn
                290                 295                 300

Ile Ile Glu Lys Glu Lys Lys Tyr Lys Leu Leu Glu Tyr Glu Leu Glu
305                 310                 315                 320

Glu Lys Asn Lys Gln Ile Asp Leu Leu Asn Lys Gln Glu Lys Glu Lys
                325                 330                 335

Glu Lys Glu Lys Glu Arg Glu Lys Glu Lys Glu Arg Glu Lys Glu Lys
```

```
                340                 345                 350
Glu Lys Glu Tyr Asp Thr Leu Ile Lys Glu Leu Lys Asp Glu Lys Ile
            355                 360                 365
Ser Ile Leu Glu Lys Val His Ser Ile Lys Val Arg Glu Met Asp Ile
        370                 375                 380
Glu Lys Arg Glu His Asn Phe Leu His Met Glu Asp Gln Leu Lys Asp
385                 390                 395                 400
Leu Lys Asn Ser Phe Val Lys Asn Asn Gln Leu Lys Val Tyr Lys
                405                 410                 415
Cys Glu Ile Lys Asn Leu Lys Thr Glu Leu Lys Lys Glu Lys Glu
            420                 425                 430
Leu Lys Asp Ile Glu Asn Val Ser Lys Glu Ile Asn Lys Leu Ile
        435                 440                 445
Asn Gln Leu Asn Glu Lys Glu Lys Gln Ile Leu Ala Phe Asn Lys Asn
    450                 455                 460
His Lys Glu Glu Ile His Gly Leu Lys Glu Glu Leu Lys Glu Ser Val
465                 470                 475                 480
Lys Ile Thr Lys Ile Glu Thr Gln Glu Leu Gln Glu Met Val Asp Ile
                485                 490                 495
Lys Gln Lys Glu Leu Asp Gln Leu Gln Glu Lys Tyr Asn Ala Gln Ile
            500                 505                 510
Glu Ser Ile Ser Ile Glu Leu Ser Lys Lys Glu Lys Glu Tyr Asn Gln
        515                 520                 525
Tyr Lys Asn Thr Tyr Ile Glu Glu Ile Asn Asn Leu Asn Glu Lys Leu
    530                 535                 540
Glu Glu Thr Asn Lys Glu Tyr Thr Asn Leu Gln Asn Asn Tyr Thr Asn
545                 550                 555                 560
Glu Ile Asn Met Leu Asn Asn Asp Ile His Met Leu Asn Gly Asn Ile
                565                 570                 575
Lys Thr Met Asn Thr Gln Ile Ser Thr Leu Lys Asn Asp Val His Leu
            580                 585                 590
Leu Asn Glu Gln Ile Asp Lys Leu Asn Asn Glu Lys Gly Thr Leu Asn
        595                 600                 605
Ser Lys Ile Ser Glu Leu Asn Val Gln Ile Met Asp Leu Lys Glu Glu
    610                 615                 620
Lys Asp Phe Leu Asn Asn Gln Ile Val Asp Leu Ser Asn Gln Ile Asp
625                 630                 635                 640
Leu Leu Thr Arg Lys Met Glu Glu Lys Glu Asn Lys Met Leu Glu Gln
                645                 650                 655
Glu Asn Lys Tyr Lys Gln Glu Met Glu Leu Leu Arg Gly Asn Ile Lys
            660                 665                 670
Ser Ser Glu Asn Ile Leu Asn Asn Asp Glu Glu Val Cys Asp Leu Lys
        675                 680                 685
Arg Lys Leu Ser Leu Lys Glu Ser Glu Met Lys Met Met Lys Glu Glu
    690                 695                 700
His Asp Lys Lys Leu Ala Glu Leu Lys Asp Asp Cys Asp Val Arg Ile
705                 710                 715                 720
Arg Glu Met Asn Glu Lys Asn Glu Asp Lys Ile Asn Met Leu Lys Glu
                725                 730                 735
Glu Tyr Glu Asp Lys Ile Asn Thr Leu Lys Glu Gln Asn Glu Asp Lys
            740                 745                 750
Ile Asn Thr Leu Lys Glu Gln Asn Glu Asp Lys Ile Asn Thr Leu Lys
        755                 760                 765
```

-continued

Glu Glu Tyr Glu His Lys Ile Asn Thr Met Lys Glu Glu Tyr Glu His
770                 775                 780

Lys Ile Asn Thr Leu Asn Glu Gln Asn Glu His Lys Ile Asn Thr Leu
785                 790                 795                 800

Asn Glu Gln Asn Glu His Lys Ile Asn Thr Met Lys Glu Glu Tyr Glu
            805                 810                 815

Asp Lys Met Asn Thr Leu Asn Glu Gln Asn Glu Asp Lys Met Asn Ser
        820                 825                 830

Leu Lys Glu Glu Tyr Glu Asn Lys Ile Asn Gln Ile Asn Ser Asn Asn
            835                 840                 845

Glu Ile Lys Ile Lys Asp Val Val Asn Glu Tyr Ile Glu Glu Val Asp
        850                 855                 860

Lys Leu Lys Val Thr Leu Asp Glu Lys Lys Gln Phe Asp Lys Glu
865                 870                 875                 880

Ile Asn Tyr Ala His Ile Lys Ala His Glu Lys Glu Gln Ile Leu Leu
                885                 890                 895

Thr Glu Met Glu Glu Leu Lys Cys Gln Arg Asp Asn Lys Tyr Ser Asp
            900                 905                 910

Leu Tyr Glu Lys Tyr Ile Lys Leu Ile Lys Ser Ile Cys Met Ile Ile
        915                 920                 925

Asn Ile Glu Cys Cys Asp Asp Ile Glu Asn Glu Asp Ile Ile Arg Arg
930                 935                 940

Ile Glu Glu Tyr Ile Asn Asn Asn Lys Gly Leu Lys Lys Glu Val Glu
945                 950                 955                 960

Glu Lys Glu His Lys Arg His Ser Ser Phe Asn Ile Leu Lys Ser Lys
            965                 970                 975

Glu Lys Phe Phe Lys Asn Ser Ile Glu Asp Lys Ser His Glu Leu Lys
        980                 985                 990

Lys Lys His Glu Lys Asp Leu Leu Ser Lys Asp Lys Glu Ile Glu Glu
            995                 1000                1005

Lys Asn Lys Lys Ile Lys Glu Leu Asn Asn Asp Ile Lys Lys Leu
        1010                1015                1020

Gln Asp Glu Ile Leu Val Tyr Lys Lys Gln Ser Asn Ala Gln Gln
        1025                1030                1035

Val Asp His Lys Lys Lys Ser Trp Ile Leu Leu Lys Asp Lys Ser
        1040                1045                1050

Lys Glu Lys Ile Lys Asp Lys Glu Asn Gln Ile Asn Val Glu Lys
        1055                1060                1065

Asn Glu Glu Lys Asp Leu Lys Lys Lys Asp Asp Glu Ile Arg Ile
        1070                1075                1080

Leu Asn Glu Glu Leu Val Lys Tyr Lys Thr Ile Leu Tyr Asn Leu
        1085                1090                1095

Lys Lys Asp Pro Leu Leu Gln Asn Gln Asp Leu Leu Ser Lys Ile
        1100                1105                1110

Asp Ile Asn Ser Leu Thr Ile Asn Glu Gly Met Cys Val Asp Lys
        1115                1120                1125

Ile Glu Glu His Ile Leu Asp Tyr Asp Glu Glu Ile Asn Lys Ser
        1130                1135                1140

Arg Ser Asn Leu Phe Gln Leu Lys Asn Glu Ile Cys Ser Leu Thr
        1145                1150                1155

Thr Glu Val Met Glu Leu Asn Lys Lys Asn Glu Leu Ile Glu
        1160                1165                1170

Glu Asn Asn Lys Leu Asn Leu Val Asp Gln Gly Lys Lys Lys Leu
        1175                1180                1185

-continued

| | | | | | | | | | | |
|---|---|---|---|---|---|---|---|---|---|---|
| Lys | Lys | Asp | Val | Glu | Lys | Gln | Lys | Lys | Glu | Ile | Glu | Lys | Leu | Asn |
| | 1190 | | | | 1195 | | | | 1200 | |

Lys Gln Leu Thr Lys Cys Asn Lys Gln Ile Asp Glu Leu Asn Glu
    1205                1210                1215

Glu Val Glu Lys Leu Asn Asn Glu Asn Ile Glu Leu Ile Thr Tyr
    1220                1225                1230

Ser Asn Asp Leu Asn Asn Lys Phe Asp Met Lys Glu Asn Asn Leu
    1235                1240                1245

Met Met Lys Leu Asp Glu Asn Glu Asp Asn Ile Lys Lys Met Lys
    1250                1255                1260

Ser Lys Ile Asp Asp Met Glu Lys Ile Lys Tyr Arg Glu Asp
    1265                1270                1275

Glu Lys Lys Arg Asn Leu Asn Glu Ile Asn Asn Leu Lys Lys Lys
    1280                1285                1290

Asn Glu Asp Met Cys Ile Lys Tyr Asn Glu Met Asn Ile Lys Tyr
    1295                1300                1305

Gly Asp Ile Cys Val Lys Tyr Glu Glu Met Ser Leu Thr Tyr Lys
    1310                1315                1320

Glu Thr Ser Leu Lys Tyr Glu Gln Ile Lys Val Lys Tyr Asp Glu
    1325                1330                1335

Lys Cys Ser Gln Tyr Asp Glu Ile Arg Phe Gln Tyr Asp Glu Lys
    1340                1345                1350

Cys Phe Gln Tyr Asp Glu Ile Asn Lys Lys Tyr Gly Ala Leu Leu
    1355                1360                1365

Asn Ile Asn Ile Thr Asn Lys Met Val Asp Ser Lys Val Asp Arg
    1370                1375                1380

Asn Asn Asn Glu Ile Ile Ser Val Asp Asn Lys Val Glu Gly Ile
    1385                1390                1395

Ala Asn Tyr Leu Lys Gln Ile Phe Glu Leu Asn Glu Glu Ile Ile
    1400                1405                1410

Arg Leu Lys Gly Glu Ile Asn Lys Ile Ser Leu Leu Tyr Ser Asn
    1415                1420                1425

Glu Leu Asn Glu Lys Asn Ser Tyr Asp Ile Asn Met Lys His Ile
    1430                1435                1440

Gln Glu Gln Leu Leu Phe Leu Glu Lys Thr Asn Lys Glu Asn Glu
    1445                1450                1455

Glu Lys Ile Ile Asn Leu Thr Ser Gln Tyr Ser Asp Ala Tyr Lys
    1460                1465                1470

Lys Lys Ser Asp Glu Ser Lys Leu Cys Gly Ala Gln Phe Val Asp
    1475                1480                1485

Asp Val Asn Ile Tyr Gly Asn Ile Ser Asn Asn Asn Ile Arg Thr
    1490                1495                1500

Asn Glu Tyr Lys Tyr Glu Glu Met Phe Asp Thr Asn Ile Glu Glu
    1505                1510                1515

Lys Asn Gly Met His Leu Ser Lys Tyr Ile His Leu Leu Glu Glu
    1520                1525                1530

Asn Lys Phe Arg Cys Met Lys Ile Ile Tyr Glu Asn Glu Asn Ile
    1535                1540                1545

Lys Ser Ser Asn Lys Ile Ile Gly Leu Tyr Asn Tyr Ser Arg Tyr
    1550                1555                1560

Tyr Gly Leu Arg Glu Asp Leu Cys Lys Glu Glu Ile Val Pro Ser
    1565                1570                1575

Lys Ile Gly Asn Ile Ser Asn Lys Asn Glu Asn Asn Asn Lys Lys

```
                    1580            1585            1590

Asn Asn Thr Cys Asp Gly Tyr Asp Glu Lys Val Thr Ile Val Leu
    1595            1600            1605

Cys Ile Ile Leu Asn Glu Ile Ile Lys Phe Leu Phe Leu Asn Asp
    1610            1615            1620

Glu Tyr Val Leu Leu Phe Glu Lys Ile His Lys Asn Val Trp Lys
    1625            1630            1635

Arg Met Tyr Ile Pro Glu Glu Ile Lys Phe Phe Ile Leu Lys Tyr
    1640            1645            1650

Ile Thr Leu Leu Asn Asn Leu Arg Asp Tyr Ile Ile Ser Val His
    1655            1660            1665

Asn Asn Met Lys Asn Glu Lys Tyr Asp Glu Cys Trp Phe Leu Phe
    1670            1675            1680

Gln His Tyr Phe Glu Arg Ser Ser Asp Val Arg Lys Glu Met Val
    1685            1690            1695

His Phe Leu Leu Glu Arg Lys Ser Gln Glu Asn Leu Ile Ser Phe
    1700            1705            1710

Lys Ser Lys Leu Lys Ser Lys Lys Glu Lys Ile Leu Thr Met Asp
    1715            1720            1725

Ile Leu Asn Phe Ser Lys Glu His Met Gln Leu Lys Thr Ile Ala
    1730            1735            1740

His Leu Arg Lys Glu Ile Asn Tyr Glu Lys Leu Ser Lys Asp Thr
    1745            1750            1755

Leu Asn Arg Asp Tyr Asn Leu Leu Leu Tyr Lys Tyr Gln Glu Cys
    1760            1765            1770

Val Ser Lys Leu Lys Arg Val Lys Asn Leu Met Lys Glu Ile Asn
    1775            1780            1785

Gln Asn Val Phe Ile Glu Lys Tyr Asp Asp Ile Ser Lys Glu Leu
    1790            1795            1800

Asp Asn Phe Ser Asp Gly Tyr Asn Glu Gln Asn Glu Gln His Val
    1805            1810            1815

Met Asp Pro Ile Leu Leu Asn Asn Asn Lys Asn Lys Asn Asn Lys
    1820            1825            1830

Leu Ile Thr Glu His Asn Asn Pro Ile Ile Asn Arg Leu Thr Asn
    1835            1840            1845

Phe Thr Gln Asn Arg Asp Ser Lys Tyr Lys Asn Lys Ile Met Asp
    1850            1855            1860

Asp Val Lys Gln Arg Lys Ile Asn Ser Thr Met Asn Asn Thr Asn
    1865            1870            1875

Lys Asn Gly Ile Asn Ile Ile Tyr Asn His Tyr Glu Asn Leu Asn
    1880            1885            1890

Lys Pro Asn Tyr Asn Asp Asn Ile Asn Arg Leu Asn Ser Tyr His
    1895            1900            1905

Gln Asn Ile His Ile Ala Asn Ser Ile His Pro Asn Arg Asn Gln
    1910            1915            1920

Asn Lys Ser Phe Leu Thr Asn Gln Ala Asn Ser Thr Tyr Ser Val
    1925            1930            1935

Met Lys Asn Tyr Ile Asn Ser Asp Lys Pro Asn Leu Asn Gly Lys
    1940            1945            1950

Lys Ser Val Arg Asn Ile Phe Asn Glu Ile Val Asp Glu Asn Val
    1955            1960            1965

Asn Lys Thr Phe Val His Lys Ser Val Phe Phe
    1970            1975
```

```
<210> SEQ ID NO 44
<211> LENGTH: 46
<212> TYPE: PRT
<213> ORGANISM: Plasmodium falciparum

<400> SEQUENCE: 44

Ile Lys Thr Met Asn Thr Gln Ile Ser Thr Leu Lys Asn Asp Val His
1               5                   10                  15

Leu Leu Asn Glu Gln Ile Asp Lys Leu Asn Asn Glu Lys Gly Thr Leu
                20                  25                  30

Asn Ser Lys Ile Ser Glu Leu Asn Val Gln Ile Met Asp Leu
            35                  40                  45

<210> SEQ ID NO 45
<211> LENGTH: 1792
<212> TYPE: PRT
<213> ORGANISM: Plasmodium falciparum

<400> SEQUENCE: 45

Met Asn Asn Asn Asn Asn Asn Asn Ser Asn Asn Asn Asn
1               5                   10                  15

Ser Asn Asn Asn Asn Gly Asn Ser Asn Asn Asn Phe Phe Ser Gly
                20                  25                  30

Lys Gly Asn Ala Leu Ser Ala Tyr Gln Asn Lys Ile Leu Asn Ile Lys
            35                  40                  45

Ser Asn Asn Asn Asn Ala His His Phe Val Asn Lys Asn Val Pro Thr
        50                  55                  60

Tyr Ser Pro Pro Asn Ile Ile Met Ala Asn Lys Lys Gly Gly Asn Phe
65                  70                  75                  80

Asn Asn Thr Ser Gly Asn Ile Ile Asn Arg Tyr Asn Val Glu Asn Asn
                85                  90                  95

Asn His Arg Asn Thr Tyr His Pro Ser Asn Asn Thr Arg Asn Ser
            100                 105                 110

Val Asn Phe Leu Asn Lys Asn Ile Leu Tyr Gly Asn Asn Asn Asn
        115                 120                 125

Asn Asn Asn Asn Asn Ile Asn Ile Thr Asn Ile Ser Asn Asn Asn
    130                 135                 140

Asn Asn Ile Asn Ile Thr Asn Ile Ser Asn Asn Asn Asn Ile Asn
145                 150                 155                 160

Ile Thr Asn Ile Ser Asn Asn Lys Gln Pro Ile Ser Ser Asn Gln
                165                 170                 175

His Pro Tyr Gln Gln Lys Gln Ser His His Asn Asn Ser Ile Asn
            180                 185                 190

Tyr Asn Glu Tyr Met Asp Glu Lys Asn Met Asn Thr Ser Gln Ser Ile
        195                 200                 205

Phe Lys Asn Met Thr Ile Gln Arg Asn Ser Gln Gln Phe Asn Thr Ser
    210                 215                 220

Asp Phe Val Asn Asn Ile Asn Ile Met Asn Ala Pro His Ile Asn Glu
225                 230                 235                 240

His Ser Asn Ile Tyr Lys Arg Asn Ser Leu Asn Ile Val Asn Asn Ala
                245                 250                 255

His Ile Ile Ser Asn Asn Met Asn Ile Gln Ser Asn Arg Asn Ser Asn
            260                 265                 270

Ile Ser Phe Pro Gln Asn Met Asn Ala Asn Ile Gly Gly Leu Lys Asn
        275                 280                 285

Ser Asn His Asn Leu Asn Asn Ile Glu Met Lys Tyr Asn Thr Leu Asn
```

```
                290              295              300
Asn Asn Met Asn Ser Ile Asn Lys Asn Thr Asn Ile Thr Asn Val Gly
305              310              315              320

Thr Leu Asn Ile Gln Met Lys Asn Asn Pro Met Asn Val Asn Ile Asn
                325              330              335

Gln Asn Asn Tyr Asn Thr Asp Phe Tyr Val Asn Glu Asn Lys Val Asn
                340              345              350

Ser Lys Asn Lys Glu Asn Asn Asn His Ile Asn Ile Glu Lys Met
                355              360              365

Asn Tyr Ile Lys Ser Asn Val Tyr Leu Asp Asn Thr Leu Val Gln Val
370              375              380

Asn Ser Asn Asn Asn Tyr Asn Met Asp Lys Asn Ile Leu Asn Asn
385              390              395              400

Asn Asn Thr Tyr Ile Ile Asn Asp Lys Lys Asn Ser Thr Val Asn Asn
                405              410              415

Asn Ile Thr Asn Met Asp Asn Asn Leu Val Pro Gly Val Met Ser Ser
                420              425              430

Met Asn Ile Pro Asp Asp Ile Lys Lys Arg Lys Lys Glu Arg Lys
                435              440              445

Lys Asn Glu Asn Ile Tyr Asn Asn Arg Asn Lys Ser Ser Ile Asn Thr
450              455              460

Glu Glu His Asn Asn Asn Ile Ile Asp Val Ala Asn Gln Asn Ser Glu
465              470              475              480

His Phe Leu Gln Asn Asn Lys Gln Tyr Gly Asn Ile Thr Asn Ile Gln
                485              490              495

Asn Asn Asn Leu Ser His Asp Met Asn Asn Tyr Ser Ile Asn Asn Ser
                500              505              510

Thr Thr Ser Asp Val Ile Gly Ile Val Glu Leu Tyr Lys Asn Ser Leu
                515              520              525

Ser Ser Lys Ala Val Asn Lys Lys Ser Lys Leu Ile Lys Asp Val
                530              535              540

Ile Asp Asp Asn Lys Lys Arg Asn Lys Lys Glu Lys Lys Lys Thr Ile
545              550              555              560

Pro Asn Asn Asp Ser Ile Ile Asn Asp Met Asn Lys Asn Lys Asn Val
                565              570              575

Glu Leu Leu Asn Glu Thr Gln Ile Phe Asp Asn Lys Asn Tyr Asp Lys
                580              585              590

Asn Asn Asp Ile His Asn Asn Ile Tyr Asn Ser Asn Asp Asn Asn Leu
                595              600              605

Ile His Asn Lys Asn Asn Val Asn Asn Asp His Thr Asn Ile Lys Glu
                610              615              620

Ala Asn Asn Asn Asn Arg Lys Ser Glu His Ser Glu Lys Asn Lys
625              630              635              640

Asp Val His Asn Tyr Tyr Ala Asn Asn Tyr Gln Cys Ile Thr Asp
                645              650              655

Glu Lys Asn Asn Lys Gln Tyr Ile Leu Trp Asn Asn Arg Thr Ile Glu
                660              665              670

Val Thr Phe Val Trp Leu Phe Ile Thr Lys Glu Phe Asn Glu Asn Arg
                675              680              685

Lys Lys Tyr Thr Ala Phe Leu Pro Tyr Leu Lys His Phe Tyr Pro Asn
                690              695              700

Arg Leu Lys Asp Leu Ile Glu Gln Leu Glu Lys Tyr Ser Leu Leu Lys
705              710              715              720
```

```
Phe Asn Tyr Ile Met His Ser Tyr Asn Met Gln Glu Glu Tyr Asn
                725                 730                 735

Lys Asn Lys Glu Pro Asn Asn Ile Asn Ser Asn Asp Asn Asn Lys
        740                 745                 750

Asn Asp Asp Asn Asn Asn Asn Asn Lys Asn Val Asp Gly Asn Asn
            755                 760                 765

Asn Asn Asn Asn Asn Ile Asn Ser Asn Asp Lys Glu Val Leu Met Asn
770                 775                 780

Gly Met Leu Leu Ser Asp Lys Ser Thr Leu Asn Ser Asn Lys Gln Ile
785                 790                 795                 800

Asp Asn Thr Leu Ile Asn Asn Ile Asn Ser Gly Phe Asn Asn Ile Ile
                805                 810                 815

Lys Asn Met Ser Ile Asp Asp Asn Thr Ile Arg Ser Ile Met Asp Asn
                820                 825                 830

Ile Glu Asn Ile Thr Lys Gly Lys Lys Gly Arg Lys Lys Lys Gln
                835                 840                 845

Thr Leu Glu Asn Asn Gly Asp Asn Ile Lys Glu Asp Ile Lys Ser Ser
        850                 855                 860

Lys Lys Asp Lys Lys Lys Asp Asn Ile Asn Asp Asn Asn Asn Asp Asn
865                 870                 875                 880

Asn Asn Asp Asn Asn Asn Asp Asn Asn Asn Asp Asn Asn Asn Asp Asn
            885                 890                 895

Asn Asn Asp Asn Asn Asp Asn Asn Asn Asn Asn Asn Asn Asn
            900                 905                 910

Asn Asn Asn Asn Asn Asn Asn Asn His Asn Asn His Asn Asp
        915                 920                 925

Asn Lys Asn Asn Gln Gly Asp Ser Lys Asn Glu Gln Glu Lys Lys Lys
        930                 935                 940

Lys Thr Arg Gln Tyr Arg Lys Lys Ser Lys Ile Thr Asn Asp Asp Asn
945                 950                 955                 960

Asn Glu Lys Ile Lys Gln Asp Asn Ile Asn Ser Asn Asn Pro Lys Asn
                965                 970                 975

Asp Leu Lys Asn Asn Glu Ile Ile Cys Ser Glu Glu Lys Asn Met Lys
            980                 985                 990

Glu Asp Asn Ile Pro Asp Asp Thr His Tyr Lys Glu Lys Arg Arg Asn
            995                 1000                1005

Thr Phe Asn Leu Phe Asn Leu Asp Glu Gly Thr Ile Asn Met Asp
    1010                1015                1020

Leu Phe Asn Leu Ser Leu Leu Glu Asn Asp Asp Ala Leu Asn Lys
    1025                1030                1035

Lys Glu Asn Asp Met Val Ser Lys Ser Asn Ile Pro Ser Ser Phe
    1040                1045                1050

Ser Ser Pro Pro Lys Glu Thr Asn Asn Lys Asn Asp Ile Asp Lys
    1055                1060                1065

Glu Gln Ser Asp Lys His Asn Asn Val Gln Glu Phe Gln Asn Leu
    1070                1075                1080

Asn Met Asn Asn Glu Lys Ser Lys Asp Leu Tyr Phe Asn Lys Asn
    1085                1090                1095

Asp Ile Asp Asn Asn Asp Asn Lys Asp Lys Ile Ile Asn Glu Thr
    1100                1105                1110

Ser Ser Gly Thr Phe Met Gln Asn Leu Lys Glu Thr Phe Tyr Glu
    1115                1120                1125

Lys Thr Lys Ala Met Phe Ser Asn Leu Leu Ser Asp Thr Lys Ile
    1130                1135                1140
```

-continued

```
Ser Lys Asp Asp Glu Leu Asn Asn Glu Val Asp Gln Asn Cys Val
1145                1150                1155

Lys Thr Ser Ser Gly Ile Leu Asn Lys Glu Glu Asn Asn Lys Lys
1160                1165                1170

Glu Asp Asp Glu Lys His Phe Asp Asp Asn Thr Asn Glu Gln Lys
1175                1180                1185

Lys Asn Val Asp Asn Gly Glu Tyr Asn Glu Met Thr Ala Glu Pro
1190                1195                1200

Gly Arg Lys Lys Arg Lys Lys Asp Val Leu Glu Arg Lys Lys Lys
1205                1210                1215

Asn Leu Asn Lys Glu Ile Ile Lys Ser Glu Lys Arg Ile Arg Lys
1220                1225                1230

Tyr Arg Thr Lys Lys Met Leu Leu Lys Glu Ala Met Glu Lys Gly
1235                1240                1245

Ile Ser Asn Asn Ile Val Glu Ser Asn Ile Thr Ala Asn Asn Asn
1250                1255                1260

Asn Asp Asn Asn Lys Asn Asn Asp Asn Asp Asn Asn Asn Asn Asn
1265                1270                1275

Asn Asp Asn Ile Ile Asn Asn Asn Asn Asn Asn Gly Asp Met Phe
1280                1285                1290

Ser Asn Ser Tyr Asp Asn Ser Tyr Ile Lys Glu Asn Lys Tyr Asn
1295                1300                1305

Lys Lys Leu Cys Phe Pro Gln Asn Asn Leu Leu Ser Asp Phe Arg
1310                1315                1320

Ser Glu Pro Ile Ile Ile Gln Gln Asp Lys Arg Lys Ile Ile Lys
1325                1330                1335

Ile Asn Thr Ile Asn Lys Ile Lys Arg Lys Tyr Lys Lys Phe Arg
1340                1345                1350

Phe Cys Ile Asn Lys Val Phe Lys Lys Lys Ser Ile Asn Asp Ile
1355                1360                1365

Ile Ala Leu Asn Glu Asn Ile His Lys Asn Lys Asp Leu Leu Thr
1370                1375                1380

Leu Phe Lys Lys Lys Asp Leu Ala Asn Leu Lys Lys Lys Asn Leu
1385                1390                1395

Ser Phe Phe Met Asp Thr Leu Lys Leu Glu Lys Ile Asp Met Leu
1400                1405                1410

Ile Met Lys Arg Ile Gln Met Cys Leu Glu Lys Ile Lys Asn Thr
1415                1420                1425

Leu Leu Leu Thr Cys Thr Ile Asn Asn Val Gln Glu Ile Val Asn
1430                1435                1440

Ile Leu Lys Lys Ala Phe Glu Lys Arg Leu Tyr Leu Met Trp Pro
1445                1450                1455

Leu Ile Glu Phe Ser Asn Lys Tyr Arg Leu Asp Gln Tyr Phe His
1460                1465                1470

Leu Leu Gly Lys Asn Lys Asn His Ile Asn Ser Ser Phe Lys Asp
1475                1480                1485

Thr Lys Leu Phe Val His Gln Asn Ile Ser Ser Leu Ile Leu Tyr
1490                1495                1500

Phe Asn Gln Arg Ser Met Asp Asp Lys Trp Val Glu Tyr Leu Lys
1505                1510                1515

Ser Gln Met Lys Pro Lys Arg Arg Arg Lys Thr Lys Met Lys
1520                1525                1530

Glu Gln Phe Leu Glu Asp Lys Pro Ile Asp Tyr Leu Asn Thr Met
```

-continued

```
             1535                1540                1545

Asn Ser Gln His Ser Asn Asn Phe Ile Gly Glu Asn Phe Ser Glu
        1550                1555                1560

Ile Glu Thr Val Glu Ser Lys Ala Asn Glu Tyr Ala Phe Val Gly
    1565                1570                1575

Tyr Asn Gln Lys Arg Leu Leu Thr Gln Ile Thr Pro Tyr Asp Tyr
    1580                1585                1590

Arg Val Val Leu Asn Ser Asn Phe Cys Asn Lys Phe Phe Thr Pro
    1595                1600                1605

Asn Trp Arg Glu Gln Gln Ser Ile Phe Ile Asp Asn Leu His Phe
    1610                1615                1620

Asp Met Val Pro Asp Thr Asp Glu Ile Lys Lys His Phe Glu Asn
    1625                1630                1635

Val Tyr Ile Arg Tyr Met Glu Tyr Asp Glu Glu Lys Leu Arg Ser
    1640                1645                1650

Lys Ser Asp Thr Lys Ser Lys Glu His Lys Lys Lys Asp Lys Lys
    1655                1660                1665

Tyr Lys Met Leu Phe Lys Lys Glu Gly Lys Gly Lys Pro Gly
    1670                1675                1680

Arg Lys Lys Lys Ile Lys Leu Glu Ile Glu Asn Val Ser Asn Glu
    1685                1690                1695

Ile Lys Ile Lys Lys Pro Arg Lys Lys Tyr Glu Arg Val Lys Pro
    1700                1705                1710

Arg Lys Ser Lys Asn Ala Met Met Asn Glu Glu Lys Ser Gly Asn
    1715                1720                1725

Ser Glu Lys Gln Ile Asn Asn Val Leu Asn Val Thr Asn Ile Glu
    1730                1735                1740

Asn Lys His Lys Ser Lys Lys Gly Arg Lys Pro Lys Glu Ser Asn
    1745                1750                1755

Leu Asn Asn Leu Asn Ile Asn Glu Asp Ile Asn Val Ala Lys Ala
    1760                1765                1770

Ser Pro Asp Thr Leu His Arg Ala Ser Leu Glu Phe Met Asn Pro
    1775                1780                1785

Asn Leu Phe Thr
    1790

<210> SEQ ID NO 46
<211> LENGTH: 29
<212> TYPE: PRT
<213> ORGANISM: Plasmodium falciparum

<400> SEQUENCE: 46

Gly Gly Leu Lys Asn Ser Asn His Asn Leu Asn Ile Glu Met Lys
1               5                   10                  15

Tyr Asn Thr Leu Asn Asn Asn Met Asn Ser Ile Asn Lys
            20                  25

<210> SEQ ID NO 47
<211> LENGTH: 2110
<212> TYPE: PRT
<213> ORGANISM: Plasmodium falciparum

<400> SEQUENCE: 47

Met Asn Glu Ile Lys Ser Glu Ser Leu Leu Gln Thr Arg Pro Phe Lys
1               5                   10                  15

Leu Gly Ile Glu Asp Ile Gln Asn Leu Gly Ser Ser Tyr Phe Ile Glu
            20                  25                  30
```

Asn Asn Glu Lys Leu Lys Lys Tyr Asn Asn Glu Ile Ser Ser Leu Lys
            35                  40                  45

Lys Glu Leu Asp Ile Leu Asn Glu Lys Met Gly Lys Cys Thr Thr Thr
 50                  55                  60

Thr Lys Ile Val Glu Pro Ala Lys Thr Pro Glu Phe Thr Phe Trp Tyr
 65                  70                  75                  80

Tyr Glu Leu Lys Glu Met Lys Gly Phe Gln Asp Leu Val Met Tyr Glu
                 85                  90                  95

Val Lys Lys Lys Lys His Phe Lys Val Leu Ser His Ser Cys Leu
                100                 105                 110

Lys Tyr Leu Ser Asn Arg Glu Lys Met Lys Ile Lys Lys Gln Glu Glu
            115                 120                 125

Glu Glu Lys Arg Leu Lys Leu Tyr Ser Lys Asn Ile Ser Ser Tyr Met
130                 135                 140

Asp Val Phe Trp Lys Lys Ile Glu Lys Leu Val Trp Glu Glu Lys Lys
145                 150                 155                 160

Arg Glu Leu Gln Gln Thr Leu Asn Lys Lys Glu Met Arg Phe Lys
                165                 170                 175

Lys Phe Val Lys Glu Ala Ile Lys Ile Lys Asp Ala Arg His Asn
            180                 185                 190

Asn Ala His Glu Leu Phe Glu Asn Lys Tyr Val Ser Met Ser Ser Asn
            195                 200                 205

Asn Asn Ser Glu Ile Val Asn Asn Ala Ser Ser Val Asp Asn Gly
            210                 215                 220

Asp Lys Glu Leu Lys Glu Asp Asp Leu Thr Asp Gln Glu Glu Glu Asp
225                 230                 235                 240

Tyr Leu Leu Asp Glu Gln Met Ser Ser Thr Asp Glu Ser Glu Asn Lys
                245                 250                 255

Glu Glu Glu Ile Asn Met Leu Asp Asp Glu Ala Asn Leu Pro Ile Glu
            260                 265                 270

Glu Leu Leu Lys Arg Met Tyr Gly Phe Lys Ser Gly Glu Asp Tyr Ile
            275                 280                 285

Asn Phe Met Glu Asn Glu Asp Ala Asn Glu Glu Asn Val Ile Glu
            290                 295                 300

Thr Ser His Asn Asp Glu Lys Ser Gly Asp Asn Ser Ile Gly Glu Asp
305                 310                 315                 320

Asp Asn Asn Asn Asp Glu Lys Gly Gly Asp Asn Asn Ile Asp Glu Asp
                325                 330                 335

Asp Asn Asn Asn Asp Glu Lys Ser Gly Asp Asn Ser Ile Gly Glu Asp
            340                 345                 350

Asp Asn Asn Asn Asp His Lys Ser Gly Asp Asn Asn Ile Asp Glu Asp
            355                 360                 365

Asp Asn Asn Asn Asp His Lys Ser Glu Asp Asn Ser Ile Gly Glu Asp
            370                 375                 380

Asp Asn Asn Asn Asp Glu Lys Gly Gly Asp Asn Asn Ile Asp Glu Asn
385                 390                 395                 400

Asp Asn Asn Ser Asp His Lys Ser Glu Asp Asn Asn Ile Asp Glu Asn
                405                 410                 415

Asp Asn Asn Ser Asp His Gln Ser Asp Gln Glu Gln Phe Asn His Glu
            420                 425                 430

Thr Lys Asp Asp Ile Ile Lys Asn Ser Ser Tyr Glu His Ile Asp Asn
            435                 440                 445

Lys Asn Tyr Tyr Asn Lys Thr Gly Glu Asp Tyr Lys Ser Asp Lys Glu

```
                450              455              460
Asn Tyr Ser Pro Thr Arg Phe His Asn Lys Leu Lys Glu Lys Tyr
465                 470                 475                 480

Asp Glu Tyr Asp Thr Lys Leu Lys Ile Glu Lys Arg Glu Glu Asn
                485                 490                 495

Lys Asn Tyr Glu Lys Asp Glu His Glu Tyr Glu Ser Asp Asn Tyr Asp
                500                 505                 510

Lys Glu Lys Ile Asn Lys Lys Glu Leu Ile Leu Leu Lys Asn Asp
                515                 520                 525

Ile Glu Asn Asp Ser Asp Glu Thr Ser Glu His Ile Lys Arg Asp Ser
530                 535                 540

Arg Ser Ser Cys Gln Lys Gln Asn Cys Glu Lys Lys Arg Ile Ile
545                 550                 555                 560

Lys Asp Glu Tyr Asn Leu Arg Arg Thr Lys Ile Ala Lys Ser Lys Pro
                565                 570                 575

Ser Ser Asp Asn Asn Ser Glu Asn Asp Asn Asn Asp Asn Asn
                580                 585                 590

Asn Asp Asn Asn Asn Asp Asn Asn Asp Asn Asn Asp Asn Asn
                595                 600                 605

Asp Asp Asn Asn Asp Asn Asn Asp Asn Asn Asp Asn Asn
610                 615                 620

Asp Asp Asn Asn Asn Glu His Lys Asn Asp Ser Asp Asn Asp Asp
625                 630                 635                 640

Ile Leu Thr Cys Asn Met Asp Glu Lys His Leu Thr Lys Ile Pro Pro
                645                 650                 655

Ile Ile Lys Ala Thr Leu Arg Asp Tyr Gln His Ala Gly Leu His Trp
                660                 665                 670

Leu Leu Tyr Leu Tyr Lys Asn Asn Ile Asn Gly Ile Leu Ala Asp Glu
                675                 680                 685

Met Gly Leu Gly Lys Thr Leu Gln Cys Ile Ser Leu Leu Ser Tyr Leu
                690                 695                 700

Ala Tyr Tyr Phe Asn Ile Trp Gly Pro His Leu Val Ile Val Pro Thr
705                 710                 715                 720

Ser Ile Leu Ile Asn Trp Glu Ile Glu Leu Lys Arg Phe Cys Pro Cys
                725                 730                 735

Phe Lys Ile Leu Ser Tyr Tyr Gly Asn Gln Asn Glu Arg Tyr Lys Lys
                740                 745                 750

Arg Val Gly Trp Phe Asn Lys Asp Ser Phe His Ile Cys Ile Ser Ser
                755                 760                 765

Tyr Ser Thr Val Val Lys Asp His Leu Val Phe Lys Arg Lys Arg Trp
770                 775                 780

Lys Tyr Ile Ile Leu Asp Glu Ala His Asn Ile Lys Asn Phe Asn Thr
785                 790                 795                 800

Lys Arg Trp Asn Ile Ile Leu Ser Leu Lys Arg Asp Asn Cys Leu Leu
                805                 810                 815

Ile Thr Gly Thr Pro Leu Gln Asn Ser Leu Glu Glu Leu Trp Ser Leu
                820                 825                 830

Leu His Phe Leu Met Pro Asn Ile Phe Thr Ser His Leu Asp Phe Lys
                835                 840                 845

Glu Trp Phe Ser Asp Pro Leu Asn Leu Ala Ile Glu Lys Ser Lys Ile
                850                 855                 860

His His Ser Lys Glu Leu Ile Asp Arg Leu His Thr Val Ile Arg Pro
865                 870                 875                 880
```

Tyr Ile Leu Arg Arg Leu Lys Lys Asn Val Glu Lys Glu Met Pro Asn
         885                 890                 895

Lys Tyr Glu His Ile Ile Lys Cys Lys Leu Thr Arg Arg Gln Gln Ile
            900                 905                 910

Leu Tyr Asp Glu Phe Ile Asn Asn Lys Asn Val Gln Asn Thr Leu Asn
            915                 920                 925

Thr Gly Asn Tyr Ile Gly Leu Met Asn Ile Leu Ile Gln Leu Arg Lys
            930                 935                 940

Val Cys Asn His Cys Asp Leu Phe Thr Asn Lys Tyr Ile Gln Thr Pro
945                 950                 955                 960

Tyr Tyr Tyr Met Leu Ser Ile Arg Tyr Phe Val Pro Arg Phe Phe Ile
                965                 970                 975

Leu Phe Glu Lys Asn Tyr Tyr Ala Asp Phe Tyr Leu Ile Leu Phe Leu
            980                 985                 990

His Asn Glu Phe Thr Ser Leu Gly Gly Arg Asp Val Thr Lys Glu Thr
            995                 1000                1005

Ser Pro Ser Ser Lys Ser Phe Asp Leu Ala His Ile Leu Thr Lys
    1010            1015            1020

His Asn Thr Asn Glu Leu Tyr Asp Asn Asn His Ile Ser Glu Leu
    1025            1030            1035

Tyr Asp Asn Asn His Ile Ser Glu Leu Tyr Asp Asn Asn His Ile
    1040            1045            1050

Ser Glu Leu Tyr Asp Asn Asn His Ile Ser Glu Leu Tyr Asp Asn
    1055            1060            1065

Pro Met Ser His Lys Asn Tyr Lys His Asn Ser Asn Gly Tyr Thr
    1070            1075            1080

Tyr Pro Asn Asp Pro Ile Asn Asn Met Asn Asn Asn Pro Ser Gly
    1085            1090            1095

Phe Thr Lys Thr Ser Glu Gln Phe Gly Gln Ile Val Ser His Glu
    1100            1105            1110

Arg Asp Asn Asn Tyr His Met Met Asp His Asn Asn Met Asn Asn
    1115            1120            1125

Leu Leu Ser Lys Glu Met Val Asn Ser Leu Arg Asn Asp Asp Asn
    1130            1135            1140

Ser Asn Asn Asn Phe Tyr Lys Tyr Ser Leu Thr Ser Asn Asn Asn
    1145            1150            1155

Asp Ser Gln Thr Ser Ile His Asp Asn Lys Gln Cys Asp Tyr Asn
    1160            1165            1170

Lys Leu Cys Ala Asp Thr Phe Asn Asn Ile Asn Ser Ile Gly Asn
    1175            1180            1185

Glu Glu Lys Arg Ser Leu Asn Val Leu Asn Glu Gln Asn Asn Asn
    1190            1195            1200

Asn Ser Lys Asp Asn Asn Asn Ile Asp Asn Asn Asn Asn Ile
    1205            1210            1215

Asp Asn Asn Asn Ile Asp Asn Asn Asn Ile Asp Asn Asn
    1220            1225            1230

Asn Asn Ile Asp Asn Asn Asn Asn Ile Asp Asn Asn Asn Asn
    1235            1240            1245

Ile Asp Asn His His Asn Asn Asn Gln His Cys Asn Tyr Asn Asp
    1250            1255            1260

Asn Trp Pro Ser Asp Tyr Pro Thr Asn Ile Ile Asn His Arg Asn
    1265            1270            1275

Ala Phe Leu Ser Ile Leu Lys Leu Leu Asn Gln Ser Asn Pro Leu
    1280            1285            1290

```
Asn Asn Asp Asn Asn Asn Asn Asn Asn Asn Asn Gly Asn Asn
1295                1300                1305
Asn Ile Tyr Asn Met Asn Arg Tyr Asn Ser Arg Asn Ser Arg Asn
    1310                1315                1320
Ser Ser Leu Ser Asn Ile Phe Ser Ser Asn Thr Ser Lys Met Asn
    1325                1330                1335
Ser Phe Gln Leu Asp Phe Leu Tyr Thr Asn Ser Phe Ile Asn Gln
    1340                1345                1350
Asp Ala Leu Cys Lys Asn Ser Phe Phe Val Asn Ile Asn Ile Glu
    1355                1360                1365
Asp Val His Ser Tyr Ile Tyr Asn Ser Ile Tyr Lys Glu Tyr Ile
    1370                1375                1380
Pro Lys Asn Ile Leu Ser Phe Ser Asp Glu Phe Leu Thr Glu Leu
    1385                1390                1395
Asn Asn Asn Tyr Asp Ile Leu Ser Leu Tyr Ile Asp Pro Tyr Asn
    1400                1405                1410
Arg Tyr Lys Ser Tyr Asn Glu Tyr Leu Tyr Lys Met Lys Glu Glu
    1415                1420                1425
Gly Thr Leu Thr Asn Gln Gln Ser Leu Gly Asp Ile Asn Asn Lys
    1430                1435                1440
His Ile Tyr His Lys Ser Thr Ser Asn Glu Asn Thr His Met Lys
    1445                1450                1455
Asn Arg Lys Thr Phe Ile Tyr Lys Tyr Asn Asn Met Phe Lys Val
    1460                1465                1470
Ile Asn Asn Asp Thr Gln Tyr Gln Asn Ile Phe Thr Asp Asp Thr
    1475                1480                1485
Asn Asn Ser Tyr Tyr Asn Ser Leu Glu His Asn Leu Trp Ile Lys
    1490                1495                1500
Arg Asn Gln Ile Asp Glu Arg Lys Lys Glu Glu Glu Glu Glu Gln
    1505                1510                1515
Asn Lys Tyr Tyr Asn Val Cys Met Asn Asn Leu Tyr Ile Leu Arg
    1520                1525                1530
Asn Glu Arg Ile Pro Ile Phe Gly Lys Asn Phe Leu Asp Leu Ile
    1535                1540                1545
Lys Lys Glu Phe Thr Lys Asp Lys Asn Ile Val Tyr Asn Tyr Thr
    1550                1555                1560
Asn Asn Val Pro Ile Asp Tyr Tyr Ser Ser Val Lys Glu Val Trp
    1565                1570                1575
Val Glu Asp Ile Cys Glu Lys Asp Asn Lys Lys Arg Lys Cys Lys
    1580                1585                1590
Arg Glu Lys Arg Trp Tyr Lys Lys Ile Lys Lys Thr Asn Asn Pro
    1595                1600                1605
Pro Glu Asp Ser Glu Val Tyr Arg Glu Asn Ser Ser Asp Val Glu
    1610                1615                1620
Lys Tyr Asn Cys Asp Val Glu Lys Asp Asn Cys Asp Asp Glu Glu
    1625                1630                1635
Lys Asp Asn Cys Asp Asp Glu Asp Met Asn Ser Asn Leu Ser Ser
    1640                1645                1650
Asn Val Tyr Gly Cys Ile Asp Ile Ser Ser Gln Asn Phe Ile His
    1655                1660                1665
Ser Arg Tyr His Asn Pro Met Met Asn Met Ser Tyr Ile Ile Glu
    1670                1675                1680
Phe Leu Phe Pro Asn Met Glu Gln Phe Leu Lys Arg His Glu Lys
```

```
                1685                1690                1695

Met Ile His Asn Phe Thr Leu Ile Asn Asn Pro Ser Val Ile Cys
        1700                1705                1710

Lys Ser His Asp Ile Arg Ile Asn Asn Asn Leu Leu Asn Tyr Ser
        1715                1720                1725

Asn Asp Lys Met Asn Pro Ile Ile Leu Gln Ile Lys Asn Ala Thr
        1730                1735                1740

Arg Val Tyr His Asp Ala Phe Leu Lys Gln Ser Ile Ile Phe Pro
        1745                1750                1755

Leu Asn Lys Asp Ile Ser Leu Gly Ser Gly Lys Leu Cys Ala Leu
        1760                1765                1770

Glu Lys Leu Leu Ser Lys Cys Lys Arg Glu Gly Asn Lys Cys Leu
        1775                1780                1785

Leu Phe Thr Gln Phe Ile Lys Met Leu Asp Ile Leu Glu Ile Phe
        1790                1795                1800

Leu Asn His Leu Asn Tyr Ser Phe Ile Arg Leu Asp Gly Ser Thr
        1805                1810                1815

Lys Val Glu Gln Arg Gln Lys Ile Val Thr Lys Phe Asn Asn Asp
        1820                1825                1830

Lys Ser Ile Phe Ile Phe Ile Ser Ser Thr Arg Ser Gly Ser Ile
        1835                1840                1845

Gly Ile Asn Leu Thr Ala Ala Asn Val Val Ile Phe Tyr Asp Thr
        1850                1855                1860

Asp Trp Asn Pro Ser Ile Asp Lys Gln Ala Met Asp Arg Cys His
        1865                1870                1875

Arg Ile Gly Gln Thr Lys Asp Val His Val Phe Arg Phe Val Cys
        1880                1885                1890

Glu Tyr Thr Val Glu Glu Asn Ile Trp Lys Lys Gln Leu Gln Lys
        1895                1900                1905

Arg Lys Leu Asp Asn Ile Cys Ile Asn Met Gly Asn Phe Asn Asn
        1910                1915                1920

Ser Asn Thr His Ser Lys Ile Thr Asp Thr Asp Pro Thr His Asn
        1925                1930                1935

Lys Asp Trp Phe Thr Asn Val Asp Thr Ile Lys Glu Val Phe Ile
        1940                1945                1950

Asn Lys Lys Asn Asn Asp Asp Asp Asp Met Tyr Lys Asp Arg
        1955                1960                1965

Leu Leu His Glu Gln Val Glu Asn Lys Asp Lys Met Asn Val Arg
        1970                1975                1980

Phe Glu Lys Thr Leu Glu His Val Glu Asp Lys Asp Asp Ile Arg
        1985                1990                1995

Ala Leu Asn Glu Thr Lys Lys Glu Thr Gln Asn Glu Ile Ser Gln
        2000                2005                2010

Asn Met Gln Val Ser Thr Asn Lys Lys Asn Ile Tyr Ile Tyr Ile
        2015                2020                2025

Asn Ile Leu Tyr Leu Asn Val Asn Phe Phe Asn Lys His Pro Leu
        2030                2035                2040

Gly Glu Phe Thr Thr Arg Asn Asp Phe Gln Asp Ser Tyr Asn Leu
        2045                2050                2055

Thr Ser Tyr Cys Phe Asn Phe Leu Asn Glu Asn Leu Thr Asp Ser
        2060                2065                2070

Leu Lys Gln Gln Ile Asp Glu Met Arg Met Lys Ile Glu Ile Glu
        2075                2080                2085
```

```
Met Met Asn Thr Gly Asp Glu Asn Met Ser Leu Ser Asp Leu Ser
    2090            2095            2100

Asn Lys Ser His Asn Ser Glu
    2105            2110
```

<210> SEQ ID NO 48
<211> LENGTH: 28
<212> TYPE: PRT
<213> ORGANISM: Plasmodium falciparum

<400> SEQUENCE: 48

```
Glu Lys Leu Lys Lys Tyr Asn Asn Glu Ile Ser Ser Leu Lys Lys Glu
1               5                   10                  15

Leu Asp Ile Leu Asn Glu Lys Met Gly Lys Cys Thr
            20                  25
```

<210> SEQ ID NO 49
<211> LENGTH: 1712
<212> TYPE: PRT
<213> ORGANISM: Plasmodium falciparum

<400> SEQUENCE: 49

```
Met Asp Ser Asp Lys Tyr Lys Lys Phe Tyr Val Tyr Asn His Gly Phe
1               5                   10                  15

Thr Lys Gln Pro Phe Tyr Glu Arg Asn Leu Asn Asp Lys Gly Ile His
            20                  25                  30

Leu Lys Glu Leu Lys Arg Leu Glu Arg Val Asp Glu Pro Arg Leu Tyr
        35                  40                  45

Asn Asn Val Asp Lys Ile Pro Asn Lys Lys Glu Ile Ile Tyr Asn Asn
    50                  55                  60

Ile Lys Ser Asn Asn Ile Gln Val Arg Val Asn Gln Asn Asn Glu
65                  70                  75                  80

Glu Lys Lys Lys Glu Glu Ala Asn Tyr Thr Cys Val Asn Asn Lys Tyr
                85                  90                  95

Val Thr Leu Lys Asn Lys Val His Val Asn Lys Tyr Val Asn Asn Ser
            100                 105                 110

Asn Ile Asn Lys Ile Lys Ile Val Pro Ile Ile Lys Cys Ser Asn Tyr
        115                 120                 125

Lys Ile Lys Asn Asn Pro Ile Ser His Leu Lys Ser Asn Tyr Glu Asn
130                 135                 140

Lys Phe Val Lys Leu Ser Asn Phe Ser Asn Ile Lys Asn Gly Cys Ser
145                 150                 155                 160

His Lys Asp Asn Val Ile Asn Glu Thr Met Asp Gln His Lys Ser Glu
                165                 170                 175

Gln Leu Asn Asn Asp Asn Ile Lys Lys Leu Leu Tyr Asp Tyr Cys Ile
            180                 185                 190

Phe Arg Glu Asp Thr Ile Lys Thr Lys Thr Asn Ile Ser Tyr Asn Lys
        195                 200                 205

Met Asn Ser Phe Lys Asp Asn Glu Glu Asn Ile Asn Tyr Met Asp Asn
    210                 215                 220

Asn Asn Ile Lys Ser Asn Ser Ser Ser Tyr Cys Ser Tyr Ser Asn Lys
225                 230                 235                 240

Ile Asn Gln Asn Asn Val Asn His Thr His Leu Lys Thr Glu Phe Leu
                245                 250                 255

Asn Glu Lys Asn Ser His Thr Gln Asn Glu Gln Ser Ile Pro Leu Leu
            260                 265                 270

Asp Gly Leu Gln Asn Asn His Asn Ser Ala Thr Lys Phe His Asn Asn
```

```
                275                 280                 285
Ile Tyr Asp Asn Asn Asn Ser Leu Val Asn Tyr Lys Ser Asp Lys Gly
            290                 295                 300
Ile Asp Leu His Asn Lys Met Met Lys Ile Glu Thr Asp Lys Asn Gly
305                 310                 315                 320
Ile Ile Thr Leu Glu Lys Lys Lys His Asp Glu Lys Tyr Tyr Asn Asn
                325                 330                 335
Ile Phe Leu Asn Pro Leu Asn Asp Asn Ser Asn Asn Val Val Ile Thr
            340                 345                 350
Thr Cys Asp Asn Lys Glu Ser Tyr Arg Asn Ser Thr Ser Asp Met Ile
        355                 360                 365
Asn Lys Ile Phe Glu Lys Met Met Asn Glu Lys Lys Asn Ile Leu Lys
    370                 375                 380
Met Lys Asn Phe Asn Asp Val Ile Lys Lys Ile Thr Met Ala Lys
385                 390                 395                 400
Glu Lys Ile Leu Asn Ser Asn Ser Thr Ile Asn Met Lys Lys Val Ser
                405                 410                 415
Phe Tyr Asn Ser Lys Asp Glu Asp Leu Phe Asn Glu Lys Glu Asn Ser
            420                 425                 430
Tyr Lys Tyr Gly Val Lys Arg Glu Asn Gln Glu Asp Ile Asn Val Ile
        435                 440                 445
Lys Asn Asn Met Lys Arg Asn Asn Ile Asn Ile Asp Asn Asn Asp Asn
    450                 455                 460
Ile Asn Ile Ile Lys Asn Asp Ser Val Ser Lys Asn Ile His Ile Asn
465                 470                 475                 480
Asn Lys Lys Lys Arg Asp Asp Asp Phe Pro Phe Asn Asn Ser Ala Gly
                485                 490                 495
Leu Leu Leu Asp Phe Asp Leu Cys Lys Arg Lys Val Leu Glu Ile Leu
            500                 505                 510
Lys Asn Val Gln Ser Ser Lys Lys Lys Asn Lys Ile Leu Thr Asn His
        515                 520                 525
Asn His Ser Ser Asp Asn Gln Asn Cys His Ser Ser Asp Asn Gln Asn
    530                 535                 540
Cys His Ser Ser Asp Asn Gln Asn Cys His Ser Ser Asp Asn Gln Asn
545                 550                 555                 560
Cys His Ser Ser Asp Asn Gln Asn Cys Asp Ser Asn Ala Cys Asn Lys
                565                 570                 575
Lys Asp Glu Glu Lys Lys Arg Lys Lys Lys Ile Lys Lys Lys Asn
            580                 585                 590
Lys Met Lys Asn Lys Ser Asn Asn Lys Ser Lys Asn Lys Arg Glu Thr
        595                 600                 605
Lys Ser Lys Lys Ile Ser Asn Asn Asn Asn Asp Asn Met Asn Asn
    610                 615                 620
Gln Cys Asp Asn Met Gly Asp Gln Arg Ile Asn Asn Glu Asn Met Asp
625                 630                 635                 640
Lys Gln Asn Val Asn Ile Gln Asn Glu Gly Asn Gly Phe Asn Asn
                645                 650                 655
Lys Asn Asn Asn Asp Leu Leu Asn Val Tyr Ile Ser Pro Asn Met Ile
            660                 665                 670
Asn His Ser Leu Ser Ser Thr Cys Glu Lys Lys Asn Lys Glu Asp Asn
        675                 680                 685
Lys Met Asn Asp Asn Lys Phe Leu Asn Ser Ser Lys Met Lys Ile
    690                 695                 700
```

-continued

```
Pro Glu Ile Ser Thr Asn Asn Ser Asn Glu Lys Ile Val Asn Val Ser
705                 710                 715                 720

Asn Asp Glu Met Leu Val Tyr His Asn Leu Thr Val Leu Asn Val Lys
                725                 730                 735

Glu Gln Gly Gly Val Thr Glu Glu Ser Ser Cys Ile Lys Arg Thr Tyr
            740                 745                 750

Phe Val Asp Gln Phe Tyr Asp Ser Tyr Asn Met Arg Asn Glu Lys Ile
        755                 760                 765

Thr Asp Asp Asn Met Gln Val Glu Asp Ile Tyr Asn Val Lys Glu Asn
    770                 775                 780

Ile Lys Arg Thr Leu Lys Gly Asp Gly His Asp Asp Val Lys Thr Asn
785                 790                 795                 800

Met Leu Ser Glu Asp Asn Ser Tyr Ala Ser Gly Leu Trp Gly Asn Glu
                805                 810                 815

Ile Asn Phe Ile Ser Asn Asn Glu Asn Cys Leu Asn Ser Tyr Asp Ile
            820                 825                 830

Ser Cys Asp Glu Lys Tyr Ile Pro Asn Glu Glu Gln Asp Glu Glu
        835                 840                 845

Leu Cys Ser Asn Asn Ile Leu Val Lys Asp Ile Glu Glu Lys Lys Met
850                 855                 860

Cys Gly Lys Leu Phe Phe Glu Glu Ile Cys Val Phe Arg Ile Asn Glu
865                 870                 875                 880

Lys Asn Glu His Gly His Glu Asn Leu Arg Lys Asn Asn His Asn Asp
                885                 890                 895

Asp Thr His Lys Met Tyr Ser Ser Tyr Glu Asn Ile Gln Asn Ile Asn
                900                 905                 910

Lys Gln Ser Thr Asn Pro Phe Cys Lys Lys Asp Glu Met Glu Lys Ser
            915                 920                 925

Gln Gly Thr Asn Leu Phe Tyr Asp Asn Tyr Ile Asn Ser Val Asp Ile
        930                 935                 940

Thr Lys Leu Glu Leu Asn Lys Asn Cys Tyr Gln His Ile Asn Tyr Glu
945                 950                 955                 960

Val Gln Asn Leu Ile Lys Lys Glu Asn Ser Tyr Ala Ala Glu Met Asn
                965                 970                 975

Val Gly Leu Val Phe Arg Lys Tyr Ile Pro Ile Leu Ile Asn Leu Ser
            980                 985                 990

Cys Asn Tyr Leu Leu Ile Lys Lys  Asn Glu Lys Asn Val  Ile Thr Cys
        995                 1000                1005

Ile Ser  Tyr Thr Asn Ile Ile  Asp Val Lys Ile Val  Lys Lys Ser
    1010                 1015                1020

Lys Lys Asn Lys Glu Arg Phe  Leu Phe Lys Ile Val  Tyr Val Phe
    1025                 1030                1035

Lys Lys Lys Glu Gln Lys Thr  Glu Lys Asn Val Thr  Leu Leu Phe
    1040                 1045                1050

Arg Ala Asn Leu Met Glu Ile  Phe Glu Lys Ile Lys  Gly Arg Val
    1055                 1060                1065

Asp Tyr Cys Ile Ile Pro Asn  Glu Asp Asp Lys Asn  Ile Gln Leu
    1070                 1075                1080

Gln Asp Lys Lys Lys Lys Lys  Gly Lys Lys Lys Glu  Leu Gln
    1085                 1090                1095

Glu Glu Lys Met Lys Lys Lys  Lys Lys Thr Gln Glu  Tyr Val Asp
    1100                 1105                1110

Ile Glu  Thr Val Tyr Glu Tyr  Val Ile Glu Lys Tyr  Lys Arg Val
    1115                 1120                1125
```

```
His Val Leu Tyr Leu Gly Arg Leu Leu Gln Ile Val Glu Lys Leu
    1130            1135            1140

Phe Lys Lys Tyr Ile Leu Lys Tyr Ser Phe His Lys Leu Arg Ile
    1145            1150            1155

Phe Tyr Glu Tyr Lys Ile Glu Met Glu Lys Leu Lys Lys Asn Tyr
    1160            1165            1170

Ile His Cys Ile Tyr Asp Ile Ser Asp Lys Leu Glu Phe Leu Ile
    1175            1180            1185

Lys Lys Lys Met Gln His Tyr Phe Asn His Ile Ile Ile Asn Ser
    1190            1195            1200

Tyr Glu Ser Ser Phe Ile Asn Tyr Gln Ile Lys Thr Asn Asp Met
    1205            1210            1215

Leu Tyr Asn Leu Leu Leu Lys Glu Lys Ser Ala Tyr Gln Asn His
    1220            1225            1230

Leu Gly Lys Asn Tyr Ile Leu Ile Leu Tyr Lys Val Leu Leu Ser
    1235            1240            1245

Met Tyr Lys Lys Lys Met Ala Ile Tyr Phe Arg Ser Phe Val Tyr
    1250            1255            1260

Asn Asn Ile Lys Val Ser Lys Lys Lys Asn Ala Phe Ala Tyr Thr
    1265            1270            1275

Leu Thr Arg Val Asn Ser Ile Leu Val Leu Tyr Glu Arg Arg Ile
    1280            1285            1290

Lys Ser Phe Ile Phe Ser Lys Leu Lys Phe Asn Tyr Asp Asn Val
    1295            1300            1305

Ser Tyr Phe Cys Phe Thr Met Tyr Lys Ile Tyr Leu Arg Arg Ile
    1310            1315            1320

Leu Phe Gly Tyr Leu Arg Ile Arg Asp Asn Arg Ile Asn Ile Lys
    1325            1330            1335

Asn Val Ile Glu Lys Asn Val Tyr Arg Leu Val Lys Leu Ile Ser
    1340            1345            1350

Lys Ile Ser Asp Asn His Lys Tyr Asn Ala Phe Leu Lys Leu Gln
    1355            1360            1365

Lys Tyr Val Tyr Glu Gln Asn Glu Lys Lys Asn Lys Met Ile Cys
    1370            1375            1380

Asp Asn Leu Ile Tyr Ala Asn Asn Glu Leu Cys Asn Asn Leu Asp
    1385            1390            1395

Lys Ile Ala Ile Glu Lys Gly Ile Asn Gln Ile Asp Cys Leu Ile
    1400            1405            1410

Lys Phe Lys Arg Lys Glu Cys Leu Met Lys Tyr Phe Tyr Thr Leu
    1415            1420            1425

Lys Gly Pro Gln Ile Asn Thr Glu Arg Phe Tyr Tyr Cys Ile Arg
    1430            1435            1440

Tyr Cys Ser Ile Phe Ser Phe Val Leu Asn Lys Ile Ile Gln Lys
    1445            1450            1455

Lys Val Gln His Ile Phe Gln Phe Val Leu Lys Thr Leu Gln
    1460            1465            1470

Arg Asn Asn Lys Asn Arg Leu Thr His Ala Ile Lys Leu Leu Gln
    1475            1480            1485

Val Leu Val Gln Lys Lys Glu Lys Lys Ser Val Ile Asp Val Leu
    1490            1495            1500

Gln Leu Tyr Asp Lys Tyr Pro Tyr Ile Phe Gln Tyr Lys Asp Leu
    1505            1510            1515

Thr Lys Ile Glu Val Phe Val Ile Cys Val Gln Asn Phe Val Thr
```

```
                    1520                1525                1530

Leu  Tyr  Asn  Arg  Lys  Leu  Leu  Asn  Phe  Leu  Leu  Lys  Leu  His
1535                     1540                     1545

Tyr  Leu  Lys  Tyr  Gln  Glu  Gln  Phe  Met  Lys  Thr  Tyr  Asn  Gly  Ile
1550                     1555                     1560

Gly  Ser  Ile  Tyr  Lys  Phe  Val  His  Val  Leu  Asp  Lys  Lys  Leu  Met
1565                     1570                     1575

Asn  Thr  Ile  Arg  Glu  Ser  Phe  Arg  Val  Ile  Leu  Gln  Asn  Asp  Lys
1580                     1585                     1590

Phe  Leu  Arg  Glu  Lys  Met  Asn  Met  Lys  Met  Glu  Gln  Met  Asp  Met
1595                     1600                     1605

Lys  Met  Glu  Lys  Ile  Asp  Val  Asn  Met  Asp  Gln  Met  Asp  Val  Lys
1610                     1615                     1620

Met  Glu  Gln  Met  Asp  Val  Lys  Met  Glu  Gln  Met  Asp  Val  Lys  Met
1625                     1630                     1635

Lys  Arg  Met  Asn  Lys  Lys  Ser  Lys  Gln  Ile  His  Val  Asn  Tyr
1640                     1645                     1650

Asn  Asn  Lys  Ala  Tyr  Ser  Ser  Ser  Ser  Pro  Ser  Pro  Met  Leu  Arg
1655                     1660                     1665

Tyr  Asn  Lys  Tyr  Lys  Asp  Met  Ser  Ser  Asn  Ser  Ala  Ser  Leu  Ile
1670                     1675                     1680

Lys  Lys  Tyr  Pro  Phe  Leu  Ile  Tyr  Asn  Ser  Glu  Ile  Ser  Pro  Asp
1685                     1690                     1695

Cys  Thr  Thr  Met  Ala  Gly  Lys  Phe  Tyr  Asn  Gln  Lys  Asn  Lys
1700                     1705                     1710

<210> SEQ ID NO 50
<211> LENGTH: 47
<212> TYPE: PRT
<213> ORGANISM: Plasmodium falciparum

<400> SEQUENCE: 50

Glu  Lys  Met  Asn  Met  Lys  Met  Glu  Gln  Met  Asp  Met  Lys  Met  Glu  Lys
1                   5                    10                       15

Ile  Asp  Val  Asn  Met  Asp  Gln  Met  Asp  Val  Lys  Met  Glu  Gln  Met  Asp
                20                       25                       30

Val  Lys  Met  Glu  Gln  Met  Asp  Val  Lys  Met  Lys  Arg  Met  Asn  Lys
            35                       40                       45

<210> SEQ ID NO 51
<211> LENGTH: 1033
<212> TYPE: PRT
<213> ORGANISM: Plasmodium falciparum

<400> SEQUENCE: 51

Met  Ser  Glu  Glu  Ser  Phe  Asp  Asp  Thr  Asn  Lys  Ala  Phe  Glu  Asn  Glu
1                   5                    10                       15

Lys  Asp  Ile  Ile  Leu  Glu  Lys  Ile  Val  Lys  Asp  Glu  Asn  Asn  Leu  Asn
                20                       25                       30

Asn  Cys  Ser  Asn  Met  Ile  Asn  Met  Asp  Asp  Val  Glu  Asn  Met  Lys  Lys
                35                       40                       45

Glu  Leu  Tyr  Val  Leu  His  Lys  Lys  Asp  Glu  Glu  Ile  Glu  Asn  Asn  Val
            50                       55                       60

Asp  Cys  Phe  Ser  Gly  Lys  Tyr  Asn  Val  Glu  Asn  Val  Ile  Asn  Leu
65                  70                       75                       80

Lys  Lys  Lys  Lys  Lys  Lys  Asp  Glu  Asp  Thr  Asp  Ser  Ser  Tyr  Tyr  Lys
                85                       90                       95
```

-continued

Thr Thr Leu Asp Glu Val Tyr Asp Thr Ser Asp Ile Ser Thr Asp Glu
            100                 105                 110

Met Leu Ser Asn Tyr Ser Ser Glu Asp Asn Asn Ile Glu Met
        115                 120                 125

Asn Ile Ile Asn Asp Phe Tyr Leu Lys Asp Asp Thr Tyr Cys Leu
130                 135                 140

Glu Trp Asn Ser Asp Ile Ile Asn Val Leu Ser Glu Glu Ile Lys Glu
145                 150                 155                 160

Lys Glu Lys Leu Leu Glu Asp Glu Asn Lys Asp Ile Cys Asn Met Lys
            165                 170                 175

Ser Arg Phe Leu Lys Leu Glu Lys Tyr Val Asn Ile Lys Lys Lys
            180                 185                 190

Ile Ile Asn Ile Lys Lys Asn Ile Glu Glu Lys Arg Lys Ile Glu Phe
            195                 200                 205

Asp Glu Lys Glu Ile Phe Lys Cys Leu Gln Ile Lys Asn Asp Phe Leu
            210                 215                 220

Lys Lys Glu Asn Lys Lys Ile Glu Leu Glu Arg Glu Lys Asn Asn Lys
225                 230                 235                 240

Lys Ile Ile Glu Thr Gln Asn Asn Ile Thr Thr Cys Gln Lys Asn Ile
            245                 250                 255

Asp Asp Ile Lys Lys Glu Leu Ile Leu Lys Glu Asn Glu Leu Asn Asp
            260                 265                 270

Phe Ile Asn Lys Ile Lys Ile Ile Gln Gln Glu Glu Tyr Glu Ile Glu
            275                 280                 285

Lys Ile Lys Leu Ser Lys Asp Lys Glu Ile Gln Asn Val Ser Tyr Asn
            290                 295                 300

Leu Glu Lys Tyr Asn Asn Glu Lys Ile Gln Gln Asp Lys Lys Tyr Glu
305                 310                 315                 320

Gln Val Lys Met Asn Asn Met Lys Phe Asp Ile Glu Leu Lys Ser Ile
            325                 330                 335

Ile Gln Glu Tyr Tyr Asp Ile Lys Lys Asp Ile Lys Asn Ile Ser Asn
            340                 345                 350

Lys Tyr Ile Cys Ile Met Asp Met Ile Lys Cys Arg Asp Lys Thr Ile
            355                 360                 365

Tyr Lys Phe Glu Lys Asp Tyr Thr Lys Thr Ile His Lys Glu Lys Gln
            370                 375                 380

Leu Gln Asn Lys Cys Leu His Lys Gln Asn Leu Ile Asn Thr Gln Lys
385                 390                 395                 400

Asp Lys Asn Ile Ile Leu Asn Asn Gln Ile Lys Lys Ile Gln Phe Asp
            405                 410                 415

Ile Asn Lys Ile Arg Lys Glu Leu Asn Asp Lys Gln Met Ser Tyr Asp
            420                 425                 430

Lys Thr Ile Ile Asp Arg Asp His Leu Asn Lys Glu Tyr Glu Tyr Glu
            435                 440                 445

Ile Val Glu Ile Lys Glu Lys Leu Gln Glu Glu Lys Lys Ser Leu Glu
            450                 455                 460

Asn Thr Leu Gln His Leu Asn Glu Thr Tyr Ile Thr Met Ser Thr Asn
465                 470                 475                 480

Tyr Glu Glu Ser Lys Asn Glu Tyr Glu Lys Glu Gln Val Asn Asn Ile
            485                 490                 495

Glu Lys Asn Asp Leu Ile Lys Ser Ser Glu Gln Ile Leu Val Gln Leu
            500                 505                 510

Gln Asn Lys Leu Gln Lys Leu Leu Asp Glu Ile Lys Ser Leu Asp Leu

```
                515                 520                 525
Glu Lys Phe Gln Leu Thr Gln Thr Leu Gln Val Ile Lys Asn Asp Tyr
530                 535                 540

Ile Thr Leu Glu Ala Asp Val Leu Gly Thr Gln Ile Lys Ile Lys Gln
545                 550                 555                 560

Ile Lys Ser Asn Ile Lys Lys Thr Glu Lys Glu Leu Glu Arg Gln Lys
                565                 570                 575

Glu Met Leu Tyr Lys Phe Asp Phe Gln Thr Gln Val Leu Thr Lys Lys
                580                 585                 590

Ile Asn Met Ile Ser Gly Ile Ser Thr Phe Glu Lys Lys Lys Glu Asn
                595                 600                 605

Gln Lys Lys Ile Ile Leu Leu Glu Lys Glu Leu Tyr Lys Asn Glu Asp
610                 615                 620

Ile Tyr Asn Thr Leu Asn Asn Glu Met Lys Arg Ile Asn Ile Glu Ile
625                 630                 635                 640

Lys Asn Ile Lys Leu Tyr Gln Asn Glu Leu Gln Glu Gln Lys Met Asn
                645                 650                 655

Tyr Lys Asn Leu Tyr Glu Lys Leu Gln Leu Glu Ile Lys Ser Leu Glu
                660                 665                 670

Ser Thr Ile Asn Asn Glu Ile Lys Glu Lys Glu Asn Ile Met Leu Ile
                675                 680                 685

Glu Leu Asn Leu Lys Ile Glu Leu Asp Lys Leu Lys Ser Thr Phe Ser
690                 695                 700

Lys His Val Asp Asn Leu Asn Ile Cys Lys Lys Glu Lys Lys Glu Asn
705                 710                 715                 720

Met Asn Asn Ala Lys Leu Ser Glu Gln Asp Ile Asn Ala His Met Glu
                725                 730                 735

Ser Leu Lys Val Ile Ile Lys Asn Ile Asn Asp Glu Ile His Lys Leu
                740                 745                 750

Asn Ile Gln Leu Tyr Glu Lys Lys Asn Lys Ser Asn Asn Leu Gln Leu
                755                 760                 765

Lys Leu Asn Ser Ile Ile Ile Cys Asn Gln Lys Asn Lys Asp Gln Lys
770                 775                 780

Asp Ile Cys Pro Asn Glu Asn Gln His Ile Tyr Tyr Lys Met Lys Ile
785                 790                 795                 800

Asp Gln Asp Ile Ile Asn Leu Lys Glu Gln Leu Lys Lys Ile Asn Glu
                805                 810                 815

Gln Ile Asp Lys Glu Asn Ile Glu Thr Lys Asn Phe Gln Arg Thr Leu
                820                 825                 830

Asp Asp Ile Ile Gln Thr Asn Lys Glu Phe Asn Asp Asn Ile Lys Ser
                835                 840                 845

Ile Asp Pro Gln Tyr Lys Ile Leu Leu Lys Lys Lys Asn Lys Leu Asn
850                 855                 860

Lys Lys Trp Glu Gln Ile Asn Asp His Ile Asn Asn Leu Glu Thr Asn
865                 870                 875                 880

Ile Asn Asp Tyr Asn Lys Lys Ile Lys Glu Gly Asp Ser Gln Leu Asn
                885                 890                 895

Asn Ile Gln Leu Gln Cys Glu Asn Ile Glu Gln Lys Ile Asn Lys Ile
                900                 905                 910

Lys Glu Ser Asn Leu Lys Val Glu Asn Asn Ile Asn Asp Leu Phe Ile
                915                 920                 925

Lys Ile Glu Arg Ala Ser Asn Gln Leu Lys Lys Asn Leu Ala Pro Thr
930                 935                 940
```

```
Thr Asn Met Met Lys Leu Lys Asn Lys Gln Ile Lys Asp Asp Glu Asn
945                 950                 955                 960

Asn Leu Ser Asn Asn Asn Asn Asn Asn Asn Asn Asn Asn Asn Asn Ile
            965                 970                 975

Asn Val Asn Val Asn Val Asn Cys Glu Pro Val Pro Leu Lys His
        980                 985                 990

Ile Phe Lys Gln Ile Gln Met Glu  Ser Leu Lys Glu Lys  Leu Ser Leu
        995                 1000                1005

Leu Met  Glu Cys Phe Lys Asn  Asn Ile Asp Asn Val  Ile Met Lys
    1010             1015                 1020

Glu Val  Phe Asn Leu Ile Glu  Thr Ala Glu
    1025             1030

<210> SEQ ID NO 52
<211> LENGTH: 55
<212> TYPE: PRT
<213> ORGANISM: Plasmodium falciparum

<400> SEQUENCE: 52

Lys Asn Lys Leu Asn Lys Lys Trp Glu Gln Ile Asn Asp His Ile Asn
1               5                   10                  15

Asn Leu Glu Thr Asn Ile Asn Asp Tyr Asn Lys Lys Ile Lys Glu Gly
            20                  25                  30

Asp Ser Gln Leu Asn Asn Ile Gln Leu Gln Cys Glu Asn Ile Glu Gln
        35                  40                  45

Lys Ile Asn Lys Ile Lys Glu
    50                  55

<210> SEQ ID NO 53
<211> LENGTH: 1711
<212> TYPE: PRT
<213> ORGANISM: Plasmodium falciparum

<400> SEQUENCE: 53

Met Asn Asn Ile Thr Ile Arg Lys Pro Leu Phe Glu Val Pro Asn Glu
1               5                   10                  15

Asn Lys Ser Asn Val Leu Lys Tyr Glu Lys Asp Asn Asp Phe Asn Asn
            20                  25                  30

Lys Lys Asn Asp Pro Ser Asn Leu Glu Ser Tyr Ile Ser Ser Thr Leu
        35                  40                  45

Pro Tyr Lys Arg Ile Glu Asn Asn His His Asn Tyr Asn Asn Ala Lys
50                  55                  60

Tyr Asp Glu Asn Asn Lys Asn Asp Asp His Ile Pro Leu Asp Leu
65              70                  75                  80

Asn Asn Lys Glu Asn Met Asn Phe Phe Val Lys Lys Asn Ile His
                85                  90                  95

Asn Ser Asn Leu Asn Tyr Asn His Asp Asn Ile Leu Gln Ser Tyr Arg
            100                 105                 110

Asn Gly Glu Ile Asn Arg Asn Tyr Asn Ile Met Asp Asn Met Tyr Asp
        115                 120                 125

Val Tyr Tyr Ile Asn Lys Ser Lys Ala Asn Leu Asn Asp Tyr Leu Lys
130                 135                 140

His Val Asn Ile Asn His Thr Ala Pro Cys Ile Gly Glu Phe Arg Thr
145                 150                 155                 160

Cys Met Asn Cys Phe Leu Asn Ile Ser Thr Leu Phe Cys Lys Thr Cys
                165                 170                 175

Asn Ile Phe Leu Cys Ala Ile Cys Asn Val Lys Leu His Asn Asn Lys
```

```
                180                 185                 190
Ser Asn His Ile Ile Asn Val Ala Ser Ser Gly Leu Tyr Glu Asn Asn
                195                 200                 205
Val Lys Phe Asn Asp Ile Ile Leu Lys Glu Lys Asp Lys Trp Leu Val
                210                 215                 220
Glu Leu Asp Asn Ser Ile Pro Ile Lys Ile Arg Glu Lys Cys Ser Val
225                 230                 235                 240
His Thr Lys Glu Tyr Ile Lys Tyr Val Cys Lys Thr Cys Lys Tyr Thr
                245                 250                 255
Leu Leu Cys Ala Asp Cys Leu Leu Asn Asp Pro Val His Val Gln Asn
                260                 265                 270
Lys Met Glu Asn Asp Met Asn Ile Ile Lys Asn Asp Met Asn Ile Met
                275                 280                 285
Glu Asn Asp Met Asn Ile Met Glu Asn Asp Met Asn Ile Ile Lys Asn
                290                 295                 300
Asp Met Asn Ile Met Glu Lys Asp Met Asn Ile Ile Lys Asn Asp Met
305                 310                 315                 320
Asn Ile Ile Lys Asn Asn Met Asn Ile Ile Lys Asn Glu Met Asn Ile
                325                 330                 335
Ile Lys Asn Val Pro Glu Gln Lys Arg Lys Asn Glu His Phe Leu Pro
                340                 345                 350
Glu Gln Val Gln Glu Asn Asn Asp Asn Lys Asn Gly Ser Lys Asn Asp
                355                 360                 365
Lys Asn Leu Lys Asp Ser Asn Lys Lys Arg Glu Asn Gln Tyr Ile
                370                 375                 380
Val Ser Ile Tyr Lys Lys Glu Thr Ser Asp Ser Asn Asn Lys Asp
385                 390                 395                 400
Ile Ile Lys Asp Val Ile Tyr Asn Asn Asp Ile Asp Lys Leu Lys Pro
                405                 410                 415
Gly Phe Lys Leu Ile Arg Gly Asn His Glu Ile Leu Thr Leu Ile Asp
                420                 425                 430
Ala Arg Asn Asp Ile Lys Glu Glu Leu Asn Asn Lys Leu Glu Ile Leu
                435                 440                 445
Cys Lys Lys Ser Leu Ile Leu Lys Asn Thr Leu Pro Ser Leu Arg Asn
                450                 455                 460
Ile Cys Lys Tyr Gly Lys Ile Thr Cys Lys Asn Asn Lys Arg Ser Ile
465                 470                 475                 480
Arg Ser Gly Phe Thr Val Thr Asn Asn Ile Leu Asn Asp Lys Lys Val
                485                 490                 495
Lys Ile His Asn Asp Leu Lys Lys Leu Gln Asp Lys Ser Thr Asn Phe
                500                 505                 510
Leu Lys Lys Leu Asp Gln Glu Arg Ile Asn Tyr Arg Asn Tyr Leu Glu
                515                 520                 525
Lys Lys Lys Ser Glu Leu Gln His Met Ile Lys Leu Ser Asn Lys Asn
                530                 535                 540
Ala Gly Leu Ala Leu Asp Tyr Tyr Val Gln Lys Leu Glu Ser Phe Lys
545                 550                 555                 560
Cys Leu Phe Phe Thr Lys Asp Asn Leu Ile Asp Ile Glu Lys Lys Leu
                565                 570                 575
Glu Val Pro His Ser Lys Ile Lys Ser Glu Phe Leu Ser Phe Leu Ile
                580                 585                 590
Glu Glu Met Lys Tyr Asp Ile Leu Asn Ser Lys Met Asn Ile Gln Asn
                595                 600                 605
```

```
Arg Cys Gln Ser Ile Thr Lys Glu Phe Glu Gln Leu Phe Asn Cys Asn
610                 615                 620

Ile Glu Ile Pro Val Tyr Pro Val His Phe Arg Asp Phe Leu Lys Lys
625                 630                 635                 640

Arg Thr Phe Asn Asn Lys Gln Asp Val His Leu Ile Ser Asn Asp Lys
                645                 650                 655

Lys Lys Lys Gln Gln Tyr Phe His Ile Leu Pro Phe Thr Asp Phe Tyr
            660                 665                 670

Met Asn Ile Glu Ile Ser Tyr Gln Ile Lys Cys Lys Arg Lys Asp Ser
            675                 680                 685

Leu His Ser Lys Trp Glu Lys Arg Thr Val Ser Val Arg Ser Ile Tyr
            690                 695                 700

Leu Cys Ile His Thr His Ser Arg Tyr Ile Lys Arg Ser Asn Lys Tyr
705                 710                 715                 720

Gln Asn Asp Glu Phe Asp Glu Asn Val Ser His Lys Asn Asp Ala Val
                725                 730                 735

Gly Ser Ile Ala Tyr Glu Met Glu Gln Asn Glu Ile Asn Glu Gln Glu
                740                 745                 750

Arg Arg Asp Gly Glu Met Leu Gly Val Asp Glu Met Glu Asn Arg Asn
                755                 760                 765

Lys Ile Glu Asn Tyr Glu His Ile Asp Asn Ala Ser Ser Glu Ile Ser
770                 775                 780

Asn Lys Glu Asn Cys Leu Ile Gln Lys Asn Met Ser Asn Asn Leu Ser
785                 790                 795                 800

Asn Asp Ile Glu Ser Ile Ile Cys Leu Ser Asn Val Glu Ile Lys Met
                805                 810                 815

Phe Asn Asp Pro Asn Ile Thr Asn Ile Thr Ile Leu Glu Lys Arg Asn
                820                 825                 830

Tyr Ser Tyr Gly Ile Glu Leu Thr Glu Tyr Asn Asp Lys Lys Asp Leu
                835                 840                 845

Val Gly Tyr Trp Leu Leu Ser Gln Asn Asn Glu Lys Asp Met Lys Glu
850                 855                 860

Leu Tyr His Ile Leu Cys Ala Ile Lys Lys Lys Asn Pro Lys Ala Ala
865                 870                 875                 880

Arg Ile Pro Ser Phe Tyr Pro Lys Ile Asn Met Asn Asn Ser Met Phe
                885                 890                 895

Asn Tyr His Glu Asn Asn Ile Ser Thr Ile Tyr Lys Asn Phe Ser Ala
                900                 905                 910

Asn Leu Ile Glu Pro Ser Tyr Phe Ile Asn Thr Ser Glu His Glu Lys
                915                 920                 925

Asp Glu Arg Asp Gly Lys Tyr Leu Glu Ala Ser Ile Asn Asp Tyr Met
930                 935                 940

Ser Asp Asp Lys Lys Lys Lys Arg Tyr Asp Ser Ile Glu Ser Leu Arg
945                 950                 955                 960

Gly Ser Asp Lys Ile Lys Asn Asp Gln Ile Tyr Gln Gly Gly His Ser
                965                 970                 975

Ser Ser Leu Leu Tyr Tyr Tyr Asp Asn Asn Asp Asn Asn Asn
                980                 985                 990

Asn Met Tyr Asp Ser Ser Ser Ser Asn His Asn Tyr Tyr Ile Leu
                995                 1000                1005

Thr Asn Asp Lys Arg Leu Asn Met Asp Asn Phe Ile Asn Asn Asn
    1010            1015            1020

Leu Glu Ile Asn Asn Ser Gln Asn Lys Val Ile Glu Lys Asn Leu
    1025            1030            1035
```

-continued

```
Glu Tyr Ile Asn Asn Val Lys Leu Thr Lys Thr Ser Asn Tyr Glu
    1040            1045                1050

Gln Ser Asn Asn Thr Asn Ser Lys Asp Glu His Asn Ile Ser Ser
    1055            1060                1065

Asp Lys Ser Lys Lys Glu Asp Thr Leu Asn Leu Ser Arg Lys Ser
    1070            1075                1080

Ser Tyr Glu Tyr Asn Asn Lys Ile Leu Gln Ser Thr Ser Asn Lys
    1085            1090                1095

Ser Leu Asn Gly Ala Tyr Glu Asn Asn Leu Phe Ser Gly Lys Lys
    1100            1105                1110

Lys Lys Asn Lys Gly Thr Val Leu Lys Asp Ile Glu His Ile Asn
    1115            1120                1125

Asp Ile Gln Asp Lys Tyr Pro Glu Asp Leu Asn Ile Asn Cys Val
    1130            1135                1140

Asn Lys Tyr Val Ile Glu Asn Glu Glu Lys His Leu Leu Pro Leu
    1145            1150                1155

Glu Leu Glu Tyr Asn Leu Val Ser Ser Asp Glu Lys Phe Gly Leu
    1160            1165                1170

Asn Lys Ile Lys Asn Asp Asn Asn Ile Ile Tyr Met Lys His Gln
    1175            1180                1185

Asn Tyr His Asn Leu Tyr Asp Asn Gln Lys Lys His Ile Leu
    1190            1195                1200

Phe Asp Thr Asn Lys Asn Val Ser Ile Gln Arg Asn Asn Asn Ile
    1205            1210                1215

Asn Ser Val Ile Lys Thr Asn His Tyr Glu Val Glu Lys Asn Asn
    1220            1225                1230

Lys Asp Gln Arg Asn Tyr Asp Asn Phe Thr Cys Asp Lys Lys Lys
    1235            1240                1245

Lys Ile Tyr Tyr Asn Ile Ile Asn Ser Asp Lys Asp Ile Tyr His
    1250            1255                1260

Asn Asn Ile Ile Tyr Thr Lys Asn Glu Lys Glu Gly Ile Gly Asn
    1265            1270                1275

Ile His Leu Asn Arg Asn Asp Lys Asp Ile Thr Asn Phe Glu Leu
    1280            1285                1290

Leu Lys Leu Asp Gly Val Lys Glu Phe Leu Asp Thr Phe Lys Asp
    1295            1300                1305

Ser Tyr Ile Asp Cys His Asn Lys Lys Glu Asn Ile Leu Asn Met
    1310            1315                1320

Thr Asn Lys Asn Lys Glu Asp His Gln Ile Ile Asp Val Ala Asp
    1325            1330                1335

Lys Ile Phe Asn Glu Thr Asn Met Ile Thr Met Asp Asn Asn Lys
    1340            1345                1350

Ile Tyr Asp Asp Lys Asn Val His Glu Lys Lys Cys Thr His Asn
    1355            1360                1365

Asp Val Ile His His Asn Met Asp Ile Leu Ser Thr Ser Ile Lys
    1370            1375                1380

Asn Asn Glu Glu Asn Leu Phe Ile Asp Thr Tyr Gln Lys Gln Asn
    1385            1390                1395

Arg Ile Gly Asp Ile Tyr Met Asn Arg Ile Asn Ile Leu Gln Glu
    1400            1405                1410

Asp Asp Asp Asp Asp Asn His Asn Asn Asn His Asn Asn Asn Asn
    1415            1420                1425

Asn Asn Asn Lys Leu Ile Leu Phe Glu Tyr Thr Lys Asn Asp Gln
```

-continued

```
                1430                1435                1440

Met Leu His Asn Asn Lys Asn Asn Leu Glu Gly Thr Glu Glu Phe
    1445                1450                1455

Ser Asp Phe Ile Glu Lys Lys Asn Lys Ile Lys Ile Lys Asn Lys
    1460                1465                1470

Asn Glu Ser Tyr His Lys Ile Asp Glu Ser Leu Leu Ser Asn Glu
    1475                1480                1485

Lys Asn Asn Lys Val Ser Leu Leu Leu Ile Asn Asn Asn Lys Asp
    1490                1495                1500

Ser Ser Ser Val Asp Asn Asn Lys Asn Asn Asn Lys Asn Asn
    1505                1510                1515

Asn Asn Lys Asn Asn Asn Asn Glu Asn Asn Asn Lys Asn Asn Lys
    1520                1525                1530

Asn Asn Asn Asn Asp Ser Phe Ser Lys Asp Asn Asn Leu Ile Asn
    1535                1540                1545

Asn Asp Asn Asn Asn Asn Asn Asn Asn Asp Ser Phe Ser Lys
    1550                1555                1560

Asp Asn Asn Leu Ile Asn Asn Asp Asn Asn Asn Asn Asn Asn
    1565                1570                1575

Asn Asn Lys Val Ile Lys Lys Glu Ile Ile Asp Lys Glu Lys
    1580                1585                1590

Asn Asp Ile His Lys Arg Asp Asn Ile Tyr Ile Lys Asp Val Ser
    1595                1600                1605

Val Ser Pro Leu Ile Asn Asn His Pro Asn Leu Asn Ser Met Arg
    1610                1615                1620

Lys Asp Arg Thr Ile Glu Pro Leu Lys Ile Ile Asn Gly Lys Asn
    1625                1630                1635

Lys Leu Ile Lys Asp Leu Lys Lys Ile Gln Glu Gln Val Glu Arg
    1640                1645                1650

Lys Ile Arg Lys Tyr Lys Ile Gln Met Asp Gln Glu Asn Lys Lys
    1655                1660                1665

Pro Pro Pro Ser Lys Asn Lys Ile Asn Met Lys Ser Ile Asn Leu
    1670                1675                1680

Asp Ile Asp Asp Asp Gln Asn Val Asp Ser Gln Gly Ile Val Asp
    1685                1690                1695

Tyr Val Leu Asn Gln Ile Gly Asn Lys Lys Met Gly Gln
    1700                1705                1710

<210> SEQ ID NO 54
<211> LENGTH: 70
<212> TYPE: PRT
<213> ORGANISM: Plasmodium falciparum

<400> SEQUENCE: 54

Gln Asn Lys Met Glu Asn Asp Met Asn Ile Ile Lys Asn Asp Met Asn
1               5                   10                  15

Ile Met Glu Asn Asp Met Asn Ile Met Glu Asn Asp Met Asn Ile Ile
            20                  25                  30

Lys Asn Asp Met Asn Ile Met Glu Lys Asp Met Asn Ile Ile Lys Asn
        35                  40                  45

Asp Met Asn Ile Ile Lys Asn Asn Met Asn Ile Ile Lys Asn Glu Met
    50                  55                  60
```

-continued

Asn Ile Ile Lys Asn Val
65                  70

<210> SEQ ID NO 55
<211> LENGTH: 24
<212> TYPE: DNA
<213> ORGANISM: Artificial Sequence
<220> FEATURE:
<223> OTHER INFORMATION: Plasmodium falciparum primer

<400> SEQUENCE: 55
tctcttctac atacgcttta ttca                                          24

<210> SEQ ID NO 56
<211> LENGTH: 25
<212> TYPE: DNA
<213> ORGANISM: Artificial Sequence
<220> FEATURE:
<223> OTHER INFORMATION: Plasmodium falciparum primer

<400> SEQUENCE: 56
gataattcgt ttaatgagga gtcca                                         25

<210> SEQ ID NO 57
<211> LENGTH: 31
<212> TYPE: DNA
<213> ORGANISM: Artificial Sequence
<220> FEATURE:
<223> OTHER INFORMATION: Plasmodium falciparum primer

<400> SEQUENCE: 57
acactttgca cagttcctat cttctcttct a                                  31

<210> SEQ ID NO 58
<211> LENGTH: 32
<212> TYPE: DNA
<213> ORGANISM: Artificial Sequence
<220> FEATURE:
<223> OTHER INFORMATION: Plasmodium falciparum primer

<400> SEQUENCE: 58
agaaggagaa gaagaaaata aagaggatga ag                                 32

SUB-REGION OF A PLASMODIUM PROTEIN WITH IMPROVED VACCINE POTENTIAL, AND MEDICAL USES THEREOF

CROSS REFERENCE TO RELATED APPLICATIONS

This application is a National Stage filing under 35 U.S.C. §371 of PCT Application No. PCT/IB2009/051875, filed on May 7, 2009. This application also claims the benefit of European Patent Application No. 08290433.5, filed on May 7, 2008. The entirety of both applications is incorporated hereby reference.

FIELD OF THE INVENTION

The invention pertains to the field of pathogen polypeptidic antigens and nucleic acids coding therefor, and their uses, notably their medical uses, for example, for the curative and/or preventive and/or palliative treatment of a disease related to said pathogen, e.g., by vaccination against said pathogen, and for the diagnosis of a disease related to said pathogen.

More specifically, the present invention relates to antigenic polypeptidic antigens deriving from Plasmodium species sequences, to antibodies directed to said antigens, to nucleic acids coding therefor, to compositions containing said antigens and/or antibodies and/or nucleic acids, as well to method of producing and using same, more specifically in the field of malaria treatment and diagnosis.

BACKGROUND OF THE INVENTION

Malaria is responsible for over a million deaths a year, with most of the victims being young children. One of the most cost-effective interventions to reduce this toll would be the development of a safe and effective vaccine against *Plasmodium falciparum*, the causative agent of the most severe form of the disease. Individuals living in malaria-endemic regions develop clinical immunity associated with high antibody titers against surface molecules of blood stages (in particular, the merozoite) of the parasite.

Vaccines against the blood stages of the parasite could reduce the morbidity and mortality, particularly among children. They could also accelerate the acquisition of natural immunity, and help maintain it through constant boosting of the immune response by naturally occurring infections.

Passive transfer studies have shown that immunoglobulins from semi-immune individuals can confer clinical immunity to individuals exposed to geographically diverse parasite strains.

Most epitopes recognized by antibodies represent three-dimensional surfaces of an antigen molecule that fit precisely the binding surfaces of the corresponding antibodies (for a review, see Corradin et al., 2007 *Endocrine, Metabolic & Immune Disorders—Drug Targets*, 7: 259-265).

These epitopes are classified into distinct groups: linear and structural epitopes. Linear epitopes are made of a continuous unstructured stretch of amino acid residues, while structural protein segment(s) which may be discontinuous (for example, loops) or not. Linear epitopes usually have flexible unfolded conformations and are located in large unstructured loops or terminal protein regions. They can be, in general, mimicked by short protein segments obtained either by protein fragment, or, more simply, by peptide synthesis. Thus, at first sight, linear epitopes do not seem to represent a major technical challenge. However, several estimates that only 10% of the antibodies elicited during an immune response are directed against linear epitopes. Thus most antibodies are raised against discontinuous structural epitopes.

Therefore, research has up to now mainly focussed on structural or conformation-dependent epitopes, and on the production of short, structurally stable protein segments, which, as isolated peptides, are able to fold into the native structure and thus be recognized by conformation-dependent antibodies. Such structural or conformation-dependent domains notably encompass globular functional domains (such as zinc-fingers, knottins, animal toxins, FGF molecules, chemokines), and structural motifs of protein made of tandem repeats, such as alpha-helical coiled coil domains. For example, WO 2007/020520 in the names of Université de Lausanne and Institut Pasteur describes *Plasmodium* peptidic antigens, such as the P27 antigen (SEQ ID NO: 27 in this PCT international application), which mimic the alpha-coiled coil domain of the native MAL6P1.37 (also referred to as PFF0165c) protein of *Plasmodium falciparum* 3D7.

By contrast, the natively unfolded or unstructured regions of *Plasmodium* proteins (which are also referred to as IUPs, standing for Intrinsically Unstructured Proteins, see Zhi-Ping Feng et al., 2006 *Molecular & Biochemical Parasitology*, 150: 256-267) do not fold in any particular unique structure. Natively unfolded or unstructured regions of *Plasmodium* proteins can be identified in the sequence of proteins by bioinformatics analysis (Oldfield et al. 2005 *Biochemistry* 44: 1989-2000; Linding et al. 2003 *Structure (Camb)* 11: 1453-1459; Coeytaux and Poupon 2005 *Bioinformatics* 21: 1891-1900; Dosztanyi et al. 2005 *Bioinformatics* 21: 3433-3434). At least 15 online services have been established to identify such structures. One of the most widely used services is DisEMBL large-scale sequence analysis (Linding et al. 2003 *Structure (Camb)* 11: 1453-1459; Zhi-Ping Feng et al., 2006 *Molecular & Biochemical Parasitology*, 150: 256-267). The DisEMBL comprise three different predictors, Loops/coils, Hot-Loops and REMARK465, which are based on the same algorithm but different training sets, to predict the ordered or disordered state of a residue (cf. dis.embl.de/html/help.html).

In malaria parasites, about 40% of genome-encoded proteins contain natively unstructured regions with segments longer than 50 amino acids. Many of these proteins have a highly hydrophilic amino acid sequence that cannot form a hydrophobic core needed to stabilize a globular structure. Some of these proteins or fragments thereof are currently being developed as vaccine candidates. These comprise the repeat region of the circumsporozoïte (CS) protein, as well as selected segments of MSP2, MSPS and GLURP of *P. falciparum*, and the N-terminal and repeat regions of the CS protein of *P. vivax*.

One of the difficulties in developing peptide antigen from such natively unfolded or unstructured regions of *Plasmodium* proteins is the difficulty of selecting candidates from the large number of predicted unstructured regions found in genomes, and their potential amyloidogenicity.

The inventors have identified polypeptides deriving from a protein of *Plasmodium falciparum*, which are unfolded or unstructured polypeptides, and which show improved properties with respect to prior art peptides or polypeptides.

The *P. falciparum* protein, from which the polypeptides of the invention derive, is the MAL6P1.37 (also referred to as PFF0165c) protein of *Plasmodium falciparum* 3D7 (accession number of the protein sequence: XP_966024). This 1103 amino acid-long protein is encoded by chromosome 6 of *P. falciparum* and only is a predicted protein, with no known function yet.

The present inventors demonstrate that unfolded or unstructured polypeptides, which derive from this predicted protein, have a high antigenicity, a high immunogenicity, and have a parasite-killing activity in the Antibody-Dependent Cellular Inhibition (ADCI) assay that is as high as, or higher than the structured P27 peptide disclosed in WO 2007/020520.

Furthermore, the total proportion of individuals who, under natural exposure to a malaria parasite, respond by specific IgG1 and IgG3, i.e., the most critical IgG subclasses, is higher for the polypeptides of the invention, such as the P27A than for other antigens, including peptide P27.

For an illustration of this effect and advantage, please see e.g., the prevalence values indicated in Table 2 in example 2 below, as well as the prevalence values indicated below the diagram of FIG. 4. The total proportion of individuals who, under natural exposure to a malaria parasite, respond by specific IgG1 and IgG3, is higher for the polypeptide of the invention P27A (anti-P27A specific IgG1: 86.7% of the individuals; anti-P27A specific IgG3: 82.2% of the individuals) than for other antigens, including peptide P27 (anti-P27 specific IgG1: 6.7%; anti-P27 specific IgG3: 95.6%).

Moreover, the polypeptides of the invention are strongly associated with clinical protection against malaria. In human beings under natural exposure to the parasite, the polypeptides of the invention induce specific antibodies (IgG1 and IgG3) that are very strongly associated with a state of resistance to malaria (statistical association, as assessed by a multivariate analysis made in accordance with the methodology described in Roussilhon et al. 2007 PLoS medicine 4(11): 1791-1803, with p<0.0014). Parasite-induced antibodies that are specific of the polypeptides of the invention are present in individuals, who resist to malaria and are absent, or are present at low titers, in individuals, who have malaria attack.

This association with resistance to malaria is much stronger for the polypeptides of the invention than for the prior art antigens, such as the P27 peptide disclosed in WO 2007/020520. Additionally, the polypeptides of the invention, in particular the conservative variant as defined herein, are different from those disclosed in this prior art.

Although there has been some progress in the treatment of malaria, the development of a safe and effective malaria vaccine remains an urgent unmet medical need for vast populations living in malaria-endemic region.

This object has been achieved by providing a polypeptide which is a fragment or variant of PFF0165c protein of *P. falciparum*, the amino acid sequence of which is i) the sequence of SEQ ID NO: 6; ii) the sequence of a fragment of said sequence of SEQ ID NO: 6; or ii) a conservative variant, which derives from said sequence of SEQ ID NO: 6 or from said fragment of SEQ ID NO: 6 by at least one conservative amino acid substitution and/or at least one conservative internal amino acid deletion.

For an illustration of this effect and advantage, please see e.g., table 3 in example 2 below, showing the F and p values of a multivariate analysis of the association with a state of resistance to malaria, wherein antibodies specific of the P27A polypeptide of the invention have the highest F ratio (28.55, with p<0.0001).

SUMMARY OF THE INVENTION

The present invention relates to polypeptides, antibodies, hybridomas, nucleic acids, vector, host cells, and uses thereof, as described below.

More particularly, the present invention relates to polypeptides, which are fragments or variants of the PFF0165c protein of *P. falciparum*. The polypeptides of the invention are sub-fragments of the fragment 1-844 (SEQ ID NO: 6 or 8) of said protein, which have retained the sequence extending from position 223 to position 326 (SEQ ID NO: 10 or 12) of said protein, or are variants of such sub-fragments.

The polypeptide of SEQ ID NO: 10 or NO: 12 has an unfolded or unstructured 3D-arrangement.

The polypeptides of the invention are efficient in the treatment of a *Plasmodium*-related disease, more particularly of malaria. They are specifically intended for the palliative and/or curative treatment of such a disease, and are specifically suitable to infants, toddlers, children under the age of 5, pregnant women.

The antibodies of the invention can be used for passive immunotherapy or for the diagnosis of a *Plasmodium*-related disease, more particularly of malaria.

The nucleic acids of the invention notably include primers and probes for the detection of *Plasmodium* species, more specifically for the detection of *Plasmodium falciparum* strain(s). They can also be used for the diagnosis of a *Plasmodium*-related disease, more particularly of malaria.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 1: nucleic acid and protein sequences of the BFFc protein of *P. falciparum* 3D7.

FIG. 5: unstructured or unfolded 3D-arrangement of P27A. Structure of the 1-160 fragment of PFF0165c, which contains the polypeptide P27A (SEQ ID NO: 10, shown in black).

DETAILED DESCRIPTION OF THE INVENTION

Figure 2:
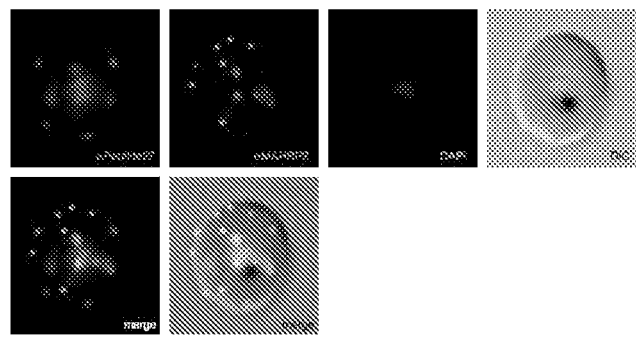
FIG. 2: human affinity-purified antibodies and murine antibodies induced by immunization against P27 and P27A specifically stain Pf-infected erythrocytes but not sporozoites.

In the present application, reference is made to the following sequences:

TABLE 1

| | SEQ ID NO: | |
|---|---|---|
| | Nucleic acid | Protein |
| Protein PFF0165c of *Plasmodium falciparum* 3D7 [mRNA accession number XM_960931; protein accession number XP_966024] | 1 | 2 |
| E292G SNP variant thereof, prevalent in certain areas such as Papua New Guinea and Tanzania | 3 | 4 |
| Polypeptide P27AA (fragment 1-844 of the protein PFF0165c of SEQ ID NO: 2) | 5 | 6 |

TABLE 1-continued

| | SEQ ID NO: | |
|---|---|---|
| | Nucleic acid | Protein |
| E292G SNP variant thereof, prevalent in certain areas such as Papua New Guinea and Tanzania (fragment 1-844 of the protein PFF0165c of SEQ ID NO: 4) | 7 | 8 |
| Polypeptide P27A (fragment 223-326 of the protein PFF0165c of SEQ ID NO: 2) | 9 | 10 |
| E292G SNP variant thereof, prevalent in certain areas such as Papua New Guinea and Tanzania (fragment 223-326 of the protein PFF0165c of SEQ ID NO: 4) | 11 | 12 |
| Polypeptide P27 (fragment 845-871 of the protein PFF0165c of SEQ ID NO: 2) | 13 | 14 |
| Polypeptide P27A-P27 (fragment 223-844 of the protein PFF0165c of SEQ ID NO: 2) | 15 | 16 |
| E292G SNP variant thereof, prevalent in certain areas such as Papua New Guinea and Tanzania (fragment 223-844 of the protein PFF0165c of SEQ ID NO: 4) | 17 | 18 |
| Polypeptide P27A' (fragment 1-326 of the protein PFF0165c of SEQ ID NO: 2) | 19 | 20 |
| E292G SNP variant thereof, prevalent in certain areas such as Papua New Guinea and Tanzania (fragment 1-326 of the protein PFF0165c of SEQ ID NO: 4) | 21 | 22 |
| Polypeptide P27A" (fragment 1-640 of the protein PFF0165c of SEQ ID NO: 2) | 23 | 24 |
| E292G SNP variant thereof, prevalent in certain areas such as Papua New Guinea and Tanzania (fragment 1-640 of the protein PFF0165c of SEQ ID NO: 4) | 25 | 26 |

In the present application, the amino acid positions are computed with respect to the sequence of the full-length PFF0165c protein, which consists of 1103 nucleotides (SEQ ID NO: 2 or 4). Please see FIG. 1.

Therefore, the sequence of SEQ ID NO: 10 is:

HNNNEKNISYDKNLVKQENDNKDEARGNDNMCGNYDIHNERGEMLDKGKS

YSGDEKINTSDNAKSCSGD<u>E</u>KVITSDNGKSYDYVKNESEEQEEKENMLNN

KKRS

The sequence of SEQ ID NO: 12 is:

HNNNEKNISYDKNLVKQENDNKDEARGNDNMCGNYDIHNERGEMLDKGKS

YSGDEKINTSDNAKSCSGD<u>G</u>KVITSDNGKSYDYVKNESEEQEEKENMLNN

KKRS

The invention relates to a polypeptide, the amino acid sequence of which is:

i) the sequence of SEQ ID NO: 6 (fragment 1-844 of the sequence of SEQ ID NO: 2);

ii) the sequence of a fragment of said sequence of SEQ ID NO: 6, said fragment having retained the sequence (SEQ ID NO: 10) extending from position 223 to position 326 of said sequence of SEQ ID NO: 6; or iii) a conservative variant, which derives from said sequence of SEQ ID NO: 6 of i) or from said fragment of SEQ ID NO: 6 of ii) by at least one conservative amino acid substitution and/or at least one conservative internal amino acid deletion, provided that said conservative variant has one the following properties:

a. said conservative variant has retained an unstructured or unfolded 3D-arrangement, said unstructured or unfolded 3D-arrangement being as defined below, e.g., as assessed by the Hot-Loops predictor of the Dis-EMBL-1.4 software, the six parameters of the software being left at their default settings;

b. said conservative variant has not acquired a globular functional domain (such as a zinc-finger, knottin, animal toxin, FGF molecule, chemokine), nor a structural motif of protein made of tandem repeats, such as an alpha-helical coiled coil domain;

c. said conservative variant has retained the property of inducing IgG1 and/or IgG3 antibodies, more particularly, specific IgG1 and/or IgG3, for example when it is injected (e.g., subcutaneously) as an immunogen in a test animal, e.g., a non-human animal, such as a mouse (for example, C3H and/or CB6F1 and/or outbred ICR mice), at a dose of 20 µg with the Montanide® ISA-720 adjuvant;

d. said conservative variant has retained the property of inducing antibodies that are specific of the *Plasmodium*-infected erythrocytes, preferably of *Plasmodium falciparum*-infected erythrocytes, but not of sporozoites, e.g., when it is injected (e.g., subcutaneously) as an immunogen in a test animal, e.g., a non-human animal, such as a mouse (for example, C3H and/or CB6F1 and/or outbred ICR mice) at a dose of 20 µg with the Montanide® ISA-720 adjuvant;

e. in the ADCI assay, said conservative variant has retained an inhibitory effect on *Plasmodium* growth (preferably on the growth of a *Plasmodium falciparum* strain such as the 3D7 strain) that is of at least 90%, preferably of at least 92%, e.g., it has retained the property of:
   inducing specific IgG1 and/or IgG3, [e.g., by subcutaneous injection of a dose of 20 µg with the Montanide® ISA-720 adjuvant in a test animal, preferably a non-human animal, such as a mouse (for example, C3H and/or CB6F1 and/or outbred ICR mice), collection of the IgG produced 10 days after said injection, and isolation of the IgG1 and/or IgG3, which specifically bind to said conservative variant],
   wherein said induced IgG1 and/or IgG3 have a SGI value of at least 90%, preferably of at least 92%, in the ADCI assay (i.e., said induced IgG1 and/or IgG3 induce at least 90%, preferably at least 92% of inhibition of a *Plasmodium falciparum* strain such as the *Plasmodium falciparum* 3D7 parasite growth in a monocyte-dependent manner);

f. said conservative variant has retained the property that, in humans under natural exposure to a malaria parasite, the total proportion of individuals having IgG1 and IgG3 antibodies that are specific of this conservative variant is higher than the total proportion of individuals having IgG1 and IgG3 antibodies that are specific of prior art peptides or polypeptides, including peptide P27 (SEQ ID NO: 14); more particularly, the proportion of individuals having IgG1 antibodies that are specific of this conservative variant is higher than the proportion of individuals having IgG1 antibodies that are specific of prior art peptides or polypeptides, including peptide P27 (SEQ ID NO: 14);

g. said conservative variant has retained the property that, in human beings under natural exposure to the parasite, it induces specific antibodies (IgG1 and IgG3) that are very strongly associated with a state of resistance to malaria;

h. said conservative variant has retained the property that parasite-induced antibodies, which are specific of said conservative variant, are present in individuals, who resist to malaria and are absent, or are present at lower titers, in individuals, who have malaria attack;

i. said conservative variant has retained the sequence of SEQ ID NO: 10, or comprises an ortholog variant sequence of said sequence of SEQ ID NO: 10 thereof, said ortholog variant sequence being the ortholog of SEQ ID NO: 10 in a *Plasmodium falciparum* strain other than the 3D7 strain, said ortholog sequence being comprised in a protein that is the chromosome 6-encoded ortholog of the PFF0165c protein in said other *Plasmodium falciparum* strain, said ortholog variant sequence having preferably at least 98%, preferably at least 99% identity with said sequence of SEQ ID NO: 10 over the entire length of SEQ ID NO: 10 and having a sequence size of 102 to 106 amino acids, preferably of 103 to 105 amino acids, advantageously of 104 amino acids, said ortholog variant sequence being most preferably the E292G variant of the sequence of SEQ ID NO: 10, i.e., the sequence of SEQ ID NO: 12 (see below).

The sequence of SEQ ID NO: 6 (fragment 1-844 of the sequence of SEQ ID NO: 2), and the fragments of said sequence of SEQ ID NO: 6, which have retained the sequence (SEQ ID NO: 10) extending from position 223 to position 326 of said sequence of SEQ ID NO: 6, possess all the properties listed under a) to i) above.

The present inventors demonstrate that the polypeptides of the invention have a high antigenicity, a high immunogenicity, and have a parasite-killing activity in the ADCI assay. The ADCI assay is well-recognized assay in the field of *Plasmodium*. A detailed description of the protocol of this assay is described in example 1 below, and has also been described in Hasnaa Bouharoun-Tayoun et al. 1995 *J. Exp. Med.* 182: 409-418.

Furthermore, the total proportion of individuals who, under natural exposure to a malaria parasite, respond by specific IgG1 and IgG3, i.e., the most critical IgG subclasses, is higher for the polypeptides of the invention, such as the P27A than for other antigens, including peptide P27.

For an illustration of this effect and advantage, please see e.g., the prevalence values indicated in Table 2 in example 2 below, as well as the prevalence values indicated below the diagram of FIG. 4. The total proportion of individuals who, under natural exposure to a malaria parasite, respond by specific IgG1 and IgG3, is higher for the polypeptide of the invention P27A (anti-P27A specific IgG1: 86.7% of the individuals; anti-P27A specific IgG3: 82.2% of the individuals) than for other antigens, including peptide P27 (anti-P27 specific IgG1: 6.7%; anti-P27 specific IgG3: 95.6%).

Moreover, the polypeptides of the invention are strongly associated with clinical protection against malaria. In human beings under natural exposure to the parasite, the polypeptides of the invention induce specific antibodies (IgG1 and IgG3) that are very strongly associated with a state of resistance to malaria (statistical association, as assessed by a multivariate analysis made in accordance with the methodology described in Roussilhon et al. 2007 PLoS medicine 4(11): 1791-1803, with $p<0.0014$). Parasite-induced antibodies that are specific of the polypeptides of the invention are present in individuals, who resist to malaria and are absent, or are present at low titers, in individuals, who have malaria attack.

This association with resistance to malaria is much stronger for the polypeptides of the invention than for the prior art antigens, such as the P27 peptide disclosed in WO 2007/020520. Additionally, the polypeptides of the invention, in particular the conservative variant as defined herein, are different from those disclosed in this prior art.

For an illustration of this effect and advantage, please see e.g., table 3 in example 2 below, showing the F and p values of a multivariate analysis of the association with a state of resistance to malaria, wherein antibodies specific of the P27A polypeptide of the invention have the highest F ratio (28.55, with $p<0.0001$).

A conservative variant of the invention has at least one, preferably at least two, more preferably at least three, even more preferably at least four, still even more preferably at least five, still even more preferably at least six, still most preferably at least seven, yet still most preferably at least eight of said properties a) to i).

The preferred combinations of the properties a) to i) listed above comprise the following combinations:

property a) and/or b); or at least one of the properties c) to e), preferably at least two of the properties c) to e), more preferably the three the properties c) and e); or at least one of the properties f) to h), preferably at least two of the properties f) to h), more preferably the three the properties f) and h); or property a) and/or b), and at least one of the properties c) to e), preferably at least two of the properties c) to e), more preferably the three the properties c) and e); or property a) and/or b), and at least one of the properties f) to h), preferably at least two of the properties f) to h), more preferably the three the properties f) and h); or at least one of the properties c) to e), preferably at least two of the properties c) to e), more preferably the three the properties c) and e), and at least one of the properties f) to h), preferably at least two of the properties f) to h), more preferably the three the properties f) and h);

property i); or property i) and at least one of the properties a) to h); or property i) and at least one of the properties a) to b); or property i) and at least one of the properties c) to e); or property i) and at least one of the properties f) to h); or property i), and at least one of the properties a) to b), and at least one of the properties c) to e); or property i), and at least one of the properties a) to b), and at least one of the properties f) to h); or property i), and at least one of the properties a) to b), and at least one of the properties c) to e), and at least one of the properties f) to h).

Most preferably, a conservative variant of the invention has all of the properties a) to i) listed above.

By "internal amino acid deletion", it is herein meant the deletion of an amino acid, which is not the very first amino acid at the N-terminus of the sequence or the very last amino acid at the C-terminus of the sequence.

Said fragment of SEQ ID NO: 6 can e.g., be:

the 223-844 fragment, which is of SEQ ID NO: 16 (fragment 223-844 of the sequence of SEQ ID NO: 6); or a sub-fragment thereof, which has retained the sequence (SEQ ID NO: 10) extending from position 223 to position 326 of said sequence of SEQ ID NO: 6; or the 1-326 fragment, which is of SEQ ID NO: 20; or a sub-fragment thereof which has retained the sequence (SEQ ID NO: 10) extending from position 223 to position 326 of said sequence of SEQ ID NO: 6; or the 1-640 fragment, which is of SEQ ID NO: 24 (the structure of which is shown in FIG. 5), or a or a sub-fragment thereof which has retained the sequence (SEQ ID NO: 10) extending from position 223 to position 326 of said sequence of SEQ ID NO: 6.

Most preferably, said fragment of SEQ ID NO: 6 is the 223-326 fragment, which is of SEQ ID NO: 10 (fragment 223-326 of the sequence of SEQ ID NO: 6).

Said conservative variant of a fragment of SEQ ID NO: 6 preferably is a variant by at least amino acid substitution.

More preferably, said at least one amino acid substitution is the E292G substitution, which is observed in certain geographical areas, such as Papua New Guinea and Tanzania.

The E292G substitution of SEQ ID NO: 6 results in the sequence of SEQ ID NO: 8 (substitution of the amino acid at position 292 in the sequence of SEQ ID NO: 6, i.e., E, by the amino acid G).

The E292G substitution of SEQ ID NO: 10 results in the sequence of SEQ ID NO: 12.

The E292G substitution of SEQ ID NO: 16 results in the sequence of SEQ ID NO: 18.

The E292G substitution of SEQ ID NO: 20 results in the sequence of SEQ ID NO: 22.

The E292G substitution of SEQ ID NO: 24 results in the sequence of SEQ ID NO: 26.

Hence, the invention more particularly relates to a polypeptide, the amino acid sequence of which is:

i) the sequence of a fragment of the sequence of SEQ ID NO: 6, said fragment sequence having retained the sequence (SEQ ID NO: 10) extending from position 223 to position 326 of said sequence of SEQ ID NO: 6; such as the sequence of SEQ ID NO: 16, 20, 24, 10; or ii) the sequence of a fragment of the sequence of SEQ ID No: 8, said fragment sequence having retained the sequence (SEQ ID NO: 12) extending from position 223 to position 326 of said sequence of SEQ ID NO: 8; such as the sequence of SEQ ID NO: 18, 22, 26, 12; or iii) a conservative variant sequence, which derives from said fragment sequences of i) or ii) by at least one conservative amino acid substitution and/or at least one conservative internal amino acid deletion, wherein the resulting conservative variant polypeptide has one, or at least one, preferably at least two, more preferably at least three, even more preferably at least four, still even more preferably at least five, yet still even more preferably at least six, most preferably at least seven, still most preferably at least eight, yet still most preferably all of the a)-i) properties, or one of the preferred combinations of the properties a) to i) as above-described.

Preferably, a conservative variant of the present invention has retained (and comprises) the sequence (SEQ ID NO: 10) extending from position 223 to position 326 of said sequence of SEQ ID NO: 6, or the sequence (SEQ ID NO: 12) extending from position 223 to position 326 of the sequence of SEQ ID NO: 8.

The sequence of a conservative variant of the invention can e.g., be the fragment of a sequence that is the ortholog of the sequence of SEQ ID NO: 6 or 8 in a *Plasmodium falciparum* strain other than the 3D7 strain, said ortholog sequence being encoded by chromosome 6 of said other *Plasmodium falciparum* strain.

The sequence of a conservative variant of the invention can e.g., be the fragment of a sequence that is the ortholog of the sequence of SEQ ID NO: 2 or 4 in a *Plasmodium* strain other than a *Plasmodium falciparum* strain, said other *Plasmodium* strain being preferably selected among the strains of *P. vivax, P. ovale, P. malariae, P. berghei, P. knowlesi, P. chabaudi, P. yoelii*, said ortholog sequence being encoded by chromosome 6 of said other *Plasmodium* strain.

Preferably, said ortholog protein has a MW of 120-140 kDa, more preferably of 125-135 kDa.

Preferably, the sequence of said ortholog protein is at least 70%, more preferably at least 80%, even more preferably at least 85%, most preferably at least 90% identical to the sequence of the protein PFF0165c of *Plasmodium falciparum* 3D7 (SEQ ID NO: 2 or 4), over the entire length of this PFF0165c protein of *Plasmodium falciparum* 3D7.

Preferably, a conservative variant of the invention derives from said sequence of SEQ ID NO: 6 or 8, or from said fragment of SEQ ID NO: 6 or 8, by one or several amino acid substitutions, wherein said one or several substitutions do not result in increasing the sequence identity score, said sequence of SEQ ID NO: 6 or 8, or said fragment of SEQ ID NO: 6 or 8, has with respect to human proteins, respectively.

Preferably, a conservative variant of the invention does not comprise a higher number of Asparagine and Glutamic Acid than said sequence of SEQ ID NO: 6 or 8, or than said fragment of SEQ ID NO: 2 or 4, from which said conservative variant derives.

Preferably, a conservative variant of the invention does not comprise a higher number of highly hydrophobic residues, preferably not a higher number of Isoleucine (I) and Valine (V), than said sequence of SEQ ID NO: 6 or 8, or than said fragment of SEQ ID NO: 6 or 8, from which said conservative variant derives.

Preferably, the sequence of a conservative variant of the invention has at least 70% identity with said sequence of SEQ ID NO: 6 or 8, or with said fragment of SEQ ID NO: 6 or 8, from which it derives. Said identity score is computed over the entire length of sequence of SEQ ID NO: 6 or 8, or of said fragment of SEQ ID NO: 6 or 8, respectively.

Preferably, the sequence of a fragment or conservative variant of the present invention consists of less than 844 amino acids, preferably of 70 to 150 amino acids, more preferably of 80 to 150 amino acids, even more preferably of 85 to 140 amino acids, still even more preferably of 90 to 120 amino acids, most preferably of 100 to 115 amino acids, for example of 104 amino acids.

The sequence of a fragment of the sequence of SEQ ID NO: 6 may comprise the sequence of SEQ ID NO: 16 or of SEQ ID NO: 20 or of SEQ ID NO: 24, or sub-fragment thereof, which has retained the sequence (SEQ ID NO: 10) extending from position 223 to position 326 of said sequence of SEQ ID NO: 6. More preferably, the sequence of a fragment of the sequence of SEQ ID NO: 6 consists of the sequence of SEQ ID NO: 10.

The sequence of a fragment of the sequence of SEQ ID NO: 8 may comprise the sequence of SEQ ID NO: 18 or of SEQ ID NO: 22 or of SEQ ID NO: 26, or sub-fragment thereof, which has retained the sequence (SEQ ID NO: 12) extending from position 223 to position 326 of said sequence of SEQ ID NO: 8.

More preferably, the sequence of a fragment of the sequence of SEQ ID NO: 8 consists of the sequence of SEQ ID NO: 12.

As the sequence of SEQ ID NO: 8 is a variant of the sequence of SEQ ID NO: 6, it can also be considered that the sequence of SEQ ID NO: 12 is a more preferred sequence of a conservative variant of the invention.

A polypeptide of the invention can be isolated from a naturally-occurring (i.e., not engineered by man) sources, e.g., by fragmentation or cleavage from a naturally-occurring protein, or produced by recombinant technology, e.g., from a genetically engineered micro-organism or plant, or by synthesis.

Preferably, said polypeptide is produced by synthesis. Any method of peptide synthesis, which the skilled person finds appropriate to synthesize said peptide, can be used. For example, polypeptides of less than about 120 amino acids, can be produced by stepwise amino acid elongation, e.g., by solid-phase peptide synthesis on a solid support such as beads of polystyrene or polyamide resin (Merrifield 1963. Journal of the American Chemical Society 85: 2149; Atherton, E.; Sheppard, R. C. (1989). *Solid Phase peptide synthesis: a practical approach*. Oxford, England: IRL Press; Stewart, J. M.; Young, J. D. (1984). Solid phase peptide synthesis, 2nd edition, Rockford: Pierce Chemical Company, 91). Longer polypeptides can be produced by fragment condensation and/or chemical ligation of peptide fragments.

Advantageously, a polypeptide of the invention is soluble in water.

As used herein, the terms "protein", "polypeptide", "polypeptidic", "peptide" and "peptidic" are used interchangeably herein to designate a series of amino acid residues connected to the other by peptide bonds between the alpha-amino and carboxy groups of adjacent residues.

A polypeptide of the invention may be chemically modified with respect to the native protein from which it derives, e.g., by glycosylation of the polypeptide or by preparing D-forms and/or "retro-inverso isomers" of the peptide.

The present application also relates to antibodies, which are directed to at least one polypeptide of the invention, more particularly which specifically bind to a polypeptide of the invention.

Preferred antibodies of the invention bind to a polypeptide of the invention, without binding to a human protein, and without binding to another *Plasmodium* protein, polypeptide or peptide, more particularly without binding to the P27 peptide disclosed in WO 2007/020520 (SEQ ID NO: 14 in the present application).

Antibodies of the invention are useful e.g., for in vitro diagnosis and/or for passive immunotherapy, as described below. When it is intended for passive immunotherapy, an antibody of the invention preferably is an Ig1 or an IgG3.

The antibody may be a polyclonal (e.g., a polyclonal serum) or a monoclonal antibody, including but not limited to fully assembled antibody, single chain antibody, Fab fragment, and chimeric antibody, humanized antibody.

The antibody of present invention may also be used in combination with other therapeutic agents such as proteins, antibodies, and/or with targeting molecules to specifically target a certain cell type, and/or to detection label, such as a radio-isotope to easily detect said antibody.

Means enabling to produce antibodies are known to the person of skilled in the art.

Animals can be immunized with a nitrated neurotrophin (or fragment or variant thereof), or an antigenic functional derivative thereof, according to a known method.

Appropriate animals notably comprise mammals, more particularly non-human mammals, such as rabbit.

For example, a mammal is injected intraperitoneally or subcutaneously with said nitrated neurotrophin (or fragment or variant thereof), or an antigenic functional derivative thereof.

Said nitrated neurotrophin (or fragment or variant thereof), or antigenic functional derivative thereof, may be diluted with, or suspended in an appropriate volume of PBS (Phosphate-Buffered Saline), physiological saline or the like.

An appropriate volume of a standard adjuvant can be mixed with the product, if necessary or desired. Illustrative standard adjuvants notably comprise Freund's (complete or incomplete) adjuvant, mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

It may be useful to conjugate said nitrated neurotrophin (or fragment or variant thereof) to a protein that is immunogenic in the species to be immunized, e.g., keyhole limpet hemocyanin (KLH), serum albumin, bovine thyroglobulin, or soybean trypsin inhibitor, by using a bifunctional or derivatizing agent, for example, maleimidobenzoyl sulfosuccinimide ester (conjugation through cysteine residues), N-hydroxysuccinimide (through lysine residues), glutaraldehyde, succinic anhydrid or $SOCl_2$.

The solution is administered to the animals several times, e.g., every 4 to 21 days. In addition, an appropriate carrier can also be used upon immunization with an immunogen.

Polyclonal antibodies are heterogeneous populations of antibody molecules, which can be derived from the sera of animals immunized with said at least one nitrated neurotrophin (or fragment or variant thereof), or an antigenic functional derivative thereof.

Monoclonal antibodies (mAb), which are homogeneous populations of antibodies to a particular antigen, may be obtained by any technique which provides for the production of antibody molecules by continuous cell lines in culture.

These include, but are not limited to the hybridoma technique of Kohler and Milstein (1975) Nature 256:495-497; and U.S. Pat. No. 4,376,110, the human B-cell hybridoma technique (Kosbor et al. (1983) Immunology Today 4:72; Cole et al. (1983) Proc. Natl. Acad. Sci. USA 80:2026-2030, and the EBV-hybridoma technique (Cole et al. (1985) Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing a mAb of this invention may be cultivated in vitro or in vivo.

Production of mAb of the invention notably comprises the collection of immunocytes, such as splenocytes, from an immunized animal, and the fusion of these immunocytes to a fusion partner.

As a partner cell to be fused with the above immunocyte, a mammalian myeloma cell can be used. Examples of a cell line of a myeloma cell that is preferably used herein include various known cell lines, such as the murine myeloma cell line SP2/0-Ag14, or a fused mouse myeloma/non-malignant B-lymphocyte cell line, such as the ATCC HB8464 cell line.

Cell fusion of the above immunocytes with myeloma cells can be basically performed according to a known method, for example, the method of Kohler and Milstein et al. (Kohler. G. and Milstein, C., Methods Enzymol. (1981) 73, 3-46).

More specifically, the above cell fusion is performed in a standard nutrition culture solution in the presence of, for example, a cell-fusion accelerator. As a cell-fusion accelerator, for example, polyethylene glycol (PEG), hemagglutinating virus of Japan (HVJ) or the like is used. If desired, an adjuvant such as dimethylsulfoxide can also be used by addition to further enhance fusion efficiency.

Any ratio of immunocytes to myeloma cells may be set for use herein. For example, it is preferable that the number of immunocytes be 1 to 10 times greater than that of myeloma cells. As a culture solution to be used for the above cell fusion, for example, a RPM11640 culture solution or a MEM culture solution which is appropriate for the growth of the above myeloma cell line, or other standard culture solutions that are used for this type of cell culture can be used. Moreover, a serum fluid such as foetal calf serum (FCS) can be used in combination therewith.

Cell fusion is performed by mixing sufficiently certain amounts of the above immunocytes and myeloma cells in the above culture solution, adding a PEG (e.g., with an average molecular weight of approximately 1000 to 6000) solution (a general concentration of 30 to 60% (w/v)) pre-heated at approximately 37° C., and then mixing the solution, so as to form target fused cells (hybridomas). Subsequently, an appropriate culture solution is added successively, and then a step of removing the supernatant by centrifugation is repeated, so that reagents for cell fusion or the like that is unfavorable for the growth of the hybridomas is removed.

The thus obtained hybridomas are selected by culturing the hybridomas in a standard selective culture solution such as a HAT culture solution (a culture solution containing hypoxanthine, aminopterin and thymidine). Culture in the above HAT culture solution is continued for a time period sufficient for the cells (unfused cells) other than the target hybridomas to die (normally, several days to several weeks). Subsequently, a standard limiting dilution method is conducted, so that screening for and monocloning of hybridomas that produce a target antibody are performed.

In addition to a method with which the above hybridomas are obtained by immunizing non-human animals with antigens, desired human antibodies having binding activity to said nitrated neurotrophin (or fragment or variant thereof) can also be obtained (see Japanese Patent Publication (Kokoku) No. 1-59878 B (1989)), by sensitizing in vitro human lymphocytes with said nitrated neurotrophin (or fragment or variant thereof), or a functional antigenic derivative thereof, and causing the sensitized lymphocytes to fuse with the human-derived myeloma cells having a permanent division potential.

The thus prepared hybridomas producing monoclonal antibodies can be passage-cultured in a standard culture solution, or can be stored for a long period in liquid nitrogen.

One example of a method employed to obtain monoclonal antibodies from the hybridomas involves culturing the hybridomas and obtaining monoclonal antibodies in the culture supernatant according to a standard method. Another method involves administering the hybridomas to mammals that are compatible with the hybridomas to cause them to proliferate, and obtaining monoclonal antibodies in the ascites. The former method is suitable to obtain antibodies of high purity. On the other hand, the latter method is suitable for the mass production of antibodies.

A monoclonal antibody that can be used in the present invention can be a recombinant monoclonal antibody that is prepared by cloning the antibody gene from the hybridoma, incorporating the gene into an appropriate vector, introducing the vector into a host, and then causing the host to produce the recombinant monoclonal antibodies by genetic engineering techniques (e.g., see Vandamme, A. M. et al., Eur. J. Biochem. (1990) 192, 767-775, 1990).

In addition to the above host cell, a transgenic animal or plant can also be used to produce a recombinant antibody.

The present invention also relates to a hybridoma secreting a monoclonal antibody of the invention.

In addition to the above antibody, artificially altered gene recombinant antibodies such as chimeric antibodies or humanized antibodies can be used for, for example, lowering heteroantigenicity against a human. These altered antibodies can be produced using a known method.

Chimeric antibodies can e.g., be obtained by ligating the DNA encoding the antibody V-region to a DNA encoding a human antibody C-region, incorporating the product into an expression vector, and then introducing the vector into a host to cause the host to produce the antibodies. Using this known method, chimeric antibodies useful in the present invention can be obtained.

Humanized antibodies are also referred to as reshaped human antibodies, which are prepared by grafting an antibody CDR (complementarity determining region) of a mammal other than a human, such as a mouse, to the CDR of a human antibody. The general gene recombination technique thereof is also known (see European Patent Application Publication EP 125023 and WO 96/02576, or any one of their US counterparts, such as e.g., U.S. Pat. No. 6,068,040).

An antibody used in the present invention is not limited to the whole molecule, and may be a fragment of the antibody or the modified product thereof, as long as it still binds to at least one nitrated neurotrophin (or fragment or variant thereof) and has retained the capacity of inhibiting and/or blocking the apoptotic effect exerted by said at least one nitrated neurotrophin (or fragment or variant thereof) on motor neurons, and/or the capacity of inhibiting and/or blocking the stimulation and/or induction effect exerted by said at least one nitrated neurotrophin (or fragment or variant thereof) on sensory ganglia.

Multivalent, preferably bivalent, antibody and a monovalent antibody are included. Examples of the fragment of an antibody include Fab, F(ab')2, Fv, Fab/c having one Fab and a complete Fc, and a single chain Fv (scFv) wherein the Fv of the H-chain or the L-chain is ligated with an appropriate linker Specifically, an antibody fragment is synthesized by treating the antibody with an enzyme such as papain or pepsin, or genes encoding these antibody fragments are constructed, the genes are introduced into expression vectors, and the genes are then expressed by appropriate host cells (see e.g., Rousseaux, J. et al., Methods in Enzymology (1989) 121, 663-669, and Bird, R. E. et al., TIBTECH (1991) 9, 132-137).

scFv is obtained by linking the H-chain V-region and the L-chain V-region of antibodies. In the scFv, the H-chain V-region and the L-chain V-region are linked via a linker, or preferably a peptide linker (Huston, J. S. et al., Proc. Natl. Acad. Sci. U.S.A. (1988) 85, 5879-5883). The H-chain V-region and the L-chain V-region in scFv may be derived from any of those described as antibodies in this specification. As a peptide linker to link the V-regions, for example, any single-stranded peptide comprising 12 to 19 amino acid residues is used.

A DNA encoding scFv can be obtained as follows. Amplification is performed by the PCR method using as templates the entire or DNA portions encoding desired amino acid sequences (of a DNA encoding the H-chain or the H-chain V-region of the above antibody, and a DNA encoding the L-chain or the L-chain V-region), and using a primer pair that specifies both ends. Amplification is then further performed by a combined use of a DNA encoding a peptide linker portion and a primer pair that specifies to cause both ends to ligate respectively to the H-chain and L-chain.

Furthermore, once a DNA encoding scFv is prepared, expression vectors containing the DNAs, and hosts transformed with the expression vectors, can be obtained according to the standard method. In addition, by the use of the host, scFv can be obtained according to the standard method.

These antibody fragments can be produced using hosts by obtaining the genes thereof in a manner similar to the above method, and then causing the expression of the genes. The "antibody" in the present invention also encompasses these antibody fragments.

While transgenic mammalian cells (e.g., Chinese hamster ovary cells) grown in culture are the industry standard for producing full length mAb, mammalian cells may be less suited for the production of antibody fragments such as Fab or scFv, and prokaryotic expression systems (e.g., *E. coli*) or other eukaryotic expression systems, such as yeast or plant cells, may preferably be used.

Furthermore, the antibody used in the present invention may be a bispecific antibody, which can also be prepared by genetic engineering techniques.

The antibodies expressed and produced as described above can be isolated from the cells or host animals, and purified to a uniform level. Isolation and purification of the antibodies to be used in the present invention can be performed using affinity columns. An example of a column using a protein A column is a Hyper D, POROS, Sepharose F. F. (Pharmacia). Other standard isolation and purification methods that are employed for proteins may be used, and there is no limitation regarding their use. For example, a chromatography column other than the above affinity column, a filter, ultrafiltration, a method of salting out, dialyses and the like may be appropriately selected and combined for use, so that antibodies can be isolated and purified (Antibodies A Laboratory Manual. Ed Harlow, David Lane, Cold Spring Harbor Laboratory, 1988).

Chemicals that mimic the function(s) of an antibody can be produced.

There are several approaches to the structure and manufacture of chemicals that mimic the function(s) of an antibody of the invention.

One approach utilizes an alternative protein framework, such as cytochrome b562, or structures comprising ribonucleic acids (RNA) (Hsieh-Wilson et al. 1996, Acc. Chem. Res. 29:164-170).

Unnatural oligomers, such as benzodiazepines, beta-turn mimics, protease inhibitors and purine derivatives have also been tested for their ability to function as antibody mimics Unnatural biopolymers, such as oligocarbamates, oligoureas and oligosulfones, have been proposed as antibody mimics Molecules with some of the recognition properties of antibodies have been created by joining various substituents to scaffolds such as xanthese or cubane, or a calixarene unit. These molecules have multiple peptide loops as the recognition site, but built around the relatively rigid organic framework formed by the scaffold.

The invention more particularly relates to those antibody mimics that have a capacity of inhibiting and/or blocking the apoptotic effect exerted by a nitrated neurotrophin (or fragment or variant thereof) on motor neurons, and/or of inhibiting and/or blocking the stimulation and/or induction effect exerted by a nitrated neurotrophin (or fragment or variant thereof) on sensory ganglia.

The invention also relates to methods for the in vitro diagnosis of a *Plasmodium*-related disease, more specifically malaria in an individual, either by using at least one polypeptide of the invention, or by using at least one antibody of the invention, as defined above, as well as to compositions (more particularly pharmaceutical compositions) and kits comprising at least part of the necessary reagents (polypeptides, antibodies . . . ) for performing these diagnosis methods.

The invention relates to a method for the in vitro diagnosis of a *Plasmodium*-related disease, more specifically malaria, in an individual suspected to be infected by one or several *Plasmodium* species, more specifically *P. falciparum*. The method of the invention comprises bringing a biological sample from said individual into contact with at least one polypeptide of the invention, under conditions enabling the formation of antigen/antibody complexes between said at least one polypeptide and the antibodies possibly present in said biological sample, and in vitro detecting the antigen/antibody complexes possibly formed.

The diagnosis method may further comprise bringing said biological sample into contact with one or several antigenic peptides originating from other *Plasmodium* antigens, such as LSA-1, LSA-3, LSA-5, SALSA, STARP, TRAP, PfEXP1, CS, MSP-3-1, MSP-3-2, MSP-3-5, MSP-3-6, MSP1, MSP2, MSP4, MSPS, AMA-1, SERP and GLURP, in particular from LSA-3, SERP and GLURP, as well as the antigens disclosed in WO 2007/020520, more specifically the P27 antigen (SEQ ID NO: 14 in the present application) or an ortholog sequence thereof from *P. vivax, P. berghei, P. knowlesi, P. chabaudi, P. yoelii*.

An alternative method of the invention for the in vitro diagnosis of a *Plasmodium*-related disease, more specifically of malaria, in an individual suspected to be infected by a *Plasmodium* species, such as *P. falciparum* comprises bringing a biological sample from said individual into contact with at least one antibody of the invention, under conditions enabling the formation of antigen/antibody complexes between said at least one antibody and the *Plasmodium*, more specifically the *P. falciparum*, antigen(s) possibly present in said biological sample, and in vitro detecting the antigen/antibody complexes possibly formed.

In the in vitro diagnosis methods of the invention, any mean appropriate to the detection of antigen/antibody complexes can be used, for example an ELISA assay.

Compositions and kits for the in vitro diagnosis of a *Plasmodium*-related disease, more specifically malaria are also contemplated by the present application.

For example, a diagnosis composition or kit of the invention may comprise at least one polypeptide according to the invention, possibly bound to a support. Such a kit can further comprise reagents for enabling the formation of antigen/antibody complexes between said antigenic polypeptide and the antibodies possibly present in a biological sample, and reagents enabling the in vitro detection of the antigen/antibody complexes possibly formed.

An alternative diagnosis composition or kit of the invention for the in vitro diagnosis of a *Plasmodium*-related disease, more specifically malaria, comprises at least one antibody of the invention, as described above, and, optionally, reagents for enabling the formation of antigen/antibody complexes between said at least one antibody and *Plasmodium* (P27A) antigens possibly present in a biological sample, and, if optionally, reagents enabling the in vitro detection of the antigen/antibody complexes possibly formed.

The application also relates to methods for the treatment, more specifically the palliative and/or curative treatment, of a *Plasmodium*-related disease, more particularly of malaria, as well as to compositions and kits for such methods.

When a composition of the invention is intended for the treatment of a *Plasmodium*-related disease, more specifically of malaria, it is a medicament, more specifically an immunogenic composition, more particularly a vaccine composition.

An immunogenic or vaccine composition of the invention comprises at least one polypeptide of the invention as an immunogen, or at least one antibody or antibody fragment of the invention, as defined above, as passive immunotherapeutic agent.

The main medical effect of the immunogenic or vaccine composition of the invention is to reduce the morbidity of the malaria disease. The immunogenic or vaccine composition of the invention is mainly a palliative and/or curative composition.

Indeed, when administered to an animal as immunogens, the polypeptides of the invention induce antibodies that mainly target the blood stages of the *Plasmodium* infection, and not the pre-erythrocytic stage. Therefore, an immunogenic or vaccine composition of the invention does not aim at preventing infection or at destroying the parasites at the pre-erythrocytic stage, but at:

reducing the morbidity and/or mortality, and/or at accelerating the acquisition of natural immunity against the parasite and/or at maintaining the natural immunity at a level appropriate that is appropriate to the patient's health.

An immunogenic or vaccine composition of the invention is intended for any patient in need thereof, more particularly for any patient, whether adult or not, who is suspected to be contaminated by a malaria-related *Plasmodium* species, such as *Plasmodium falciparum*. An immunogenic or vaccine composition of the invention is more specifically intended for infants, toddlers, children under the age of 5, pregnant women.

The preferred target patients are those from countries, where *P. falciparum* is endemic, especially in sub-Sahara Africa, where it is responsible for at least a million deaths per year.

Said at least one antigenic polypeptide of the invention can be conjugated with a carrier protein, such as keyhole limpet hemocyanin, horseshoe crab hemocyanin, or bovine serum albumin An immunogenic or vaccine composition of the invention, which comprises at least one antigenic polypeptide of the invention as an immunogen, may further contain at least one vaccination adjuvant, such as:

Freund's adjuvant, either complete or incomplete; Titermax® gold adjuvant; alum; LPS such as bacterial LPS; gamma-linolenic acid (GLA), such as GLA-57, GLA-27, GLA-58, GLA-59, GLA-60; Montanide® ISA 720;

Mineral salts, e.g., aluminium hydroxide and aluminium or calcium phosphate gels;

Oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilised water-in-oil emulsion);

Particulate adjuvants, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG);

Microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self organise into liposomes), OM-174 (lipid A derivative), CpG motifs (synthetic oligonucleotides containing immunostimulatory CpG motifs), modified LT and CT (genetically modified bacterial toxins to provide non-toxic adjuvant effects);

Endogenous human immunomodulators, e.g., hGM-CSF or hIL-12 (cytokines that can be administered either as protein or plasmid encoded), Immudaptin (C3d tandem array);

Inert vehicles, such as gold particles.

Said at least one adjuvant preferably is alum, Montanide® ISA 720, or a GLA.

An immunogenic or vaccine composition of the invention may contain at least two different adjuvants, e.g., two different adjuvants selected from alum, Montanide® ISA 720 and GLA, more preferably alum and a GLA.

An immunogenic or vaccine composition of the invention may comprise several polypeptides of the invention, e.g. two or three polypeptides of the invention, or several antibodies or antibody fragments of the invention, e.g. two or three antibodies or antibody fragments of the invention of the invention.

An immunogenic or vaccine composition of the invention, which comprises at least one antigenic polypeptide of the invention as an immunogen, may comprise at least one anti-*Plasmodium* immunogenic compound other than a polypeptide of the invention, more particularly at least one other protein, polypeptide or peptide having anti-*Plasmodium* immunogenic properties.

In addition to said at least one polypeptide of the invention, an immunogenic or vaccine composition of the invention may for example comprise at least anti-Plasmodium immunogenic protein, polypeptide or peptide, which derives from, or is a fragment of, a *Plasmodium* protein selected from a MSP2 protein of *P. falciparum*, a MSPS protein of *P. falciparum* (MSP-3-1, MSP-3-2, MSP-3-5, MSP-3-6), a MSP4 protein of *P. falciparum*, a MSPS protein of *P. falciparum*, a GLURP protein of *P. falciparum*, a LSA protein (LSA-1, LSA-3, LSA-5) a SALSA protein, a STARP protein, a TRAP protein, a PfEXP1 protein, an AMA-1 protein, a SERP protein, a N-terminal and repeat region of the CS protein of *P. vivax*, the *Plasmodium* peptides described in WO 2007/020520, more specifically the PFF0165c-derived P27 peptide disclosed under SEQ ID NO: 27 in WO 2007/020520, which is herein referred to as SEQ ID NO: 14 (KKRNVEEELHSLRKNY-NIINEEIEEIT) or an ortholog sequence thereof from *P. vivax, P. berghei, P. knowlesi, P. chabaudi, P. yoelii*.

An immunogenic or vaccine composition of the invention can be a liquid solution, suspension, emulsion, tablet, pill, capsule, sustained release formulation, or powder.

An immunogenic or vaccine composition of the invention may be in the form of a kit-of-part composition.

For example, the immunogenic or vaccine composition of the invention may contain said at least one polypeptide of the invention and at least one other component, such as at least one adjuvant and/or at least one anti-Plasmodium immunogenic compound other than a polypeptide of the invention, in at least two distinct containers, preferably in at least two distinct vials, or in vials that keep said at least polypeptide of the invention separate from the other compounds of the composition until medical use is made of the composition. More preferably, an immunogenic or vaccine composition of the invention is a kit-of-part composition containing said at least one polypeptide of the invention and at least one adjuvant in separate containers, so that these two ingredients are kept separate until medical use thereof.

Preferably, said at least one polypeptide of the invention is contained in the immunogenic or vaccine composition of the invention under the form of a powder, more specifically under lyophilized form.

The immunogenic or vaccine composition of the invention may comprise one or several doses of said at least one polypeptide of the invention, the quantity of one dose being determined and/or adjusted by the physician taking due account of the patient's health, notably of the state of the patient's immunity system, and taking due account of the patient's medical features, such as age and weight. Illustrative doses are doses of 8 to 100 µg per adult person, preferably of 9 to 60 µg per adult person, e.g., of 10, 25 or 50 µg per adult person.

When formulated as a multidose composition, the immunogenic or vaccine composition of the invention may for example comprise said at least one polypeptide of the invention in a quantity corresponding to 2 to 20 individual doses, e.g., to 3 to 15 individual doses, said individual doses being either mixed together in the same container or vial or contained in individual containers or vials.

The administration schedule is to be determined by the physician depending on the patient's health, the stage of the *Plasmodium* infection, the patient's age, the patient's weight, and of the dose to be or that has already be administered. Typically, two or three doses at monthly interval are expected to be efficient in the treatment, more specifically the palliative and/or curative treatment of the disease.

The administration mode will be selected by the physician, and preferably is an administration by injection, more specifically an intramuscular injection.

The immunogenic or vaccine composition of the invention may further comprise at least one pharmaceutically and/or physiologically acceptable vehicle (diluent, excipient, additive, pH adjuster, emulsifier or dispersing agent, preservative, surfactant, gelling agent, as well as buffering and other stabilizing and solubilizing agent, etc.).

Appropriate pharmaceutically acceptable vehicles and formulations include all known pharmaceutically acceptable vehicles and formulations, such as those described in "Remington: The Science and Practice of Pharmacy", $20^{th}$ edition, Mack Publishing Co.; and "Pharmaceutical Dosage Forms and Drug Delivery Systems", Ansel, Popovich and Allen Jr., Lippincott Williams and Wilkins.

In general, the nature of the vehicle will depend on the particular mode of administration being employed. For instance, parenteral formulations usually comprise, in addition to the one or more contrast agents, injectable fluids that include pharmaceutically and physiologically acceptable fluids, including water, physiological saline, balanced salt solutions, buffers, aqueous dextrose, glycerol, ethanol, sesame oil, combinations thereof, or the like as a vehicle. The medium also may contain conventional pharmaceutical adjunct materials such as, for example, pharmaceutically acceptable salts to adjust the osmotic pressure, buffers, preservatives and the like. The carrier and composition can be sterile, and the formulation suits the mode of administration.

For solid compositions (e.g., powder, pill, tablet, or capsule forms), conventional nontoxic solid carriers can include, for example, pharmaceutical grades of mannitol, lactose, starch, sodium saccharine, cellulose, magnesium carbonate, or magnesium stearate. In addition to biologically-neutral carriers, pharmaceutical compositions to be administered can contain minor amounts of auxiliary substances, such as wetting or emulsifying agents, preservatives, and pH buffering agents and the like, for example sodium acetate or sorbitan monolaurate.

The composition can be formulated with traditional binders and carriers, such as triglycerides.

Preferably, an immunogenic or vaccine composition of the invention is kit-of-part composition comprising at least one, preferably several vials of a polypeptide of the invention under lyophilized form, wherein said polypeptide of the invention is intended to be dissolved in at least one adjuvant prior to administration thereof.

The invention also relates to a kit, which comprises at least one immunogenic or vaccine composition of the invention, and optionally a leaflet containing appropriate instructions for the use thereof as an immunogenic or vaccine composition, more particularly for the treatment of a *Plasmodium*-related disease, more specifically of malaria.

In view of what precedes, the present application also relates to methods for the treatment of an individual in need thereof, by active and/or passive immunotherapy, i.e., by at least one administration of at least one polypeptide of the invention, or of a nucleic acid coding therefore, preferably by injection, and/or by at least one administration of at least one antibody of the invention.

Also part of the present invention are nucleic acids (DNAs or RNAs) coding for a polypeptide of the invention, according to the universal genetic code and taking due account of the degeneracy of this genetic code, as well as oligonucleotide primers, which specifically amplify a sequence coding for a polypeptide of the invention (or a fragment thereof which is specific of such a sequence), preferably under stringent conditions, as well as oligonucleotide probes, which specifically hybridize to a polypeptide of the invention, preferably under stringent conditions.

Nucleic acids coding for a polypeptide of the invention advantageously comprise:

i) the sequence of SEQ ID NO: 5 (fragment 1-844 of the sequence of SEQ ID NO: 1);

ii) the sequence of a fragment of said sequence of SEQ ID NO: 5, said fragment having retained the sequence (SEQ ID NO: 9) extending from position 223 to position 326 of said sequence of SEQ ID NO: 5; or iii) a conservative variant thereof, which derives from said sequence of SEQ ID NO: 5 of i) or from said fragment of SEQ ID NO: 5 of ii) by at least one conservative amino acid substitution and/or at least one conservative internal amino acid deletion, said conservative variant having retained the property of coding for a polypeptide, which has one, or at least one, preferably at least two, more preferably at least three, even more preferably at least four, still even more preferably at least five, yet still even more preferably at least six, most preferably at least seven, still most preferably at least eight, yet still most preferably all of the a)-i) properties, or one of the preferred combinations of the properties a) to i) as above-described.

The invention more particularly relates to a nucleic, the sequence of which is:

i) the sequence of a fragment of the sequence of SEQ ID NO: 5, said fragment sequence having retained the sequence (SEQ ID NO: 9) extending from position 223 to position 326 of said sequence of SEQ ID NO: 5; such as the sequence of SEQ ID NO: 15, 19, 9; or ii) the sequence of a fragment of the sequence of SEQ ID No: 7, said fragment sequence having retained the sequence (SEQ ID NO: 11) extending from position 223 to position 326 of said sequence of SEQ ID NO: 7; such as the sequence of SEQ ID NO: 17, 21, 11; or iii) a conservative variant sequence, which derives from said fragment sequences of i) or ii) by at least one conservative amino acid substitution and/or at least one conservative internal amino acid deletion, said conservative variant having retained the property of coding for a polypeptide, which has one, or at least one, preferably at least two, more preferably at least three, even more preferably at least four, still even more preferably at least five, yet still even more preferably at least six, most preferably at least seven, still most preferably at least eight, yet still most preferably all of the a)-i) properties, or one of the preferred combinations of the properties a) to i) as above-described.

A primer must be sufficiently long to prime the synthesis of the desired extension product. The exact length of the primer will depend upon many factors, including temperature, source of primer and use of the method.

A primer of the invention advantageously consist of 14-30 nucleotides, preferably of 15-29, more preferably of 16-28, most preferably of 17-25 nucleotides, the sequences of which are suitable for use as forward or reverse primer, in the amplification of at least one nucleic acid encoding a polypeptide of the invention.

By "consisting of 14-30 nucleotides", it is meant "consisting of 14, 15, 16, 17, 18, 19, 20, 21, 22, 23, 24, 25, 26, 27, 28, 29 or 30 nucleotides".

A primer pair of the invention is a pair of two primers, which anneals to Plasmodium nucleic acid at such positions that the primer pair enables the specific amplification of an amplicon, said amplicon consisting of, or essentially consisting of, a nucleic acid coding for a polypeptide of the invention, or of a fragment of such a nucleic acid that is sufficiently specific to ascertain that the amplicon was contained in a nucleic acid coding for a polypeptide of the invention. By an "amplicon essentially consisting of", it is herein meant that the sequence that is amplified from the target Plasmodium nucleic acids consists of the indicated sequence, but that the amplicon sequence may further contain detection-related arm (s), such as beacon or scorpion arm(s), at its 5' and/or 3' ends.

The application also relates to a primer or a primer pair of the invention, for use in the detection of Plasmodium species, more specifically of Plasmodium falciparum strain(s), or for use in the diagnosis of a Plasmodium-related disease, such as malaria.

A probe must be sufficiently long to specifically hybridize to a polypeptide of the invention, preferably under stringent conditions.

A probe of the invention advantageously consists of 20-200 nucleotides, preferably of 25-100 nucleotides.

The application also relates to a probe of the invention, for use in the detection of Plasmodium species, more specifically of Plasmodium falciparum strain(s), or for use in the diagnosis of a Plasmodium-related disease, such as malaria.

The invention also relates to a PCR system, comprising at least one primer or primer pair of the invention and at least one probe of the invention.

The application also relates to a PCR system of the invention, for use in the detection of Plasmodium species, more specifically of Plasmodium falciparum strain(s), or for use in the diagnosis of a Plasmodium-related disease, such as malaria. Usually, the PCR system is part of a kit which, optionally, contains instructions to use.

Also embraced by the scope of the invention is a kit for the in vitro diagnosis of malaria in an individual likely to be infected by a Plasmodium species which contains: a polypeptide of the invention, the reagents for the constitution of the medium appropriate for carrying out the antigen-antibody reaction and the reagents making possible the detection of the complex formed.

The invention also pertains to a recombinant cloning and/or expression vector, comprising at least one nucleic acid of the invention. In a vector of the invention, said at least one nucleic acid can be under the control of a promoter and regulatory elements homologous or heterologous vis-à-vis a host cell, for expression in said host cell.

An expression vector as described in the above paragraph can advantageously be used for the preparation of a medicament for genetic immunisation against Plasmodium species, more specifically against P. falciparum.

A recombinant or genetically engineered host cell, for example a bacterium, a yeast, an insect cell, or a mammalian cell, which is transformed by an expression vector as described above, is also part of the present invention.

The invention also pertains to a nucleic acid vaccine (e.g. polynucleotide vaccine) comprising at least one nucleic acid, vector or host cell of the invention.

Several aspects and advantages of the present invention are illustrated in the following figures and experimental data.

The following definitions apply throughout the text of the present application.

In the context of the present invention, 'amino acid' or 'amino acid residue' means any amino acid residue known to those skilled in the art (see e.g.: Sewald et al., 2002; IUPAC nomenclature under www.chem.qmul.ac.uk/iupac/AminoAcid/).

This encompasses naturally occurring amino acids (including for instance, using the three-letter code, Ala, bAla, Arg, Asn, Asp, Cys, Gln, Glu, Gly, His, Ile, Leu, Lys, Met, Phe, Pro, Ser, Thr, Trp, Tyr, Val), as well as rare and/or synthetic amino acids and derivatives thereof (including for instance Aad, Abu, Acp, Ahe, Aib, Apm, Dbu, Des, Dpm, Hyl, MeLys, MeVal, Nva, HAO, NCap, Abu, Aib, MeXaa and the like (see e.g.: (Milner et al., 1993; Aurora et al., 1998; Obrecht et al., 1999; Maison et al., 2001; Formaggio et al., 2003; Nowick et al., 2003).

Said amino acid residue or derivative thereof can be any isomer thereof, especially any chiral isomer, e.g., the L- or D-isoform.

By amino acid derivative, we hereby mean any amino acid derivative as known in the art (see e.g.: Sewald et al., 2002; IUPAC nomenclature under www.chem.qmul.ac.uk/iupac/AminoAcid/).

For instance, amino acid derivatives include residues derivable from natural amino acids bearing additional side chains, e.g. alkyl side chains, and/or heteroatom substitutions. Further examples of amino acid derivatives comprise amino acid bearing chemical modifications such the one fund in mimetic peptides or peptidomimetics, which are compounds containing non-peptidic structural elements that are capable of mimicking or antagonizing the biological action(s) of a natural parent peptide. A peptidomimetic usually does no longer have classical peptide characteristics such as enzymatically scissille peptidic bonds.

Preferably, said amino acid belongs to the group of the non-essential amino acids. Preferred non-essential amino acids are glycine, alanine, proline, serine, cysteine, tyrosine, asparagines, glutamine, aspartic acid, glutamic acid, arginine, histidine.

Appropriate amino acids may be accurately selected by selecting those amino acids which are in lower amounts in the patient into which the drug is to be administered. Dosage and administration regimen can be determined as a function of the patient's level in said amino acid. Preferred dosage and administration regimen are those which intend to increase the patient's amino acid level up to the normal standard level.

Unfolded or unstructured regions can de determined by identification of amino acid stretches, which have a highly hydrophilic amino acid sequence. Such stretches have no hydrophobic core.

Hydropathy index of standard amino acids is as follows (Kyte and Doolittle 1982. J. Mol. Biol. 157 (1): 105-132):

| Amino acids sorted by increasing hydropathy index | | | | | | | | | | | | | | | | | | | |
|---|---|---|---|---|---|---|---|---|---|---|---|---|---|---|---|---|---|---|---|
| R | K | N | D | Q | E | H | P | Y | W | S | T | G | A | M | C | F | L | V | I |
| -4.5 | -3.9 | -3.5 | -3.5 | -3.5 | -3.5 | -3.2 | -1.6 | -1.3 | -0.9 | -0.8 | -0.7 | -0.4 | 1.8 | 1.9 | 2.5 | 2.8 | 3.8 | 4.2 | 4.5 |

The larger the value of the hydropathy index is, the more hydrophobic the amino acid. The most hydrophobic amino acids are isoleucine (4.5) and valine (4.2). The most hydrophilic ones are arginine (−4.5) and lysine (−3.9).

Hydrophobic amino acid residues notably include P, Y, W, S, T, G, A, M, C, F, L, V, I.

The person of average skill in the art uses a computer tool to predict unstructured or unfolded regions, such as the DisEMBL software (DisEMBL-1.4), which is available on dis-.embl.de/html/help.html. The DisEMBL software provides three predictors, namely the Loops/coils predictor, the Hot-loops predictor and the REMARK-465 predictor.

The Loops/coils predictor uses the Definition of Secondary Structure of Proteins (DSSP) program. Executables of the DSSP program are available from www.embl-heidelberg.de/dssp/or from ftp.embl-heidelberg.de. With the Loops/coils predictor, residues are assigned as belonging to one of several secondary structure types. Residues as alpha-helix ('H'), 3_10-helix ('G') or beta-strand ('E') are considered to ordered residues, and all other states ('T', 'S', 'B', 'I', ' ') are considered to be loops (also known as coils). Loops/coils are not necessarily disordered; however, protein disorder is only found within loops. It follows that one can use loop assignments as a necessary but not sufficient requirement for disorder.

The Hot-loops predictor constitutes a subset of the Loops/coils predictor, namely those loops with a high degree of mobility as determined from C-alpha temperature (B-)factors. It follows that highly dynamic loops should be considered protein disorder.

Missing coordinates in X-Ray structure as defined by REMARK-465 entries in PDB. Non assigned electron densities most often reflect intrinsic disorder, and are used early on in disorder prediction.

Preferably, the Hot-Loops or the REMARK465 predictor of the DisEMBL software is being used.

Most preferably, the identification of an unstructured or unfolded region of *Plasmodium* protein is made with the Hot-Loops predictor of the DisEMBL-1.4 software, the six parameters of the software being left at their default settings.

The term "sequence identity" has its ordinary meaning in the field. The terms "identical" or percent "identity" in the context of two or more polypeptide sequences, refer to two or more sequences that are the same, or have a specified percentage of amino acid residues that are the same (i.e., at least 70% identity, preferably at least 75%, 80%, 85%, 90%, or 95% identity over a specified region), when compared and aligned for maximum correspondence. A preferred example of algorithm that is suitable for determining percent sequence identity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used to determine percent sequence identity for the polypeptides of the invention. Software for performing BLAST analyses is publicly available through the National Center for Biotechnology Information www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The person of average skill in the art usually consider that the following eight groups each contain amino acids that are conservative substitutions for one another:
 1) Alanine (A), Glycine (G);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V);
 6) Tyrosine (Y), Tryptophan (W);
 7) Serine (S), Threonine (T); and
 8) Cysteine (C), Methionine (M);
 (see, e.g., Creighton, Proteins (1984).

The term "treatment" or "treating" herein encompasses curative treatment, preventive treatment as well as palliative treatment, more specifically palliative treatment and curative treatment.

The term "palliative treatment" herein reflects that the fact that the treatment concerned focuses on the blood stages of the *Plasmodium* infection, and therefore that it does not aim at preventing infection or at destroying the parasites at the pre-erythrocytic stage, but at:
 reducing the morbidity and/or mortality, and/or at
 accelerating the acquisition of natural immunity against
  the parasite and/or at maintaining the natural immunity
  at a level appropriate that is appropriate to the patient's
  health.

The term "carrier" or "carrier molecule" means an immunogenic molecule containing antigenic determinants recognized by T cells. A carrier molecule can be a protein or can be a lipid. A carrier protein is conjugated to a polypeptide to render the polypeptide immunogenic, or to further increase its immunogenicity. Carrier proteins include keyhole limpet hemocyanin, horseshoe crab hemocyanin, and bovine serum albumin Freund's adjuvant, either complete or incomplete; Titermax® gold adjuvant; alum; LPS such as bacterial LPS; gamma-linolenic acid (GLA), such as GLA-57, GLA-27, GLA-58, GLA-59, GLA-60; Montanide® ISA 720;

Mineral salts, e.g., aluminium hydroxide and aluminium or calcium phosphate gels;

Oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), Montanide ISA-51 and ISA-720 (stabilised water-in-oil emulsion);

Particulate adjuvants, e.g., virosomes (unilamellar liposomal vehicles incorporating influenza haemagglutinin), AS04 ([SBAS4] Al salt with MPL), ISCOMS (structured complex of saponins and lipids), polylactide co-glycolide (PLG);

Microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self organise into liposomes), OM-174 (lipid A derivative), CpG motifs (synthetic oligonucleotides containing immunostimulatory CpG motifs), modified LT and CT (genetically modified bacterial toxins to provide non-toxic adjuvant effects);

Endogenous human immunomodulators, e.g., hGM-CSF or hIL-12 (cytokines that can be administered either as protein or plasmid encoded), Immudaptin (C3d tandem array);

Inert vehicles, such as gold particles.

The term "adjuvant" is as defined by EMEA, i.e., a component that potentiates the immune responses to an antigen and/or modulates it towards the desired immune responses. These adjuvants include for instance.

Other novel types of adjuvants not listed above may be under development and are also encompassed by the present application.

"Stringent hybridization conditions" are defined herein as conditions that allow specific hybridization of two nucleic acid especially two DNA molecules at about 65° C., for example in a solution of 6×SSC, 0.5% SDS, 5×Denhardt's solution and 100 µg/ml of denatured non specific DNA or any solution with an equivalent ionic strength, and after a washing step carried out at 65° C., for example in a solution of at most 0.2×SSC and 0.1% SDS or any solution with an equivalent ionic strength. However, the stringency of the conditions can be adapted by the skilled person as a function of the size of the sequence to be hybridized, its GC nucleotide content, and any other parameter, for example following protocols described by Sambrook et al, 2001 (Molecular Cloning: A Laboratory Manual, 3$^{rd}$ Edition, Laboratory Press, Cold Spring Harbor, N.Y.).

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

Each of the relevant disclosures of all references cited herein is specifically incorporated by reference.

The present invention is illustrated by the following examples, which are given for illustrative purposes only.

EXAMPLES

Example 1

In Vitro Blood Stage Killing of *P. Falciparum* by Antibodies to the Gene Products, by the ADCI Mechanism 2.A. Materials and Methods: The ADCI Assay
2.A.1. Introduction The Antibody Dependent Cellular Inhibition (ADCI) assay is designed to assess the capability of antibodies to inhibit the in vitro growth of *Plasmodium*, more particularly of *Plasmodium falciparum* in the presence of monocytes. Studies have shown that antibodies that proved protective against *P. falciparum* blood stages by passive transfer in humans are unable to inhibit the parasite in vitro unless they are able to cooperate with blood monocytes. It has also been shown that antibodies that were not protective in vivo had no effect on *P. falciparum* growth in the ADCI assay. The ADCI is therefore an in vitro assay the results of which reflect the protective effect of anti-malarial antibodies observed under in vivo conditions in humans.

The antibodies able to cooperate with monocytes should be obviously cytophilic: IgG1 and IgG3 isotypes are efficient in ADCI while IgG2, IgG4 and IgM are not efficient. This is consistent with the findings that in sera from protected individuals, cytophilic anti-*P. falciparum* antibodies are predominant, while in non-protected patients the antibodies produced against the parasite are mostly non-cytophilic.

The results suggest that ADCI likely involves the following succession of events: at the time of schizonts rupture, the contact between some merozoite surface component and cytophilic antibodies bound to monocytes via their Fc fragment triggers the release of soluble mediators which diffuse in the culture medium and block the division of surrounding intra-erythrocytic parasites.

The major steps of the ADCI protocol are:
(i). Serum IgG preparation using ion exchange chromatography
(ii). Monocyte isolation from a healthy blood donor
(iii). Preparation of *P. falciparum* parasites including synchronization and schizont enrichment.
(iv). Parasite culture, for 96 hrs, in the presence of antibodies and monocytes.
(v). Inhibition effect assessed by microscopic observation and parasite counting.

The ADCI assay is also described in Hasnaa Bouharoun-Tayoun et al. 1995 *J. Exp. Med.* 182: 409-418.

2.A.2. Materials
IgG Preparation
1. Tris buffer: 0.025 M Tris-HCl, 0.035 M NaCl, pH 8.8.
2. Phosphate Buffer Saline (PBS), pH 7.4.
3. GF-05-Trisacryl filtration column (IBF, Biothecnics, Villeneuve La Garenne, France).

4. DEAE-Trisacryl ion exchange chromatography column (IBF).
5. G25 Filtration column
6. Amicon filters and tubes for protein concentration (Mol. Wt. cut off: 50,000 Da).
7. Sterile Millex filters, 0.22 lam pore size (Millipore Continental Water Systems, Bedford Mass.).
8. Spectrophotometer equipped with Ultra Violet lamp.

Monocyte Preparation
1. Heparinized blood collected from a healthy donor, 20-40 mL volume.
2. Ficoll-Hypaque density gradient (Pharmacia LKB Uppsala, Sweden).
3. Hank's solution supplemented with $NaHCO_3$, pH 7.0.
4. RPMI 1640 culture medium supplemented with 35 mM Hepes and 23 mM $NaHCO_3$; prepare with mineral water; store at 4° C.
5. Reagents for non-specific esterase (NSE) staining: fixing solution, nitrite, dye, buffer and substrate
6. 96-well sterile plastic plates (TPP, Switzerland).
7. Refrigerated centrifuge.
8. $CO_2$ incubator.
9. Inverted microscope.

Parasite Preparation
1. RPMI 1640 culture medium (see above).
2. 10% Albumax stock solution; store at 4° C. for up to 1 month.
3. 5% Sorbitol for parasite synchronization.
4. Plasmagel for schizont enrichment.
5. Reagents for fixing and staining of thin smears: methanol, eosine, methylene blue.

2.A.3. Methods

IgG preparation

IgGs are extracted from human sera (see Note 1) as follows:
1. Dilute the serum at a ratio of 1 to 3 in Tris buffer.
2. Filter the diluted serum through a GF-05 Trisacryl gel filtration column previously equilibrated in the Tris buffer. Ensure that the ratio of serum to filtration gel is 1 volume of undiluted serum to 4 volumes of GF-05 gel.
3. Pool the protein-containing fractions
4. Load over a DEAE-Trisacryl ion exchange chromatography column previously equilibrated with Tris buffer. Ensure that the ratio of serum to filtration gel is 1 volume of undiluted serum to 4 volumes of DEAE gel.
5. Collect fractions of 1 mL volume.
6. Measure the optical density (OD) of each fraction using a 280 nm filter.
7. Calculate the IgG concentration as follows:

$$IgG \text{ concentration (mg/mL)} = \frac{OD\ 280\ nm}{1.4}$$

8. Pool the fractions containing IgGs.
9. Concentrate the IgG solution using Amicon filters. Amicon filters are first soaked in distilled water for 1 hour and than adapted to special tubes in which the IgG solution is added.
10. Centrifuge the tubes at 876 g for 2 hr at 4° C. This usually leads to a 25-fold concentration.
11. Perform a final step of gel filtration using a G25 column previously equilibrated in RPMI culture medium.
12. Collect the IgG fractions in RPMI.
13. Measure the optical density (OD) of each fraction using a 280 nm filter.
14. Calculate the IgG concentration.
15. Pool the fractions containing IgGs.
16. Sterilize the IgG fractions by filtration through 0.22 µm pore size filters.
17. Store the sterile IgG solution at 4° C. for up to 1 month (or add Albumax for longer storage—but not recommended—).

Monocyte Preparation

The procedure for monocyte preparation is based on that described by Boyum (*Scand. J. Clin. Lab. Invest.* 1968, 21, 77-89) and includes the following steps:
1. Dilute the heparinized blood 3-fold in Hank's solution.
2. Carefully layer two volumes of diluted blood onto 1 volume of Ficoll-Hypaque (maximum volume of 20 mL of diluted blood per tube).
3. Centrifuge at 560 g for 20 min at 20° C.
4. Remove the mononuclear cell layer at the Ficoll/plasma interface.
5. Add 45 mL of Hank's solution to the mononuclear cell suspension.
6. Centrifuge at 1000 g for 15 min at 20° C.
7. Carefully resuspend the pelleted cells in 45 mL of Hank's solution.
8. Centrifuge again at 1000 g for 15 min at 20° C. Repeat this washing step twice more.
9. Finally, centrifuge at 180 g for 6 min at 20° C., to remove any platelets that remains in the supernatant.
10. Resuspend the mononoclear cells in 2 mL of RPMI.
11. Calculate the mononuclear cell concentration (i.e. lymphocytes plus monocytes) in the cell suspension: dilute a 20 µL aliquot of the cell suspension 3-fold in RPMI and count cell numbers using a hemocytometer (Malassez type for example).
12. Determine the number of monocytes using the Non Specific Esterase (NSE) staining technique:
    (i). In microtube A, add 40 µL of mononuclear cell suspension to 40 µL of fixing solution.
    (ii). In microtube B, mix the NSE staining reagents in the following order: 60 µL of nitrite, 60 µL of dye, 180 µL of buffer, and 30 µL of substrate
    (iii). Add the mixture in microtube B to the cells in microtube A.
    (iv). Take a 20 µL sample of the stained cells and measure the proportion of monocytes:lymphocytes:monocytes will be colored in brown whereas the lymphocytes will be uncolored. Usually the proportion of monocytes is 10-20% of the total mononuclear cells.
13. Adjust the cell suspension to a concentration of $2 \times 10^5$ monocytes per 100 µL, with RPMI.
14. Aliquot the cell suspension in a 96-well plate at 100 µL/well.
15. Incubate for 90 min at 37° C., 5% $CO_2$. During this incubation, monocytes will adhere to the plastic.
16. Remove the non-adherent cells and wash the monocytes by adding, and thoroughly removing, 200 µL of RPMI in each well.
17. Repeat this washing procedure 3 times in order to remove all the non-adherent cells.
18. At least 95% of the recovered cells will be monocytes. Control for the cell appearance and the relative homogeneity of cell distribution in the different wells by observation using an inverted microscope (see Notes 2, 3, and 4)

Parasite Preparation

*P. falciparum* strains are cultivated in RPMI 1640 supplemented with 0.5% Albumax. Parasites are synchronized by Sorbitol treatments as follows:
1. Dilute the sorbitol stock to 5% in mineral water.
2. Centrifuge the asynchronous parasite culture suspension at 1200 rpm for 10 min at 20° C.
3. Resuspend the pellet in the 5% sorbitol solution. This will lead to the selective lysis of schizont infected RBC without any effect on the rings and young trophozoites.

When required, schizonts are enriched by flotation on plasmagel as follows:
1. Centrifuge cultures containing asynchronous parasites at 250 g for 10 min at 20° C.
2. Resuspend the pellet at a final concentration of 20% red blood cells (RBC), 30% RPMI, 50% plasmagel.
3. Incubate at 37° C. for 30 min Schizont-infected RBC will remain in the supernatant, whereas young trophozoite-infected and uninfected RBC will sediment.
4. Collect carefully the supernatant, by centrifugation at 250 g for 10 min at 20° C.
5. Prepare a thin smear from the pelleted cells, stain, and determine the parasitemia by microscopic examination.
6. Usually, using this method, synchronous schizont infected RBC are recovered at ~70% parasitemia.

For the ADCI assay, synchronized early schizont parasites are used. Usually the parasitemia is 0.5-1.0% and the hematocrit 4%.

The ADCI Assay
1. After the last washing step, add in each monocyte containing well:
    (i). 40 µL of RPMI supplemented with 0.5% Albumax (culture medium).
    (ii). 10 µL of the antibody solution to be tested. Usually the IgGs are used at 10% of their original concentration in the serum (~20 mg/mL for adults from hyperendemic areas, and ~12 mg/mL for children from endemic area and primary attack patients). (see Note 5).
    (iii). 50 µL of parasite culture, at 0.5% parasitemia and 4% hematocrit.
2. Control wells consist of the following elements:
    (i). Monocytes (MN) and parasites with normal IgG (N IgG) prepared from the serum of a donor with no history of malaria.
    (ii). Parasite culture with IgG to be tested without MN.
3. Maintain the culture at 37° C. for 96 hrs in a candle-jar (or a low $O_2$, 5% $CO_2$ incubator).
4. Add 50 µL of culture medium to each well after 48 and 72 hrs.
5. Remove the supernatant after 96 hrs. Prepare thin smears from each well, stain, and determine the parasitemia by microscopic examination. In order to ensure a relative precision in the parasite counting, a minimum of 50,000 red blood cells (RBC) should be counted and the percentage of infected RBC calculated (see Notes 6 and 7).
6. Calculate the specific Growth Inhibitory Index (SGI), taking into account the possible inhibition induced by monocytes or antibodies alone:

> SGI=100×(1−[Percent parasitemia with MN and Abs/Percent parasitemia with Abs]/[Percent parasitemia with MN+N IgG/Percent parasitemia with N IgG])

2.A.4. notes
1. IgG preparation from sera to be tested is an essential step because a non-antibody dependent inhibition of parasite growth has frequently been observed when unfractionated sera were used, probably due to oxidized lipids.
2. Monocyte (MN) function in ADCI is dependent upon several factors such as water used to prepare RPMI 1640. Highly purified water, such as Millipore water, although adequate for parasite culturing, leads to a poor yield in the number of MN recovered after adherence to the plastic wells. On the other hand, water which contains traces of minerals, such as commercially available Volvic water, or glass-distilled water, provide consistently a good monocyte function.
3. Improved monocyte adherence can be obtained by coating the culture wells with fibronectin i.e. coating with autologous plasma from the MN donor, followed by washing with RPMI 1640, prior to incubation with mononuclear cells.
4. MN from subjects with a viral infection (e.g. influenza) are frequently able to induce a non IgG dependent inhibition of parasite growth. This non-specific inhibition effect could prevent the observation of the IgG-dependent inhibition in ADCI. Therefore, MN donors suspected of having a viral infection, or who have had fever in the past 8 days, should be avoided. The results from ADCI are not reliable when the direct effect of MN alone is greater than 50% inhibition. The preparation of MN in medium containing heterologous serum, such as FCS, results in the differenciation of MN, their progressive transformation into macrophages which have lost their ADCI promoting effect.
5. If required, murine IgG can be tested in ADCI with Human MN. The IgG2a isotype is able to bind to the human Fc γ receptor II present on monocytes shown to be involved in the ADCI mechanism.
6. A possible variation of the ADCI assay is the assessment of a competition effect between protective cytophilic antibodies (adults from hyperendemic area) directed to the merozoite surface antigens, and non-protective antibodies (children from endemic area and primary attack patients) which recognize the same antigens but are not able to trigger the monocyte activation because they do not bind to Fc gamma receptors. Therefore non-cytophilc Ig directed to the "critical" antigens may block the ADCI effect of protective antibodies. Each IgG fraction should be used at 10% of its original concentration in the serum.
7. The ADCI assay protocol can be modified and performed as a two-step ADCI with short-term activation of monocytes according to the following procedure:
    (i). Incubate MN for 12-18 hrs with test Ig and synchronous mature schizonts infected RBC, at 5-10% parasitemia. During this first culture time, infected RBC rupture occurs and merozoites are released.
    (ii). Collect supernatants from each well and centrifuge them at 700 g.
    (iii). Distribute the supernatants in a 96-well plate, at 100 µL/well
    (iv). Add to each well 100 µL of *P. falciparum* asynchronous culture containing fresh medium, at 0.5-1% parasitemia, 5% hematocrit (particular care is taken to reduce to a minimum the leucocyte contamination of the RBC preparation used for this second culture).
    (v). At 36 hr of culture, add 1 mCi of $^3H$ hypoxanthine to each well.
    (vi). At 48 hr of culture, harvest cells and estimate $^3H$ uptake by counting in a liquid scintillation counter.

Example 2

Structure

The unfolded or unstructured 3D-arrangement of the P27A polypeptide is illustrated by FIG. 5.

Life Cycle Stage of Expression

The protein PFF0165c/MAL6P1.37 (Pf27) investigated by Villard et al (Plos One 2: e645) is predicted to be expressed during the blood stage of *Plasmodium falciparum* infection (PlasmoDB). Indeed, human affinity-purified antibodies and murine antibodies induced by immunization against P27 and P27A specifically stain *Plasmodium falciparum*-infected erythrocytes, but not sporozoites (FIG. 2).

Figure 3:
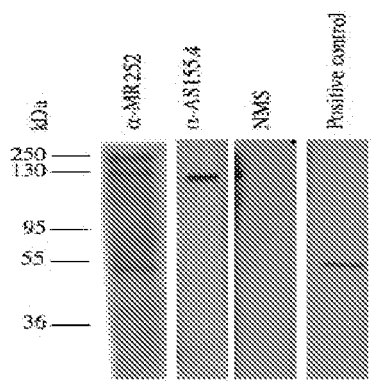
FIG. 3: Western blots of lysates of infected erythrocytes (human affinity-purified antibodies and murine antibodies induced by immunization against P27 and P27A).

In Western blots of lysates of infected erythrocytes (FIG. 3), these antibodies also reacted specifically with a protein of the expected molecular weight (about 130 kD), as well as with a small number of bands of lower molecular weight, which may represent degradation products.

Accessibility

Immunofluorescence staining of *Plasmodium falciparum*-infected erythrocytes by human affinity-purified antibodies against P27 and P27A, and also antibodies induced in mice against P27A and P27, is localised to cytoplasm and the periphery of infected erythrocytes. However it is not co-localized with the Maurer's cleft associated histidine rich protein (MAHRP) (FIG. 2).

Protein Function

The biological and biochemical functions of the malaria protein PFF0165c (Pf 27) are still unknown and have not been investigated in the course of our preclinical studies.

In Vivo Protection

Detailed immuno-epidemiological studies show that cytophilic human antibodies strongly correlate with acquired clinical protection from malaria.

In Vitro Inhibition

Human affinity-purified antibodies specific for P27 and P27A, as well as murine antibodies induced by immunization were extremely potent in the ADCI assays (i.e., as active as purified immunoglobulin pool prepared from sera of adults living in malaria-endemic areas) (Villard et al., Plos One 2: e645).

Results are normalized with respect to the Pool of Immune African Globulins (PIAG; cf. Hasnaa Bouharoun-Tayoun et al. 1990 J. Exp. Med. 172: 1633-1641), which is used as a reference showing 100% activity.

The results are as follows:

with immunopurified human antibodies (final concentration of 15 µg/mL): for P27, the SGI is of 106%, and for P27A, the SGI is of 80-85%;

with the sera from immunized mice:

for P27, with ICR mice, final titer of Indirect Fluorescent Antibody (IFA) in the well at ¹/₄₀, SGI=100%;

for P27A, with C3H mice, final titer of Indirect Fluorescent Antibody (IFA) in the well at ¹/₂₀, SGI=92%;

for P27+P27A, with C3H mice, final titer of Indirect Fluorescent Antibody (IFA) in the well at ¹/₄₀, SGI=120%.

Diversity (e.g. Sequence and Antigen Diversity (Minimal Sequence Variation))

Genetic diversity of P27 and P27A was assessed by using in vitro cultured strains and field samples of Pf from two malaria endemic areas. PCR primers were designed for amplifying the two regions within Pf27 corresponding to P27 and P27A. Nucleotides were aligned to screen for polymorphism within the sequences corresponding to the two peptides.

```
P27 forward primer:
TCTCTTCTACATACGCTTTATTCA        (SEQ ID NO: 55)

P27 reverse primer:
GATAATTCGTTTAATGAGGAGTCCA       (SEQ ID NO: 56)

P27A forward primer:
ACACTTTGCACAGTTCCTATCTTCTCTTCTA (SEQ ID NO: 57)

P27A reverse primer:
AGAAGGAGAAGAAGAAAATAAAGAGGATGAAG (SEQ ID NO: 58)
```

P27—No polymorphism whatsoever was observed in 46 Tanzanian blood samples, 17 samples from Papua New Guinea and 8 in vitro culture strains.

P27A—shows limited polymorphism with essentially a single SNP (E292G, see preceding Section) being distributed worldwide and reaching a high prevalence (6/19 samples from Papua New Guinea—frequency 0.31, 38/63 samples from Tanzania-frequency 0.6, and 4/11 isolates from PlasmoDB. This gives an overall frequency of 0.52). Two additional SNPs in P27A were each only observed in one isolate from PlasmoDB by microarray, a technique prone to false positives (Kidgell et al. PLoS Pathog. 2006, 2:e57).

Orthologs of Pf27 are found in other species of *Plasmodium—P. vivax, P. knowlesi, P. chabaudi, P. yoelii* and *P. berghei* (PlasmoDB).

Seroepidemiological Data

Below are the antibody prevalence* and mean OD measured by ELISA of individual endemic-area sera against P27 and P27A (Villard et al., cited supra).

*percent of donors whose serum gave an OD value in ELISA exceeding mean OD+3 standard deviations of negative controls (naïve European donors).

TABLE 2

|  | Burkina Faso (N = 37) | | Tanzania (N = 42) | |
| --- | --- | --- | --- | --- |
|  | % prevalence | Mean OD | % prevalence | Mean OD |
| Peptide 27 | 54 | 0.265 | 69 | 0.237 |
| Peptide 27A | 76 | 0.673 | 76 | 0.688 |

IgG1 and IgG3, known to be associated with antibody-dependent cellular inhibition and protection against intracellular organisms, are the predominant IgG subclasses in the anti-peptide antibodies.

Further studies were performed among inhabitants of Dielmo, Senegal. The first study involved 45 individuals among whom 22 had no malaria attacks during 3-year of follow-up period and 23 had one or more malaria attacks during the same period. Both have the same age-distribution.

These results were confirmed among 102 Ndiop inhabitants while also adjusting for age and occurrence of malaria attacks.

Figure 4:
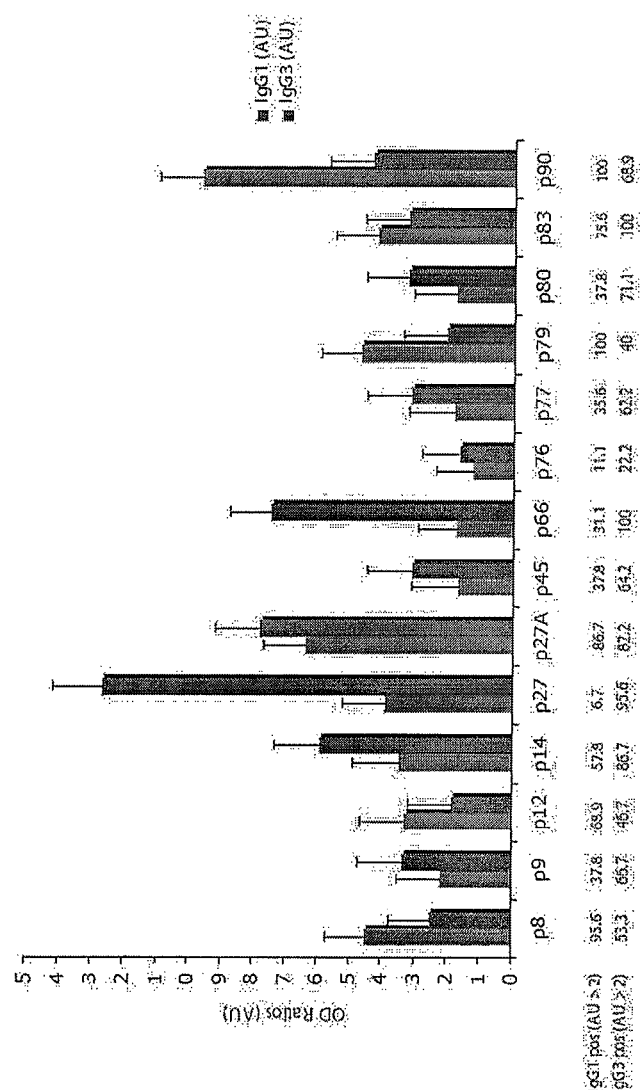
FIG. 4: prevalence of cytophilic IgG subclass and association with protection were studied against the 14 initial peptides/genes selected. IgG1=left column (in red); IgG3=right column (in blue). Geometric means, 95% confidence intervals and prevalence of anti-peptide antibody responses determined in the village of Ndiop.

The prevalence, cytophilic IgG subclass and association with protection were studied against the 14 initial peptides/genes selected (FIG. 4). Please see the prevalence values indicated below the diagram of FIG. 4: the total proportion of individuals responding by IgG1 and IgG3, i.e., the most critical IgG subclasses, is higher for the polypeptide of the invention P27A (IgG1: 86.7%; IgG3 82.2%) than for the prior art peptide P27 (IgG1 6.7%; IgG3 95.6%). Indeed, the proportion of individuals responding by IgG1 is drastically higher for P27A (82.2%) than for P27 (6.7%). The peptides of FIG. 4 are shown in Table 5 below.

TABLE 5

| N° Parmed | N° GPC | Name of the gene in PlasmoDB | |
|---|---|---|---|
| p14 | 27 | MAL6P1.37 (PFF0165c) | Predicted Protein Sequence of 1103aa (in underlined characters: fragment of the protein corresponding to peptide 27)<br>MSNKKRSKNENDESTSLPLENSELLIEYIHNLKSCLNVYRREIQEKNKYISIIKNDLSFH<br>ECILTNVNVVWSVFNNDLLNLLCNNEQKEEGEEIIKQRNIGDEINEYNNLTKLQNDENIK<br>NNNMIKEDLEDDANQNILMKSPYYNIENFLQVFLKYINKKKKVKVKVKDEGKKEKIEDK<br>KYEQDDEEENEEEEEEEEEEGEEENKEDEEFFKTFVSFNLYHNNNEKNISYDKNLVKQE<br>NDNKDEARGNDNMCGNYDIHNERGEMLDKGKSYSGDEKINTSDNAKSCSGDEKVITSDNG<br>KSYDYVKNESEEQEEKENMLNNKKRSLECNPNEAKKICFSLEEKIGTVQSVKLKEYNELS<br>KENIEKNKHDDNNICNYLSHNEGENVIEREDKLFNKLNNKNYRNEEEKKKNQINFDYLKK<br>KIKNNQDVFEETIQKCFLINLKKTLNLINKIMYLKNVEFRKYNLDYIRKINYEKCFYYKN<br>YIDIKKKISELQKDNESLKIQVDRLEKKKATLIYKLNNDNIRKHILDNNIKDYQNGIDNS<br>KVSYFDEGENPYNRNNKNYRTDNKNSDDNNNNNNYYYNNYNSDDNYNSEDNEYNNGNYRF<br>RNNYKKDSLNEDDVKKNPLKVCHKINSDSNIFVNFENIITKQNIIHSEPFRNLLKESNEL<br>YITLKEKEKENIILKNEILKMENKDEEYEHLLNNTIEDKKELTRSIKELEINMMTCNME<br>KDKISNKVNTLEYEINVLKNIDKNQTMQLQQKENDILKMKLYIEKLKLSEKNLKDKIILL<br>ENEKDKMLSGIHIKDNSFNEESKSEEGKIQLRDIQNDNDEKYDDEKKRFKELFIENQKLK<br>EELN<u>KKRNVEEELHSLRKNYNIINEEIEEIT</u>KEFEKKQEQVDEMILQIKNKELELLDKFN<br>NKMNKAYVEEKLKELKNTYEEKMKHINNIYKKHDDFVNIYLNLFFQARKNAILSDSQREE<br>QMNLFIKLKDKYDIIFQKKIELTDILKNVYDCNKKLIGHCQDLEKENSTLQNKLSNEIKN<br>SKMLSKNLSKNSDDHLLIEENNELRRRLICSVCMENFRNYIIIKCGHIYCNNCIFNNLKT<br>RNRKCPQCKVPFDKKDLQKIFLD<br>(SEQ ID NO: 27)<br>p27: KKRNVEEELHSLRKNYNIINEEIEEIT<br>(SEQ ID NO: 28) |
| p27A | 27A | MAL6P1.37 (PFF0165c) | Predicted Protein Sequence of 1103aa (in underlined characters: fragment of the protein corresponding to peptide 27A)<br>MSNKKRSKNENDESTSLPLENSELLIEYIHNLKSCLNVYRREIQEKNKYISIIKNDLSFH<br>ECILTNVNVVWSVFNNDLLNLLCNNEQKEEGEEIIKQRNIGDEINEYNNLTKLQNDENIK<br>NNNMIKEDLEDDANQNILMKSPYYNIENFLQVFLKYINKKKKVKVKVKDEGKKEKIEDK<br>KYEQDDEEENEEEEEEEEEEGEEENKEDEEFFKTFVSFNLY<u>HNNNEKNISYDKNLVKQE<br>NDNKDEARGNDNMCGNYDIHNERGEMLDKGKSYSGDEKINTSDNAKSCSGDEKVITSDNG<br>KSYDYVKNESEEQEEKENMLNNKKRS</u>LECNPNEAKKICFSLEEKIGTVQSVKLKEYNELS<br>KENIEKNKHDDNNICNYLSHNEGENVIEREDKLFNKLNNKNYRNEEEKKKNQINFDYLKK<br>KIKNNQDVFEETIQKCFLINLKKTLNLINKIMYLKNVEFRKYNLDYIRKINYEKCFYYKN<br>YIDIKKKISELQKDNESLKIQVDRLEKKKATLIYKLNNDNIRKHILDNNIKDYQNGIDNS<br>KVSYFDEGENPYNRNNKNYRTDNKNSDDNNNNNNYYYNNYNSDDNYNSEDNEYNNGNYRF<br>RNNYKKDSLNEDDVKKNPLKVCHKINSDSNIFVNFENIITKQNIIHSEPFRNLLKESNEL<br>YITLKEKEKENIILKNEILKMENKDEEYEHLLNNTIEDKKELTRSIKELEINMMTCNME<br>KDKISNKVNTLEYEINVLKNIDKNQTMQLQQKENDILKMKLYIEKLKLSEKNLKDKIILL<br>ENEKDKMLSGIHIKDNSFNEESKSEEGKIQLRDIQNDNDEKYDDEKKRFKELFIENQKLK<br>EELNKKRNVEEELHSLRKNYNIINEEIEEITKEFEKKQEQVDEMILQIKNKELELLDKFN<br>NKMNKAYVEEKLKELKNTYEEKMKHINNIYKKHDDFVNIYLNLFFQARKNAILSDSQREE<br>QMNLFIKLKDKYDIIFQKKIELTDILKNVYDCNKKLIGHCQDLEKENSTLQNKLSNEIKN<br>SKMLSKNLSKNSDDHLLIEENNELRRRLICSVCMENFRNYIIIKCGHIYCNNCIFNNLKT<br>RNRKCPQCKVPFDKKDLQKIFLD<br>(SEQ ID NO: 29)<br>p27A:<br>HNNNEKNISYDKNLVKQENDNKDEARGNDNMCGNYDIHNERGEMLDKGKSYSGDEKINTS<br>DNAKSCSGDEKVITSDNGKSYDYVKNESEEQEEKENMLNNKKRS<br>(SEQ ID NO: 30) |
| P3 | 14 | PFC0245c | Predicted Protein Sequence of 3933aa (in underlined characters: fragment of the protein corresponding to peptide 14)<br>MIKKSEESKRLLRKKLNNDITNILLLFEKVQEWADLSNILQKLYLTIEKYELFVNVSSKF<br>LLFRRLSQCLNPLLPSGVHSKALIIYSSIFKKVEMDFFINNIHILCSGIFEFMLHCTINL<br>KTIYFKNIKSILRLKENVYIFAYALLLSLFNVVDSDNNILLYIYSINNYIGENIFFNNIW<br>LLLLRHPEIRTNILNFLEASFSPQIYLLSKERIKMLLPYKDHLVLSSIIYCLNDKNILNQ<br>RITLSLLINNFPLSHVPNKKNKKKIIDKSKSNDYHMDKPPYSPFNASTSSVILNNSNMDS<br>MNDNRINENNINNNDNKRHNIQINNDYLFGDMMNKQNDTTIMQSNKMLNRHNIIGEQHLD<br>DDLLSSIHDDNSEKKNNNNFMLLNENNKISTSKEHLDNMHNRGIKSHEDIMGSNQNKMNL<br>SNDEKDHWGGNLNSKVGNYDDKNICGKKHLGLKSEYGQVSYDESLERRLNNNNNNNNNNN<br>NNNNNNGDNLKYQGSVDYDEHDISMSTENDKYGKMGNENMNDVFISKGKMMRKGYEDDGH<br>HHINDDDNLNYDDNEDDEYGNYHNNNYNDRNYFNEYDEDDQYENNNNNNHSNNNNMLH<br>LGSVDRNRRKQLKKKINNIGQTNNYDDDEEEEDEEEEDNNNNTSYNNNNNNSSSSSSIFF<br>SDTSKKLIARNVIFLLKKSDIGLNRRIFKYLYLYESNDEKNFKDKEINFENYKIYCETII<br>DILENKSDDYNYSIAEVIYILFKNKDYININRYIMEQVFLYLLNFCYKNREDTSIKSFLK<br>NMLNLNLISYENILNIFLYTFYYLRRNDDLFVHYTNIYIKKYINLLNIMTFFVEFIKHMN<br>KYLYIQFLFHFNLATLKLMNFLNLKIINIIKKYSHVKDLNEKYFIDSNDVVSGRHSTLYY<br>FYFFVTHYNNYYLNKCLSIIVKDILPQNPSNRKMGNYQSHYYANNKHMLYMNTHEIHSAR<br>MEEYSNKIQKVGFKNEIVDRKNKYDNNEYSESEIKMRAVDNSMNYIKRKVKKKNMESKDS<br>SNSMSNMEINTNSTMANRLNHMQHIQHDGISSMEHMNNKINDNNNNNVNYFFDGNNSNN<br>NNNNNILENNNKLYFDKGYNGNYSKIENDQSFHNILMKYKFKLKQNLIDAIIKNHELYFF |

TABLE 5-continued

| Nº Parmed | Nº GPC | Name of the gene in PlasmoDB | |
|---|---|---|---|
| | | | TNNCEYIIFLFYNYHLLIEKEKLNKSCFYFLKNILNNCTCENKNKFYFWCFLFLHIIRIN
FNKSLLKNYKIKEAGDDTDDDDDDDDDDEEEDDDDEDDDDEDDEEEDDEEDLGVDGLK
NMSSKKGKKKKKKSVHKNKLMNKKYGRGGSSKYYYYLTSDKEIMLHGGMMGGVNYSDMEH
DEDNLDVDDEDEQMFSYNKNKIRNKHFGELNKMKYMNEDITNNNNNINNNSNNNNNNKNN
INNNNNNNNNNNNNNNNNLNNLNNFNNNVSINNGNNKYRNYFRSTEEELLFNKRFVEFLLP
YSNNIAKYIFQYIKILKKNKKFIKLFFDINYLYFFCDNMFCLKILKKSLKCKDNHELTIN
VKVILEYIINSKTNEYHIIHSNFYNLTHDVFKLYNRRNNLINYYLIKYIMRNKENLSYIF
DNIIISMFDLITEIENLYEKIEMMKKDLSYSMMNNNDHVYDPNGMIEAADQRKSHYVSLK
DNMNNMNNMNNVNNMNNVNNMNNVNNNVNNVNYHNNTINNNNNNNNFSNHTSYVNEKT
QENNYHNLMNTYEKYLKKLKCKFDYISYFFLNMENFMLWLYKHKISKKIYHSRNKMTLTN
YEKNMAIIICYICTEGNINSFFFRNYLDVFFILFLKIIYLNENISELNNSANNIIQKEKN
NLKHNSLLEFKRDTLSMLNNIFNINHNKKFEYMKILNLYYRQIIHHLLFLYYYFTVKKYY
VLQLQLVHFIRYILPLYEKNIDKKFLTNESTEKDKVFKRMKYNNYEEFISASKYHFEIIN
RNNYNMKNDVFIFSILRKSMTIIFNLNEQVLYKEVLKTIIDLIENIIDEKEVKNYYLTVF
FLDLLYIIKMEDQKKKKNIFFIMKFCQFLIEIFKLIYRDEMKNELKCDKKFQDDNITIDI
IENALSNNKMSTASFCTIFSIKTDDKFVNVQHKNISNLFSVIFNLYAFLKKKIKLYYKHN
KHLINNDDKNNVVNNNSYIYYDNNSNVYNNNNTNIYNNNNNNENNAFNNNMPNNSNIMNN
MNNMNDIYHISQHTNNNIRYNDVSSCGARGHNINSNENVNQNDLNNNSNYNYNRGMNNMN
GDINNINGDINNMNGDINNMNGDINNMNGDINNMGDINNMGGNFKNPNSYNNNNNMNS
YYSHNSSDYHKDNDNMRNNVNSSNSNFHNNNQDVQIMNRKNDSDGNVGNFDNNSTYSYMN
NVNNDISMRLTNINNNNNINIINNNNNNNNNLFAYNKNNPNALVNNMNNQDKPDQHNNSHQ
YMYKENDMNQFGNSNYNNMDNTNNKFYNNYNYGKNVEGHTIYDNNNNNNNSNNGAVNIN
SVQGENNVMSRNNILFNHNVNNNEYYFSQKNEDNMASMNNNHHNNYHNNNNNHHNNNINN
HHNNNINNHHNMNRNNNIYSEDSKTNECYSMREKMGDVNVAYNSNFYDDKNNYTHMKNDL
IKNEQKNNYGFCNNHENTFIYNCKNRMNRNNYAFNMGSKKNKKIMLLKVCLSNIISINKL
LYFITRPEFLFIDNLYSIFKDYIKNRNEYNKERLSKSDYYYEQREKLYKEHRRKMNRQNI
RTDSSNNNNNNNINSNNNNNNNNNNNNNNNNNNNNNIYNNNNYYYSSSINKVSFDDDEKI
EVESFLDHNGVVGSNKKIKREKIREYFKKEKNLLKKLNFMTKFSKNTIKKSMIVMNNSDE
CIEKKKLSFSLTLLTEFDDVILIKIIDDLLNYYEKYKSKINLNEFMYFLFNIYLNICTLT
KRIINHFIDFIFSFIKKITQTSQNIMSSLWFLYILFIIENNHIYVFNDKLQKKIIVEQIS
ILIQISLYSYYSKNVKNNYNIQTPLPNFVQPFNIYYIIQNYFINNNYFHIKKNNKNIRYF
YIKNLKLIEKNFNINDYSEIAAINALSFLLMCFYHTVNYNGTNKSYICESSVNIFYEHFS
KYISLIYNNSLQNIFYRYVFLLIMNLLIDYNANSKYYIKKITFDLYSYITNVDIRCIKAL
STLFKKLNETNIDELLLVPTSSIFSLKFNIINSRINYINKLSLIILAGNRNFYLCHLPKI
AENISEYIKFCNDLKLYREILILICIIIIKNDENEIYIIPTFISLILQIYHVERIKYKM
AVENINNIDKDDDNYIYDFNSYNNKDVLSLLKTLLIIINILIKRNVSFINFYSWIFFKDI
SIKKNRLEQQNREPGNLMIYPGHKTLVYNNKKKKQKNVVRYVSSSSDKDESSVYNISVDE
ENSLKTQGRFFDDTYYKRKDNSGYTNKMKNFNSLTYEDKSSLMTGNQTSSTKDVGGMVNN
AIRQNIEQNNMIHPNQINNNNNNNNNNNVYNFNDFTNSMNQPNVINNNKKKKAFTTDDY
FVKYDENQKVTKQTKLNHHNEDNLNDTITVYLNSNQEDYLYESKNNFTSIRSEHISSMVD
IKKGSILNSNNILTNDNNTNNNIHSNIHNGSSSNNNNNNNSVCTGIKLDESKFVPFLDII
ERIYSPNNILNKKYVSSEELKNEKSTRTYNSSLQEGSDYDEEEDEEYDVDADVDVDVDVD
DDDDDDVDIVDVDVDDVVVDYNYYDNENNSVKIIDVDERKRSVHFYPQHLDGNTLKKNLY
YNDNYLREYILSTKNELSGYSSFENNLSSSSVNSIKSNFSNTFSKDNINKNIITDDTSDD
NDMMNSNNNMNSMMVPYNMHMTDDEFQENINNNNNNNNNNDNMYLSSDDGYPSQSNHKW
IHFNSLLNYDIHELSKKKKKKKKKISIHSCKNLPLVLVYLSKKIKLNFYKYSMKKPKEET
IILLKELNSVENDINDLFLEVDLNEVYYDFLIR
(SEQ ID NO: 31)
p14: GMNNMNGDINNINGDINNMNGDINNMNGDINNMNGDINNMN
(SEQ ID NO: 32) |
| p13 | 66 | PFL0250w | Predicted Protein Sequence of 781aa (in underlined characters: fragment of the protein corresponding to peptide 66)
MSYNDGSEEENDSNTYIPDEKKKKKKKNNKNAYALINEVNYSQEDEQEVIHNTNSEDETS
NRKGNGCVYSLSDQNVEDHIISLPEYLDLINNNNNNSNSYKMKKEKKKKKKKKKNQTDEE
NMKNKKDHIYQNNITNQQNDIKNDYKKINHHNMNNKKNKIFCQDDQNIFNINHTFQIHET
VQNNLIIPPSETCLASDIIQPSDTTQSNTYLNEATASQNDDNNNEDSSNEMGMFKKIFYR
IKKIIVDKKGTPITNENDVDNDMCELNVMENNMNNIHSNNNNISTHMDDVIEDESNEEVF
VINRNTDGYINTRENINVSTHVTRQMINLSELNPNDLLCNVSEYEEGQNINSLWNDNNNN
NNNNNNFLVGSLNALHPINHNLRNENIHNDNINNTHINYDNNNSYESPIHILSFSPKNI
YNKISSYINEHITHIKEKIKKYWLERVQEANTQLNSPRPVHTRNTTNINTNIININEDND
DPSCVQILFFMGLICKFPILWIIGSIVFCITPSEHRKTKTWSLVNTFFALLSIIYFITTT
NFRLRKPTFFVILEQNVENKNTYPKGILKYNNMIHHKHIIDQSSLHKWKDLHTNKVYKT
SENYFLNRNFLSSQKPDSNILLSDTIYKLLNRIQVTVTFGKGNIYSSDNIEKIKPFFQNL
RINMDPISYDKLTMTDEDIPDDFFGSGLRCERTYNNHNQNINEPQQNKEKEKWYLFWKEE
EINNSHNKNIYNISIPVGEIFFFKSEYNCRIAFLYPKSILYDQNDIPSNFVEIQKIIIKP
F
(SEQ ID NO: 33)
p66: MCELNVMENNMNNIHSNNNNISTHMDDVIE
(SEQ ID NO: 34) |

TABLE 5-continued

| N° Parmed | N° GPC | Name of the gene in PlasmoDB | |
|---|---|---|---|
| p8 | 9 | PFB0145c | Predicted Protein Sequence of 1979aa (in underlined characters: fragment of the protein corresponding to peptide 9)<br>MVFTFKNKKKKKEASSDKVSKESFNEEDNENNEKREKSDSWYKKIIETKGKSKTKYKNDN<br>SLDDNINEDIINNNNNNNDNNNDNNNDNNNDNNNDNNNENNNDNNNFNNYSDEIS<br>KNIIHKDNELENQLKDTLKSISSLSNKIVNYESKIEELEKELKEVKDKNIDNNDYENKLK<br>EKEDFVKQKIDMLNEKENLLQEKELDINKREKKINEKEKNIIKKEETFHNIEKEYLEKNK<br>ERETISIEIIDIKKHLEKLKIEIKEKKEDLENLNKKLLSKENVLKELKGCVKEKNETINS<br>LNDNIIEKEKKYKLLEYELEEKNKQIDLLNKQEKEKEKEKEREKEKEREKEKEYDTLI<br>KELKDEKISILEKVHSIKVREMDIEKREHNFLHMEDQLKDLKNSFVKNNNQLKVYKCEIK<br>NLKTELEKKEKELKDIENVSKEEINKLINQLNEKEKQILAFNKNHKEEIHGLKEELKESV<br>KITKIETQELQEMVDIKQKELDQLQEKYNAQIESISIELSKKEKEYNQYKNTYIEEINNL<br>NEKLEETNKEYTNLQNNYTNEINMLNNDIHMLNGNIKTMNTQISTLKNDVHLLNEQIDKL<br>NNEKGTLNSKISELNVQIMDLKEEKDFLNNQIVDLSNQIDLLTRKMEEKENKMLEQENKY<br>KQEMELLRGNIKSSENILNNDEEVCDLKRKLSLKESEMKMMKEEHDKKLAELKDDCDVRI<br>REMNEKNEDKINMLKEEYEDKINTLKEQNEDKINTLKEQNEDKINTLKEEYEHKINTMKE<br>EYEHKINTLNEQNEHKINTLNEQNEHKINTMKEEYEDKMNTLNEQNEDKMNSLKEEYENK<br>INQINSNNEIKIKDVVNEYIEEVDKLKVTLDEKKKQFDKEINYAHIKAHEKEQILLTEME<br>ELKCQRDNKYSDLYEKYIKLIKSICMIINIECCDDIENEDIIRRIEEYINNNKGLKKEVE<br>EKEHKRHSSFNILKSKEKFFKNSIEDKSHELKKKHEKD<u>LLSKDKEIEEKNKKIKELNNDI</u><br><u>KKL</u>QDEILVYKKQSNAQQVDHKKKSWILLKDKSKEKIKDKENQINVEKNEEKDLKKKDDE<br>IRILNEELVKYKTILYNLKKDPLLQNQDLLSKIDINSLTINEGMCVDKIEEHILDYDEEI<br>NKSRSNLFQLKNEICSLTTEVMELNNKKNELIEENNKLNLVDQGKKKLKKDVEKQKKEIE<br>KLNKQLTKCNKQIDELNNEEVEKLNNENIELITYSNDLNNKFDMKENNLMMKLDENEDNIK<br>KMKSKIDDMEKEIKYREDEKKRNLNEINNLKKKNEDMCIKYNEMNIKYGDICVKYEEMSL<br>TYKETSLKYEQIKVKYDEKCSQYDEIRFQYDEKCFQYDEINKKYGALLNINITNKMVDSK<br>VDRNNNEIISVDNKVEGIANYLKQIFELNEEIIRLKGEINKISLLYSNELNEKNSYDINM<br>KHIQEQLLFLEKTNKENEEKIINLTSQYSDAYKKKSDESKLCGAQFVDDVNIYGNISNNN<br>IRTNEYKYEEMFDTNIEEKNGMHLSKYIHLLEENKFRCMKIIYENENIKSSNKIIGLYNY<br>SRYYGLREDLCKEEIVPSKIGNISNKNENNNKKNNTCDGYDEKVTIVLCIILNEIIKFLF<br>LNDEYVLLFEKIHKNVWKRMYIPEEIKFFILKYITLLNNLRDYIISVHNNMKNEKYDECW<br>FLFQHYFERSSDVRKEMVHFLLERKSQENLISFKSKLKSKKEKILTMDILNFSKEHMQLK<br>TIAHLRKEINYEKLSKDTLNRDYNLLLYKYQECVSKLKRVKNLMKEINQNVFIEKYDDIS<br>KELDNFSDGYNEQNEQHVMDPILLNNNKNKNNKLITEHNNPIINRLTNFTQNRDSKYKNK<br>IMDDVKQRKINSTMNNTNKNGINIIYNHYENLNKPNYNDNINRLNSYHQNIHIANSIHPN<br>RNQNKSFLTNQANSTYSVMKNYINSDKPNLNGKKSVRNIFNEIVDENVNKTFVHKSVFF<br>(SEQ ID NO: 35)<br>p9: LLSKDKEIEEKNKKIKELNNDIKKL<br>(SEQ ID NO: 36) |
| p15 | 45 | PF11_0207 | Predicted Protein Sequence (in underlined characters: fragment of the protein corresponding to peptide 45)<br>MAKKKQIHLNIIDFQKYYQTDDLLLDTSISTEKKTVDNQKFIRKNRTLEKDEVVQNIDW<br>RTFDNEKEKETNNENTSNVNKIKSPGLEKKNFKKSNDVITLGARNKNKSTNLNADDIDFT<br>NLRNKKKEDDIDFTNLRNKKKEDDLDFSNLRNKKKEEEDVDFSNLRNKKKEDDVDFSNVR<br>NKKKEDDLDFSNVRNKKKEDDVNFSDVRNKKKEDDLDFSNVRNKKKEDDVNFSDVRNKKK<br>EDDLDFSNVRNKKKEDDVNFSDVRNKKKEDALDFSNVRNKKKEDDLDFSNVRNKNKEDDM<br>DFSNVRNKKKEDDLDFSNVRNKKKEDDLDFSNVRNKKKEDDLNFSNVRNKKKEDDLDFSN<br>VRNKNKEDDMDFSNVRNKKKEDDMDFSNVRNKKKEDDLDFSNVRNKKKEDDLDFSNVRNK<br>KKEDDLDFSNLRNKKKEESKENDTNKSEKPLYLRRLEEYRKKKKLESQANDTAMKMHEKE<br>QIDDIQERKEEIKEEFKEEVKEEIKEIKEEIKEVKEEIKEEIKEEIKEVKEEI<u>KEEIKEE</u><br><u>IKEVKEEIKEVKEEIKEVKEEIKEE</u>IKEVKEEIKEEIKEEIKEVKEEIKEEVK<br>EEIKEVKEEIKEVKEEIKEVKEEIKEVKEEIKEVKEEIKEVKEEIKEEIKEVKEEIKE<br>EIKEIKEELKNDISSETTKEEKNTEHKKEETEKKKFIPKRVIMYQQELKEKEERNLKLLE<br>QQRKEREMRLQLIRSKTQGTSSTFIPSAKLKHLESLKEEKKKEVKTNIQPKDNNNNNNNN<br>NNNNNNIAVLKNNKNEEQNVIKKKSIFLEIAEKTENAKIVEKTDIEEIAKKKREELYKKQ<br>LEKITKKNEEHLKYNNIYKHDVNIIKNFYNEIKDKIIQNYYFNQDDCISLCSILKTDDCN<br>YMESHVPFYVVISIFMLSLPQKLQNDDYFKRASNIKNLLIYLKEVQFYPYKVKISTLIRR<br>NIIN<br>(SEQ ID NO: 37)<br>P45: EEIKEEIKEVKEEIKEVKEEIKEVKEEIKEVKEEIKE<br>(SEQ ID NO: 38) |
| p25 | 90 | PFD0520c | Predicted Protein Sequence of 213aa (in underlined characters: fragment of the protein corresponding to peptide 90)<br>MRHKISENEIINKIDSINLKEVKDASACMNNYTNFISIKLKKNREGIIHSIQRIKHLEGL<br><u>TKKLNKELSEGNKELEKLEKNIKELEETNNTLENDIKV</u>EMNKGNLYKSRLALLKKNKVRI<br>SKAQEIIDKDIIYMKSRINIMRENADKNNQKYDKIVSQKDKMHQEMEKFKKDRKNLQLNL<br>KNTRKNHEFLKNKMQNLVLTMKKSTADDKRFQY<br>(SEQ ID NO: 39)<br>p90: TKKLNKELSEGNKELEKLEKNIKELEETNNTLENDIKV<br>(SEQ ID NO: 40) |

TABLE 5-continued

| N° Parmed | N° GPC | Name of the gene in PlasmoDB | |
|---|---|---|---|
| p2 | 12 | PFB0145c | Predicted Protein Sequence of 1979aa (in underlined characters: fragment of the protein corresponding to peptide 12)<br>MVFTFKNKKKKKEASSDKVSKESFNEEDNENNEKREKSDSWYKKIIETKGKSKTKYKNDN<br>SLDDNINEDIINNNNNNNNDNNNDNNNDNNNDNNNDNNNENNNDNNNFNNYSDEIS<br>KNIIHKDNELENQLKDTLKSISSLSNKIVNYESKIEELEKELKEVKDKNIDNNDYENKLK<br>EKEDFVKQKIDMLNEKENLLQEKELDINKREKKINEKEKNIIKKEETFHNIEKEYLEKNK<br>ERETISIEIIDIKKHLEKLKIEIKEKKEDLENLNKKLLSKENVLKELKGCVKEKNETINS<br>LNDNIIEKEKKYKLLEYELEEKNKQIDLLNKQEKEKEKEKEREKEKEREKEKEYDTLI<br>KELKDEKISILEKVHSIKVREMDIEKREHNFLHMEDQLKDLKNSFVKNNNQLKVYKCEIK<br>NLKTELEKKEKELKDIENVSKEEINKLINQLNEKEKQILAFNKNHKEEIHGLKEELKESV<br>KITKIETQELQEMVDIKQKELDQLQEKYNAQIESISIELSKKEKEYNQYKNTYIEEINNL<br>NEKLEETNKEYTNLQNNYTNEINMLNNDIHMLNGNIKTMNTQISTLKNDVHLLNEQIDKL<br>NNEKGTLNSKISELNVQIMDLKEEKDFLNNQIVDLSNQIDLLTRKMEEKENKMLEQENKY<br>KQEMELLRGNIKSSENILNNDEEVCDLKRKLSLKESEMKMMKEEHDKKLAELKDDCDVRI<br>REMNEKNEDKINMLKEEYEDKINTLKEQNEDKINTLKEQNEDKINTLKEEYEHKINTMKE<br>EYEHKINTLNEQNEHKINTLNEQNEHKINTMKEEYEDKMNTLNEQNEDKMNSLKEEYENK<br>INQINSNNEIKIKDVVNEYIEEVDKLKVTLDEKKKQFDKEINYAHIKAHEKEQILLTEME<br>ELKCQRDNKYSDLYEKYIKLIKSICMIINIECCDDIENEDIIRRIEEYINNNKGLKKEVE<br>EKEHKRHSSFNILKSKEKFFKNSIEDKSHELKKKHEKDLLSKDKEIEEKNKKIKELNNDI<br>KKLQDEILVYKKQSNAQQVDHKKKSWILLKDKSKEKIKDKENQINVEKNEEKDLKKKDDE<br>IRILNEELVKYKTILYNLKKDPLLQNQDLLSKIDINSLTINEGMC<u>VDKIEEHILDYDEEI</u><br><u>NKSRSNLFQLKNEICSLTTEVMELNNKKNELIEENNKLNLVDQGKKKLKKDVEKQKKEIE</u><br><u>KL</u>NKQLTKCNKQIDELNEEVEKLNNENIELITYSNDLNNKFDMKENNLMMKLDENEDNIK<br>KMKSKIDDMEKEIKYREDEKKRNLNEINNLKKKNEDMCIKYNEMNIKYGDICVKYEEMSL<br>TYKETSLKYEQIKVKYDEKCSQYDEIRFQYDEKCFQYDEINKKYGALLNINITNKMVDSK<br>VDRNNNEIISVDNKVEGIANYLKQIFELNEEIIRLKGEINKISLLYSNELNEKNSYDINM<br>KHIQEQLLFLEKTNKENEEKIINLTSQYSDAYKKKSDESKLCGAQFVDDVNIYGNISNNN<br>IRTNEYKYEEMFDTNIEEKNGMHLSKYIHLLEENKFRCMKIIYENENIKSSNKIIGLYNY<br>SRYYGLREDLCKEEIVPSKIGNISNKNENNNKKNNTCDGYDEKVTIVLCIILNEIIKFLF<br>LNDEYVLLFEKIHKNVWKRMYIPEEIKFFILKYITLLNNLRDYIISVHNNMKNEKYDECW<br>FLFQHYFERSSDVRKEMVHFLLERKSQENLISFKSKLKSKKEKILTMDILNFSKEHMQLK<br>TIAHLRKEINYEKLSKDTLNRDYNLLLYKYQECVSKLKRVKNLMKEINQNVFIEKYDDIS<br>KELDNFSDGYNEQNEQHVMDPILLNNNKNKNNKLITEHNNPIINRLTNFTQNRDSKYKNK<br>IMDDVKQRKINSTMNNTNKNGINIIYNHYENLNKPNYNDNINRLNSYHQNIHIANSIHPN<br>RNQNKSFLTNQANSTYSVMKNYINSDKPNLNGKKSVRNIFNEIVDENVNKTFVHKSVFF<br>(SEQ ID NO: 41)<br>p12:<br>VDKIEEHILDYDEEINKSRSNLFQLKNEICSLTTEVMELNNKKNELIEENNKLNLVDQGK<br>KKLKKDVEKQKKEIEKL<br>(SEQ ID NO: 42) |
| P7 | 8 | PFB0145c | Predicted Protein Sequence of 1979aa (in underlined characters: fragment of the protein corresponding to peptide 8)<br>MVFTFKNKKKKKEASSDKVSKESFNEEDNENNEKREKSDSWYKKIIETKGKSKTKYKNDN<br>SLDDNINEDIINNNNNNNNDNNNDNNNDNNNDNNNDNNNENNNDNNNFNNYSDEIS<br>KNIIHKDNELENQLKDTLKSISSLSNKIVNYESKIEELEKELKEVKDKNIDNNDYENKLK<br>EKEDFVKQKIDMLNEKENLLQEKELDINKREKKINEKEKNIIKKEETFHNIEKEYLEKNK<br>ERETISIEIIDIKKHLEKLKIEIKEKKEDLENLNKKLLSKENVLKELKGCVKEKNETINS<br>LNDNIIEKEKKYKLLEYELEEKNKQIDLLNKQEKEKEKEKEREKEKEREKEKEYDTLI<br>KELKDEKISILEKVHSIKVREMDIEKREHNFLHMEDQLKDLKNSFVKNNNQLKVYKCEIK<br>NLKTELEKKEKELKDIENVSKEEINKLINQLNEKEKQILAFNKNHKEEIHGLKEELKESV<br>KITKIETQELQEMVDIKQKELDQLQEKYNAQIESISIELSKKEKEYNQYKNTYIEEINNL<br>NEKLEETNKEYTNLQNNYTNEINMLNNDIHMLNGN<u>IKTMNTQISTLKNDVHLLNEQIDKL</u><br><u>NNEKGTLNSKISELNVQIMDLKEEKDFLNNQIVDLSNQIDLLTRKMEEKENKMLEQENKY</u><br>KQEMELLRGNIKSSENILNNDEEVCDLKRKLSLKESEMKMMKEEHDKKLAELKDDCDVRI<br>REMNEKNEDKINMLKEEYEDKINTLKEQNEDKINTLKEQNEDKINTLKEEYEHKINTMKE<br>EYEHKINTLNEQNEHKINTLNEQNEHKINTMKEEYEDKMNTLNEQNEDKMNSLKEEYENK<br>INQINSNNEIKIKDVVNEYIEEVDKLKVTLDEKKKQFDKEINYAHIKAHEKEQILLTEME<br>ELKCQRDNKYSDLYEKYIKLIKSICMIINIECCDDIENEDIIRRIEEYINNNKGLKKEVE<br>EKEHKRHSSFNILKSKEKFFKNSIEDKSHELKKKHEKDLLSKDKEIEEKNKKIKELNNDI<br>KKLQDEILVYKKQSNAQQVDHKKKSWILLKDKSKEKIKDKENQINVEKNEEKDLKKKDDE<br>IRILNEELVKYKTILYNLKKDPLLQNQDLLSKIDINSLTINEGMCVDKIEEHILDYDEEI<br>NKSRSNLFQLKNEICSLTTEVMELNNKKNELIEENNKLNLVDQGKKKLKKDVEKQKKEIE<br>KLNKQLTKCNKQIDELNEEVEKLNNENIELITYSNDLNNKFDMKENNLMMKLDENEDNIK<br>KMKSKIDDMEKEIKYREDEKKRNLNEINNLKKKNEDMCIKYNEMNIKYGDICVKYEEMSL<br>TYKETSLKYEQIKVKYDEKCSQYDEIRFQYDEKCFQYDEINKKYGALLNINITNKMVDSK<br>VDRNNNEIISVDNKVEGIANYLKQIFELNEEIIRLKGEINKISLLYSNELNEKNSYDINM<br>KHIQEQLLFLEKTNKENEEKIINLTSQYSDAYKKKSDESKLCGAQFVDDVNIYGNISNNN<br>IRTNEYKYEEMFDTNIEEKNGMHLSKYIHLLEENKFRCMKIIYENENIKSSNKIIGLYNY<br>SRYYGLREDLCKEEIVPSKIGNISNKNENNNKKNNTCDGYDEKVTIVLCIILNEIIKFLF<br>LNDEYVLLFEKIHKNVWKRMYIPEEIKFFILKYITLLNNLRDYIISVHNNMKNEKYDECW<br>FLFQHYFERSSDVRKEMVHFLLERKSQENLISFKSKLKSKKEKILTMDILNFSKEHMQLK<br>TIAHLRKEINYEKLSKDTLNRDYNLLLYKYQECVSKLKRVKNLMKEINQNVFIEKYDDIS<br>KELDNFSDGYNEQNEQHVMDPILLNNNKNKNNKLITEHNNPIINRLTNFTQNRDSKYKNK |

TABLE 5-continued

| N° Parmed | N° GPC | Name of the gene in PlasmoDB | |
|---|---|---|---|
| | | | IMDDVKQRKINSTMNNTNKNGINIIYNHYENLNKPNYNDNINRLNSYHQNIHIANSIHPN RNQNKSFLTNQANSTYSVMKNYINSDKPNLNGKKSVRNIFNEIVDENVNKTFVHKSVFF (SEQ ID NO: 43) p8: IKTMNTQISTLKNDVHLLNEQIDKLNNEKGTLNSKISELNVQIMDL (SEQ ID NO: 44) |
| P9 | 76 | MAL13P1.30 4 | Predicted Protein Sequence of 1792aa (in underlined characters: fragment of the protein corresponding to peptide 76) MNNNNNNNNNSNNNNNSNNNNNGNSNNNFFSGKGNALSAYQNKILNIKSNNNNAHHFVNK NVPTYSPPNIIMANKKGGNFNNTSGNIINRYNVENNNHRNTYHPSNNNTRNSVNFLNKNI LYGNNNNNNNNNNNNINITNISNNNNNINITNISNNNNNINITNISNNNKQPISSNQHPYQ QKQSHHHNNSINYNEYMDEKNMNTSQSIFKNMTIQRNSQQFNTSDFVNNINIMNAPHINE HSNIYKRNSLNIVNNAHIISNMNIQSNRNSNISFPQNMNANI<u>GGLKNSNHNLNNIEMKY NTLNNNMNSINK</u>NTNITNVGTLNIQMKNNPMNVNINQNNYNTDFYVNENKVNSKNKENNN NHINIEKMNYIKSNVYLDNTLVQVNSNNNYNMDKNILNNNNNTYIINDKKNSTVNNNITN MDNNLVPGVMSSMNIPDDIKKRKKKERKKNENIYNNRNKSSINTEEHNNNIIDVANQNSE HFLQNNKQYGNITNIQNNNLSHDMNNYSINNSTTSDVIGIVELYKNSLSSKAVNKKKSKL IKDVIDDNKKRNKKEKKKTIPNNDSIINDMNKNKNVELLNETQIFDNKNYDKNNDIHNNI YNSNDNNLIHNKNNVNNDHTNIKEANNNNNRKSEHSEKNKDVHNYYANNYQCITDEKNN KQYILWNNRTIEVTFVWLFITKEFNENRKKYTAFLPYLKHFYPNRLKDLIEQLEKYSLLK FNYIMHSSYNMQEEYNKNKEPNNINSNDNNNKNDDNNNNNNKNVDGNNNNNNNINSNDKE VLMNGMLLSDKSTLNSNKQIDNTLINNINSGFNNIIKNMSIDDNTIRSIMDNIENITKGK KKGRKKKQTLENNGDNIKEDIKSSKKDKKKDNINDNNNDNNNDNNNDNNNDNNNDNNNDN NNDNNNNNNNNNNNNNNNNNNNHNNHNDNKNNQGDSKNEQEKKKKTRQYRKKSKITNDDN NEKIKQDNINSNNPKNDLKNNEIICSEEKNMKEDNIPDDTHYKEKRRNTFNLFNLDEGTI NMDLFNLSLLENDDALNKKENDMVSKSNIPSSFSSPPKETNNKNDIDKEQSDKHNNVQEF QNLNMNNEKSKDLYFKNDIDNNDNKDKIINETSSGTFMQNLKETFYEKTKAMFSNLLSD TKISKDDELNNEVDQNCVKTSSGILNKEENNKKEDDEKHFDDNTNEQKKNVDNGEYNEMT AEPGRKKRKKDVLERKKKNLNKEIIKSEKRIRKYRTKKMLLKEAMEKGISNNIVESNITA NNNNDNNKNNDNDNNNNNDNIINNNNNGDMFSNSYDNSYIKENKYNKKLCFPQNNLLS DFRSEPIIIQQDKRKIIKINTINKIKRKYKKFRFCINKVFKKKSINDIIALNENIHKNKD LLTLFKKKDLANLKKKNLSFFMDTLKLEKIDMLIMKRIQMCLEKIKNTLLLTCTINNVQE IVNILKKAFEKRLYLMWPLIEFSNKYRLDQYFHLLGKNKNHINSSFKDTKLFVHQNISSL ILYFNQRSMDDKWVEYLKSQMKPKRRRRKTKMKEQFLEDKPIDYLNTMNSQHSNNFIGEN FSEIETVESKANEYAFVGYNQKRLLTQITPYDYRVVLNSNFCNKFFTPNWREQQSIFIDN LHFDMVPDTDEIKKHFENVYIRYMEYDEEKLRSKSDTKSKEHHKKDKKYKMLFKKKEGKG KPGRKKKIKLEIENVSNEIKIKKPRKKYERVKPRKSKNAMMNEEKSGNSEKQINNVLNVT NIENKHKSKKGRKPKESNLNNLNINEDINVAKASPDTLHRASLEFMNPNLFT (SEQ ID NO: 45) p76: GGLKNSNHNLNNIEMKYNTLNNNMNSINK (SEQ ID NO: 46) |
| p12 | 77 | PF08_0048 | Predicted Protein Sequence of 2110aa (in underlined characters: fragment of the protein corresponding to peptide 77) MNEIKSESLLQTRPFKLGIEDIQNLGSSYFIENN<u>EKLKKYNNEISSLKKELDILNEKMGK CTTTT</u>KIVEPAKTPEFTFWYYELKEMKGFQDLVMYEVKKKKHFKVLSHSCLKYLSNREK MKIKKQEEEEKRLKLYSKNISSYMDVFWKKIEKLVWEEKKRELQQTLNKKKEMRFKKFVK EAIKKIKDARHNNAHELFENKYVSMSSNNNSEIVNNNASSVDNGDKELKEDDLTDQEEED YLLDEQMSSTDESENKEEEINMLDDEANLPIEELLKRMYGFKSGEDYINFMENEDDANEE NVIETSHNDEKSGDNSIGEDDNNNDEKGGDNNIDEDDNNNDEKSGDNSIGEDDNNDHKS GDNNIDEDDNNNDHKSEDNSIGEDDNNNDEKGGDNNIDENDNNSDHKSEDNNIDENDNNS DHQSDQEQFNHETKDDIIKNSSYEHIDNKNYYNKTGEDYKSDKENYSPTRFHNKLKKEKY DEYDTKLKIEKREEENKNYEKDEHEYESDNYDKEKINKKKELILLKNDIENDSDETSEHI KRDSRSSCQKQNCEKKRRIIKDEYNLRRTKIAKSKPSSDNNNSENDNNNDNNNDNNNDNN DDNNDDNNDDNNDDNNDDNNDDNNDDNNEHKNDSDDNDDILTCNMDEKHLTKIPPIIKA TLRDYQHAGLHWLLYLYKNNINGILADEMGLGKTLQCISLLSYLAYYFNIWGPHLVIVPT SILINWEIELKRFCPCFKILSYYGNQNERYKKRVGWFNKDSFHICISSYSTVVKDHLVFK RKRWKYIILDEAHNIKNFNTKRWNIILSLKRDNCLLITGTPLQNSLEELWSLLHFLMPNI FTSHLDPKEWFSDPLNLAIEKSKIHHSKELIDRLHTVIRPYILRRLKKNVEKEMPNKYEH IIKCKLTRRQQILYDEFINNKNVQNTLNTGNYIGLMNILIQLRKVCNHCDLFTNKYIQTP YYYMLSIRYFVPRFFILFEKNYYADFYLILFLHNEFTSLGGRDVTKETSPSSKSFDLAHI LTKHNTNELYDNNHISELYDNNHISELYDNNHISELYDNPMSHKNYKHNSN GYTYPNDPINNMNNNPSGFTKTSEQFGQIVSHERDNNYHMMDHNMMNNLLSKEMVNSLRN DDNSNNNFYKYSLTSNNNDSQTSIHDNKQCDYNKLCADTFNNINSIGNEEKRSLNVLNEQ NNNNSKDNNNNIDNNNNIDNNNNIDNNNNIDNNNNNIDNNNNIDNHHNNQHCN YNDNWPSDYPTNIINHRNAFLSILKLLNQSNPLNNDNNNNNNNNNGNNNIYNMNRYNSRN SRNSSLSNIFSSNTSKMNSFQLDFLYTNSFINQDALCKNSFFVNINIEDVHSYIYNSIYK EYIPKNILSFSDEFLTELNNNYDILSLYIDPYNRYKSYNEYLYKMKEEGTLTNQQSLGDI NNKHIYHKSTSNENTHMKNRKTFIYKYNNMFKVINNDTQYQNIFTDDTNNSYYNSLEHNL WIKRNQIDERKKEEEEQNKYYNVCMNNLYILRNERIPIFGKNFLDLIKKEFTKDKNIVY NYTNNVPIDYYSSVKEVWVEDICEKDNKKRKCKREKRWYKKIKKTNNPPEDSEVYRENSS DVEKYNCDVEKDNCDDEEKDNCDDEDMNSNLSSNVYGCIDISSQNFIHSRYHNPMMNMSY IIEFLFPNMEQFLKRHEKMIHNFTLINNPSVICKSHDIRINNNLLNYSNDKMNPIILQIK NATRVYHDAFLKQSIIFPPLNKDISLGSGKLCALEKLLSKCKREGNKCLLFTQFIKMLDIL |

TABLE 5-continued

| N° Parmed | N° GPC | Name of the gene in PlasmoDB | |
|---|---|---|---|
| | | | EIFLNHLNYSFIRLDGSTKVEQRQKIVTKFNNDKSIFIFISSTRSGSIGINLTAANVVIF<br>YDTDWNPSIDKQAMDRCHRIGQTKDVHVFRFVCEYTVEENIWKKQLQKRKLDNICINMGN<br>FNNSNTHSKITDTDPTHNKDWFTNVDTIKEVFINKKNNDDDDDMYKDRLLHEQVENKDKM<br>NVRFEKTLEHVEDKDDIRALNETKKETQNEISQNMQVSTNKKNIYIYINILYLNVNFFNK<br>HPLGEFTTRNDFQDSYNLTSYCFNFLNENLTDSLKQQIDEMRMKIEIEMMNTGDENMSLS<br>DLSNKSHNSE<br>(SEQ ID NO: 47)<br>p77: EKLKKYNNEISSLKKELDILNEKMGKCT<br>(SEQ ID NO: 48) |
| p20 | 79 | PFB0315w | Predicted Protein Sequence of 1712aa (in underlined characters: fragment of the protein corresponding to peptide 79)<br>MDSDKYKKFYVYNHGFTKQPFYERNLNDKGIHLKELKRLERVDEPRLYNNVDKIPNKKEI<br>IYNNIKSNNIQVRVNQNNNEEKKKEEANYTCVNNKYVTLKNKVHVNKYVNNSNINKIKIV<br>PIIKCSNYKIKNNPISHLKSNYENKFVKLSNFSNIKNGCSHKDNVINETMDQHKSEQLNN<br>DNIKKLLYDYCIFREDTIKTKTNISYNKMNSFKDNEENINYMDNNNIKSNSSSYCSYSNK<br>INQNNVNHTHLKTEFLNEKNSHTQNEQSIPLLDGLQNNHNSATKFHNNIYDNNNSLVNYK<br>SDKGIDLHNKMMKIETDKNGIITLEKKKHDEKYYNNIFLNPLNDNSNNVVITTCDNKESY<br>RNSTSDMINKIFEKMMNEKKNILKMKNFNDVIKKKITMAKEKILNSNSTINMKKVSFYNS<br>KDEDLFNEKENSYKYGVKRENQEDINVIKNNMKRNNINIDNNDNINIIKNDSVSKNIHIN<br>NKKKRDDDFPFNNSAGLLLDFDLCKRKVLEILKNVQSSKKKNKILTNHNHSSDNQNCHSS<br>DNQNCHSSDNQNCHSSDNQNCHSSDNQNCDSNACNKKDEEKKRKKKKIKKKNKMKNKSNN<br>KSKNKRETKSKKISNNNNNDNMNNQCDNMGDQRINNENMDKQNVNIQNEGNGFNNNKNNN<br>DLLNVYISPNMINHSLSSTCEKKNKEDNKMNDNKFLNSSSKMKIPEISTNNSNEKIVNVS<br>NDEMLVYHNLTVLNVKEQGGVTEESSCIKRTYFVDQFYDSYNMRNEKITDDNMQVEDIYN<br>VKENIKRTLKGDGHDDVKTNMLSEDNSYASGLWGNEINFISNNENCLNSYDISCDEKYIP<br>NEEEQDEELCSNNILVKDIEEKKMCGKLFFEEICVFRINEKNEHGHENLRKNNHNDDTHK<br>MYSSYENIQNINKQSTNPFCKKDEMEKSQGTNLFYDNYINSVDITKLELNKNCYQHINYE<br>VQNLIKKENSYAAEMNVGLVFRKYIPILINLSCNYLLIKKNEKNVITCISYTNIIDVKIV<br>KKSKKNKERFLFKIVYVFKKKEQKTEKNVTLLFRANLMEIFEKIKGRVDYCIIPNEDDKN<br>IQLQDKKKKGKKKKELQEEKMKKKKKTQEYVDIETVYEYVIEKYKRVHVLYLGRLLQIV<br>EKLFKKYILKYSFHKLRIFYEYKIEMEKLKKNYIHCIYDISDKLEFLIKKKMQHYFNHII<br>INSYESSFINYQIKTNDMLYNLLLKEKSAYQNHLGKNYILILYKVLLSMYKKKMAIYFRS<br>FVYNNIKVSKKKNAFAYTLTRVNSILVLYERRIKSFIFSKLKFNYDNVSYFCFTMYKIYL<br>RRILFGYLRIRDNRINIKNVIEKNVYRLVKLISKISDNHKYNAFLKLQKYVYEQNEKKNK<br>MICDNLIYANNELCNNLDKIAIEKGINQIDCLIKFKRKECLMKYFYTLKGPQINTERFYY<br>CIRYCSIFSFVLNKIIQKKVQHIFFQFVLKTLQRNNKNRLTHAIKLLQVLVQKKEKKSVI<br>DVLQLYDKYPYIFQYKDLTKIEVFVICVQNFVTLYNRKLLLNFLLKLHYLKYQEQFMKTY<br>NGIGSIYKFVHVLDKKLMNTIRESFRVILQNDKFLR<u>EKMNMKMEQMDMKMEKIDVNMDQM<br>DVKMEQMDVKMEQMDVKMKRMNK</u>KKKSQIHVNYNNKAYSSSSPSPMLRYNKYKDMSSNSA<br>SLIKKYPFLIYNSEISPDCTTMAGKFYNQKNK<br>(SEQ ID NO: 49)<br>p79: EKMNMKMEQMDMKMEKIDVNMDQMDVKMEQMDVKMEQMDVKMKRMNK<br>(SEQ ID NO: 50) |
| p21 | 80 | MAL8P1.12 | Predicted Protein Sequence of 1033aa (in underlined characters: fragment of the protein corresponding to peptide 80)<br>MSEESFDDTNKAFENEKDIILEKIVKDENNLNNCSNMINMDDVENMKKELYVLHKKDEEI<br>ENNVDCFSGDKYNVENVINLKKKKKKDEDTDSSYYKTTLDEVYDTSDISTDEMLSNYSSS<br>EDNNNIEMNIIINDFYLKDDNTYCLEWNSDIINVLSEEIKEKEKLLEDENKDICNMKSRFL<br>KLEKYVNIKKKKIINIKKNIEEKRKIEFDEKEIFKCLQIKNDFLKKENKKIELEREKNNK<br>KIIETQNNITTCQKNIDDIKKELILKENELNDFINKIKIIQQEEYEIEKIKLSKDKEIQN<br>VSYNLEKYNNEKIQQDKKYEQVKMNNMKFDIELKSIIQEYYDIKKDIKNISNKYICIMDM<br>IKCRDKTIYKFEKDYTKTIHKEKQLQNKCLHKQNLINTQKDKNIILNNQIKKIQFDINKI<br>RKELNDKQMSYDKTIIDRDHLNKEYEYEIVEIKEKLQEEKKSLENTLQHLNETYITMSTN<br>YEESKNEYEKEQVNNIEKNDLIKSSEQILVQLQNKLQKLLDEIKSLDLEKFQLTQTLQVI<br>KNDYITLEADVLGTQIKIKQIKSNIKKTEKELERQKEMLYKFDFQTQVLTKKINMISGIS<br>TFEKKKENQKKIILLEKELYKNEDIYNTLNNEMKRINIEIKNIKLYQNELQEQKMNYKNL<br>YEKLQLEIKSLESTINNEIKEKENIMLIELNLKIELDKLKSTFSKHVDLNLICKKEKKEN<br>MNNAKLSEQDINAHMESLKVIIKNINDEIHKLNIQLYEKKNKSNNLQLKLNSIIICNQKN<br>KDQKDICPNENQHIYYKMKIDQDIINLKEQLKKINEQIDKENIETKNFQRTLDDIIQTNK<br>EFNDNIKSIDPQYKILLK<u>KKNKLNKKWEQINDHINNLETNINDYNKKIKEGDSQLNNIQL<br>QCENIEQKINKIKE</u>SNLKVENNINDLFIKIERASNQLKKNLAPTTNMMKLKNKQIKDDEN<br>NLSNNNNNNNNNNNINVNVNCEPVPLEKHIFKQIMESLKEKLSLLMECFKNNIDNV<br>IMKEVFNLIETAE<br>(SEQ ID NO: 51)<br>p80: KNKLNKKWEQINDHINNLETNINDYNKKIKEGDSQLNNIQLQCENIEQKINKIKE<br>(SEQ ID NO: 52) |

TABLE 5-continued

| N° Parmed | N° GPC | Name of the gene in PlasmoDB | |
|---|---|---|---|
| p23 | 83 | PFC0345w | Predicted Protein Sequence of 1711aa (in underlined characters: fragment of the protein corresponding to peptide 83)<br>MNNITIRKPLFEVPNENKSNVLKYEKDNDFNNKKNDPSNLESYISSTLPYKRIENNHHNY<br>NNAKYDENNKNDDDHIPLDLNNKENMNFFVNKKNIHNSNLNYNHDNILQSYRNGEINRNY<br>NIMDNMYDVYYINKSKANLNDYLKHVNINHTAPCIGEFRTCMNCFLNISTLFCKTCNIFL<br>CAICNVKLHNNKSNHIINVASSGLYENNVKFNDIILKEKDKWLVELDNSIPIKIREKCSV<br>HTKEYIKYVCKTCKYTLLCADCLLNDPVHVQNKMENDMNIIKNDMNIMENDMNIMENDMN<br>IIKNDMNIMEKDMNIIKNNMNIIKNEMNIIKNVPEQKRKNEHFLPEQVQENND<br>NKNGSKNDKNLKDSNKKKRENQYIVSIYKKEETSDSNNKDIIKDVIYNNDIDKLKPGFKL<br>IRGNHEILTLIDARNDIKEELNNKLEILCKKSLILKNTLPSLRNICKYGKITCKNNKRSI<br>RSGFTVTNNILNDKKVKIHNDLKKLQDKSTNFLKKLDQERINYRNYLEKKKSELQHMIKL<br>SNKNAGLALDYYVQKLESFKCLFFTKDNLIDIEKKLEVPHSKIKSEFLSFLIEEMKYDIL<br>NSKMNIQNRCQSITKEFEQLFNCNIEIPVYPVHFRDFLKKRTFNNKQDVHLISNDKKKKQ<br>QYFHILPFTDFYMNIEISYQIKCKRKDSLHSKWEKRTVSVRSIYLCIHTHSRYIKRSNKY<br>QNDEFDENVSHKNDAVGSIAYEMEQNEINEQERRDGEMLGVDEMENRNKIENYEHIDNAS<br>SEISNKENCLIQKNMSNNLSNDIESIICLSNVEIKMFNDPNITNITILEKRNYSYGIELT<br>EYNDKKDLVGYWLLSQNNEKDMKELYHILCAIKKKNPKAARIPSFYPKINMNNSMFNYHE<br>NNISTIYKNFSANLIEPSYFINTSEHEKDERDGKYLEASINDYMSDDKKKKRYDSIESLR<br>GSDKIKNDQIYQGGHSSSLLYYYDNNNDDNNNNMYDSSSSSNHNYYILTNDKRLNMDNFI<br>NNNLEINNSQNKVIEKNLEYINNVKLTKTSNYEQSNNTNSKDEHNISSDKSKKEDTLNLS<br>RKSSYEYNNKILQSTSNKSLNGAYENNLFSGKKKKNKGTVLKDIEHINDIQDKYPEDLNI<br>NCVNKYVIENEEKHLLPLELEYNLVSSDEKFGLNKIKNDNNIIYMKHQNYHNLYDDNQKK<br>HILFDTNKNVSIQRNNNINSVIKTNHYEVEKNNKDQRNYDNFTCDKKKKIYYNIINSDKD<br>IYHNNIIYTKNEKEGIGNIHLNRNDKDITNFELLKLDGVKEFLDTFKDSYIDCHNKKENI<br>LNMTNKNKEDHQIIDVADKIFNETNMITMDNNKIYDDKNVHEKKCTHNDVIHHNMDILST<br>SIKNNEENLFIDTYQKQNRIGDIYMNRINILQEDDDDDNHNNNHNNNNNNNKLILFEYTK<br>NDQMLHNNKNNLEGTEEFSDFIEKKNKIKIKNKNESYHKIDESLLSNEKNNKVSLLLINN<br>NKDSSSVDNNKNNNNKNNNNKNNNNENNNKNNKNNNNDSFSKDNNLINNDNNNNNNNNDS<br>FSKDNNLINNDNNNNNNNNNKVIKKEIIDDKEKNDIHKRDNIYIKDVSVSPLINNHPNLN<br>SMRKDRTIEPLKIINGKNKLIKDLKKIQEQVERKIRKYKIQMDQENKKPPPSKNKINMKS<br>INLDIDDDQNVDSQGIVDYVLNQIGNKKMGQ<br>(SEQ ID NO: 53)<br>p83:<br>QNKMENDMNIIKNDMNIMENDMNIMENDMNIIKNDMNIMEKDMNIIKNDMNIIKNNMNII<br>KNEMNIIKNV<br>(SEQ ID NO: 54) |

The latter was performed using all the data in a multivariate analysis (following the methodology described in Roussilhon et al. 2007, PLoS medicine 4(11) e320 1791-1803). Please see Table 3 below.

In the multivariate analysis, when age was systematically controlled for each statistical test (Table 3 below), antibodies to peptide P27 were high when the number of malaria attacks was low after 1 and 3 years of active and daily clinical follow-up of the villagers. Indeed after 1 year, high anti-P27 IgG1 antibodies were associated with a low number of malaria attacks during the first year following the sampling (F ratio=8.92 and p=0.0047). After 3 years, high anti-P27 IgG1 levels remained associated with less malaria attacks observed during the 3 year period following the sampling (F ratio=12.14; p=0.0012). Similarly, after 3 years, absence of malaria attacks was found associated with high anti-P27 IgG1 response levels (OR=13.17 [1.27-195.84]; p=0.0408).

In the same conditions of statistical analysis applied for other peptides, anti-P27A IgG3 were found at high levels in individuals presenting with a low number of clinical attacks (F ratio=8.33 and p=0.0062 after 1 year of survey).

When anti-P27A responses were tested among a higher number of Ndiop inhabitants (n=102), the association between high antibody responses and reduced malaria attacks was confirmed. After 1 year: F ratio=13.27; p=0.0004 when using the number of malaria attacks as a continuous variable; OR=42.55 [4.05-610.07]; p=0.003, when malaria attacks were tested as a dichotomous variable (presence or absence of attacks); and after 3 years: F ratio=27.84; p<0.0001 when using the number of malaria attacks as a continuous variable, Odds ratio (OR)=68.69 [4.27-1717.64]; p=0.0051, when malaria attacks were tested as a dichotomous variable (presence or absence of attacks).

In non linear multivariate analysis (when testing the occurrence of malaria attacks as a Poisson distribution), anti-P27A IgG3 (p=0.002) was present at high levels when the number of malaria attacks was reduced.

TABLE 3

F ratios were calculated with regard to the number of malaria attacks identified 1 or 3 years after the blood samplings:

| Anti-peptide IgG: | F ratios (1 year): | p values (1 year): | F ratios (3 years): | p values (3 years): |
|---|---|---|---|---|
| IgG3-pMR198 | 5.43 | 0.025 | 1.29 | 0.262 |
| IgG1-p12 | 5.57 | 0.023 | 2.11 | 0.154 |
| IgG3-p14 | 6.77 | 0.013 | 2.5 | 0.122 |
| IgG3-p8 (LR148A) | 7.57 | 0.009 | 8.14 | 0.007 |
| IgG3-p9 | 0.645 | 0.427 | 3.74 | 0.06 |
| IgG3-p76 | 2.71 | 0.107 | 4.25 | 0.046 |
| IgG3-p77 | 7.17 | 0.011 | 3.31 | 0.076 |
| IgG3-p66 | 11.62 | 0.0015 | 3.96 | 0.053 |
| IgG1-p27 | 8.94 | 0.005 | 11.74 | 0.001 |
| Igg1-p45 | 2.26 | 0.14 | 1.47 | 0.233 |
| IgG3-p79 | 2.9 | 0.096 | 4.45 | 0.041 |
| IgG3-p80 | 3.25 | 0.079 | 4.19 | 0.047 |

TABLE 3-continued

F ratios were calculated with regard to the number of malaria
attacks identified 1 or 3 years after the blood samplings:

| Anti-peptide IgG: | F ratios (1 year): | p values (1 year): | F ratios (3 years): | p values (3 years): |
|---|---|---|---|---|
| IgG1-p83 | 9.06 | 0.003 | 14.54 | 0.0002 |
| IgG1-p90 | 4.41 | 0.042 | 0.88 | 0.354 |
| IgG1-pAS202.13 | 3.22 | 0.0803 | 9.22 | 0.0042 |
| IgG1-pLR179A | 3.4 | 0.072 | 6.88 | 0.013 |
| IgG3-p27A | 13.35 | 0.0004 | 28.55 | <0.0001 |

Due to the number of tests carried out, individual p values ≤ 0.0014 still remain significant in this Table.
Numbering corresponding here to Giampetro Corradin indications.

Table 3: The antibody responses found in Ndiop were tested in multivariate analysis by stepwise regression. The number of malaria attacks identified during the 3 years following the serum sampling were used as a continuous variable. Both age and Log 10-transformed antibody responses were simultaneously tested as explanatory variables.

The F ratio, (i.e., the ratio of the mean square for the effect divided by the mean square of the error) was calculated, and F statistics were used in order to determine that the effect test was null. By testing the hypothesis that the lack of fit was zero, the F test indicated if all parameters of an individual effect were null. The probabilities indicated in the Table correspond to the significance levels determined for the F ratio values (i.e., the probability that given that the null hypothesis is true, an even larger F statistic would occur due to random error). Using Bonferroni correction (i.e., taking into account that 18 different statistical tests were carried out), individual p values<0.0028 can still be considered as significant.

Antigenicity/Immunogenicity

The peripheral blood mononuclear cells (PBMCs) of 9 out of 17 (53%)* adult Nigerian donors proliferated when stimulated with P27A, with a mean stimulation index (SI) of 4.0. Two of the 17 (13%)* donors also gave significant T cell stimulation with P27 (mean SI=3.1).
*SI is considered significant when>than twice the negative control Antigen Size and Solubility P27 and P27A are 27 and 104 amino acids long respectively. They are readily soluble in aqueous solutions.

Antigenicity:

Peptides P27 and P27A are immunogenic, both alone and in combination, in 3 strains of mice (CB6F1, C3H and ICR) when given subcutaneously with Montanide® ISA 720. Table 4 shows ELISA titres and numbers of responding mice/number immunised with P27, P27A individually and in combination. Each mouse was injected with 20 μg of each peptide together with Montanide subcutaneously at 0, 3 and 8 weeks. Antibody titers were assessed 10 days after the second and third immunizations. No significant increase in antibody titers was observed between the second and third immunizations.

Strains of mice, such as CB6F1, C3H and ICR, are commercially available, e.g., from Charles Rivers Laboratories, Harlan, Taconic.

For example, ICR mice are available from Taconic (Corporate Office USA Taconic One Hudson City Centre Hudson NY 12534) under reference IcrTac:ICR.

C3H mice (haplotype $H2^k$) are available under strain code 025 from Charles River Laboratories, and CB6F1 mice are available under strain code 176 also from Charles River Laboratories (Charles River Laboratories, Inc. 251 Ballardvale Street Wilmington, Mass. 01887-1000).

TABLE 4

| | Peptide 27 | | Peptide 27A | | COMBINED | |
|---|---|---|---|---|---|---|
| | Mean Ab titer ± SD (×10³) | No of responders | Mean Ab titer SD (×10³) | No of responders | Mean Ab titer | No of responders |
| CB6F1 | 16.7 ± 10.5 | 4/4 | 24.3 ± 0 | 4/4 | ongoing | ongoing |
| C3H | 145.8 ± 118.8 | 4/5 | 182.2 ± 72.9 | 4/4 | 218.7-182.2 | 4/4 |
| ICR | 10.8 ± 9.4 | 3/5 | ongoing | ongoing | ongoing | ongoing |

Weak responses were obtained when mice were immunised with P27 and alum or GLA; however, alum is known to be a weaker adjuvant in mice than in humans. Assays of the immunogenicity of P27A with these adjuvants are currently ongoing.

The sera of mice immunized with peptides P27 and P27A in Montanide® ISA 720 localize the malaria antigen to the cytoplasm and the periphery of infected erythrocytes in IFAT.

In Western blots of lysates of infected erythrocytes, these antibodies also reacted specifically with a protein of the expected molecular weight (about 130 kD), as well as with a small number of bands of lower molecular weight, which may represent degradation products

MAIN CONCLUSIONS

The putative random coil segment of Pf27 was selected and chemically synthesized as P27A. P27A was recognized in ELISA by 76% of adult sera from Burkina Faso, Tanzania and 86% in Ndiop, Senegal;

Human purified antibodies specific for P27A also stained the cytoplasm and periphery of infected erythrocytes. Their activity in the ADCI assay was high, i.e., comparable to that of P27.

T cells from 9/17 adults living in endemic areas responded to P27A (average SI=4).

Longitudinal follow-up study in a malaria-endemic region revealed that high titers of antibodies against P27A were associated with clinical protection from malaria.

Peptides P27 and P27A induced high-titer antibodies in CB6F1, C3H and outbred ICR mice when injected subcutaneously, alone and in combination, together with Montanide ISA 720 adjuvant. The sera of these mice also reacted specifically with the cytoplasm and the periphery of Pf-infected erythrocytes in IFAT.

The invention claimed is:

1. An isolated polypeptide, the amino acid sequence of the polypeptide consisting of:
the sequence of SEQ ID NO: 6;
the sequence of a fragment of said sequence of SEQ ID NO: 6, said fragment comprising the sequence extending from position 223 to position 326 of said sequence of SEQ ID NO: 6; or
a conservative variant, which differs from said sequence of SEQ ID NO: 6 or from said fragment of SEQ ID NO: 6 by one conservative amino acid substitution, provided that said conservative variant has at least one of the following properties a)-i):
a) said conservative variant has an unstructured or unfolded 3D-arrangement;
b) said conservative variant does not comprise a globular functional domain or a protein structural motif comprising tandem repeats;
c) said conservative variant induces IgG1 and/or IgG3 antibodies;
d) said conservative variant has induces antibodies wherein the antibodies are specific to *Plasmodium*-infected erythrocytes but not to sporozoites;
e) in an ADCI assay, said conservative variant has an inhibitory effect on *Plasmodium* growth wherein the inhibitory effect is at least 92%;
f) said conservative variant has a property that, in humans under natural exposure to a malaria parasite, the total proportion of individuals having IgG1 and IgG3 antibodies that are specific to the conservative variant is higher than the total proportion of individuals having IgG1 and IgG3 antibodies that are specific to peptide P27 (SEQ ID NO: 14);
g) said conservative variant has a property that, in human beings under natural exposure to the parasite, it the conservative variant induces specific IgG1 and IgG3 antibodies that are very strongly associated with a state of resistance to malaria;
h) said conservative variant has a property that parasite-induced antibodies that are specific to said conservative variant are present in individuals who are resistant to malaria and are absent, or are present at lower titers, in individuals, who have malaria; or
i) said conservative variant comprises the sequence of SEQ ID NO: 10 or comprises an ortholog variant sequence of said sequence of SEQ ID NO: 10, said ortholog variant sequence having at least 98% identity with said sequence of SEQ ID NO: 10 over the entire length of SEQ ID NO: 10, said ortholog variant sequence consisting of 102 to 106 amino acids.

2. The isolated polypeptide of claim 1, wherein said conservative variant comprises:
the sequence of SEQ ID NO: 10, or
the E292G ortholog variant of said sequence of SEQ ID NO: 10, wherein the E292G ortholog variant is SEQ ID NO: 12.

3. The isolated polypeptide of claim 1, wherein the sequence of said conservative variant is the fragment of an ortholog sequence, said ortholog sequence being the ortholog of the sequence of SEQ ID NO: 6 in a *Plasmodium falciparum* strain other than the 3D7 strain, said ortholog sequence being encoded by chromosome 6 of said other *Plasmodium falciparum* strain.

4. The isolated polypeptide of claim 1, wherein the sequence of said conservative variant is the fragment of an ortholog sequence, said ortholog sequence being the ortholog of the sequence of SEQ ID NO: 6 in a *Plasmodium* strain other than a *Plasmodium falciparum* strain, said ortholog sequence being encoded by chromosome 6 of said other *Plasmodium* strain.

5. The isolated polypeptide of claim 1, wherein the sequence of said conservative variant is the sequence of SEQ ID NO: 18 or NO: 22 or NO: 26, or a sub-fragment thereof, which has retained the sequence of SEQ ID NO: 12.

6. The isolated polypeptide of claim 1, wherein the sequence of said fragment is the sequence of SEQ ID NO: 16 or NO: 20 or NO: 24, or a sub-fragment thereof, which has retained the sequence of SEQ ID NO: 10.

7. A medicament comprising the isolated polypeptide of claim 1 as an active ingredient.

8. A method for treating malaria in an individual comprising the step of:
administering the isolated polypeptide of claim 1,
wherein the individual is selected from the group consisting of infants, toddlers, children under the age of 5, and pregnant women.

9. An isolated antibody, which specifically binds to the isolated polypeptide of claim 1, or a Fab, a F(ab')2, a Fv, a Fab/c fragment thereof, or a scFv thereof.

10. The antibody of claim 9, which is an IgG1 or an IgG3.

11. The antibody of claim 9, which is a monoclonal antibody.

12. A hybridoma, secreting the monoclonal antibody of claim 11.

13. An immunogenic composition comprising at least one isolated polypeptide according to claim 1.

14. The immunogenic composition of claim 13, which further comprises at least one isolated polypeptide comprising the sequence of SEQ ID NO: 14 or an ortholog thereof in a *Plasmodium* species selected from the group consisting of *P. vivax*, *P. ovale*, *P. malariae*, *P. berghei*, *P. knowlesi*, *P. chabaudi*, and *P. yoelii*.

15. A kit for the in vitro diagnosis of malaria in an individual likely to be infected by a *Plasmodium* which contains: i) an isolated polypeptide according to claim 1, ii) the reagents for the constitution of the medium appropriate for carrying out the antigen-antibody reaction and iii) the reagents making possible the detection of the complex formed.

16. The isolated polypeptide of claim 1 wherein said unstructured or unfolded 3D-arrangement is established by assessment with the Hot-Loops predictor of the DisEMBL-1.4 software, the six parameters of the software being left at their default settings.

17. The isolated polypeptide of claim 1 wherein the globular functional domain is a zinc-finger, knottin, animal toxin, FGF molecule, or a chemokine.

18. The isolated polypeptide of claim 1 wherein the tandem repeat is an alpha-helical coiled coil domain.

19. The isolated polypeptide of claim 1 wherein the conservative variant differs from said sequence of SEQ ID NO:6 or from said fragment of SEQ ID NO:6 by one conservative amino acid substitution at position 292.

20. The isolated polypeptide of claim 1 wherein said substitution is a E292G substitution.

21. A composition comprising at least one antibody according to claim 9.

* * * * *